(12) United States Patent
Zanda et al.

(10) Patent No.: US 8,580,820 B2
(45) Date of Patent: Nov. 12, 2013

(54) TUBULYSIN COMPOUNDS WITH HIGH CYTOTOXICITY, PHARMACEUTICAL COMPOSITIONS THEREOF, AND METHOD OF USE THEREOF

(75) Inventors: Matteo Zanda, Gandino (IT); Monica Sani, Noviglio (IT); Paolo Lazzari, Pula (IT)

(73) Assignee: Kemtech S.r.L., Cagliari (IT)

( * ) Notice: Subject to any disclaimer, the term of this patent is extended or adjusted under 35 U.S.C. 154(b) by 171 days.

(21) Appl. No.: 12/841,976

(22) Filed: Jul. 22, 2010

(65) Prior Publication Data

US 2011/0200581 A1    Aug. 18, 2011

(30) Foreign Application Priority Data

Jul. 22, 2009 (IT) .............. MI2009A1296

(51) Int. Cl.
| | | |
|---|---|---|
| *A01N 43/40* | (2006.01) | |
| *A61K 31/445* | (2006.01) | |
| *C07D 401/00* | (2006.01) | |
| *C07D 405/00* | (2006.01) | |
| *C07D 409/00* | (2006.01) | |
| *C07D 411/00* | (2006.01) | |
| *C07D 413/00* | (2006.01) | |
| *C07D 417/00* | (2006.01) | |
| *C07D 419/00* | (2006.01) | |
| *C07D 421/00* | (2006.01) | |
| *C07D 277/00* | (2006.01) | |

(52) U.S. Cl.
USPC ............ 514/317; 514/326; 546/209; 548/200

(58) Field of Classification Search
USPC .................. 514/317, 326; 546/209; 548/200
See application file for complete search history.

(56) References Cited

U.S. PATENT DOCUMENTS

| | | |
|---|---|---|
| 2005/0239713 A1 | 10/2005 | Domling et al. |
| 2005/0249740 A1 | 11/2005 | Domling et al. |
| 2006/0128754 A1 | 6/2006 | Hoefle et al. |

FOREIGN PATENT DOCUMENTS

| | | |
|---|---|---|
| WO | WO 98/13375 A1 | 4/1998 |
| WO | WO 2004/046170 A2 | 6/2004 |
| WO | WO 2006/067633 A2 | 6/2006 |
| WO | WO 2008/112873 A2 | 9/2008 |
| WO | WO 2008/138561 A1 | 11/2008 |
| WO | WO 2009/012958 A2 | 1/2009 |
| WO | WO 2009/055562 A1 | 4/2009 |

OTHER PUBLICATIONS

Vippagunta et al. Advanced Drug Delivery Reviews, 2001, vol. 48, pp. 3-26.*
Zhiyoung Wang et al., Structure-activity and High-content Imaging Analyses of Novel Tubulysins, Chemical Biology & Drug Design, 2007, 70, (2), 75-86.
Hillary M. Peltier et al., The Total Synthesis of Tubulysin D, J. Am. Chem. Soc., 2006, 128, pp. 16018-16019.
Florenz Sasse et al., Tubulysins, New Cytostatic Peptides from Myxobacteria Acting on Microtubuli Production, Isolation, Physicochemical and Biological Properties, The Journal of Antibiotics, Sep. 2000, 53, 9, pp. 879-885.
Alexander Dömling et al., Total Synthesis of Tubulysin U and V, Angew. Chem. Int. Ed., 2006, 45, pp. 7235-7239.
Gurmeet Kaur et al., Biological Evaluation of Tubulysin A: a potential antcancer and antiangiogenic natural product, Biochem. J. 2006, 396, pp. 235-242.
Mohamed W. Khalil et al., Mechanism of Action of Tubulysin, an Antimitotic Peptide from Myxobacteria, ChemBioChem, 2006, 7, pp. 678-683.
Heinrich Steinmetz et al., Isolation, Crystal and Solution Structure Determination, and Biosynthesis of Tubulysins-Powerful Inhibitors of Tubulin Polymerization from Myxobacteria, Angew. Chem. Int. Ed., 2004, 43, pp. 4888-4892.
Bhooma Raghavan et al., Cytotoxic Simplified Tubulysin Analogues, J. Med. Chem., 2008, 51 (6), pp. 1530-1533.

(Continued)

*Primary Examiner* — Samira Jean-Louis
(74) *Attorney, Agent, or Firm* — Arent Fox LLP

(57) ABSTRACT

Tubulysine compounds of formula (A) having a high cytotoxicity (A)

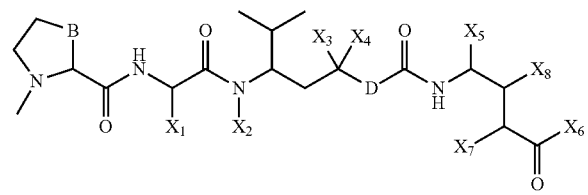

wherein:
B is selected from $CH_2$, $CH_2$—$CH_2$ or $CH_2$—$CH_2$—$CH_2$,
D is an aromatic linker,
$X_1$ is alkyl or alkenyl,
$X_2$ is selected from the $X_{2a}$, substituted or non substituted, selected from: aryl, heteroaryl, arylalkyl, cycloalkylalkyl, heterocycloalkylalkyl, or heteroarylalkyl,
$X_{2b}$: alkylene-O-alkyl, wherein alkylene is $C_2$-$C_{10}$,
$X_{2c}$: $CH_2$—O-alkyl,
$X_3$ is selected from H, or together with $X_4$ forms the group =O,
$X_4$ is selected from H, halogen, OH, SH, alkyl, alkenyl, $(OR_5)_n$—$OR_6$, $OC(O)R_7$, $NR_6R_7$, or together with $X_4$ forms the group =O,
$R_5$ is an alkylene,
n is zero or an integer from 1 to 10,
$R_6$ and $R_7$, equal to or different from each other, have the following meanings:
  z1: H, alkyl,
  z2 substituted or non substituted: aryl, heteroaryl, cycloalkyl, heterocycloalkyl, arylalkyl, heteroarylalkyl, cycloalkylalkyl, heterocycloalkyl-alkyl,
$X_5$ is z2, or has the meaning of z3-alkyl, alkenyl,
$X_6$ is selected from $NR_8R_9$, $OR_8$, NH—$NR_8R_9$, $SR_8$, $R_{10}$, wherein $R_8$ and $R_9$, equal to or different from each other, have the same meanings of $R_6$, $R_{10}$ has the same meanings as $R_6$ but excluding H,
$X_7$ is z3 or H,
$X_8$ is selected from z3, H, halogen, OH, SH, $OCH_3$.

11 Claims, No Drawings

(56) References Cited

OTHER PUBLICATIONS

Andrew W. Patterson et al., Design, Synthesis, and Biological Properties of Highly Potent Tubulysin D Analogues, Chem, Eur. J., 2007, 13, pp. 9534-9541.
Monica Sani et al., Total Synthesis of Tubulysins U and V, Angew. Chem. Int. Ed., 2007, 46, pp. 3526-3529.
Andrew W. Patterson et al., Expedient Synthesis of N-Methyl Tubulysin Analogues with High Cytotoxicity, J. Org. Chem., 2008, 73 (12), pp. 4362-4369.
Peter Wipf et al., Total Synthesis of N-Desacetoxybulsin H, Org. Lett., 2007, pp. 1605-1607.
Gregory K. Friestad et al., Stereoselective Mn-Mediated Coupling of Functionalized Lodides and Hydrazones: A Synthetic Entry to the Tubulysin γ-Amino Acids, Org. Lett., 2004, 6 (19), pp. 3249-3252.
Peter Wipf et al., Synthesis of the Tubuvaline-Tubuphenylalanine (Tuv-Tup) Fragment of Tubulysin, Org. Lett., 2004, 6 (22), 4057-4060.
Ranganathan Balasubramanian et al., Total Synthesis and Biological Evaluation of Tubulysin U, Tubulysin V, Their Analogues, J. Med. Chem., 2009, 52 (2), pp. 238-240.
Remington, The Science and Practice of Pharmacy, vol. II, 1995, p. 1457.
E.J. Corey et al., Highly Enantioselective Borane Reduction of Ketones Catalyzed by Chiral Oxazaborolidines, Mechanism and Synthetic Implications, J. Am. Chem. Soc., 1987, 109, pp. 5551-5553.
E.J. Corey et al., A Stable and Easily Prepared Catalyst for the Enantioselective Reduction of Ketones. Applications to Multistep Syntheses, J. Am. Chem. Soc., 1987, 109, pp. 7925-7926.
Manasi Das et al., Ligand-Based Targeted Therapy for Cancer Tissue, Expert Opinion Drug Deliv., 2009, 6 (3), pp. 285-304.
Sumith A. Kularatne et al., Prostate-Specific Membrane Antigen Targeted Imaging and Therapy of Prostate Cancer Using a PSMA Inhibitor as a Homing Ligand, Molecular Pharmaceutics, 2009, 6, (3), pp. 780-789.
Woo-Dong Jang et al., Bioinspired Application of Dendrimers; From Bio-Mimicry to Biomedical Applications. Progress in Polymer Science, 2009, 24, pp. 1-23.
Thomas Schluep et al., Polymeric Tubulysin-Peptide Nanoparticles with Potent Antitumor Activity, 2009, 15 (1), pp. 181-189.
E. Garcia-Garcia et al., Colloidal carriers and Blood-Brian Barrier (BBB) Translocation: A way to Deliver Drugs to the Brian?, International Journal of Pharmaceutics, 2005, 298, pp. 274-292.
Jörg Kreuter, Nanoparticlate Systems for Brain Delivery of Drugs, Advanced Drug Delivery Reviews, 2001, 47, pp. 65-81.
Marla Teresa Peracchia et al., Synthesis of a Novel Poly(MePEG cyanoacrylate-co-alkyl cyanoacrylate) Amphiphilic Copolymer for Nanoparticle Technology, Macromolecules, 1997, 30, pp. 846-851.
Luca Costantino et al., Peptide-Derivatized Biodegradable Nanoparticles able to Cross the Blood-Brain Barrier, Journal of Controlled Release, 2005, 108, pp. 84-96.
Barbara Stella et al., Design of Folic Acid-Conjugated Nanoparticles for Drug Targeting, J. of Pharmaceutical Sciences, Nov. 2000, 89, (11), pp. 1452-1464.
Rajib K. Mitra et al., Physicochemical Investigations of Microemulsification of Eucalyptus Oil and Water Using Mixed Surfactants (AOT+Brij-35) and Butanol, J. Colloid and Interface Science, 2005, 283, pp. 565-577.
Cathy E. McNamee et al., Physicochemical Characterization of PEG1500-12-acyloxy-stearate Micelles and Liquid Crystalline Phases, Langmuir, 2005, 21, pp. 8146-8154.
Spomenka Simovic et al., Dry Hybrid Lipid-Silica Microcapsules Engineered from Submicron Lipid Droplets and Nanoparticles as a Novel Delivery System for Poorly Soluble Drugs, Molecular Pharmaceutics, 2009, 6, (6), pp. 861-872.
E. Atherton et al., The Fluorenylmethoxycarbonyl Amino Protecting Group, The Peptides, 1987, 9, pp. 1-39, Academic Press, San Diego, CA.
Greg B. Fields et al., Solid Phase Peptide Synthesis Utilizing 9-Fluorenylmethoxycarbonyl Amino Acids, Int. J. Peptide Protein Res., 1990, 35, pp. 161-214.
Cornelia Halin et al., Antibody-Based Targeting of Angiogenesis, News Physiol. Sci., 2001, 16, pp. 191-194.
E. El-Emir et al., Characterisation and Radioimmunotherapy of LI9-SIP, An Anti-Angiogenic Antibody Against the Extra Domain B of Fibronectin, in Colorectal Tumour Models, British Journal of Cancer, 2007, 96, pp. 1862-1870.

\* cited by examiner

```
                     SEQUENCE LISTING

<160> NUMBER OF SEQ ID NOS: 28

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Val Arg Tyr
1

<210> SEQ ID NO 2
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Cys Asn Gly Arg Cys Val Ser Gly Cys Ala Gly Arg Cys
1               5                   10

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Asn Gly Arg Ala His Ala
1               5
```

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Asn Gly Arg Gly
1               5

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Cys Val Leu Asn Gly Arg Met Glu Cys
1               5

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Cys Asn Gly Arg Cys
1               5

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Cys Asn Gly Arg Cys Gly
1               5

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Leu Asn Gly Arg Glu
1               5

<210> SEQ ID NO 9
<211> LENGTH: 5
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 9

Tyr Asn Gly Arg Thr
1               5

<210> SEQ ID NO 10
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Leu Gln Cys Ile Cys Thr Gly Asn Gly Arg Gly Glu Trp Lys Cys Glu
1               5                   10                  15

<210> SEQ ID NO 11
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Leu Gln Cys Ile Ser Thr Gly Asn Gly Arg Gly Glu Trp Lys Cys Glu
1               5                   10                  15

<210> SEQ ID NO 12
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Cys Ile Cys Thr Gly Asn Gly Arg Gly Glu Trp Lys Cys
1               5                   10

<210> SEQ ID NO 13
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Cys Ile Ser Thr Gly Asn Gly Arg Gly Glu Trp Lys Cys
1               5                   10

<210> SEQ ID NO 14
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Met Arg Cys Thr Cys Val Gly Asn Gly Arg Gly Glu Trp Thr Cys Tyr
1               5                   10                  15
```

```
<210> SEQ ID NO 15
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Met Arg Cys Thr Ser Val Gly Asn Gly Arg Gly Glu Trp Thr Cys Tyr
1               5                   10                  15

<210> SEQ ID NO 16
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Cys Thr Cys Val Gly Asn Gly Arg Gly Glu Trp Thr Cys
1               5                   10

<210> SEQ ID NO 17
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Cys Thr Ser Val Gly Asn Gly Arg Gly Glu Trp Thr Cys
1               5                   10

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Cys Asn Gly Arg Cys Gly Val Arg Tyr
1               5

<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(9)
<223> OTHER INFORMATION: Cyclic

<400> SEQUENCE: 19

Cys Val Leu Asn Gly Arg Met Glu Cys
1               5

<210> SEQ ID NO 20
<211> LENGTH: 5
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: misc_feature
<222> LOCATION: (1)..(5)
<223> OTHER INFORMATION: Cyclic

<400> SEQUENCE: 20

Cys Asn Gly Arg Cys
1               5

<210> SEQ ID NO 21
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(6)
<223> OTHER INFORMATION: Cyclic

<400> SEQUENCE: 21

Cys Asn Gly Arg Cys Gly
1               5

<210> SEQ ID NO 22
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(6)
<223> OTHER INFORMATION: Beta-Ala

<400> SEQUENCE: 22

Ala Leu Ala Leu Ala Ala Cys Asn Gly Arg Cys Gly Val Arg Tyr
1               5                   10                  15

<210> SEQ ID NO 23
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NH2
<220> FEATURE:
<221> NAME/KEY: MOD_RES
<222> LOCATION: (1)..(2)
<223> OTHER INFORMATION: Beta-Ala
<220> FEATURE:
<223> OTHER INFORMATION: C-term COO-Resin

<400> SEQUENCE: 23

Ala Ala Cys Asn Gly Arg Cys Gly Val Arg Tyr
1               5                   10

<210> SEQ ID NO 24
<211> LENGTH: 4
<212> TYPE: PRT
<213> ORGANISM: Artificial Sequence
<220> FEATURE:
```

-continued

```
<223> OTHER INFORMATION: Description of Artificial Sequence: Synthetic
      peptide
<220> FEATURE:
<223> OTHER INFORMATION: N-term NH2
<220> FEATURE:
<223> OTHER INFORMATION: C-term COO-Resin

<400> SEQUENCE: 24

Ala Leu Ala Leu
1

<210> SEQ ID NO 25
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Ala Leu Ala Leu
1

<210> SEQ ID NO 26
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(6)
<223> OTHER INFORMATION: Beta-Ala

<400> SEQUENCE: 26

Gly Phe Leu Gly Ala Ala Cys Asn Gly Arg Cys Gly Val Arg Tyr
1               5                   10                  15

<210> SEQ ID NO 27
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NH2
<220> FEATURE:
<223> OTHER INFORMATION: C-term COO-Resin

<400> SEQUENCE: 27

Gly Phe Leu Gly
1

<210> SEQ ID NO 28
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Gly Phe Leu Gly
1
```

TUBULYSIN COMPOUNDS WITH HIGH CYTOTOXICITY, PHARMACEUTICAL COMPOSITIONS THEREOF, AND METHOD OF USE THEREOF

The present invention relates to synthetic tubulysine compounds having a high cytotoxicity, with antimitotic and/or antiangiogenic properties, the corresponding solvates and pharmaceutically acceptable salts, their use for the treatment of tumoural diseases and/or diseases associated to angiogenesis, and a process for their preparation with high yields.

As it is known, tubulysines are natural compounds obtainable by fermentation from culture media of myxobacteria strains. Examples of mixobacteria are Cystobacter, Archangium Gephyra, Angiococcus disciformis now classified as Pyxicoecus fallax. Tubulysines have been isolated for the first time by Hofle and Reichenbach as described in WO 98/13,375.

Their general formula of is the following:

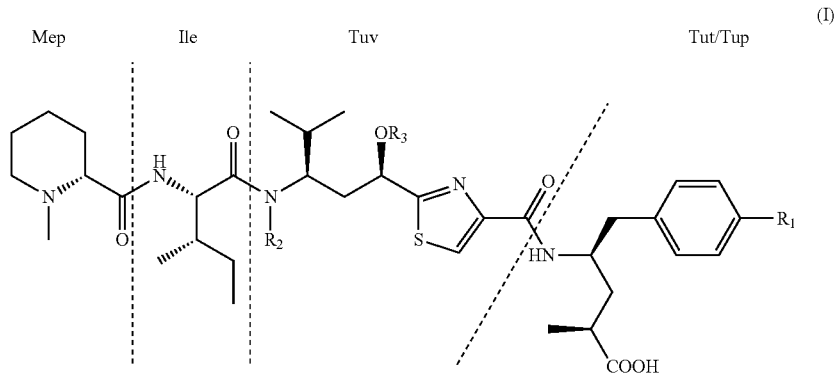

(I)

wherein:
Mep=N-methyl pipecolinic acid,
Ile=isoleucine,
Tuv=tubuvaline,
Tut/Tup=tubutyrosine/tubuphenylalanine.
The natural compounds comprised in formula (I) are in particular the following:

| | | | |
|---|---|---|---|
| Tubulisine A: | $R_1 = OH$ | $R_2 = CH_2OC(O)$-isobutyl | $R_3 = C(O)CH_3$, |
| Tubulisine B: | $R_1 = OH$ | $R_2 = CH_2OC(O)$-n-propyl | $R_3 = C(O)CH_3$, |
| Tubulisine C: | $R_1 = OH$ | $R_2 = CH_2OC(O)$-ethyl | $R_3 = C(O)CH_3$, |
| Tubulisine D: | $R_1 = H$ | $R_2 = CH_2OC(O)$-isobutyl | $R_3 = C(O)CH_3$, |
| Tubulisine E: | $R_1 = H$ | $R_2 = CH_2OC(O)$-n-propyl | $R_3 = C(O)CH_3$, |
| Tubulisine F: | $R_1 = H$ | $R_2 = CH_2OC(O)$-ethyl | $R_3 = C(O)CH_3$, |
| Tubulisine U: | $R_1 = H$ | $R_2 = H$ | $R_3 = C(O)CH_3$, |
| Tubulisine V: | $R_1 = H$ | $R_2 = H$ | $R_3 = H$. |

Natural tubulysines have received a remarkable interest for the high cytotoxicity shown towards a wide spectrum of cell lines. Tubulysines bind to tubuline inducing tubuline polymerization. In particular these compounds have been found effective in inhibiting various cell lines showing $GI_{50}$ values (Growth Inhibition of 50%) at the nanomolar level, even lower than this. As described by H. M. Peltier et al. in J. Am. Chem. Soc., 128, 2006, 16018-16019, tubulysines resulted more effective in inhibiting cell growth even from 20 to 1,000 times more than known antitumoural products as hepotylones, vinblastine and taxol. Among the various tubulysines, tubulysine D resulted the most active. However also tubulysine A has shown interesting antimitotic properties and promising antiangiogenic effects. See for example the following papers: F. Sasse et al., The Journal of Antibiotics, 53, 2000, 879-885; A. Dömling et al., Angew. Chem. Int. Ed., 45, 2006, 7235-7239; G. Kaur et al., Biochem J., 396, 2006, 235-242; M. W. Khalil et al., ChemBioChem, 7, 2006, 678-683; H. Steinmetz et al., Angew. Chem. Int. Ed., 43, 2004, 4888-4892; B. Raghavan et al., J. Med. Chem., 51, 2008, 1530-1533.

The process leading to the isolation of natural tubulysines is based on fermentation and has low yields. Generally the tubulysine concentrations in the final solution obtained from the process are lower than 10 mg/liter, even after several chromatographic purification steps. See for example the cited publications by A. Dömling and B. Raghavan.

The clinical applications of natural tubulysines up to now have therefore been limited due to the very poor availability of these compounds. The limits of the fermentation process for obtaining tubulysines have directed several research groups to study processes for the total synthesis of tubulysines, with particular reference to tubulysines A, B, C, D, U and V and their analogues. The various strategies of chemical synthesis adopted for the total synthesis of tubulysines and their analogues have recently been published in several publications. See for example H. M. Peltier (already mentioned), A. W. Patterson et al., Chem. Eur. J., 13, 2007, 9534-9541; M. Sani et al., Angew. Chem. Int. Ed., 46, 2007, 35263529; A. W. Patterson et al., J. Org. Chem., 73, 2008, 4362-4369; P. Wipf et al., Org. Lett., 9, 2007, 1605-1607; G. K. Friestad at al., Org. Lett., 6, 2004, 3249-3252; P. Wipf et al., Org. Lett., 6, 2004, 4057-4060; B. Raghavan et al., J. Med. Chem., 52, 2009, 238-240.

Tubulysine analogues and synthesis processes for their obtainment are described in US 2005/0239.713, US 2006/0128,754, WO 2009/012,958.

US 2005/0239,713 describes synthetic tubulisine analogues having the following general formula (II):

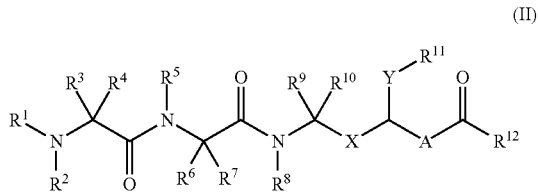

(II)

wherein:
A is an heteroaryl substituent having 5 or 6 atoms,
X is O, S or $NR^{13}$ or $CR^{14}R^{15}$,
Y is O, S, or $NR^{16}$,
$R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$ have the meaning of H, alkyl, alkenyl, alklnyl, heteroalkyl, aryl, heteroaryl, cycloalkyl, alkylcycloalkyl, heteroalkylcycloalkyl, heterocycloalkyl, arylalkyl, heteroarylalkyl: or two of the above mentioned substituents from $R^{1-}$ to $R^{16}$ are components of a cycloalkylic or heterocycloalkylic ring.

In this patent application the derivatives of formula (IA) (formula (I)) of patent application US 2005/0239,713) are excluded from the compounds of formula (II):

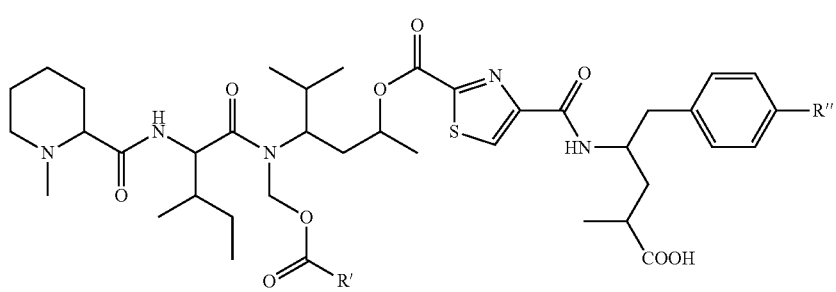

(IA)

wherein R' has the meaning of H, alkyl, alkenyl, aryl, or heteroaryl and R" has the meaning of H, OH, alkyl, aryl, or heteroaryl.

US 2006/0128,754 describes the synthesis of tubulysine derivatives having general formula (III) (formula I of patent application US 2006/0128,754):

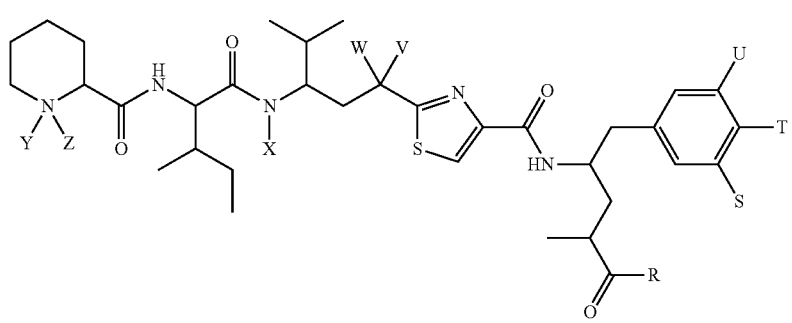

(III)

wherein:
S and U have the meaning of H, halogen, $NO_2$, or $NHR^{23}$,
T has the meaning of H or $OR^{24}$,
R has the meaning of H, alkyl, aryl, $OR^{21}$, $NR^{21}R^{22}$, or $NH-(CH_2)_{2-4}$,
X has the meaning of H, alkyl, alkenyl, or $CH_2OR^{29}$,
V has the meaning of H, $OR^{27}$, halogen or, together with W, of oxygen,
W has the meaning of H, alkyl or, together with V, of oxygen,
Y has the meaning of oxygen, when Z is $CH_3$, or of a free electronic doublet when Z is $CH_3$ or $COR^{31}$,
Z is $CH_3$ or $COR^{31}$, $R^{31}$ has the meaning of alkyl, $CF_3$, or aryl,
$R^{21}$ and $R^{22}$ have the meaning of H, alkyl, or aryl,
$R^{23}$ has the meaning of H, HCO, or $C_{1-4}$ alkyl-CO,
$R^{24}$ has the meaning of H, alkyl, aryl, $COR^{25}$, $P(O)(OR^2)_2$, or $SO_3R^{26}$,
$R^{25}$ has the meaning of alkyl, alkenyl, aryl, or heteroaryl,
$R^{26}$ has the meaning of H, alkyl, or metal ion,
$R^{27}$ has the meaning of H, alkyl, or $COR^{28}$,
$R^{28}$ has the meaning of alkyl, alkenyl or aryl,
$R^{29}$ has the meaning of H, alkyl, alkenyl, aryl or $COR^{30}$,
$R^{30}$ has the same meanings as $R_{25}$.

Patent application WO 2009/012,958 describes the synthesis of tubulysine analogues having general formula (IV):

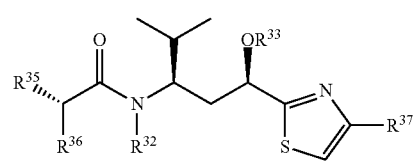

(IV)

wherein:
$R^3$ has the meaning of H, substituted or non substituted alkyl, substituted or non substituted heteroalkyl, $R^3$ has the same meanings as $R^{32}$ and also the meaning of an acyl group $(C(O)R^{34})$,
$R^{34}, R^{35}, R^{36}, R^{37}$ have the meanings mentioned in the patent application.

US 2005/0249,740 describes conjugated compounds containing tubulysine for the treatment of tumours, having general formula:

$$U'-V'-W'$$

wherein U' is a tubulysine or a tubulysine analogue of the above described formula (II), V' is a linker (for example a direct bond or an alkylene), W' is a polymer (for example polyethylenglycol) or a biomolecule (for example an antibody). These conjugated compounds show a high selectivity towards cancer cells. Further, they are able to reduce, in human beings and in animals, the side effects associated with the administration of tubulysines as such.

The need was felt to have available tubulysine compounds, characterized by a high cytotoxicity, being easily obtainable by a synthesis process in high yields. In particular the need was felt to have available tubulysine compounds having a cytotoxicity towards tumoural cell lines, expressed as GI50, lower than 10 nM ($GI_{50}<10^{-9}M$), preferably lower than 0.1 nM.

The Applicant has surprisingly and unexpectedly found a new class of tubulysine compounds solving the above mentioned technical problem.

It is an object of the present invention tubulysine compounds having formula (A):

(A)

wherein:
B is selected from $CH_2$, $CH_2$—$CH_2$ or $CH_2$-$CH_2$-$CH_2$,
D is an aromatic linker selected from phenyl, or heteroaryl with 5 or 6 atoms in the ring,
$X_1$ is alkyl or alkenyl,
$X_2$ is selected from the following groups:
  $X_{2a}$, substituted or non substituted, is selected from: aryl, heteroaryl, arylalkyl, cycloalkylalkyl, heterocycloalkylalkyl, or heteroarylalkyl,
  $X_{2b}$: alkylene-O-alkyl, wherein alkylene is $C_2$-$C_{10}$,
  $X_{2c}$: $CH_2$—O-alkyl,
$X_3$ has the meaning of H, or together with $X_4$ forms the group: =O,
$X_4$ is selected from: H, halogen, OH, SH, alkyl, alkenyl, $(OR_5)_n$—$OR_6$, $OC(O)R_7$, $NR_6R_7$, or together with $X_4$ forms the group: =O,
$R_5$ is an alkylene, n is zero or an integer from 1 to 10,
$R_6$ and $R_7$, equal to or different from each other, have the following meanings: z1: H, alkyl, z2, substituted or non substituted, is selected from: aryl, heteroaryl, cycloalkyl, heterocycloalkyl, arylalkyl, heteroarylalkyl, cycloalkylalkyl or heterocycloalkylalkyl, $X_5$ is z2, or it has the meaning of z3, z3 being alkyl or alkenyl,
$X_6$ has the meaning of H, $NR_8R_9$, $OR_8$, NH—$NR_8R_9$, $SR_8$, $R_{10}$, wherein $R_8$ and $R_9$, equal to or different from each other, have the same meanings as $R_6$, $R_{10}$ has the same meaning of $R_6$, but excluding H, $X_7$ is z3 or H,
$X_8$ is selected from z3, H, halogen, OH, SH or $OCH_3$.

The compounds of the present invention show unexpectedly and surprisingly a high cytotoxicity as they show towards tumoural cell lines $GI_{50}$ values lower than 10 nM, preferably lower than 0.1 nM. Furthermore they are obtainable by a synthesis process having high yields, thus very valuable from an industrial point of view.

The compounds of formula (A) comprise both geometrical isomers, for example cis-trans, and stereoisomers and their corresponding mixtures. Therefore the compounds of formula (A) of the present invention, depending on the substituents, can contain chiral centres in their structure.

Furthermore the atoms present in the molecules of the compounds of formula (A) can be in the corresponding isotopic forms.

When $X_2$=$X_{2a}$, one or more hydrogen atoms, preferably of the aryl, heteroaryl, arylalkyl, cycloalkylalkyl, heterocycloalkylalkyl or heteroarylalkyl ring, can be substituted with one or more groups, equal to or different from each other, selected from halogen, OH, O-aryl, SH, $OCH_2O$ (this substituent binds to two adjacent positions of the ring), $C_1$-$C_7$ alkyl, $C_1$-$C_7$ alkylthio, $C_1$-$C_7$ alkoxy, $C_1$-$C_7$ haloalkyl, $C_1$-$C_7$ haloalkoxy, $SO_2NH_2$, cyano, nitro, isothiocyanate, phenyl, cycloalkyl, saturated or unsaturated heterocycle, heteroaryl, amino optionally mono- or bisubstituted with a $C_1$-$C_7$ alkyl chain.

The phenyl, cycloalkyl, saturated or unsaturated heterocycle and heteroaryl substituents of $X_{2a}$ are optionally substituted with one or more groups, equal to or different from each other, selected from halogen, OH, O-aryl, SH, $OCH_2O$, $C_1$-$C_7$ alkyl, $C_1$-$C_7$ alkylthio, $C_1$-$C_7$ alkoxy, C1-C7 haloalkyl, $C_1$-$C_7$ haloalkoxy, $SO_2NH_2$, cyano, isothiocyanate, phenyl, cycloalkyl, saturated or unsaturated heterocycle, heteroaryl, nitro, amino optionally mono- or bi-substituted with a $C_1$-$C_7$ alkyl chain.

When $R_6$, $R_7$, $X_8$, $R_5$, $R_9$, $R_{10}$ have the meaning of $z_2$, one or more hydrogen atoms, preferably of the aryl, heteroaryl, cycloalkyl, heterocycloalkyl, arylalkyl, heteroarylalkyl, cycloalkylalkyl or heterocycloalkylalkyl ring, can optionally be substituted with one or more groups (optional substituents), equal to or different from each other, selected from the optional substituent groups of $X_{2a}$.

When $X_5$ has the meaning of Z2, one or more hydrogen atoms, preferably of the aryl, heteroaryl, cycloalkyl, heterocycloalkyl, arylalkyl, heteroarylalkyl, cycloalkylalkyl or heterocycloalkylalkyl ring, can optionally be substituted with one or more of the following groups (optional substituents): COOH, $C(O)R_6$, $OC(O)R_{94}$, wherein $R_6$ is as defined above and $R_{94}$, substituted or non substituted is selected from alkyl, cycloalkyl, alkenyl, aryl, heteroaryl.

When $R_{94}$ has the meaning of cycloalkyl, alkenyl, aryl or heteroaryl, one or more hydrogen atoms can optionally be substituted with one or more groups, equal to or different from each other, selected from the substituent groups of $X_{2a}$.

Preferably the compounds of formula (A) wherein contemporaneously the substituents have the meanings reported hereinafter, are excluded from the compounds of the present invention:
$X_2$=$x_{2C}$ B=$CH_2$—$CH_2$,
$X_1$=$C(CH_3)(CH_2$—$CH_3)$
$X_3$=H or, together with $X_4$, forms group: =O,
$X_4$ is selected from H, halogen, OH, $OR_{90}$, O-Q(O)—$R_{91}$, or together with $X_3$ forms the group: =O, wherein $R_{90}$ has the meaning of $C_1$-$C_4$ alkyl or $C_3$-$C_4$ cycloalkyl, and $R_{91}$ is selected from alkyl, alkenyl, aryl, cycloalkyl, $X_5$ is a benzyl substituent wherein the aromatic ring is substituted in para position with $Q_2$ and in meta positions with $Q_1$ and $Q_3$ substituents, $Q_2$ being hydrogen or $OR_{92}$, and $Q_1$ and $Q_3$, equal to or different from each other, are selected from hydrogen, halogen, $NO_2$ or $NH_2$, wherein:

$R_{92}$ is selected from H, $C_1$-$C_7$ alkyl, aryl or $C(O)R_{94}$, $R_{94}$ being as defined above, $X_6$ is H, alkyl, cycloalkyl, aryl, $OR_{97}$, or $NR_{97}R_{98}$, wherein $R_{97}$ and $R_{98}$, equal to or different from each other, are selected from H, alkyl, cycloalkyl or aryl, $X_7$=$CH_3$, $X_8$=H.

In this patent application, where not otherwise specified, the following definitions hold: by alkyl it is meant a saturated $C_1$-$C_{20}$ hydrocarbon chain, linear, branched when possible, substituted or non substituted, wherein one or more hydrogen atoms can optionally be substituted with halogen atoms. Preferably the hydrocarbon chain is $C_1$-$C_{12}$, for example methyl, ethyl, n-propyl, isopropyl, n-butyl, isobutyl, sec-butyl, tert-butyl, by alkylene it is meant a bivalent aliphatic $C_1$-$C_{20}$ chain, linear or when possible branched, having at each end. one free valence, substituted or non substituted, wherein one or more hydrogen atoms can optionally be substituted with halogen atoms. Preferably the bivalent aliphatic chain is $C_1$-$C_8$, for example vinyl, allyl, propen-l-yl, propen-2-yl, but-1-en-lyl, but-l-en-2-yl, but-l-en-3-yl, but-l-en-4-yl, but-2-en-1yl, but-2-en-2-yl, 2-methyl-propen-l-yl, 2-methyl-propen-3-yl, by alkenyl it is meant a mono-. or poly-unsaturated $C_2$-$C_{20}$ hydrocarbon chain, preferably mono-unsaturated, wherein the unsaturation is a double bond, said chain being a linear or when possible branched chain, substituted or non substituted, wherein one or more hydrogen atoms can optionally be substituted with halogen atoms. Preferably the hydrocarbon chain is $C_2$-$C_{12}$, by alkenylene it meant a bivalent mono- or poly-unsaturated $C_2$-$C_{20}$ hydrocarbon chain, wherein the unsaturation is a double bond, linear or when possible branched, having at each end one free valence, substituted or non substituted, wherein one or more hydrogen atoms can optionally be substituted with halogen atoms, preferably the hydrocarbon. chain is $C_2$-$C_8$, by alkynyl it is meant a mono- or poly-unsaturated $C_2$-$C_{20}$ hydrocarbon chain, preferably mono-unsaturated, wherein the unsaturation is a triple bond, said chain being linear or when possible branched, substituted or non substituted, wherein one or more hydrogen atoms can optionally be substituted with halogen atoms, preferably the hydrocarbon chain is $C_2$-$C_2$, by alkynylene it is meant a bivalent mono- or poly-unsaturated $C_2$-$C_{20}$ chain, wherein the eunsaturation is a triple bond, linear or branched when possible, having at each end one free valence, substituted or non substituted, wherein one or more hydrogen atoms can optionally be substituted with halogen atoms, preferably the bivalent hydrocarbon chain is $C_2$-$C_8$, by halogen it is meant one atom selected from fluorine, chlorine, bromine, iodine, by haloalkyl it is meant an alkyl as defined above, wherein one or more hydrogen atoms are substituted with halogen atoms. Examples of haloalkyl are trifluoromethyl, 1-bromo-nbutyl, pentachloroethyl, etc., by aryl it is meant an aromatic monocyclic radical, or a condensed aromatic polycyclic radical, having from 6 to 20 carbon atoms, by arylalkyl it is meant an alkyl as defined above, preferably $C_1$-$C_7$, linked to one aryl as defined above.

Benzyl can for example be mentioned, by cycloalkyl it is meant: an aliphatic monocyclic ring, optionally containing one or more unsaturations but with the proviso that the structure is not aromatic, said ring having from 3 to 10 carbon atoms, preferably from 4 to 9 carbon atoms, or—a polycyclic structure from 7 to 19 carbon atoms, by heterocycloalkyl it is meant a cycloalkyl as defined above wherein one or more carbon atoms are substituted with heteroatoms, equal to or different from each other, selected from S, O, N. When the ring is monocyclic, preferably the number of heteroatoms is not higher than 2, by heteroaryl it is meant an aryl as defined above, except that the monocyclic radical is $C_5$-$C_6$ wherein at least one or more carbon atoms are substituted with one or more heteroatoms, equal to or different from each other, selected from S, O, N. When the radical is monocyclic preferably the number of heteroatoms is not higher than 2, by heteroarylalkyl it is meant an alkyl as defined above, preferably $C_1$-$C_7$, linked to an heteroaryl as defined above, by cycloalkylalkyl it is meant an alkyl as defined above, preferably $C_1$-$C_7$, linked to a cycloalkyl as defined above, by heterocycloalkylalkyl it is meant an alkyl as defined above, preferably $C_1$-$C_7$, linked to an heterocycloalkyl as defined above, by heteroalkylene it is meant a group having the following meanings: —RA-O-Ya-, —Ra—S-Ya, —RA-N(Rb)-Ya-, —Ra—CO-Ya-, —Ra—O—CO-Ya-, —Ra—CO—O-Ya, —Ra—CO—N(Rb)-Ya-, —Ra—N(Rb)—CO-Ya, —Ra—O—CO—N(Rb)-Ya-, —Ra—N(Rb)—CO—O-Ya-, —Ra—N(Rb)—CO—N(Rc)-Ya-, —Ra—O—CO—O-Ya-, —Ra—N(Rb)—C(=NRd)-N(Rc)-Ya-, —Ra—CS-Ya-, —Ra—O—CS-Ya-, —Ra—CS—O-Ya-, —Ra—CS—N(Rb)-Ya-, —Ra—N(Rb)—CS-Ya-, —Ra—O—CS—N(Rb)-Ya-, —Ra—N(Rb)—CS—O-Ya-, —Ra—N(Rb)—CS—N(Rc)-Ya-, —RaO—CS—O-Ya-, —Ra—S—CO-Ya-, —Ra—CO—S-Ya-, —Ra—S—CO—N(Rb)-Ya-, —Ra—N(Rb)—CO—S-Ye-, —Ra—S—CO—O-Ya-, —Ra—O—CO—S-Ya-, —Ra—S—CO—S-Ya-, —Ra—S—CS-Ya-, —Ra—CS—S-Ya-, —Ra—S—CS—N(Rb)-Ya-, —Ra—N(R'b)—CS—S-Ya-, —Ra—S—CS—S-Ya-, —Ra—O—CS—S-Ya-, wherein:

Ra is a group selected from $C_1$-$C_6$ alkylene, $C_2$-$C_6$ alkenylene or $C_2$-$C_6$ alkynylene, Rb is selected from an hydrogen atom, a group selected from $C_1$-$C_6$ alkyl, $C_2$-$C_6$ alkenyl or $C_2$-$C_6$ alkynyl, Rc is hydrogen or a group selected from $C_1$-$C_6$ alkyl, $C_2$-$C_6$ alkenyl or $C_2$-$C_6$ alkynyl, Rd is hydrogen or a group selected from $C_1$-$C_6$ alkyl, $C_2$-$C_6$ alkenyl or $C_2$-$C_6$ alkynyl, Ya is a covalent bond or a group selected from $C_1$-$C_6$ alkylene, $C_2$-$C_6$ alkenylene or $C_2$-$C_6$ alkynylene, wherein each heteroalkyl group contains at least one carbon atom, and one or more hydrogen atoms can be substituted 'by fluorine or chlorine atoms, by alkylcycloalkyl it is meant a cycloalkyl as defined above, linked to one alkyl as defined above, by heteroalkylcycloalkyl it is meant a cycloalkyl as defined above, linked to an heteroalkyl as defined above, by (hetero)arylene, (hetero)cycloalkylene, arylalkylene, (heteroaryl)alkylene, and (heteroalkyl)cycloalkylene, respectively an aryl, an heteroaryl, a cycloalkyl, an heterocycloalkyl, an arylalkyl, an heteroarylalkyl, an alkylcycloalkyl, an heteroalkylcycloalkyl, as defined above wherein one hydrogen atom is substituted by a single bond, are meant, by alkylenearylalkylene it is meant an arylene with two alkylene chains from 1 to 20 carbon atoms linear or branched when possible.

By radical of a compound of the invention, or radical of a compound of formula (A), it is meant the compound of formula (A) having one or more free valences, derived from the removal of one or more hydrogen atoms or of a group $X_6$, with formation in the latter case of a —C(O)— group. Preferably the radicals of the compounds of formula (A) are monovalent or bivalent, still more preferably, they are monovalent.

Where not otherwise indicated in the present patent application:
$X_2$, $X_5$, $R_6$, $R_7$, $R_8$, $R_9$ and $R_{10}$ have the above mentioned meanings and are optionally substituted with the above mentioned substituent groups.

The preferred compounds of the invention are those of formula (A) wherein B, $X_1$, $X_2$, $X_3$, $X_4$, $X_5$, $X_6$, $X_7$ and $X_8$ are as defined above and D is an heteroaryl group having 5 or 6 atoms.

The most preferred compounds are those of formula (A) wherein B, $X_1$, $X_2$, $X_3$, $X_{4r}$, $X_5$, $X_6$, $X_7$ and $X_8$ are as defined above and D has the meaning of formula (V):

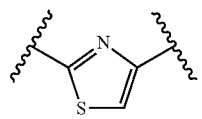

(V)

The compounds of formula (A) still more preferred are those wherein:
B is $CH_2$—$CH_2$,
D is an heteroaryl of formula (V),
$X_1$ is a $C_1$-$C_6$ alkyl,
$X_2$ is selected from the following groups: monocyclic aryl, monocyclic heteroaryl, monocyclic arylalkyl, monocyclic cycloalkylalkyl, monocyclic heterocycloalkylalkyl or monocyclic heteroarylalkyl, alkylene-O-alkyl, wherein alkylene is $C_2$-$C_4$,
$X_3$ is as defined above,
$X_4$ is selected from $C_1$-$C_6$ alkyl, $C_2$-$C_6$ alkenyl, $(OR_5)_nOR_6$, $OC(O)R_7$, or together with $X_3$ forms a group: =O,
$R_5$ is $C_1$-$C_2$ alkylene, n is zero or an integer from 1 to 4,
$R_6$ and $R_7$, equal to or different from each other, are selected from H or $C_1$-$C_6$ alkyl,
$X_5$ is selected from monocyclic arylalkyl, monocyclic heteroarylalkyl, monocyclic cycloalkylalkyl, monocyclic heterocycloalkylalkyl, alkyl, or alkenyl,
$X_6$ is selected from H, $NR_8R_9$, $OR_8$, NH—$NR_8R_9$, $SR_8$ or $R_{10}$, wherein $R_8$, $R_9$ and $R_{10}$ equal to or different from each other, are selected from alkyl, aryl, heteroaryl, cycloalkyl or heterocycloalkyl, or $R_8$ and $R_9$ are hydrogen,
$X_7$ is selected from $C_1$-$C_6$ alkyl or C2-00 alkenyl,
$X_8$ is H.

Preferred examples of the compounds of formula (A) are those of formula (AI):

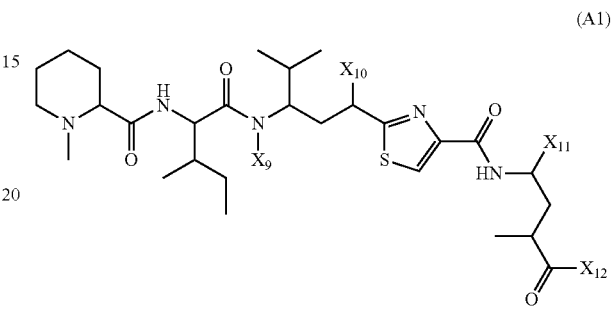

(A1)

wherein:
$X_9$ is selected from: monocyclic arylalkyl, monocyclic cycloalkylalkyl, monocyclic heterocycloalkylalkyl, or monocyclic heteroarylalkyl, optionally substituted with the groups which are optional substituents of $X_{2a}$,
  $CH_2$—$CH_2O$-alkyl wherein alkyl is $C_1$-$C_3$, wherein $C_3$ is linear or branched,
$X_{10}$ is selected from $(OR_{10})_m$—$OR_{11}$ or $OC(O)R_{12}$,
$R_{10}$ is a $C_1$-$C_2$ alkylene, m is zero or an integer from 1 to 3,
$R_{11}$ and $R_{12}$, equal to or different from each other, are selected from H, $CH_3$,
$X_{11}$ is selected from monocyclic arylalkyl or monocyclic heteroarylalkyl, non substituted or substituted, optionally substituted with the groups which are optional substituents of $X_5$, when $X_5$=$Z_2X_{12}$ is selected from H, $NR_{8a}R_{9a}$, $OR_{8a}$, or NH—$NR_{8a}R_{9a}$, wherein $R_{8a}$ and $R_{9a}$, equal to or different from each other, are selected from H, alkyl, monocyclic aryl, monocyclic heteroaryl, monocyclic cycloalkyl, monocyclic heterocycloalkyl, wherein monocyclic aryl, monocyclic heteroaryl, monocyclic cycloalkyl, monocyclic heterocycloalkyl are non substituted or optionally substituted with those groups which are optional substituents of $R_8$ and $R_9$.

The still more preferred compounds of the invention are reported hereinafter:

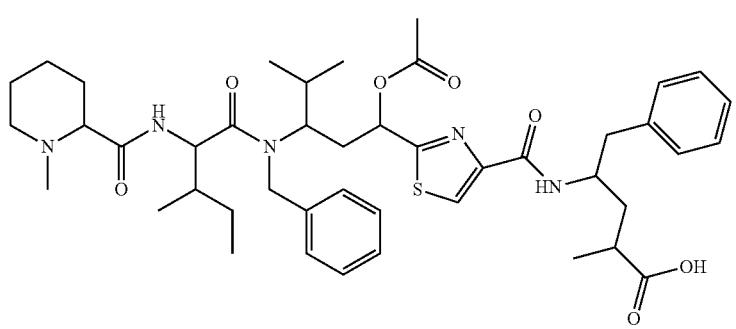

(AI)

-continued
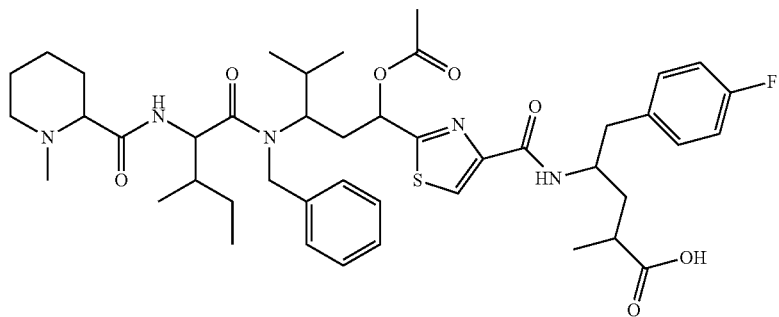
(AII)
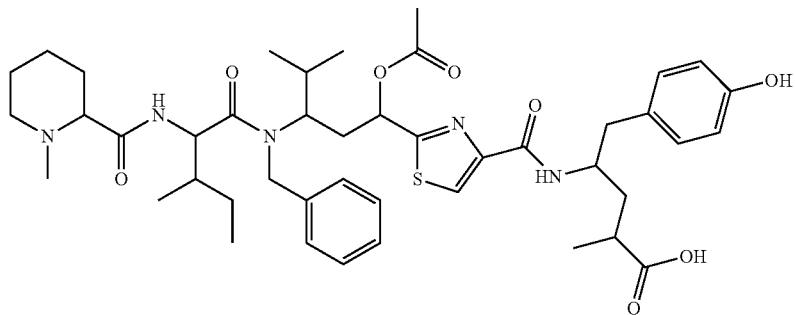
(AIII)
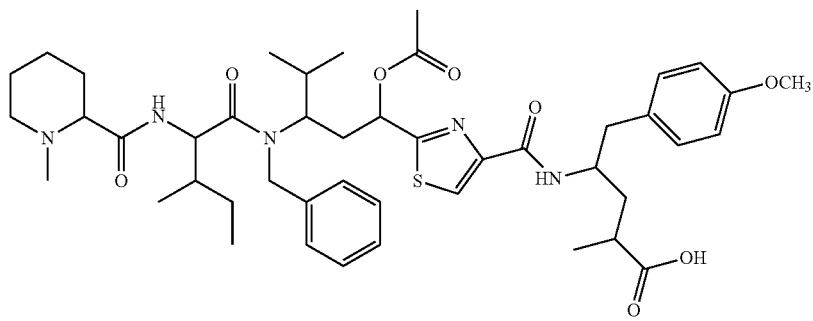
(AIV)
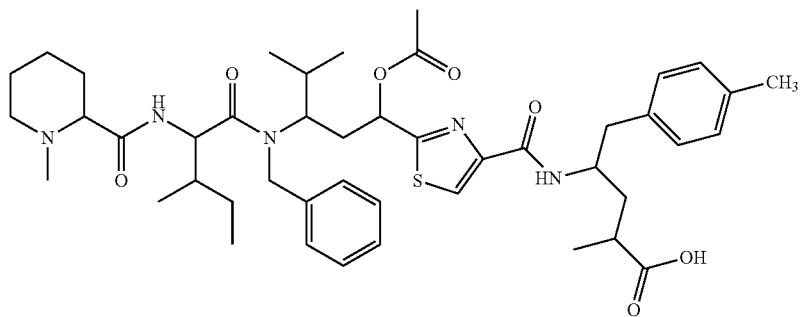
(AV)
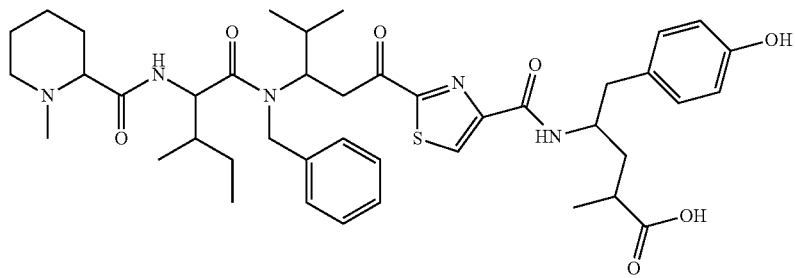
(AXLV)

-continued
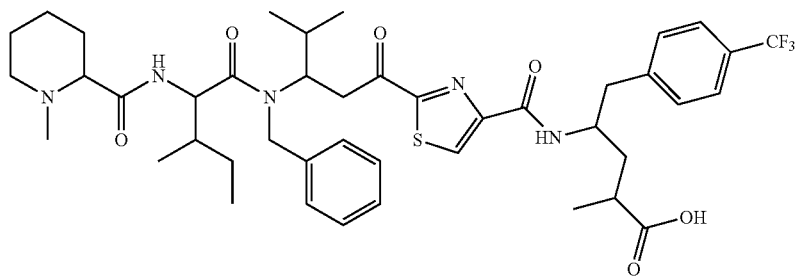
(AXLVIII)
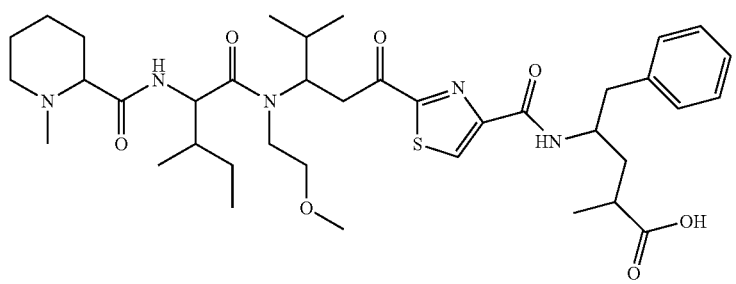
(AL)
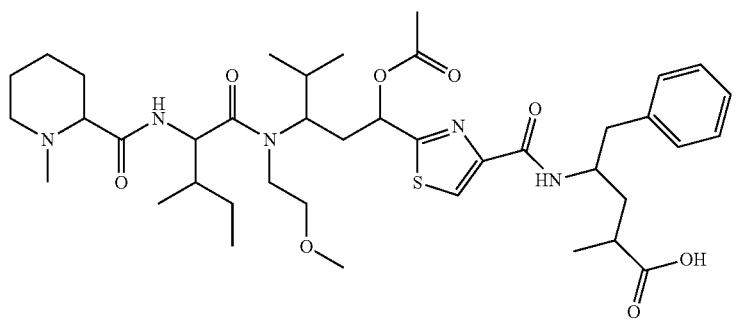
(AVIII)
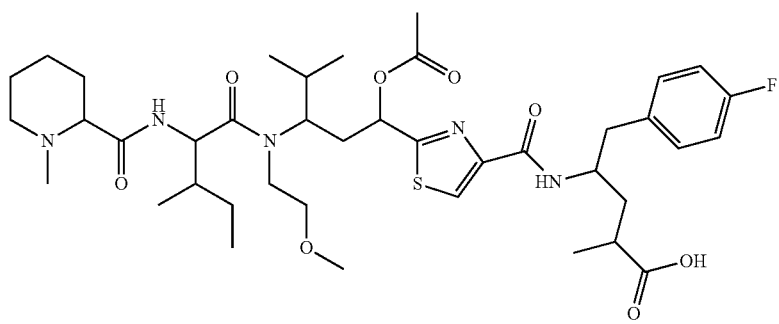
(AIX)
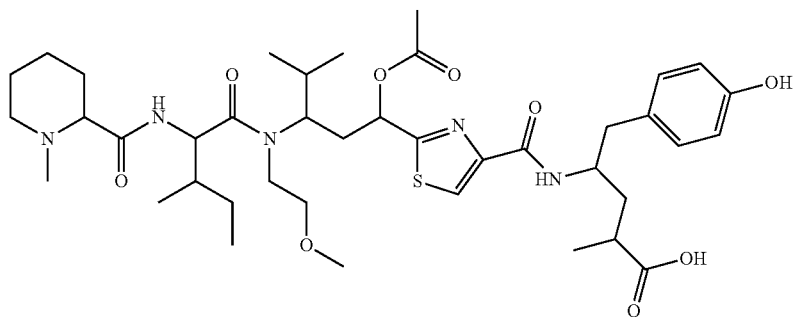
(AX)

(AXI)
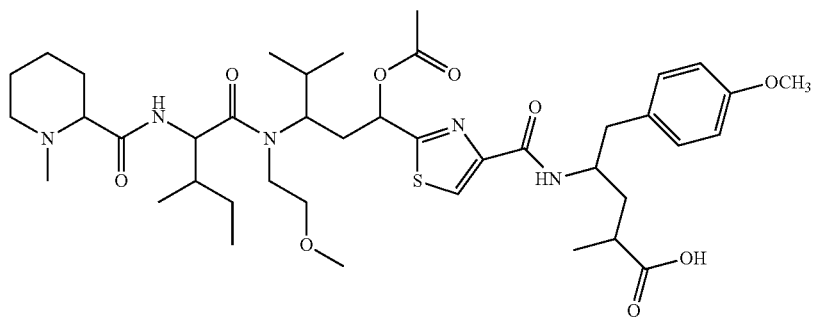
(AXII)
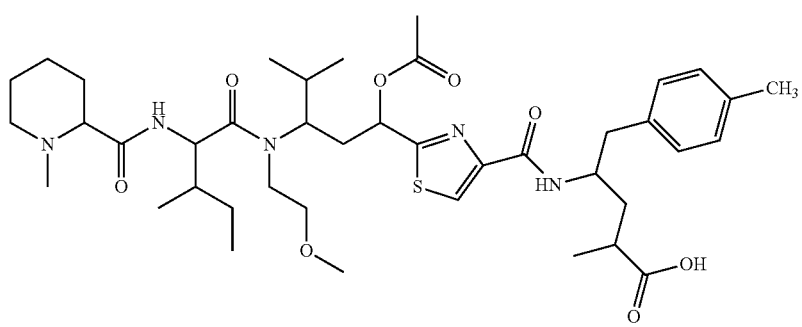
(AXIII)
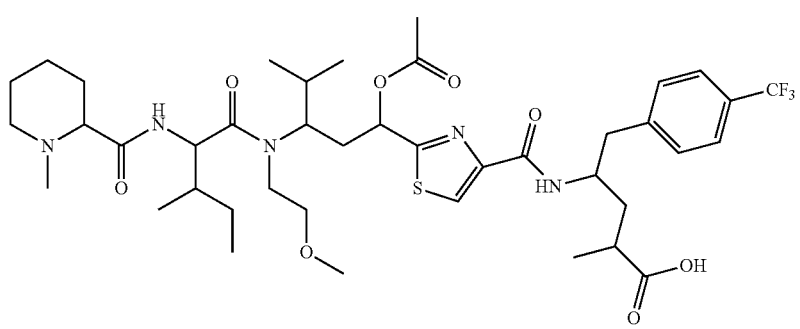
(AXIV)
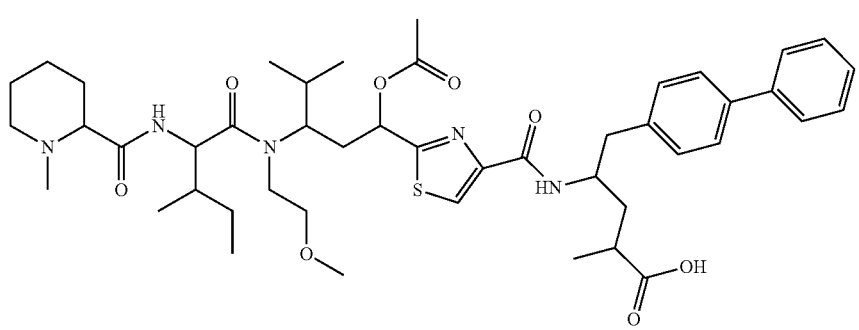
(AXV)
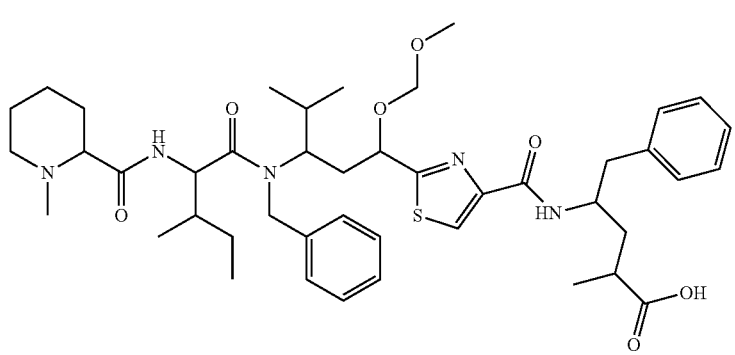

-continued
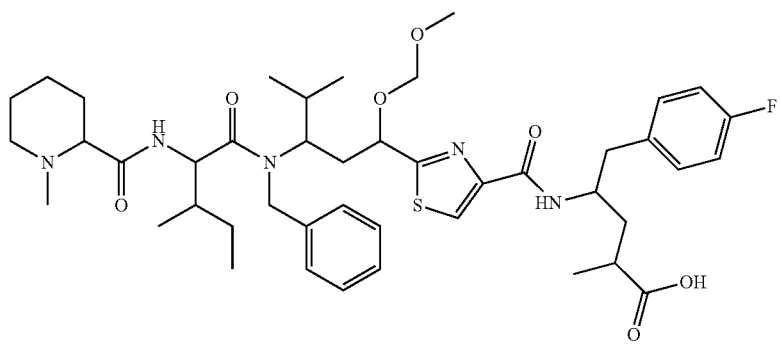
(AXVI)
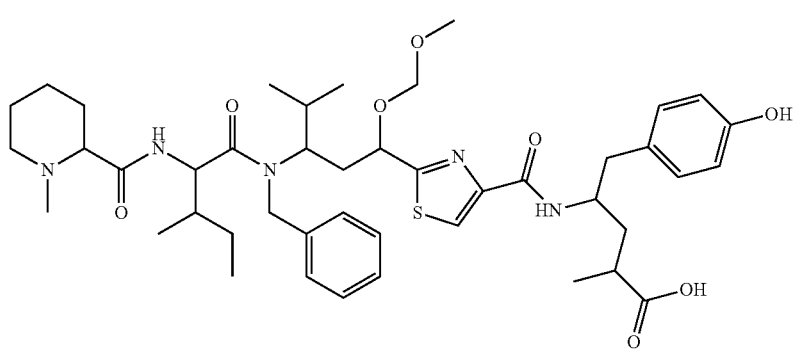
(AXVII)
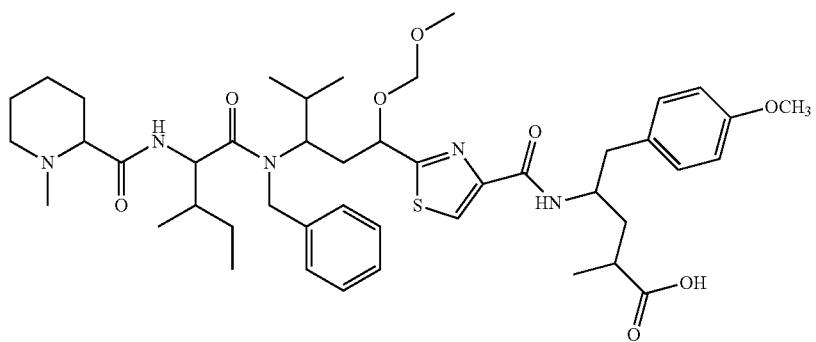
(AXVIII)
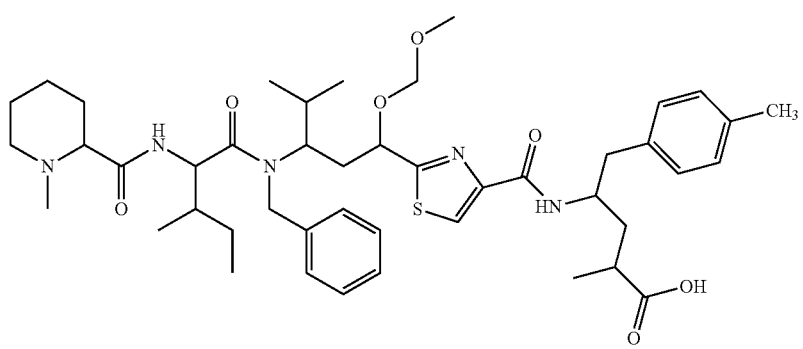
(AXIX)

-continued
(AXX)
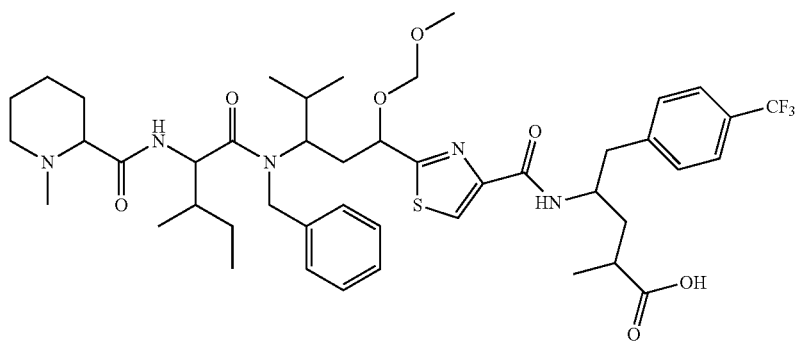
(AXXI)
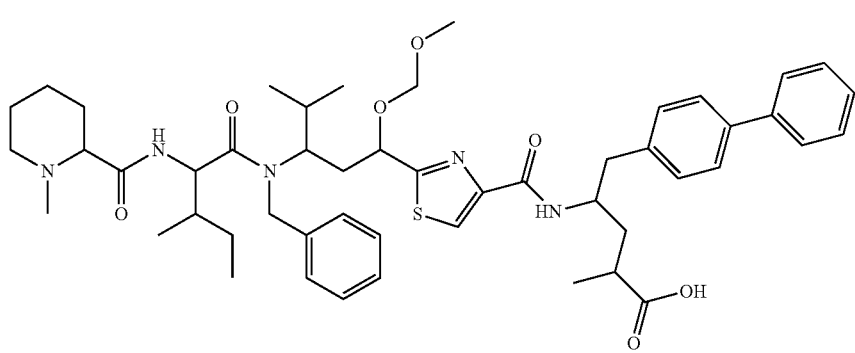
(AXXII)
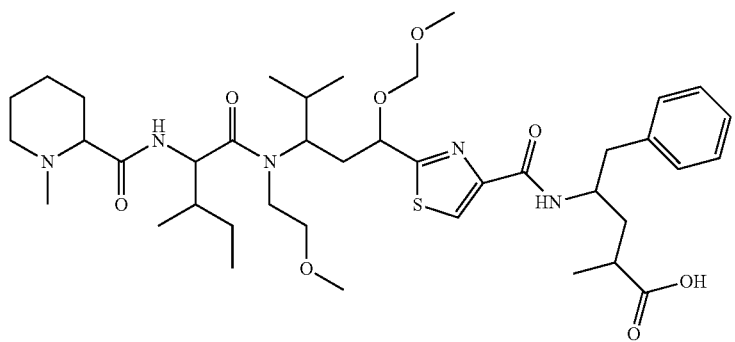
(AXXIII)
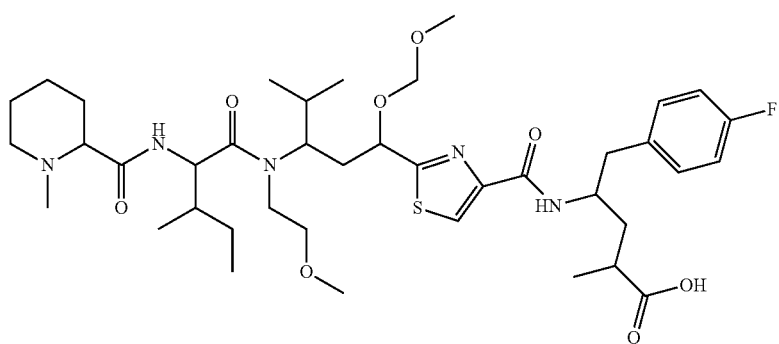

-continued
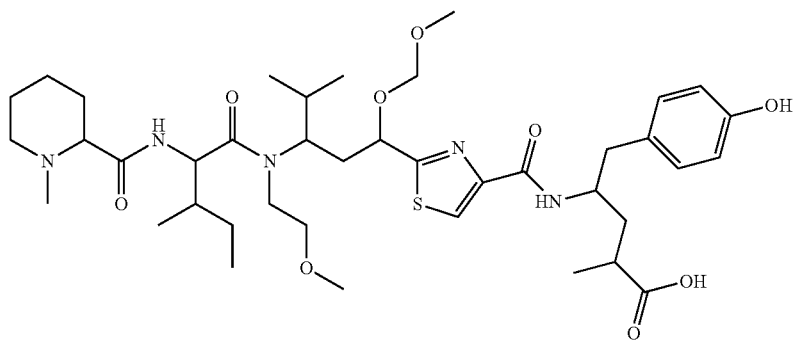
(AXXIV)
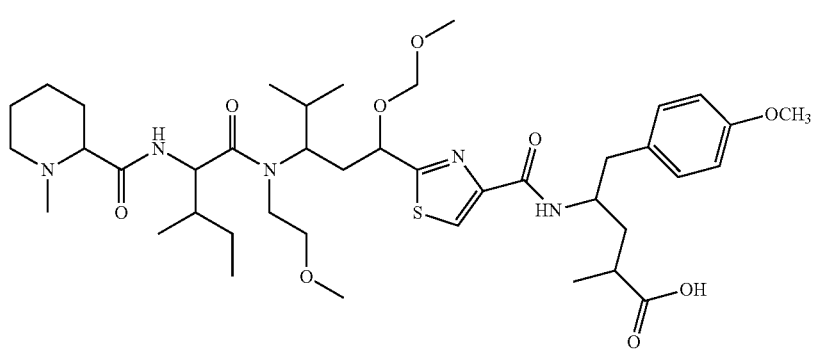
(AXXV)
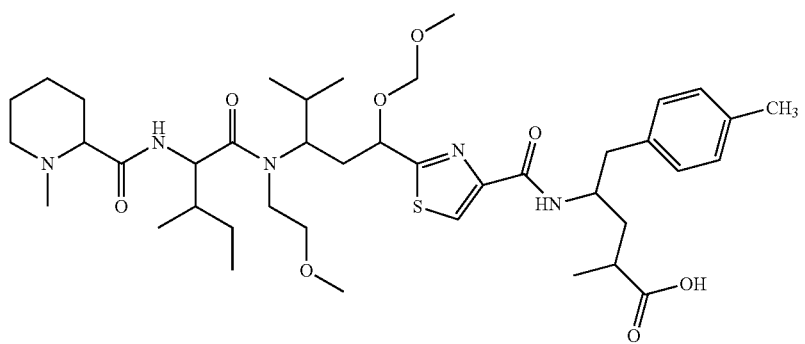
(AXXVI)
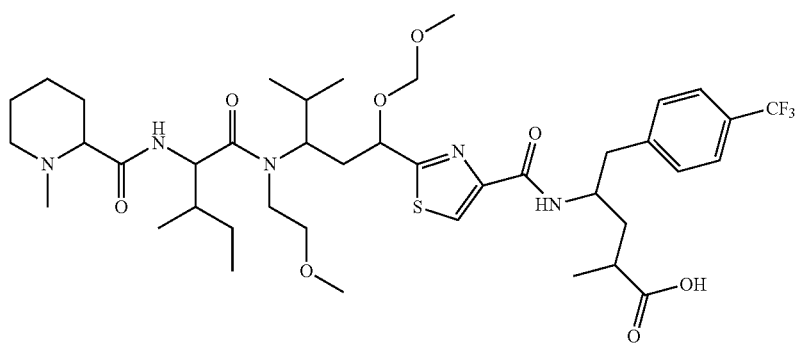
(AXXVII)

-continued
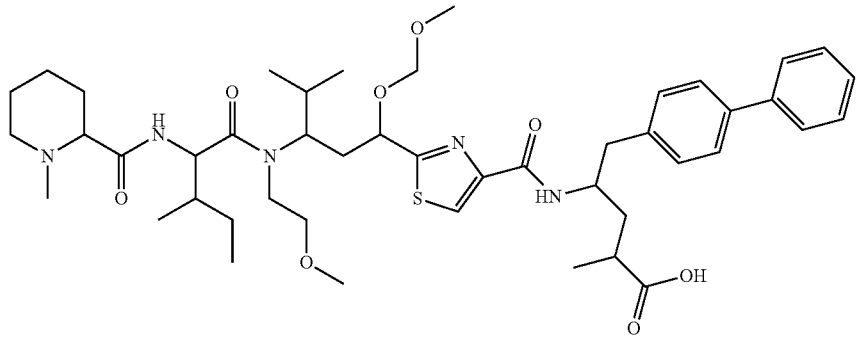
(AXXVIII)
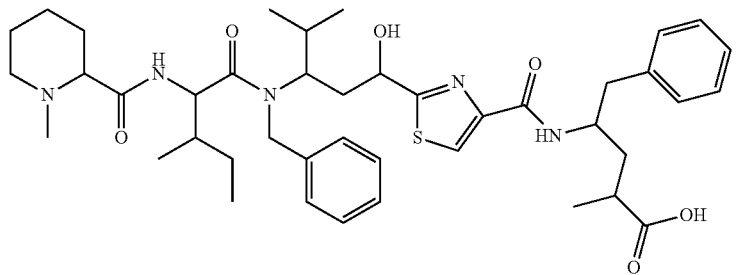
(AXXIX)
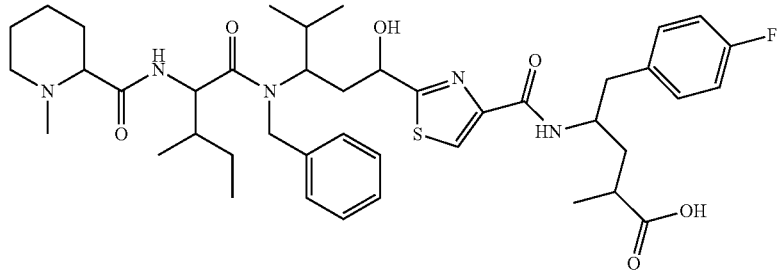
(AXXX)
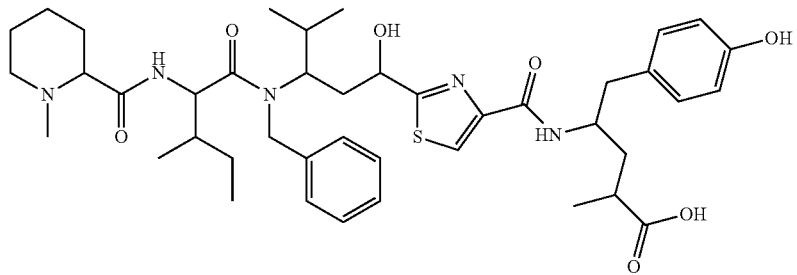
(AXXXI)
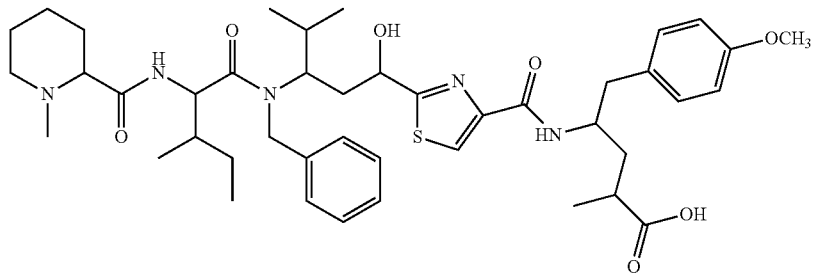
(AXXXII)

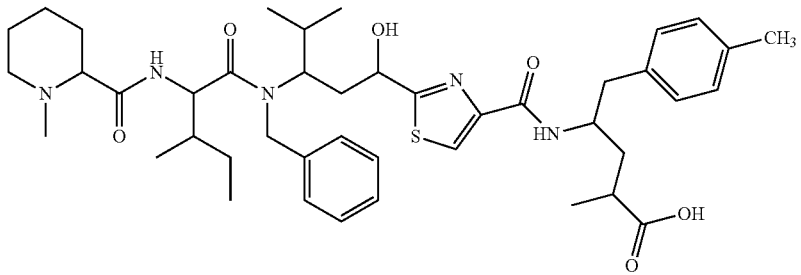
(AXXXIII)
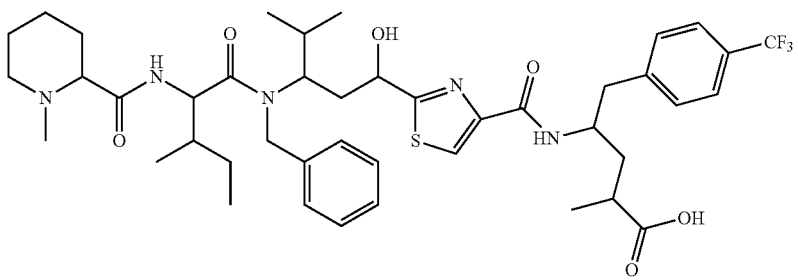
(AXXXIV)
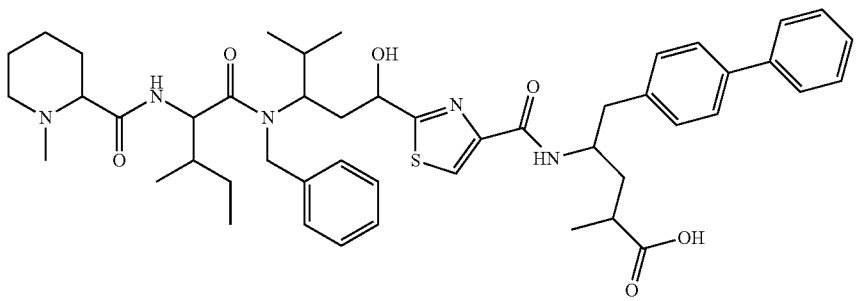
(AXXXV)
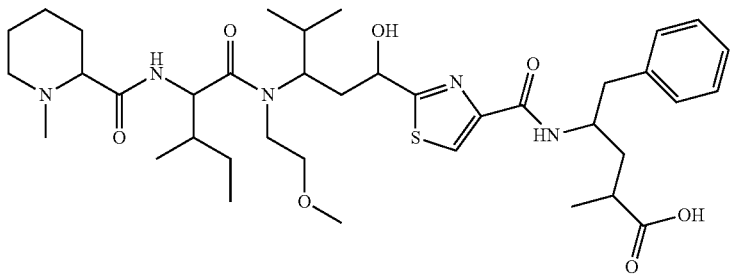
(AXXXVI)
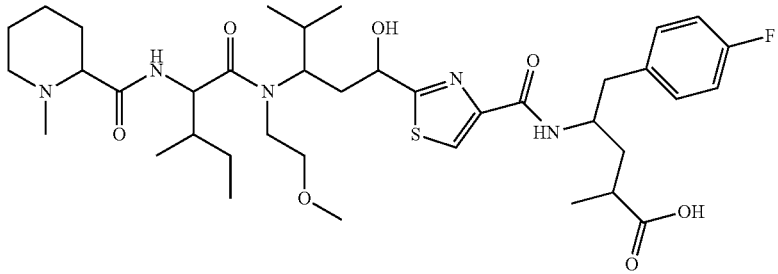
(AXXXVII)

-continued
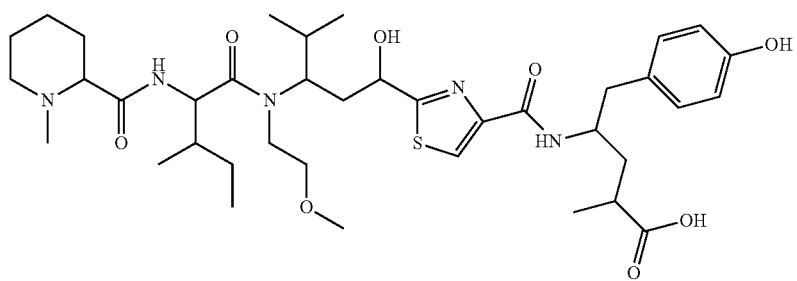
(AXXXVIII)
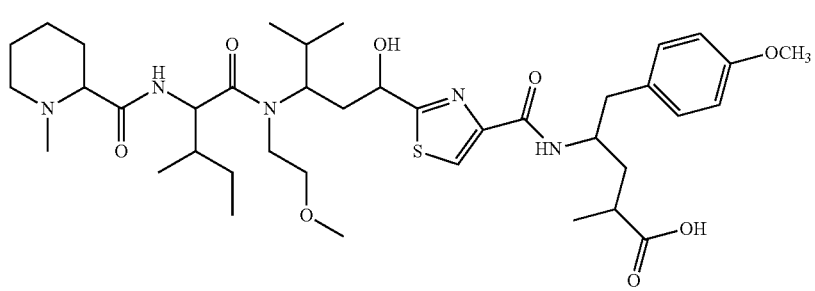
(AXXXIX)
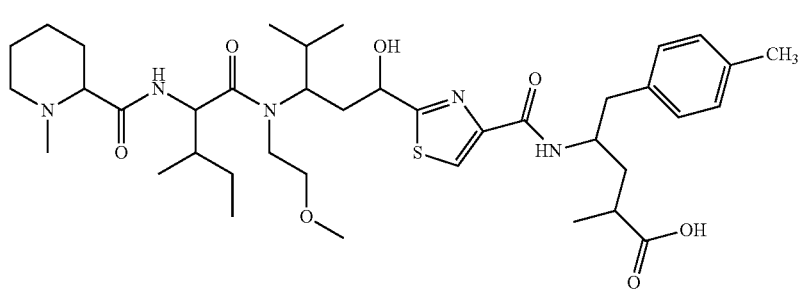
(AXL)
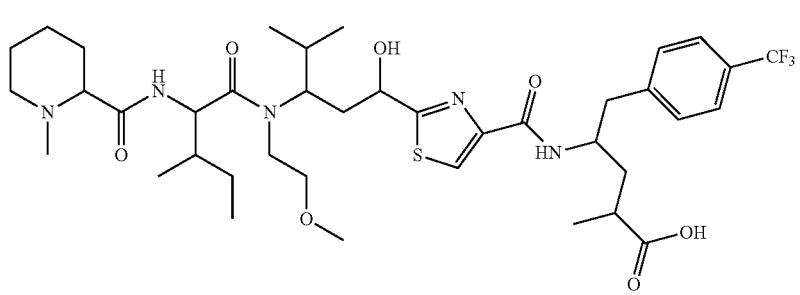
(AXLI)
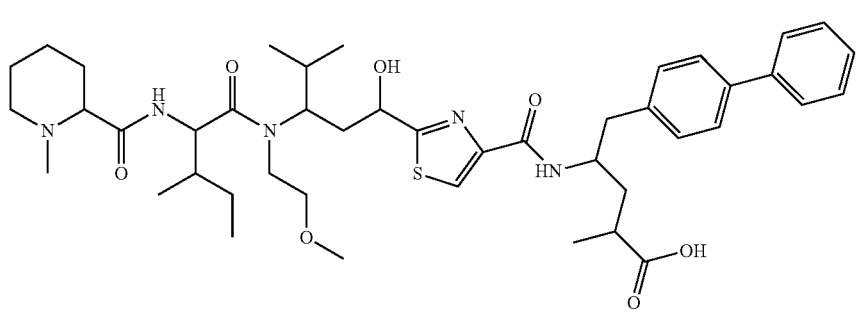
(AXLII)

-continued
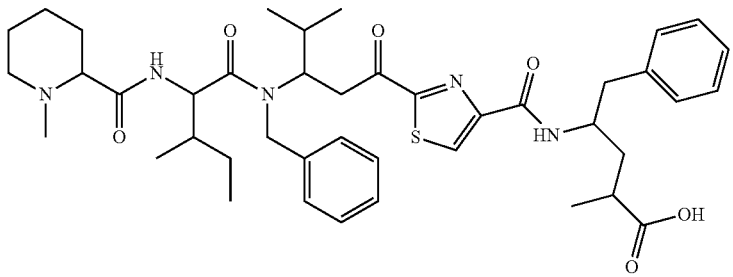
(AXLIII)
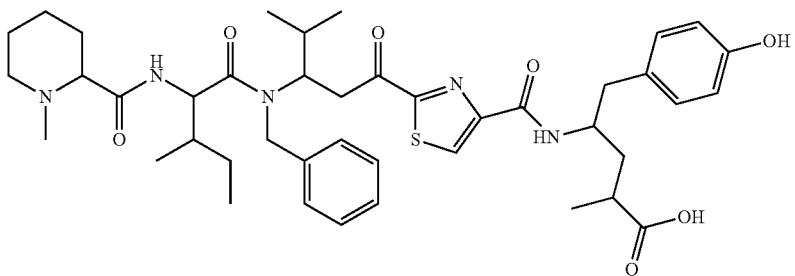
(AXLV)
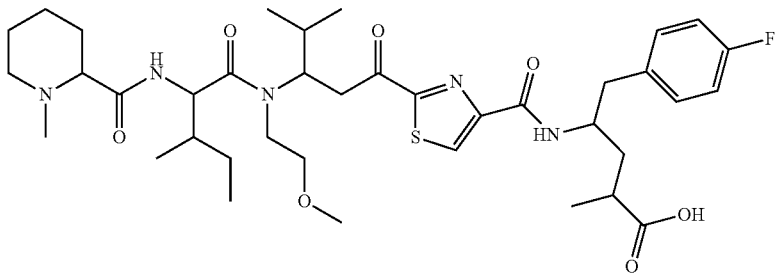
(ALI)
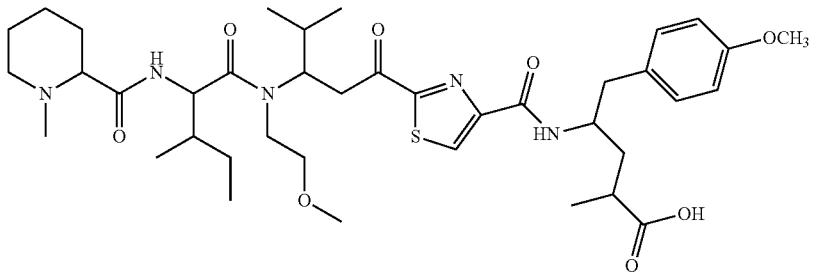
(ALIII)
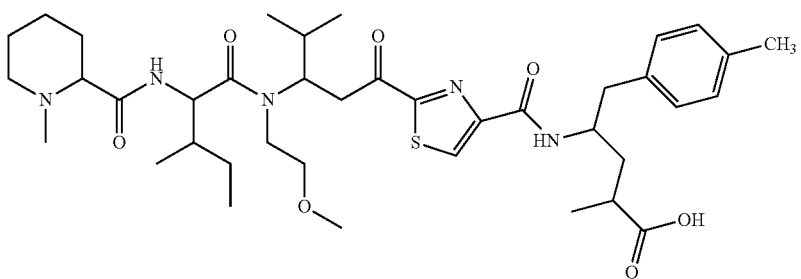
(ALIV)

-continued
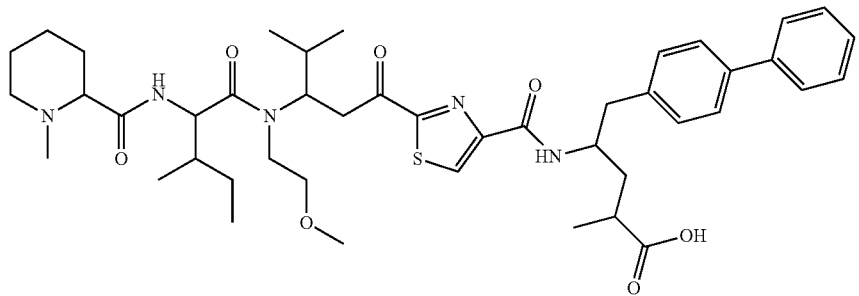
(ALVI)
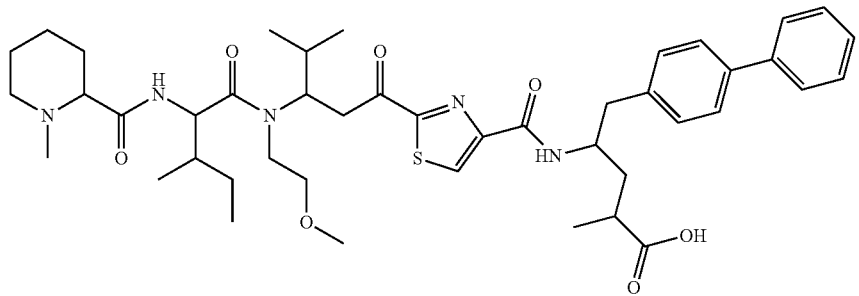
(ALVI)
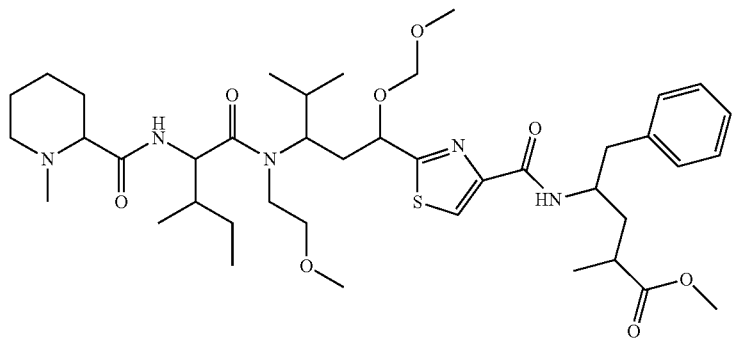
(ALVII)
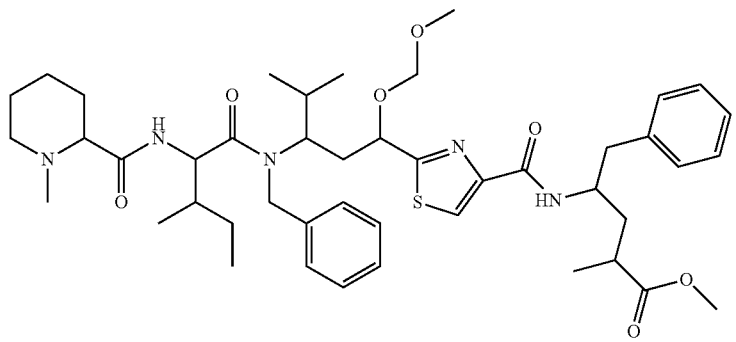
(ALVIII)
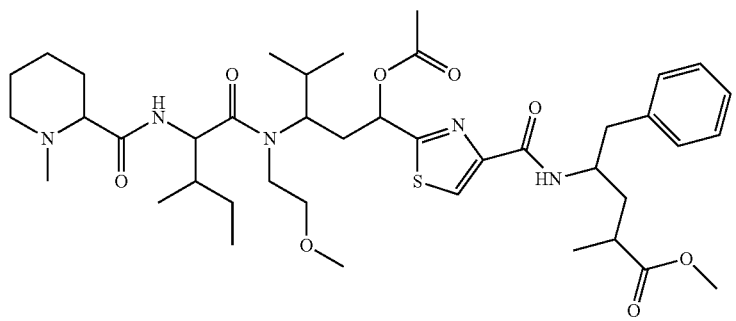
(ALIX)

(ALX)
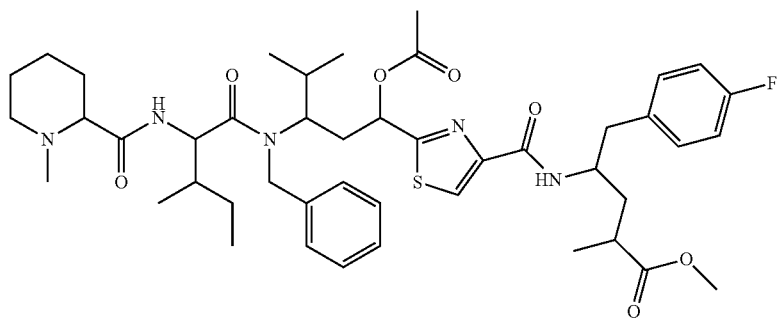
(ALXI)
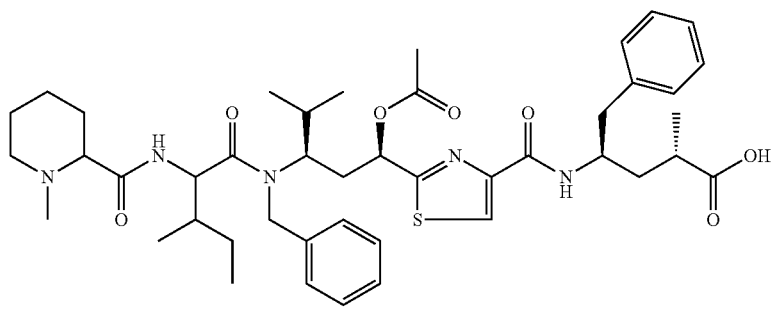
(ALXII)
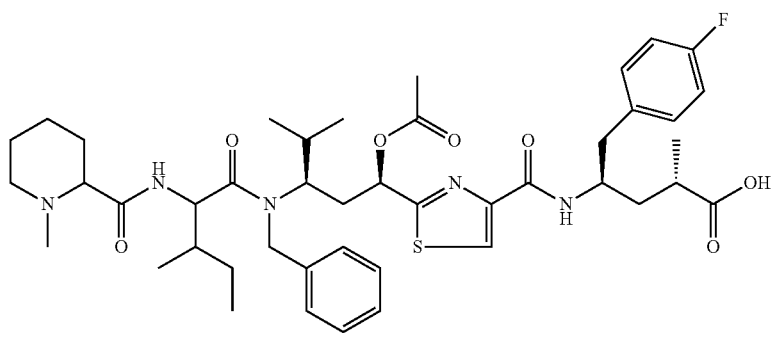
(ALXIII)
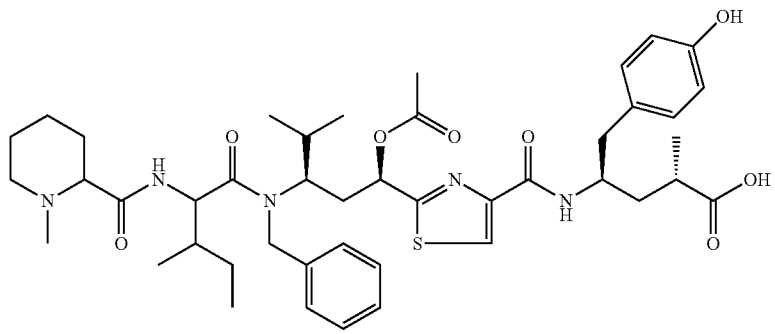
(ALXIV)
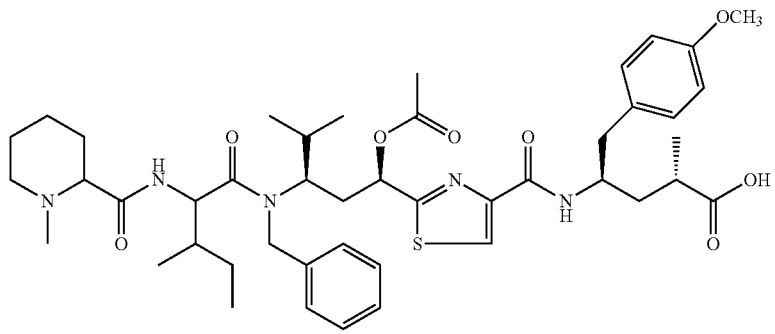

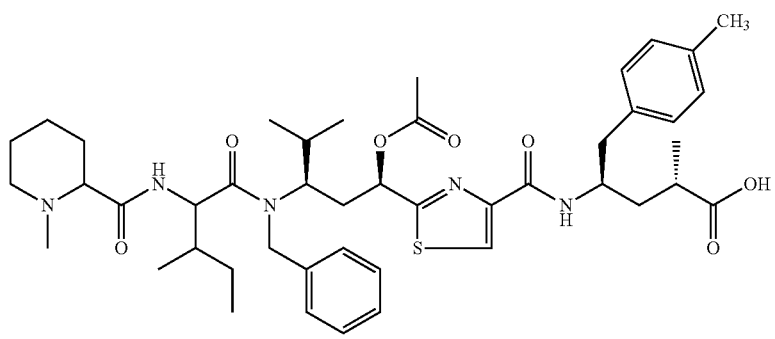
(ALXV)
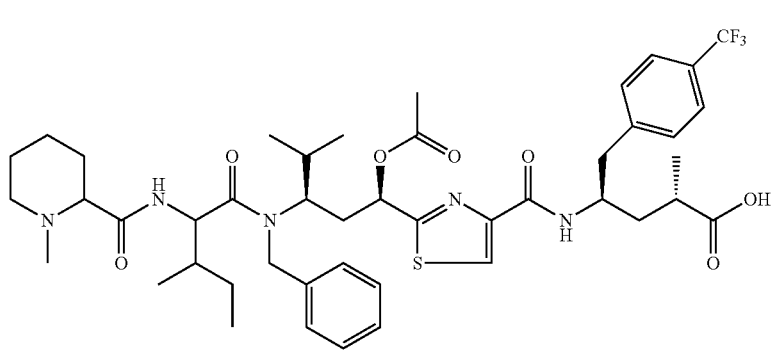
(ALXVI)
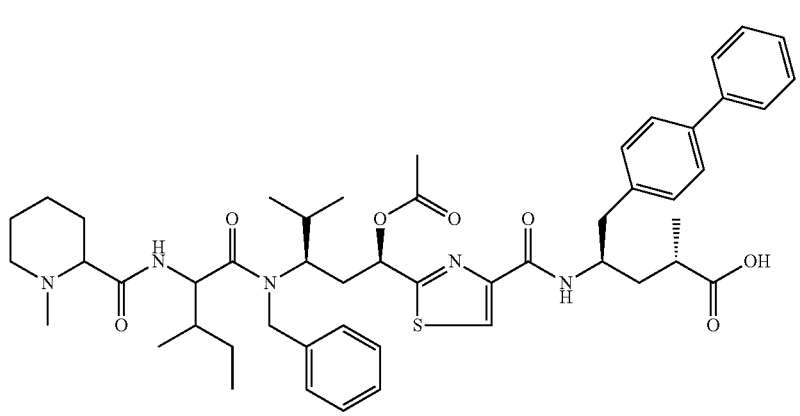
(ALXVII)
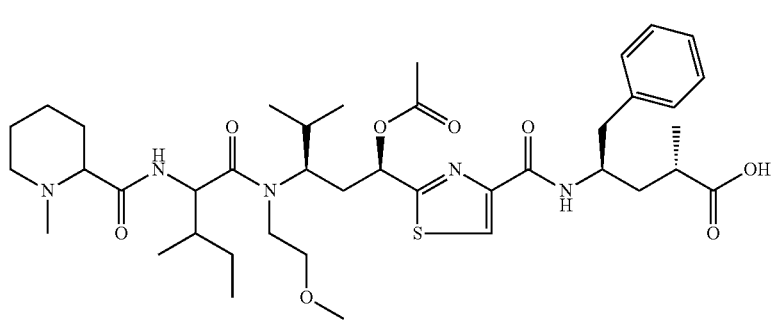
(ALXVIII)

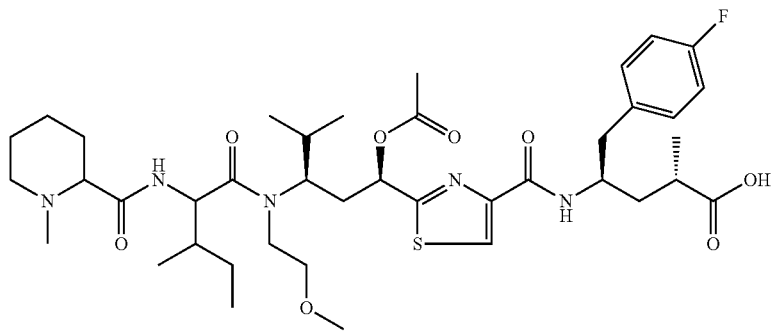
(ALXIX)
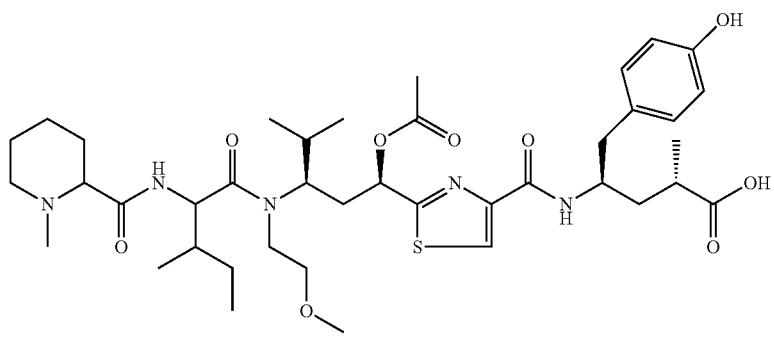
(ALXX)
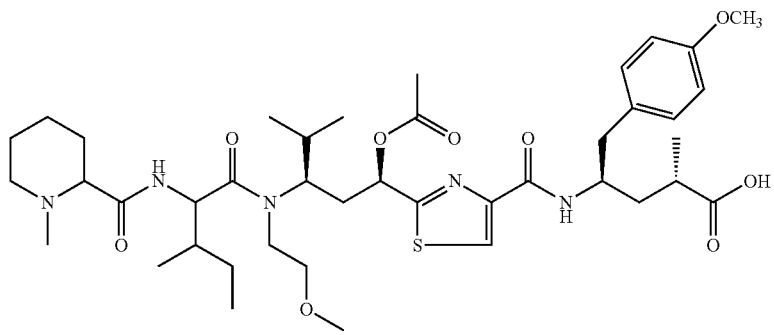
(ALXXI)
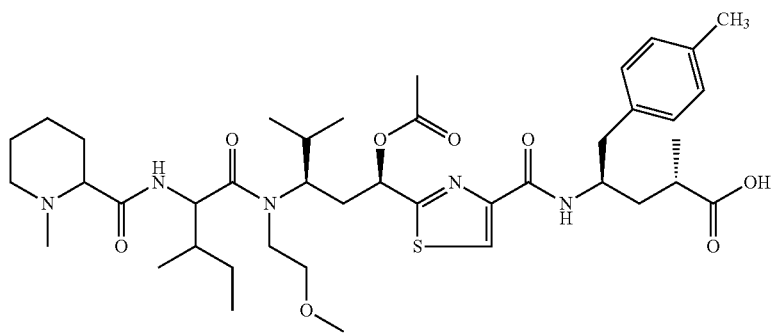
(ALXXII)

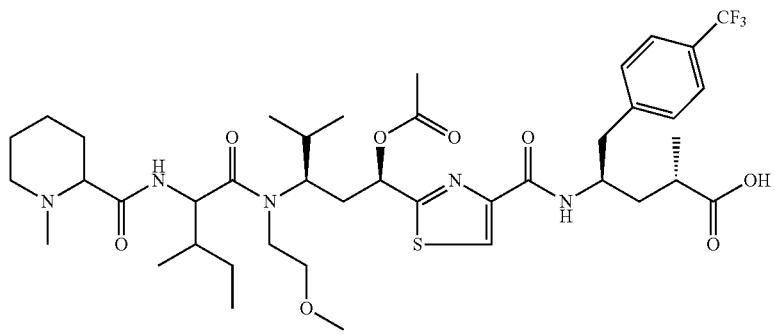
(ALXXIII)
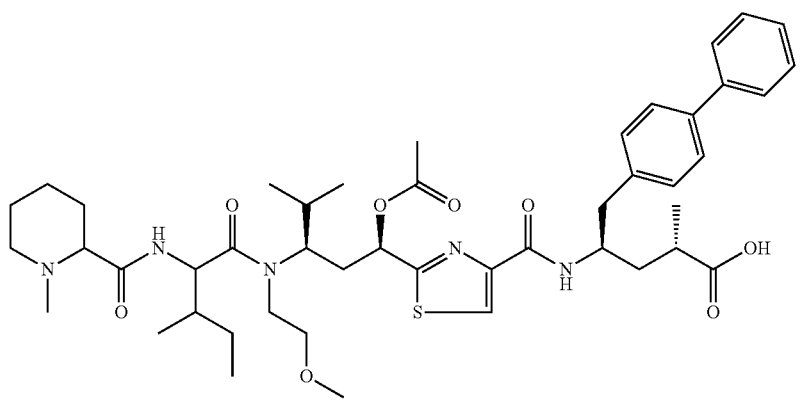
(ALXXIV)
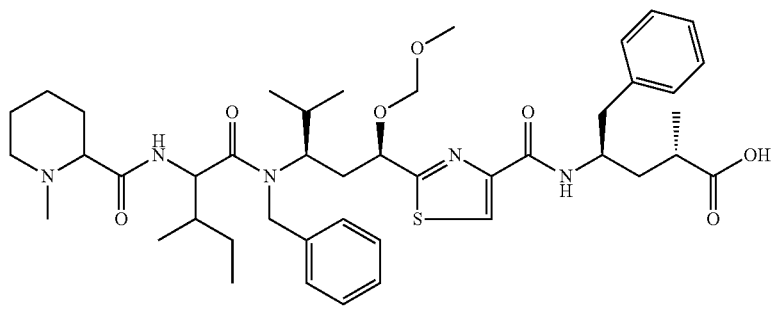
(ALXXV)
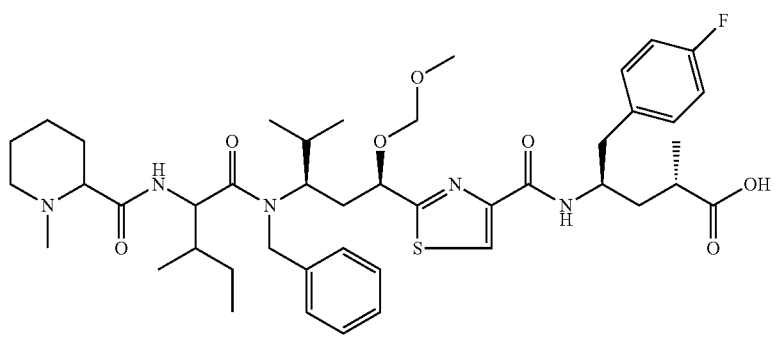
(ALXXVI)

-continued
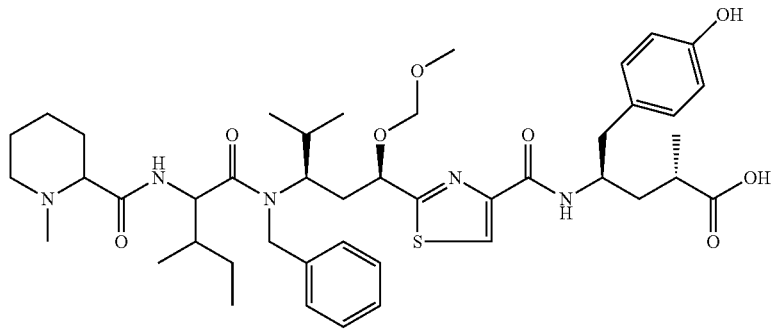
(ALXXVII)
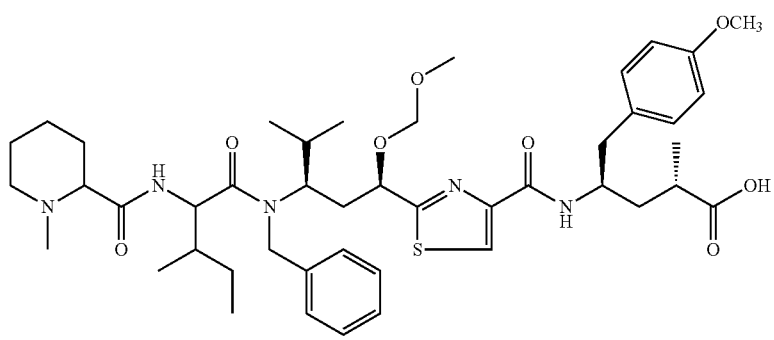
(ALXXVIII)
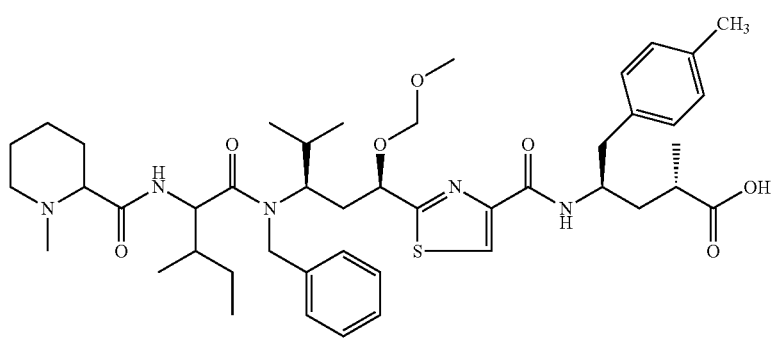
(ALXXIX)
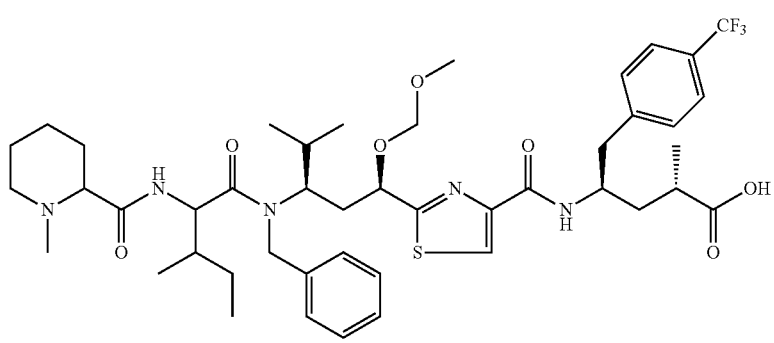
(ALXXX)

(ALXXXI)
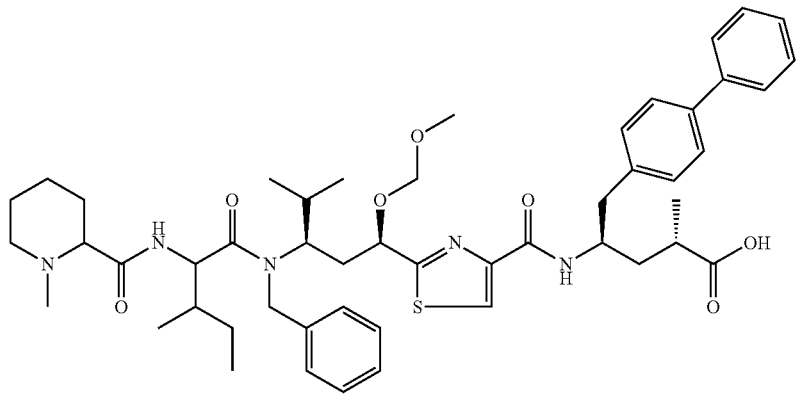
(ALXXXII)
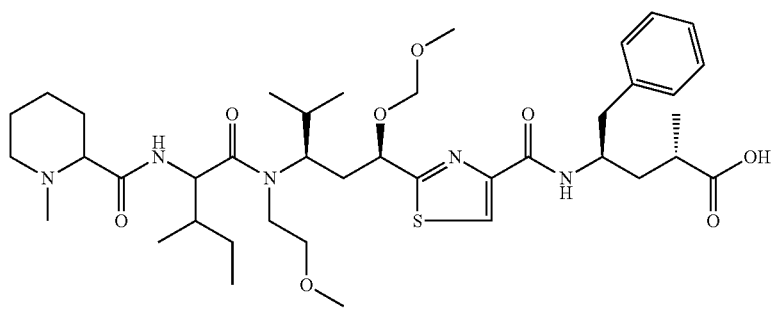
(ALXXXIII)
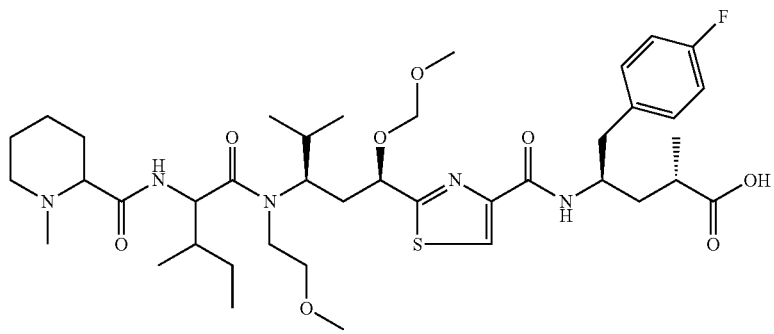
(ALXXXIV)
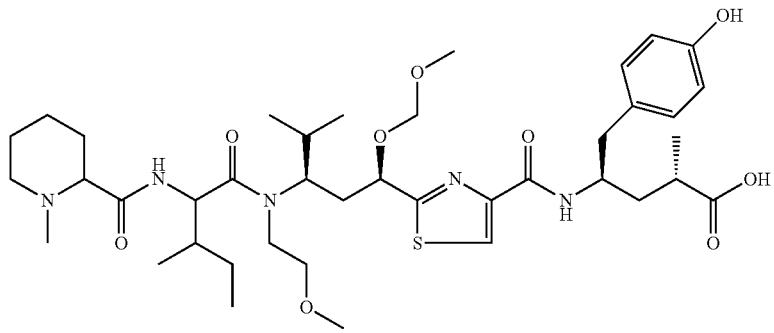

-continued
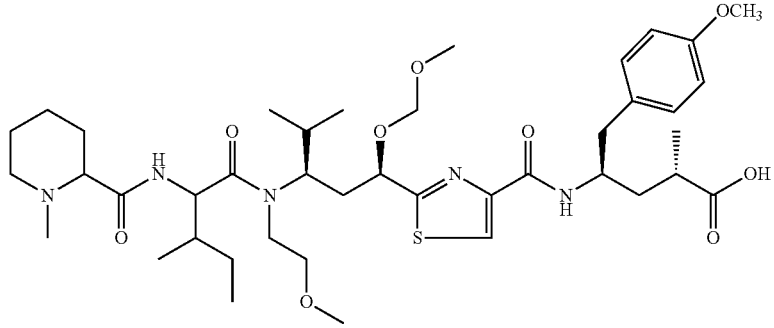
(ALXXXV)
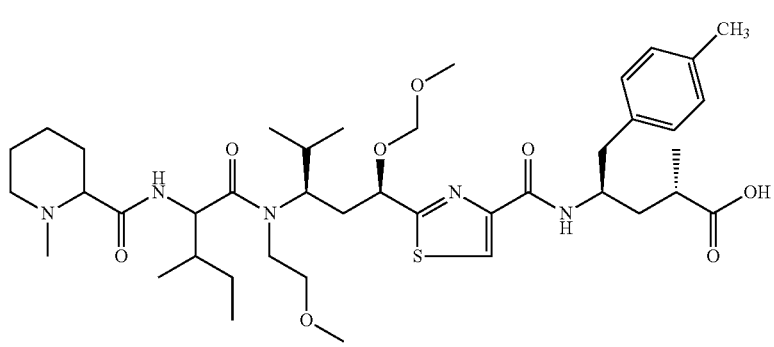
(ALXXXVI)
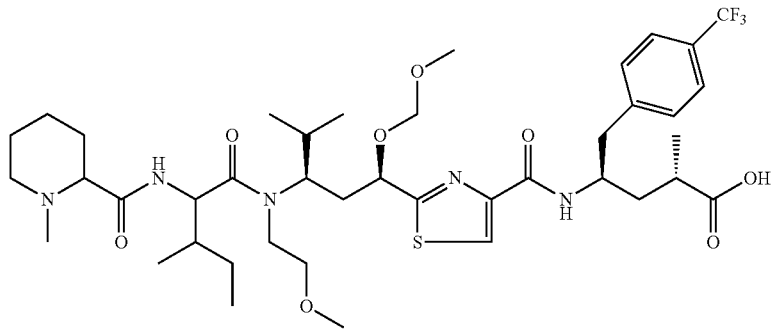
(ALXXXVII)
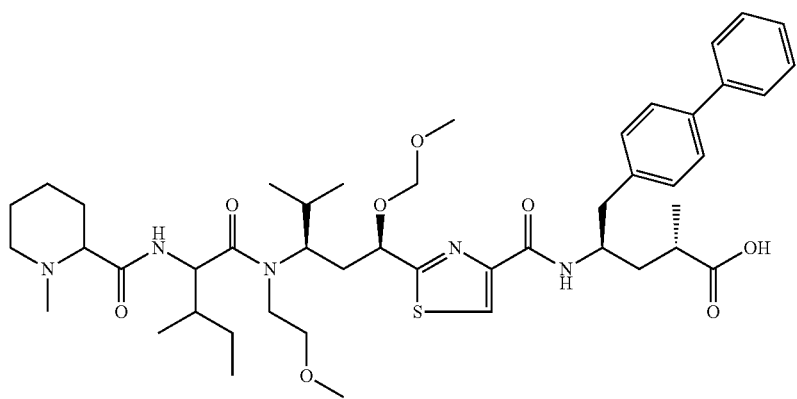
(ALXXXVIII)

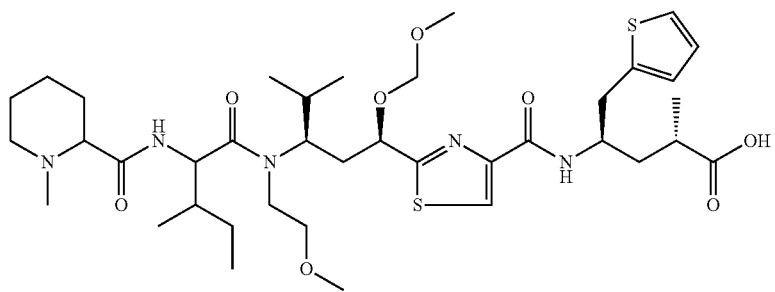
(AIXC)
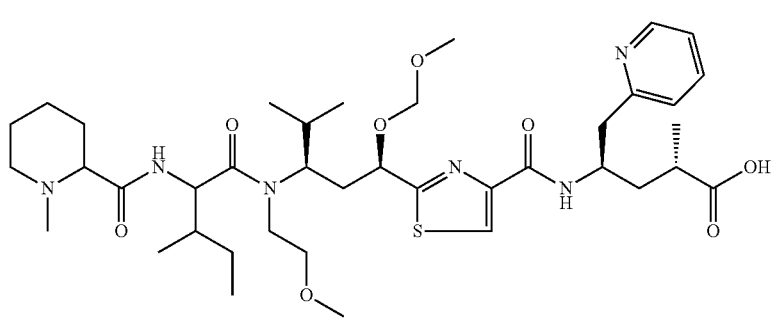
(AXC)
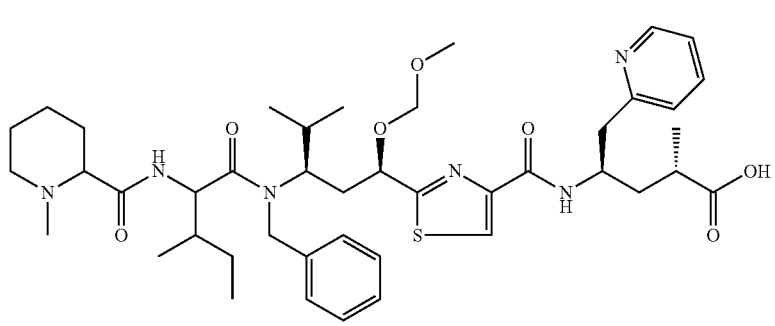
(AXCI)
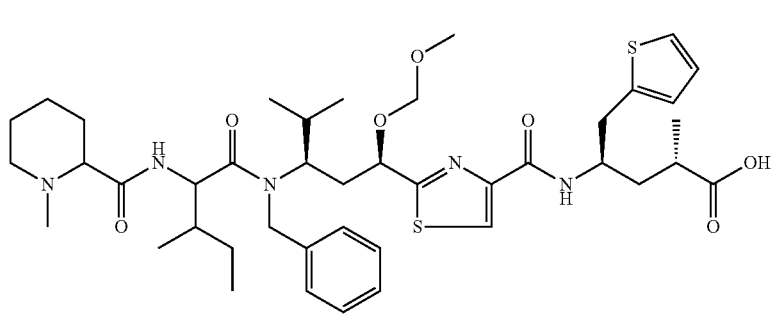
(AXCII)
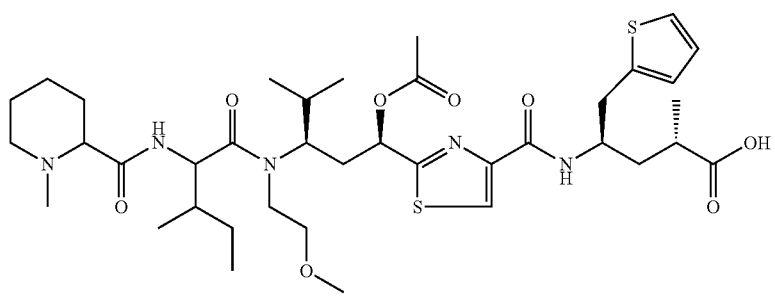
(AXCIII)

-continued
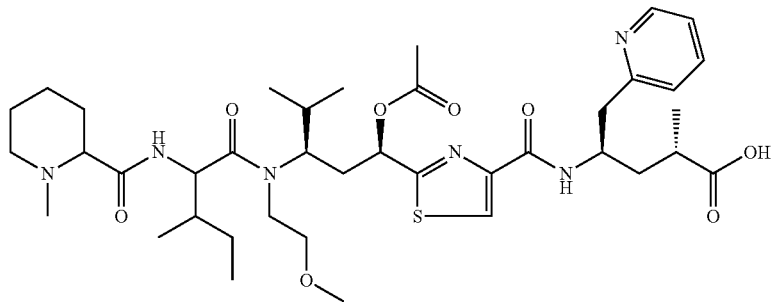
(AXCIV)
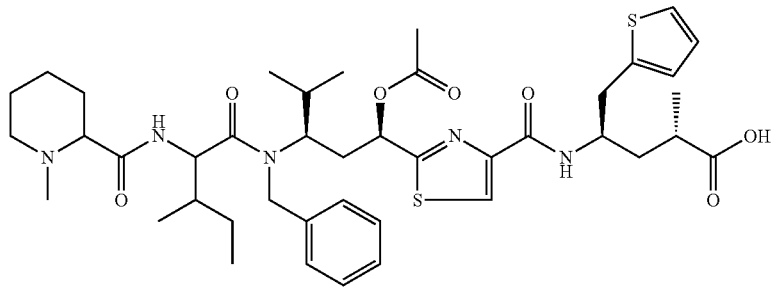
(AXCV)
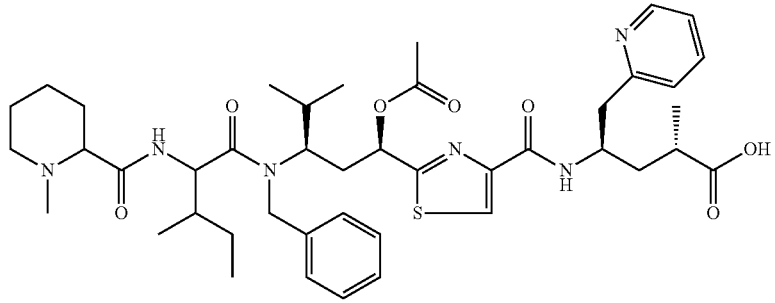
(AXCVI)
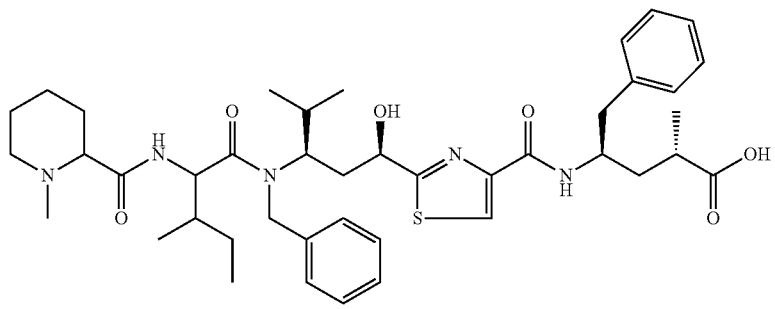
(AXCVII)
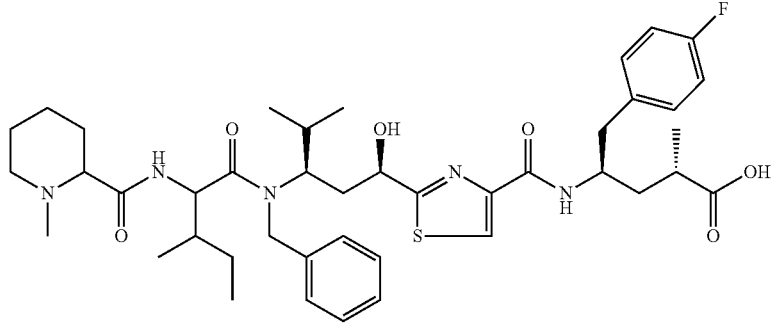
(AXCVIII)

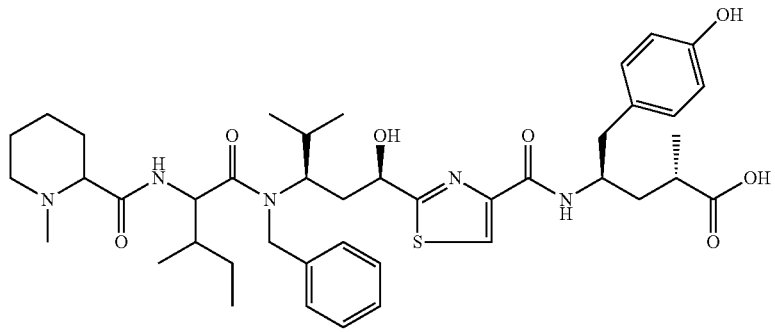
(AIC)
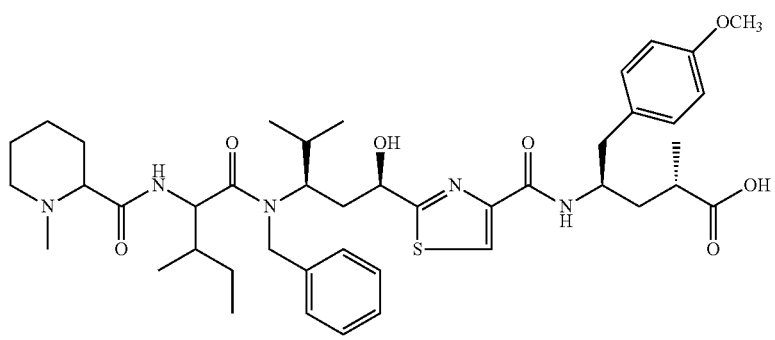
(AC)
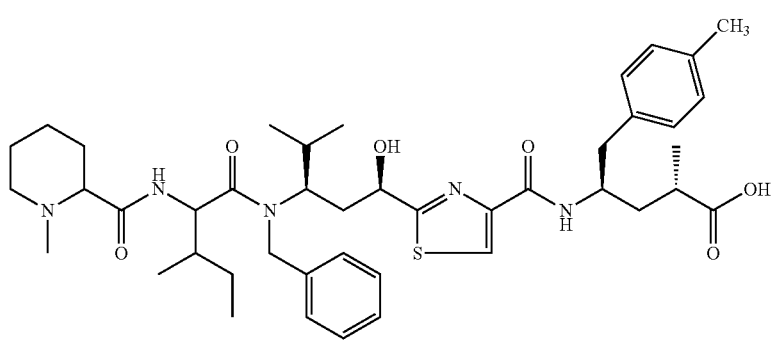
(ACI)
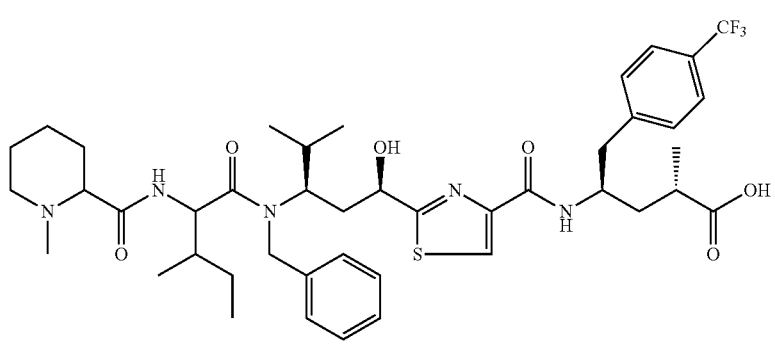
(ACII)

-continued
(ACIII)
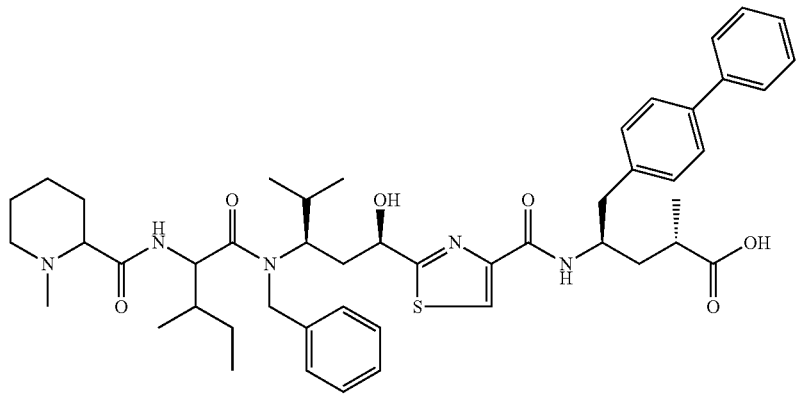
(ACIV)
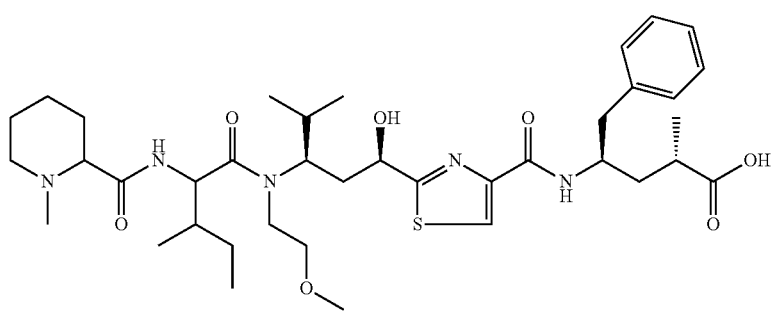
(ACV)
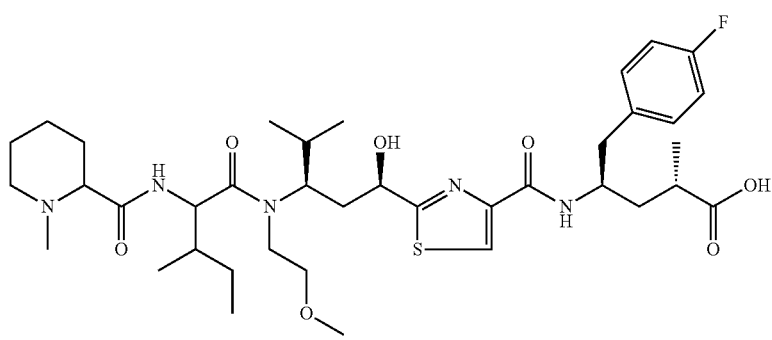
(ACVI)
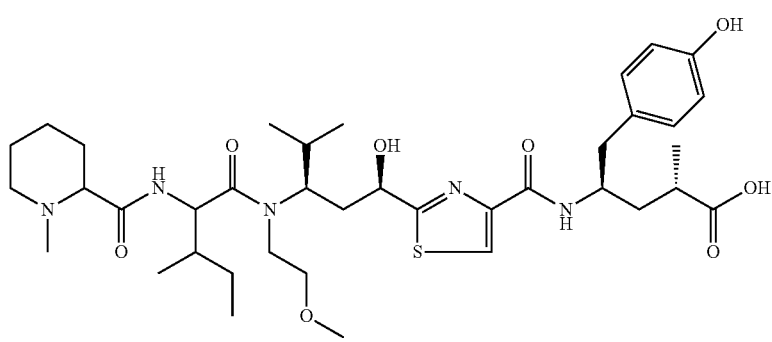

-continued
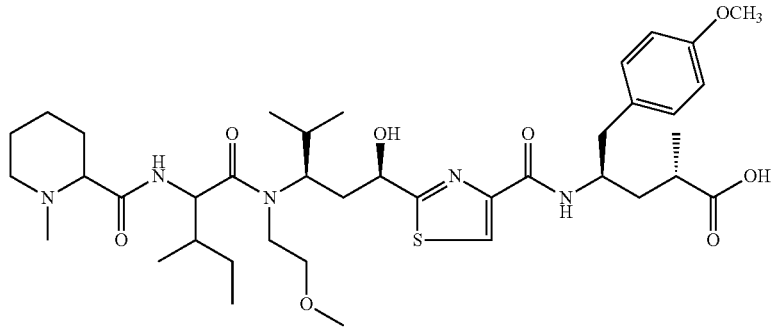
(ACVII)
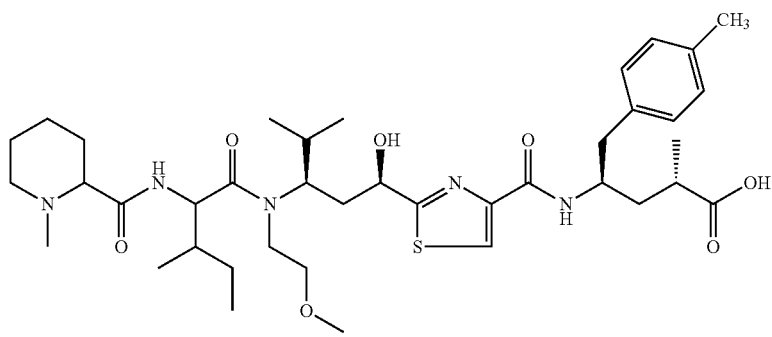
(ACVIII)
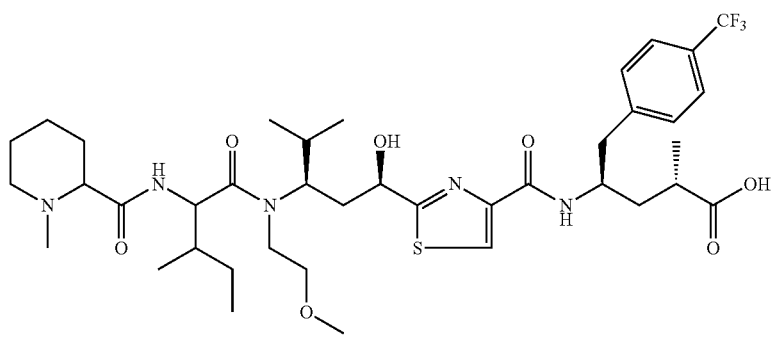
(ACIX)
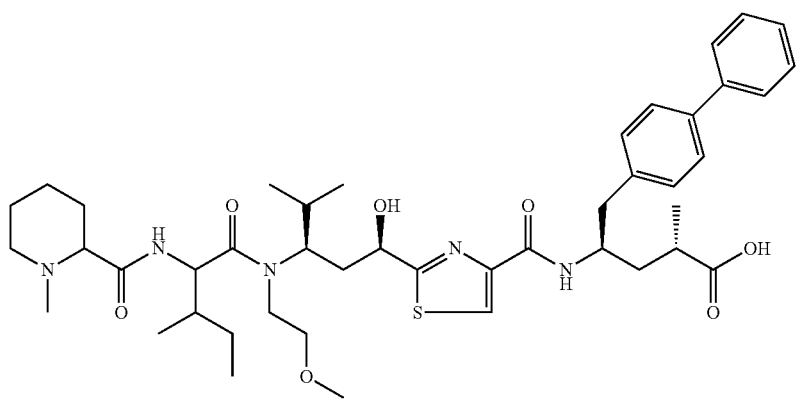
(ACX)

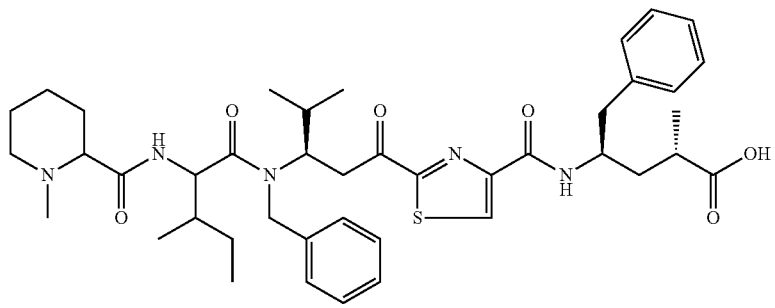
(ACXI)
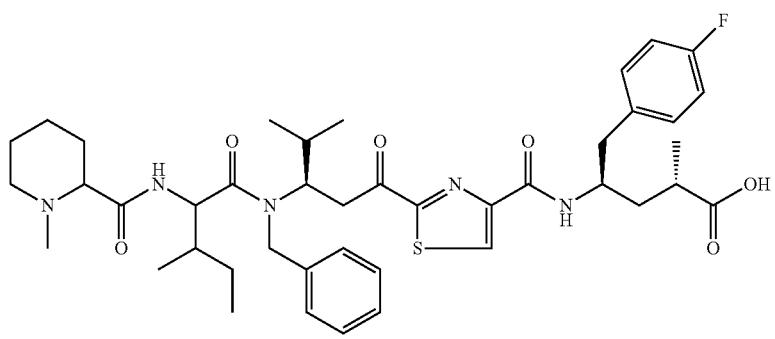
(ACXII)
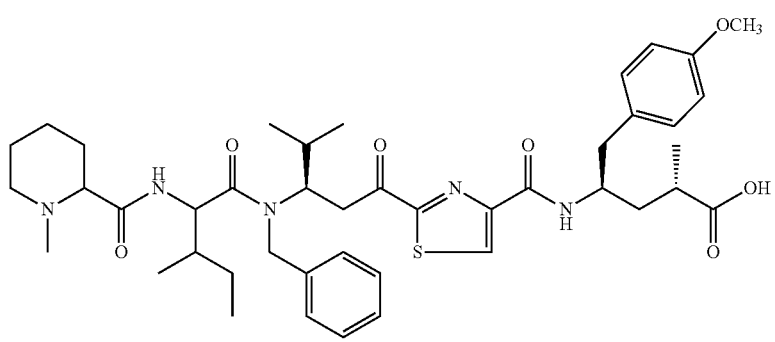
(ACXIII)
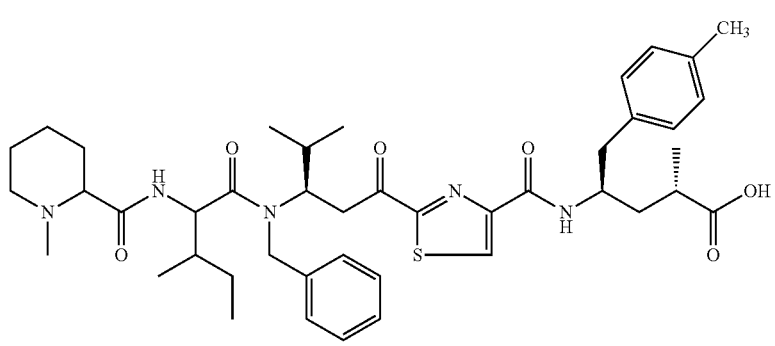
(ACXIV)

(ACXV)
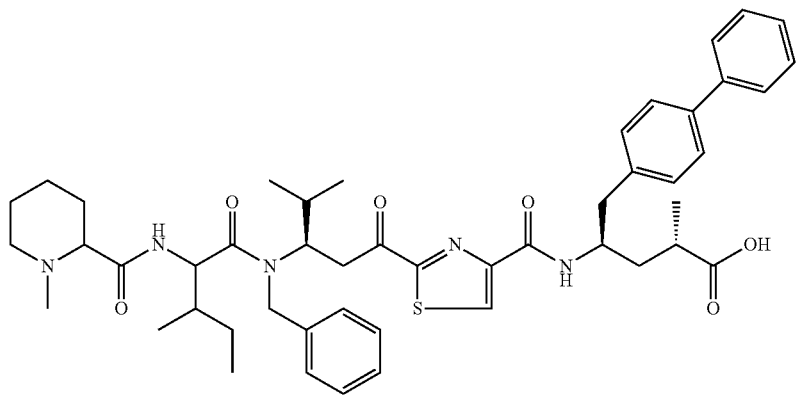
(ACXVI)
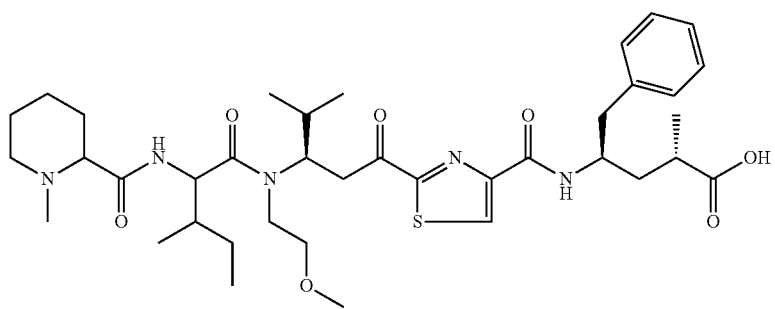
(ACXVII)
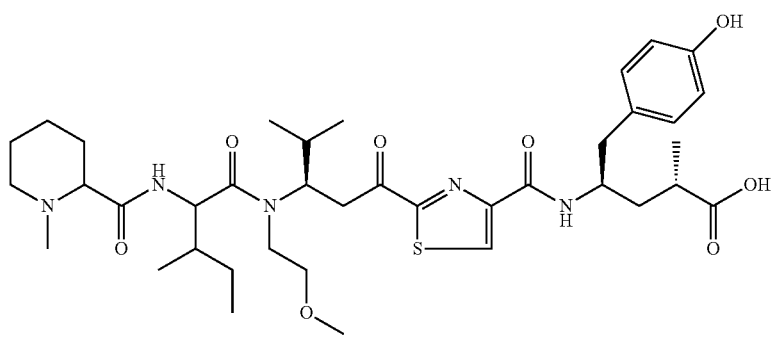
(ACXVIII)
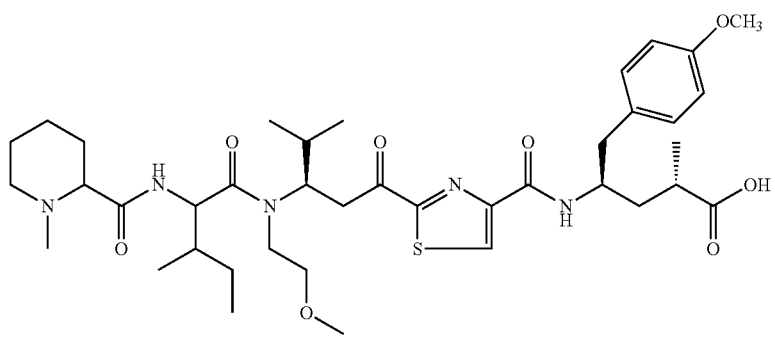

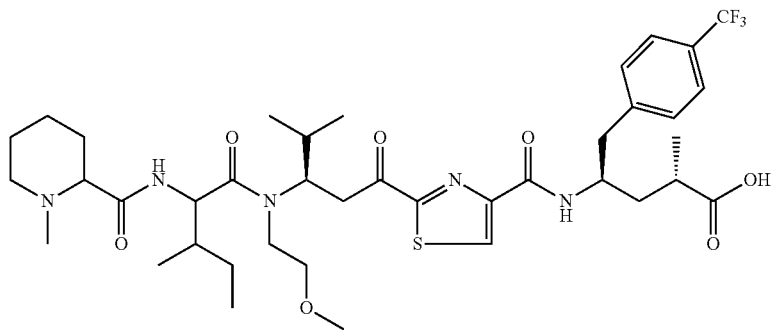
(ACXIX)
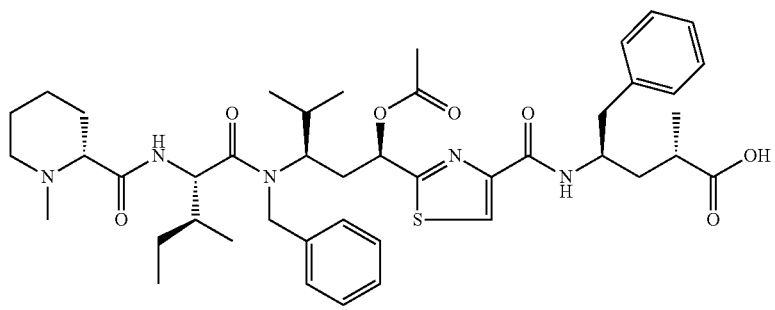
(ACXX)
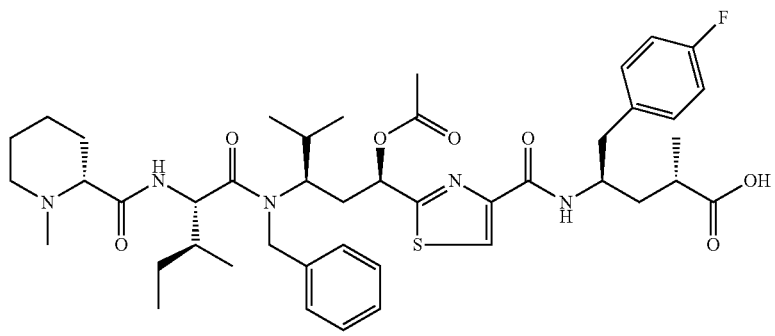
(ACXXI)
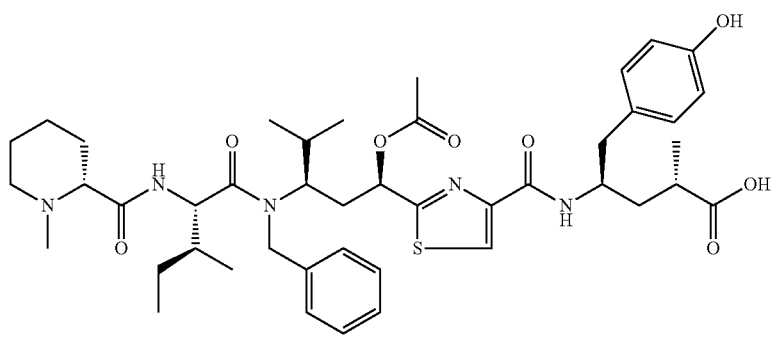
(ACXXII)
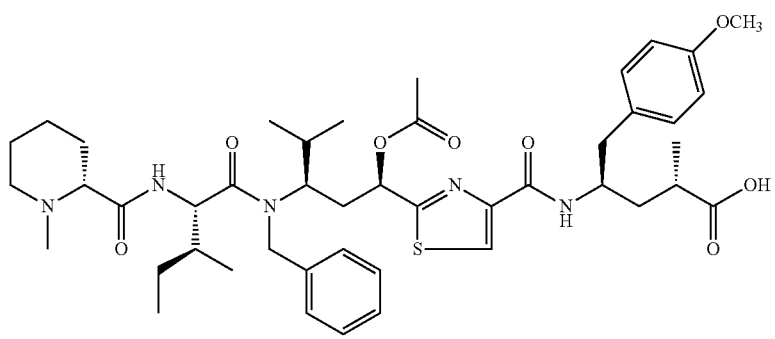
(ACXXIII)

(ACXXIV)
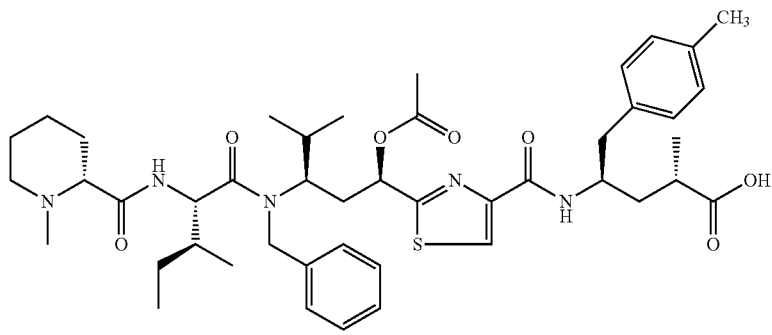
(ACXXV)
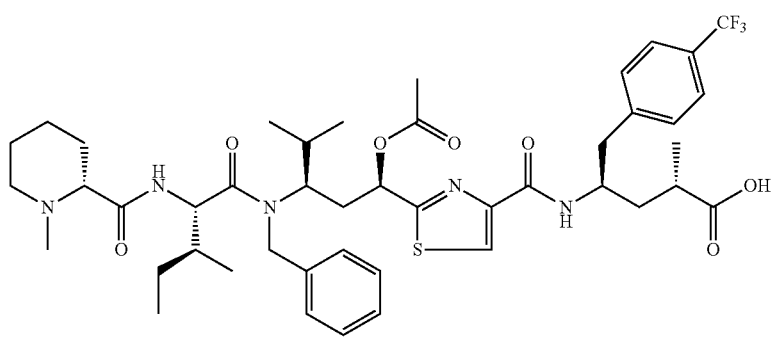
(ACXXVI)
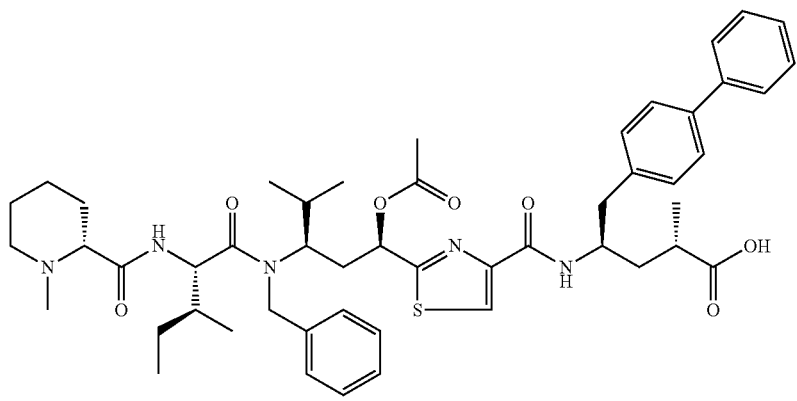
(ACXXVII)
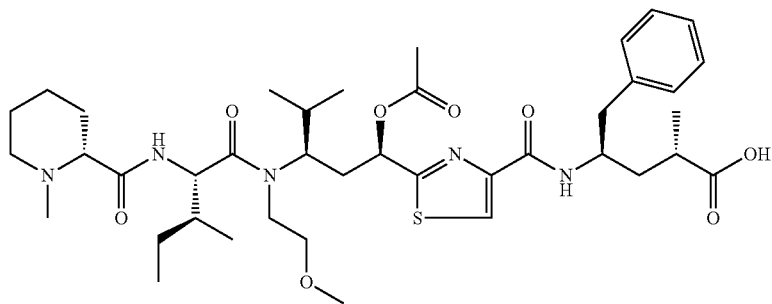

-continued
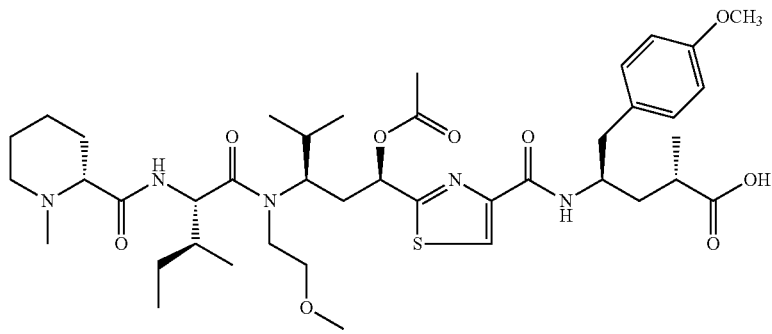
(ACXXVIII)
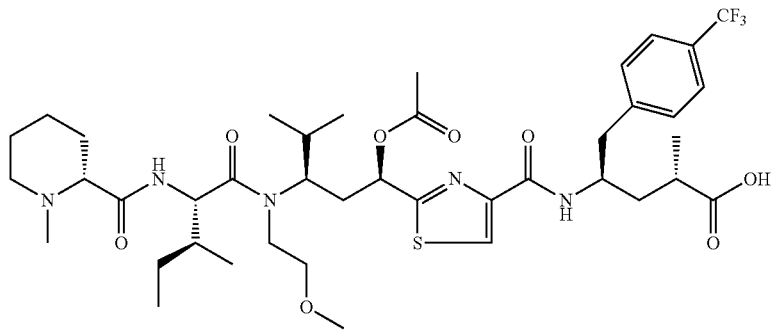
(ACXXIX)
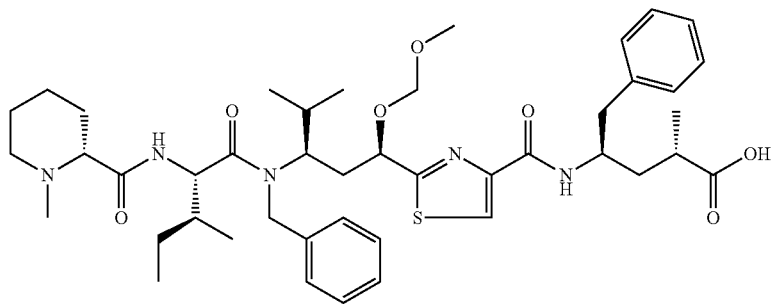
(ACXXX)
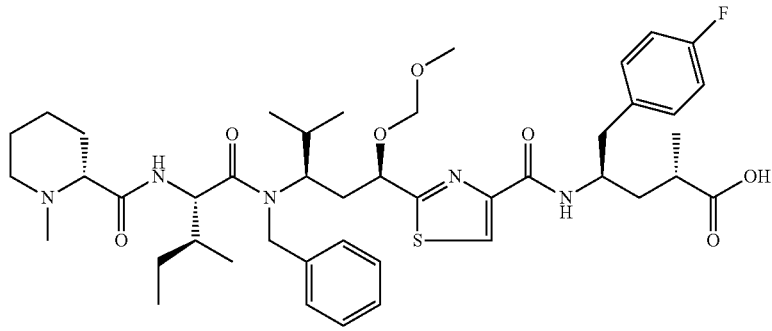
(ACXXXI)
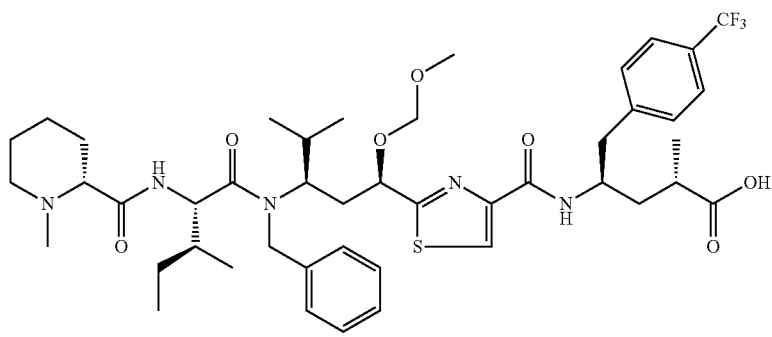
(ACXXXII)

(ACXXXIII)
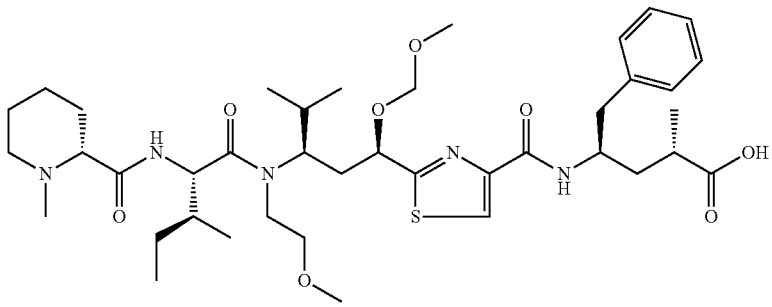
(ACXXXIV)
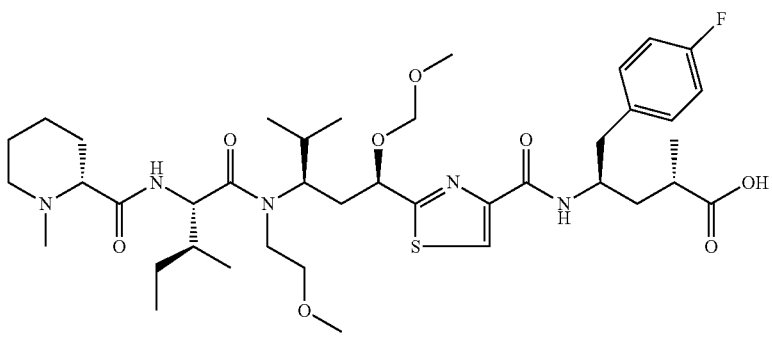
(ACXXXV)
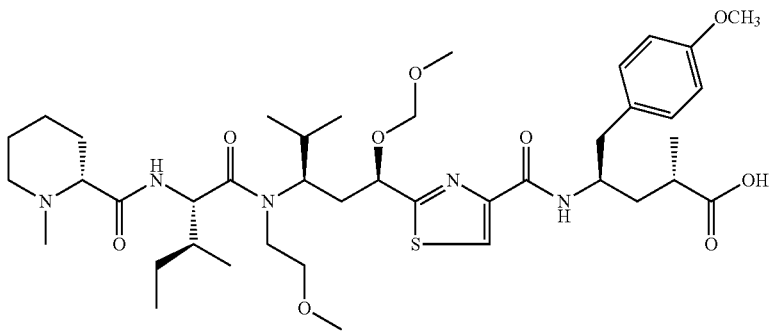
(ACXXXVI)
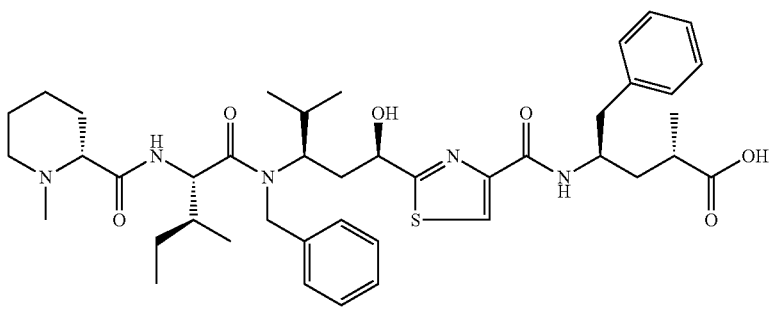
(ACXXXVII)
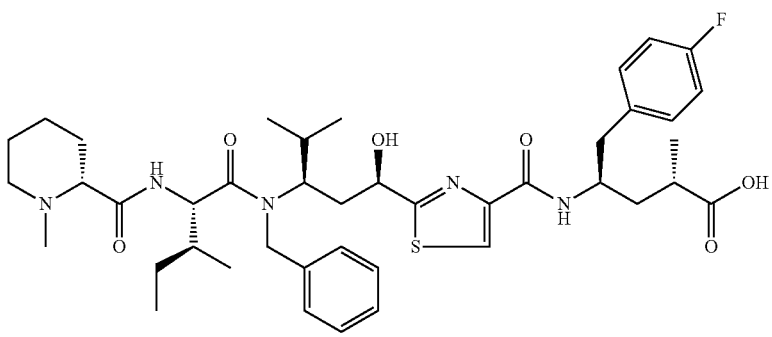

-continued

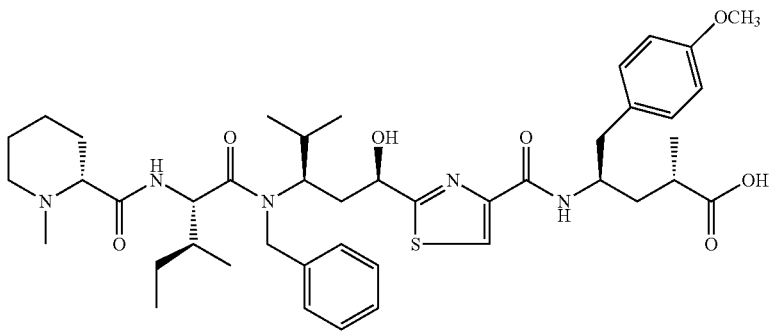

(ACXXXVIII)

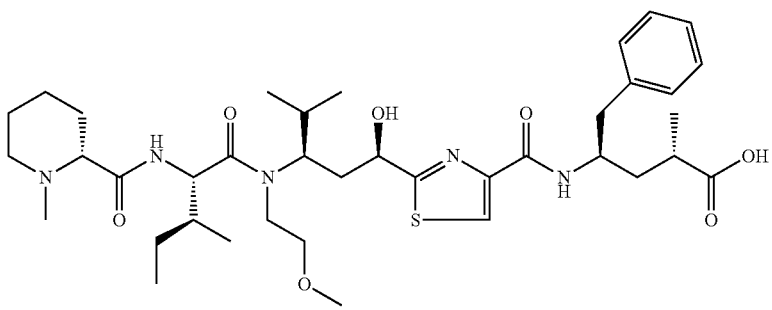

(ACIXL)

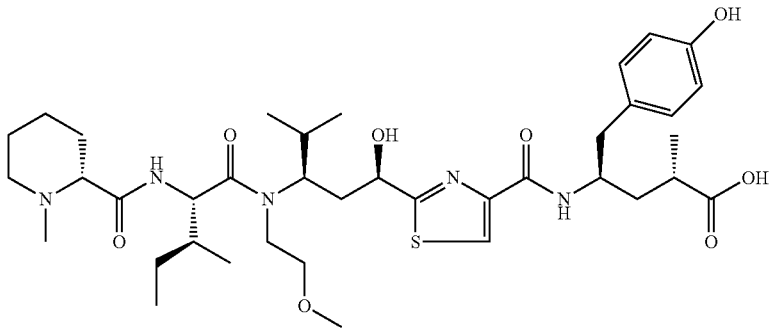

(ACXL)

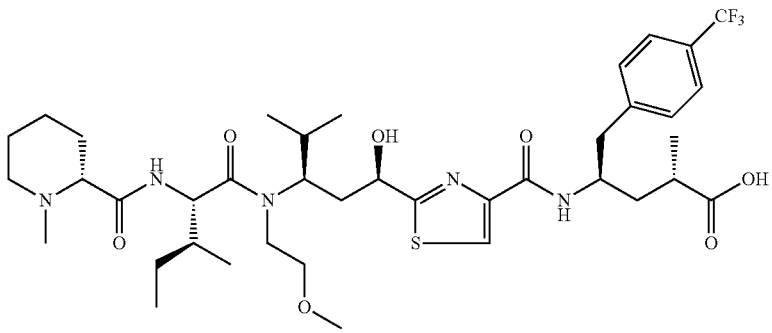

(ACXLI)

The hydrates, solvates and pharmaceutically acceptable salts of the compounds of the invention, comprising the various isomers, stereoisomers and the mixtures thereof, are a further object of the present invention.

The meaning of the hydrate and solvate terms is well known to the skilled in the art. In particular, by hydrate it is meant the compound containing one or more hydration water molecules, generally from 1 to 10. By solvate it is meant that the compound contains one or more molecules of solvent different from water. By pharmaceutically acceptable salts are meant all the salts obtained by treating the compounds of the invention with organic or inorganic acids, or with organic or inorganic bases, acceptable from the pharmaceutical point of view. For example hydrochlorides, sulphates, fumarates, oxalates, citrates, hydrogensulphates, succinates, paratoluensulphonates, quaternary ammonium salts can be mentioned. See the volume: "Remington, The Science and Practice of Pharmacy", vol. II, 1995, page 1457.

A further object of the present invention is a process for preparing the compounds of general formula (A) when X4 is selected from halogen, NR6R-7, SH, $(OR_5)_n$—$OR_6$, alkyl or alkenyl, comprising the following steps:

A-1) reaction of an acid of formula (B) with an aminoester of formula (D) and to yield a compound of formula (E)

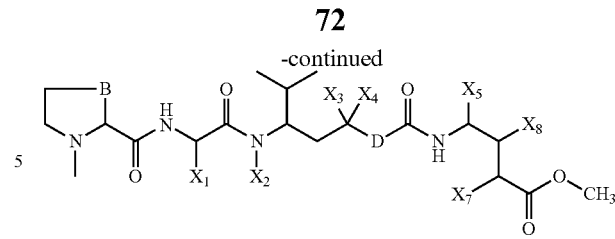

(F)

A-4) hydrolysis of the ester group located at one end of the chain of compound (F) and subsequent treatment with an organic or inorganic acid AnionH to give compound (G), which corresponds to the salified compounds of formula (A) wherein $X_6$=OH,

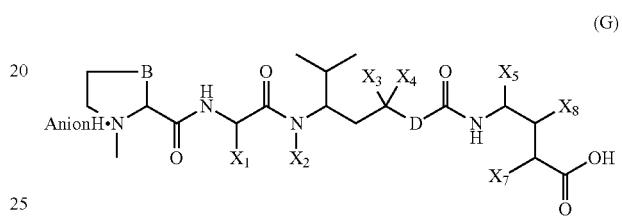

(G)

A-5) neutralization of compound (G) with an organic base to give the compound (H'), corresponding to the compounds of formula (A) wherein $X_6$=OH,

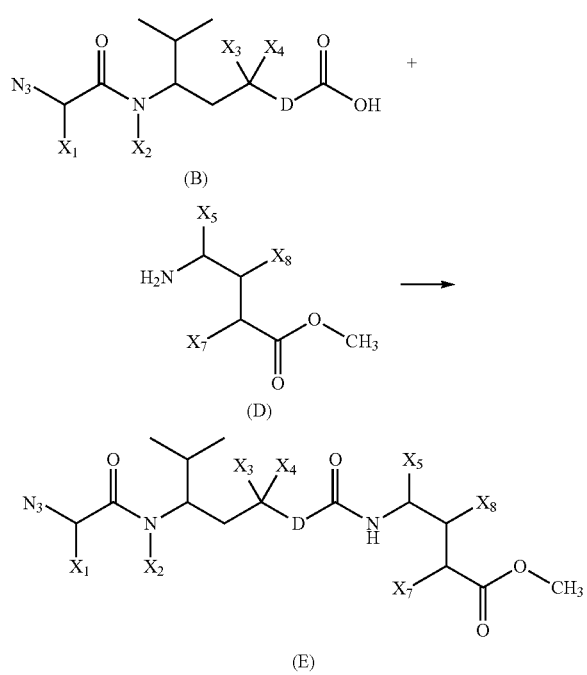

the aminoester (D) is optionally in the form of the corresponding salt (compound (Da)) with an organic or inorganic acid (AnionH, wherein Anion is the acid anion),

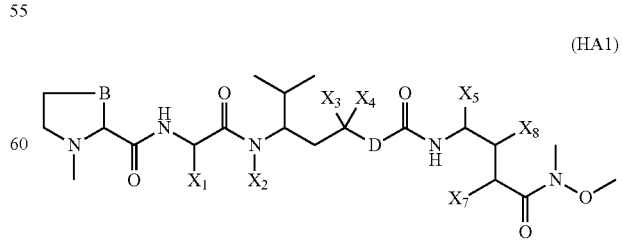

(H')

Depending on the meaning of $X_6$, the following steps A-6), A-7), A-8) are carried out:

A-6) synthesis of the compounds of formula (A) wherein $X_6$ is selected from one of the following groups: $NR_8R_9$, $OR_8$, NH—$NR_8R_9$ or $SR_8$, by reaction of the carboxylic acid function of compound (H') with the precursors of the $X_6$ groups, A-7) in the alternative to A-6), synthesis of the compounds of formula (A) wherein $X_6$ is $R_{10}$, by reacting compound (H') with $CH_3$—O—NH—$CH_3$ and $CH_3S(O)_2Cl$, in an inert solvent in the presence of an organic base, to yield the compound (HA1)

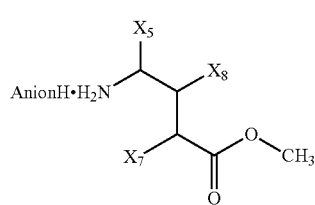

(Da)

A-2) hydrogenation of the compound of formula (E) to give the aminoester of formula (E'), wherein the end azide group ($N_3$) is converted into a primary amine group, A-3) reaction of the aminoester (E') with the heterocyclic acid (F1) to give the ester (F),

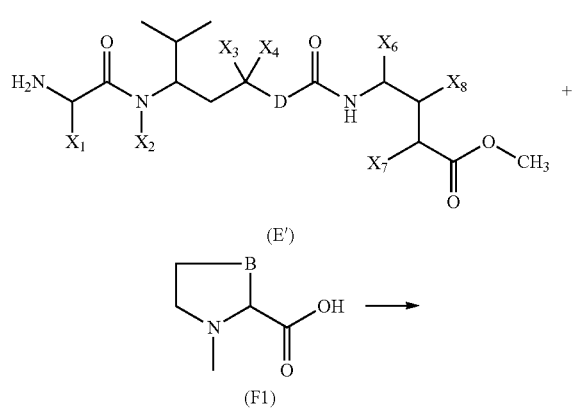

(HA1) and subsequent reaction of (HA1) with a Grignard reactant $R_{10}MgBr$,

A-8) to prepare the compounds of formula (A) wherein $X_6$ is H, the carboxylic acid group of compound (H') is reduced to an aldehyde group.

Step A-1) is carried out by adding an amine (D), or the corresponding salt with an AnionH acid, to a solution of an acid of formula (B), previously dissolved in an inert solvent and added of a coupling reactant and of an organic base. At the end of the reaction, water is added and a final extraction with an organic solvent is carried out. The organic solution is recovered and washed, firstly with an acid aqueous solution, then with a basic aqueous solution and lastly with a saline aqueous solution. The organic phase is recovered and dehydrated. Compound (E) is obtained by removing the solvent under reduced pressure.

The AnionH acid with which the aminoester (D) can be salified is a weak or strong organic or inorganic acid, selected from those that do not affect groups $X_5$, $X_7$ and $X_8$ and the ester function $^-COOCH_3$ of compound (D). For example the following ones can be mentioned: HCl, $CF_3COOH$, COOH.

A solvent which can be used in the reaction is for example dimethylformamide (DMF). The coupling reactant is for example selected from DCC (dicyclohexylcarbodiimide), mixture EDC (1-ethyl-3-(3-dimethylaminopropyl)carbo-diimide)/HOBt (1-hydroxy benzotriazole), the mixture HOAt (1-hydroxy-7-azabenzo triazole)/HATU (2-(1H-7-azabenzotriazol-1-yl)-1,1,3,3-tetra-methyl uroniumhexafluorophosphate-methanaminium), preferably HOAt/HATU is used. The used organic base is for example diphenylethylamine (DIPEA), triethylamine, pyridine, preferably triethylamine.

The reaction time is generally comprised in the range 1-5 hours. Preferably the organic solvent which can be used for the extraction of the reaction mixture is for example ethyl ether. The washings of the organic phase are for example carried out, in sequence, with an 1N HCl 1N aqueous solution, with an aqueous $NaHCO_3$ saturated solution and with an aqueous NaCl saturated solution.

Step A-2) is carried out by using a catalyst, preferably Pd/C, under an hydrogen atmosphere. As a solvent, an alcohol, for example methanol, can be used. The reaction time is generally in the range 8-20 hours.

Step A-3) is carried out by using as a coupling reactant and as organic base, respectively, the compounds which have been reported in step A-1). Preferably as coupling reactant, HOAt/HATU is used and, as a base, triethylamine is used.

Step A-4) is carried out by adding to a solution of the methyl ester (F) in an inert organic solvent, an aqueous solution of an inorganic base. At the end of the reaction, the mixture is acidified at pH values lower than 3 with an inorganic or organic AnionH acid, and the reaction product is extracted with an inert organic solvent, which is separated and then removed under reduced pressure yielding compound (G). In step A-4) as a solvent, THF can be used and as an inorganic base LiOH. At the end of the reaction, the mixture is acidified at a pH lower than 3, preferably at pH equal to or lower than 2, for example with trifluoroacetic acid. As extraction solvent, ethyl acetate can be used.

The neutralization step A-5) is carried out by using an organic base, for example triethylamine or pyridine.

In step A-6) compound (H') is reacted with a coupling reactant and an organic base, selected respectively from those mentioned above in step A-1). The precursors of the substituent $X_6$ that are used are the following compounds: $NHR_8R_9$, $HOR_8$, $NH2-NR_8R_9$, $HSR_8$. As a solvent, dichloromethane can be used, the coupling reactant is an HOAt/HATU mixture, the organic base is for example triethylamine.

Step A-8) can be carried out by direct reduction of the carboxylic function of compound (H') to aldehyde, for example by using diisobutylaluminum hydride, $NaAlH_4$, lithiumtri-t-butoxyaluminum hydride, $Pd/BaSO_4$, under an hydrogen atmosphere. Alternatively in a first step the acid is reduced to a primary alcohol, for example by using $LiAlH_4$, diborane, $BH_3.THF$ complex. In a further step the primary alcohol is oxidized to aldehyde for example by using the mixture oxalyl chloride/dimethylsulphoxide (DMSO)/triethylamine, or Dess-Martin periodinane (DMPER).

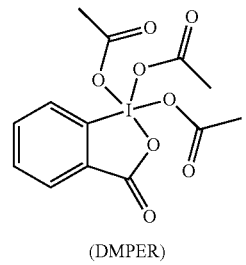 [SMILES: CC(=O)OI1(OC(C)=O)(OC(C)=O)OC(=O)c2ccccc21]

(DMPER)

Preferably in the direct reduction from acid to alcohol the acid is used in the activated form, for example as an ester, preferably a methyl or ethyl ester, or as an acyl chloride. When $X_4$ is selected from OH or of $OC(O)R_7$, the process for obtaining the compounds of formula (A) comprises the following steps in succession:

A-1') the same as a-1) but using (B) wherein $X_4$—OH and obtaining a compound of formula ($E^I$)

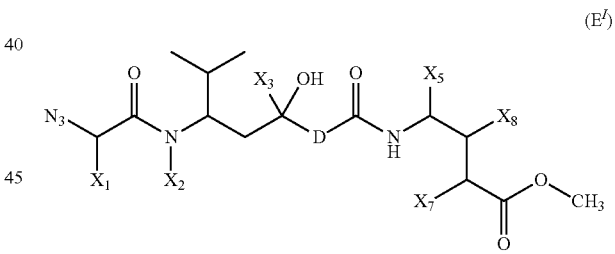

($E^I$)

A-2') the same as A-2) but using ($E^I$) to give the aminoester of formula ($E^{II}$)

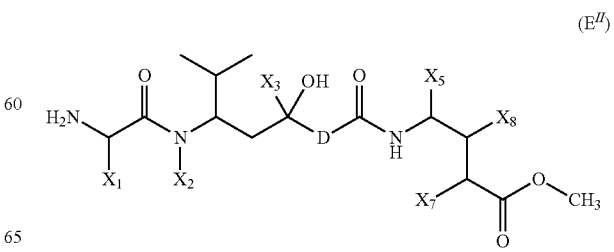

($E^{II}$)

A-3') the same as A-3) but using (E^{II}) to give the ester (F^{I})

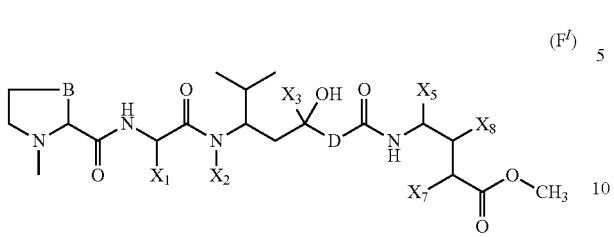

(F^{I})

A-4') the same as a-4 but using compound (F^{I}) to obtain compound (G')

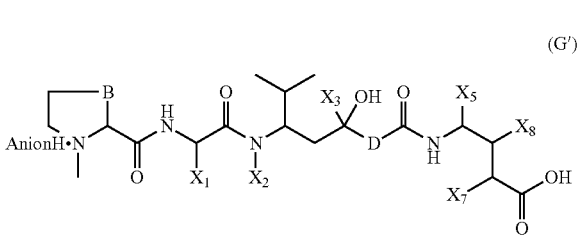

(G')

A-5') the same as A-5) but using compound (G') to obtain compound (G^{A})

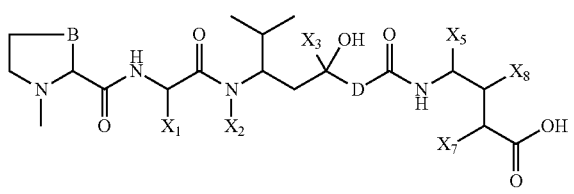

(G^{A})

said acid (G^{A}) corresponds to the compounds of formula (A) wherein $X_4$ and $X_6$ have the meaning of OH, step A-7') Step A-8) is repeated but using (G^{A}) as the starting compound to obtain (G'') corresponding to the compounds (A) wherein $X_4$=OH and $X_6$=H

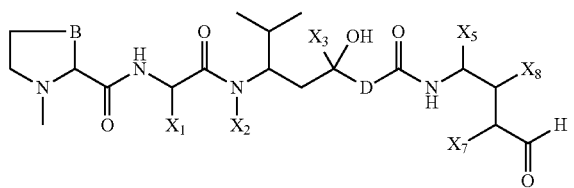

(G'')

step A-8') acylation of the hydroxyl of compound (G'), or of the corresponding hydroxyl group in the compound (G^{A}), with an acid of formula $R_7C(O)OH$, obtaining compound (H), which corresponds to the compounds of formula (A) wherein $X_4$=OC(O)$R_7$ and $X_6$ is OH,

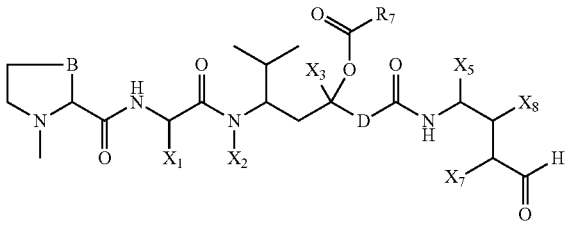

(H)

A-8'') step A-8') is repeated but using as starting compound (G'') to obtain compound (H'') corresponding to the compounds of formula (A) wherein $X_4$=OC(O)$R_7$ and $X_6$ is H,

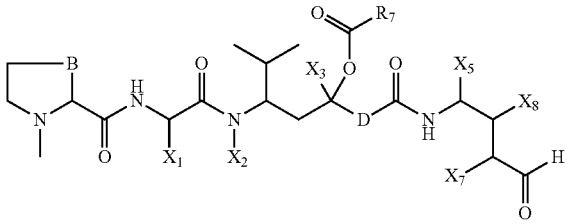

(H'')

repetition of step A-6) but using compound (H) or (H'') obtaining the compounds of formula (A) wherein $X_6$ has the meaning as in step A-6) and $X_4$=OC(O)$R_7$. repetition of step A-6) but using compound (H) and obtaining the compounds of formula (A) wherein $X_6$ is $R_{10}$ and $X_4$=OC(O)$R_7$.

In steps A-8') and A-8'') acylation is carried out by using an active derivative of the acid of formula $R_7C(O)OH$, selected from the following group: acyl chlorides, anhydrides, mixed anhydrides, imidazolides, ester-amide adducts, linear or branched when possible $C_1$-$C_4$ alkyl esters. The reaction is generally carried out in the presence of an organic base, selected for example from those used in step A-1). At the end, the reaction product is extracted from the reaction mixture by using an inert organic solvent, which is afterwards removed under reduced pressure, yielding the compound of formula (H) and (H''), respectively. Preferably the active derivative of the acid is the corresponding anhydride $[R_7C(O)]_2O$ and the base is pyridine. Generally the reaction time is in the range 8-24 hours. The product is purified by flash chromatography.

The acid of formula (B) used in step A-1) is prepared by a synthesis process comprising the following steps (see Scheme 1): s1-a) reaction of an acid of formula (B0) with an amine of formula $X_2$—$NH_2$, obtaining the compound (B01), s1-b) reaction of compound (B01) with the enone of formula (B2) to give compound (B1).

Then, depending on the various meanings of $X_4$ in the compound of formula (A), the steps described hereinafter are carried out:

when $X_4$ together with $X_3$ forms the group =O, step s1-c) hydrolysis of the end ester group of (B1) is carried out, when $X_3$=H and $X_4$ has the meanings of alkyl, alkenyl or $NR_6R_7$ the following steps are carried out in sequence: s1-d) reaction of the ketone group of (B1) with the precursor of group $X_4$ and thus obtaining (B4), s1-d') hydrolysis of the end ester group of (B4) obtaining compound (B), when $X_3$=H and $X_4$=OH the following steps are carried out in sequence: s1-e) reduction of the keto group of (B1)

obtaining compound (B3), s1-e') hydrolysis of the terminal ester group of (B3) obtaining compound (B), when $X_3$=H and $X_4$ is selected from: halogen, SH, $(OR_5)_n$—$OR_6$ the following steps are carried out in sequence: s1-f) reaction of the hydroxyl of (B3) in position D, with the corresponding precursors of the above mentioned $X_4$ groups, obtaining compound (B4), s1-f') hydrolysis of the terminal ester group of (B4) obtaining compound (B).

inorganic salt is added and compound (B1) is recovered by extraction with an organic solvent, for example anhydrous tetrahydrofurane (THF). The non nucleophilic organic base is preferably KENDS and the inorganic salt in the acid aqueous solution can be for example ammonium chloride.

The reaction is carried out at temperatures lower than 0° C., preferably comprised between −80° C. and −20° C., still more preferably between −80° C. and −60° C. The reaction time

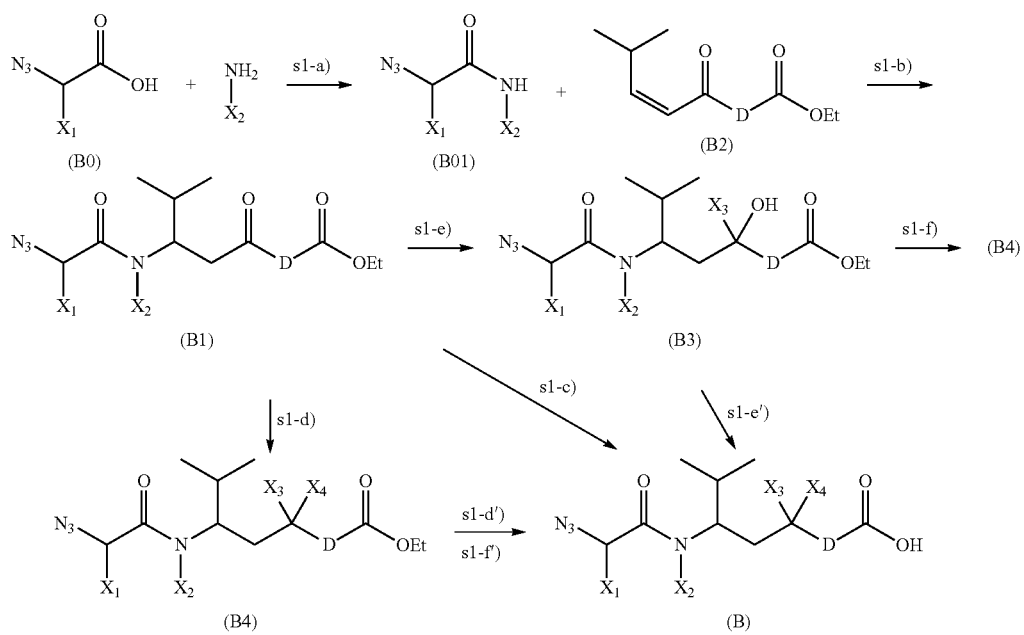

SCHEME 1

In Scheme 1: when (54) is obtained from (B1) $X_4$-alkyl, alkenyl, $NR_6R_7$; when (B4) is obtained from (B3) $X_4$=halogen, SH, $(OR_5)_n$—$OR_6$; when (B) is obtained from (B1), $X_3$ together with $X_4$ forms the group =O Step s1-a) is preferably carried out by reacting the amine with an active derivative of the acid (B0) in a solvent, inert under the reaction conditions. The compounds which can be used as active derivatives of the acid (B0) belong to the same group reported for the active derivatives of the acid $R_7C(O)OH$ in step A-8'). The acid (B0) can be prepared according to known procedures, see for example J. Am. Chem. Soc., 128, 2006, 16018-16019. The reaction takes place in the presence of an organic base. The reaction product is recovered from the reaction mixture for example by adding an acid aqueous solution of an inorganic salt and subsequent extraction with an organic solvent, for example dichloromethane. The organic base can be selected among those used in step A-1), preferably DIPEA. The added acid aqueous solution of an inorganic salt is for example an acid solution of ammonium chloride. The reaction time is generally in the range from 20 minutes to four hours. The reaction temperatures are preferably comprised between 0° C. and 10° C.

Step s1-b) is carried out by dissolving compound (B01) in an inert solvent and then adding an organic non nucleophilic base, for example LiHMDS (Lithio HexaMethylDiSilazide) or NaHMDS or KHMDS. Then a solution containing the enone of formula (B2) is added. The enone can be synthesized as described in Angew. Chem. Int. Ed., 16, 2007, 3526-3529. At the end of the reaction, an acid aqueous solution of an generally ranges from 30 minutes to 5 hours. The reaction product is purified by column chromatography.

Step s1-c) is carried out by dispersing compound (B1) in a mixture of water with an organic solvent, then adding an inorganic base. The reaction product is isolated by adding to the reaction mixture an organic solvent, then recovering and acidifying the aqueous phase. The organic solvent used for the starting dispersion of (B1) is for example selected from dioxane, methanol, THF, more preferably is THF. The inorganic base is selected from Na(OH), K(OH), Li(OH), more preferably Li(OH). The organic solvent added at the end of the reaction is for example ethyl acetate and the acid used for acidifying the aqueous phase can be for example hydrochloric acid. The final pH is lower than 3, preferably equal to or lower than 2. Step s1-d) is carried out by reacting compound (B1) with the phosphorus hylides of formula $Ph_3P$=$C(R_{50})H$ or $Ph_3P$=$C(R_{50})R_{51}$, wherein Ph is phenyl and $R_{50}$ and $R_{51}$, equal to or different from each other, are selected from H, $C_1$-$C_{19}$ alkyl, $C_1$-$C_{19}$ alkenyl. Then a selective reduction of the formed double bond is carried out for example, by using hydrogen in the presence of Pd/C.

Step s1-d') is carried out as described in s1-c).

Step s1-e) is carried out by adding first to a solution of the catalyst in an inert solvent a reducing agent, compound (B1) obtained in s1-b), and then an organic protic solvent. It is obtained the compound of formula (B3). The catalyst is preferably a chiral catalyst, more preferably is (S)—CBS, wherein CBS is the chiral derivative reactant CBS of borohydride developed by Corey, Bakshi and Shibita (J. Am. Chem.

Soc., 109, 1987, 5551-5553; *J. Am. Chem. Soc.,* 109, 1987, 7925-7926). The inert solvent is for example THF, the reducing agent is preferably borane complexed with dimethylsulphide. The organic protic solvent is for example methanol. The reaction product is preferably purified by column chromatography. The reaction is carried out at temperatures comprised between −10° C. and 40° C., preferably between 0° C. and 25° C. The reaction time is generally in the range from 4 to 16 hours.

Step s1-e') is carried out as described in s1-c).

Step s1-f) is carried out with different reactions depending on the meaning of $X_4$ of compound (B), as indicated hereinafter:

When $X_4$ is bromine or chlorine, compound (B3) is reacted with triphenylphosphine and, with carbon tetrabromide or carbon tetrachloride, respectively.

When $X_4$ is fluorine, compound (B3) is reacted with bis(2-methoxyethyl)aminosulfurtrifluonde (Deoxo-fluorreagent) at temperatures in the range −80° C.--−20° C., preferably at temperatures at −80° C.--−60° C., most preferably −80° C.--−70° C. When $X_4$ is iodine, compound (B3) is reacted with diethylaminoazodicarboxylate (DEAD), triphenylphosphine and methyl iodide.

When $X_4$ is the group (OR5)nOR6 and n=0, compound (B3) is reacted with $R_6Br$ and a metal hydride, preferably NaH; when n is different from zero, compound (B3) is reacted with $BrR_5(OR_5)_{n-1}OR_6$.

When $X_4$ is SH, compound (B3) is reacted with DEAD, triphenylphosphine and $CH_3C(O)SH$.

Step s1-f') is carried out as described in s1-c).

The synthesis of compound (D) used in step A-1) is carried out with different processes, depending on the meanings of $X_8$ in formula' (A).

When $X_8$=H, the process comprises the following steps (see Scheme 2): preparation of compound (D1), preparation of the compound of formula (D2) when $X_7$=H in formula (A), when $X_7$ in formula (A) is different from H the compound (D3) is prepared, preparation of compound of formula (D5), synthesis of (96) by reaction respectively of (D2) or of (D3) with (D5), conversion of (D6) into (D7), reaction of (D7) to yield (D).

When $X_8$ is different from H, and is selected from halogen, OH, SH, alkyl, alkeriyl, $OCH_3$, compound (D) is prepared starting from compound (D5) by the process described later (Scheme 3).

More in particular Scheme 2 is described. The process comprises in sequence the following steps: s2-a) reaction of an alcohol of formula $X_{15}$—OH, wherein $X_{15}$ is selected from alkyl or cycloalkyl, with bromoacetylbromide, yielding compound (D1).

Depending on $X_7$ in the compound of formula (A), the following steps take place.

When $X_7$=H the following steps are carded out, in sequence: s2-b) reaction of (D1) with triphenylphosphine yielding compound (D2), s2-c) oxidation of an aminoalcohol of formula (D4), wherein the amine group has a protecting group $X_{17}$, to aminoaldehyde (D5), s2-d) reaction of compound (D2) with (D5) yielding the unsaturated aminoester (D6), s2-e) reduction of the double bond C=C of compound (D6) yielding compound (97), s2-f) removal of the protecting group $X_{17}$ from the amine group of (D7) by using a strong acid and subsequent methylation reaction of the carboxylic group, yielding compound (D) wherein $X_8$=H.

When in (D) $X_7$ is selected from alkyl or alkenyl, a compound (D) is obtained by carrying out step s2-b) reaction of (D1) with triphenyl phosphine to give (D2), then followed, in the order, by the following steps: step s2-g): reaction of (D2) with an aliphatic iodide of formula wherein $X_{7a}$ is alkyl or alkenyl, yielding compound (D3), step s2-c) oxidation of an aminoalcohol (D4) to aminoaldehyde (D5), step s2-d) wherein (D5) is reacted with compound (D3) to give (D6), then steps s2-e) and s-2f) to obtain compound (D).

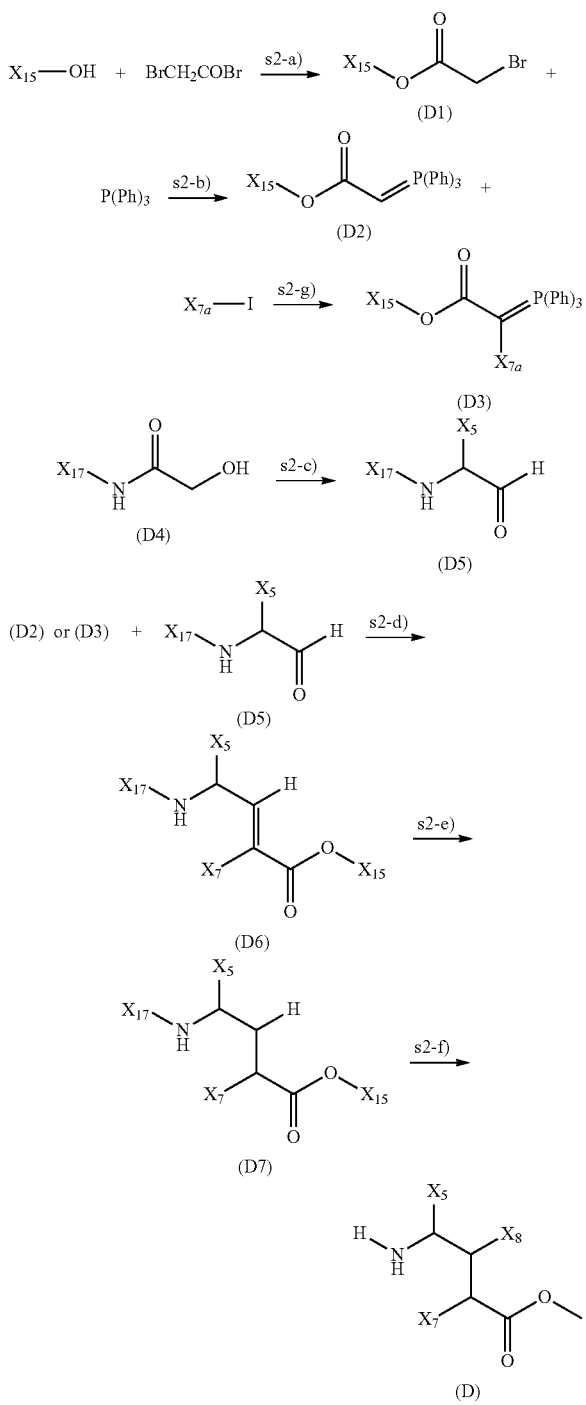

SCHEME 2

(D1), (D2), (D3), (D4), (D5), (D6), (D7), (D)

OH is for example (−)Menthol. As a suitable inert solvent, THF can be used. As an aqueous solution of an inorganic acid to be added at the end of the reaction, a diluted HCl solution can be used. The reaction mixture can for example be extracted with ethyl acetate. The extracted organic phase is washed with a saturated aqueous solution of NaCl. The obtained crude product after removal of the solvent is purified by flash chromatography. The reaction temperature ranges from −10° C. to 40° C., preferably from 0° C. to 3° C. The reaction time generally ranges from one to five hours.

In step s2-b) (D1) is reacted with triphenylphosphine (PPh₃) in an inert organic solvent, that is removed at the end of the reaction. The obtained solid is dissolved in an organic solvent, to which an aqueous solution of a strong inorganic base is then added. At the end of the reaction the organic phase is recovered. After dehydration and evaporation of the solvent, compound (D2) is obtained. A suitable inert organic solvent is for example THF. The reaction is carried out at the reflux temperature of the solvent for a time generally comprised between one and five hours. A suitable solvent for dissolving the solid residue is for example toluene. As strong inorganic base, Na(OH) can for example be used. The compound is reacted in the presence of the base for a time generally comprised between 30 minutes and 3 hours. The reaction temperature is in the range 15° C.-35° C.

In step s2-c) the protecting group $X_{17}$ of (D4) is selected from those stable under reducing conditions. The reaction is carried out starting from the aminoalcohol compound (D4) which is oxidized to aldehyde (D5) in an inert organic solvent, by using an oxidizing agent riot affecting the aldehyde stability. For example a suitable oxidizing agent no effecting the aldehyde stability. For example a suitable oxidizing agent is selected from the mixture oxalyl chloride/dimethylsulphoxide (DMSO/triethyl-amine, Dess-Martin periodinane (DMPER).

At the end of the reaction a saline aqueous solution is added to the reaction mixture that is extracted with an inert organic solvent. The obtained organic phase is dehydrated and the solvent subsequently removed obtaining the aldehyde (95). In step s2-c) preferably the reactant compound (D4) is used in the corresponding isomeric form (D4a), to obtain the isomer compound (D5a) of (D5):

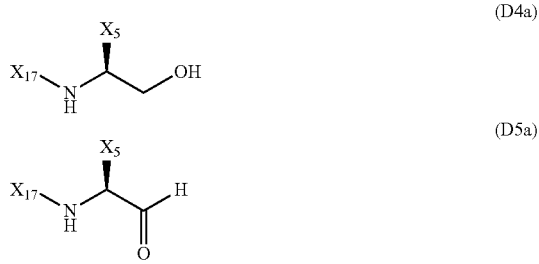

Compounds (D4) and (D4a) are available on the market or can be synthesized according to well known methods to the skilled in the art. See for example the synthesis method reported in the example.

Preferably $X_{17}$ is BOC (Ter-butyloxycarbonyl derivative). Preferably the oxidant is Dess-Martin periodinane (DMPER).

A suitable reaction solvent is dichloromethane. The reaction is carried out at room temperature. NaHCO3 is added to the reaction mixture. The reaction time generally ranges from 1 to 5 hours. The saline aqueous solution added at the end of the reaction can be for example a saturated solution of NaHCO₃/Na₂S₂O₃. A suitable solvent for the final extraction is dichloromethane.

In step s2-d) (D3) or (D2) is reacted with compound (D5) in an inert organic solvent. At the end of the reaction a saline aqueous solution is added, the organic phase recovered, washed with 'a saline aqueous solution, dehydrated and evaporated to give compound (D6).

A suitable organic solvent for the reaction is for example dichloromethane. The reaction temperature generally ranges from 0° C. to 4° C. The reaction time generally ranges from 1 to 5 hours. At the end of the reaction a NaHSO₄ aqueous solution is preferably added. A suitable solvent for the final extraction is for example dichloromethane. The reaction product is purified by flash chromatography.

In step s2-e) compound (D6) is solubilized in an inert organic solvent and the double bond C═C is reduced with a reducing agent. At the end the reaction mixture is filtered, the organic phase recovered and the solvent evaporated obtaining the compound of formula (D7). A suitable inert organic solvent is for example ethyl acetate. The reduction reaction is preferably carried out by using Pd/C under an hydrogen atmosphere. The reaction time is generally comprised between one and four hours.

The compound (D7) that is obtained in this step is a mixture of diastereoisomers. Preferably from the mixture of stereoisomers (D7) the diastereoisomers (D7a) and (D7b) are separated by flash chromatography. Preferably for the subsequent steps of the process, (D7a) is used. The flash chromatography is carried out for example by using an n-hexane/ethyl acetate mixture for example in 4:1 v/v ratio.

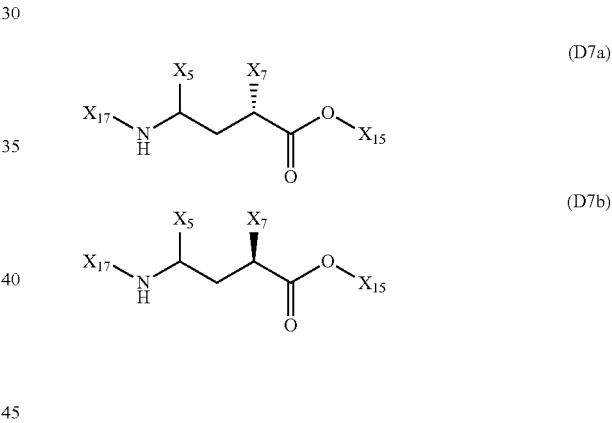

More preferably by flash chromatography (D7aa) is isolated from the isomer (07a), when in s2-c) the isomeric form (D4a) is used

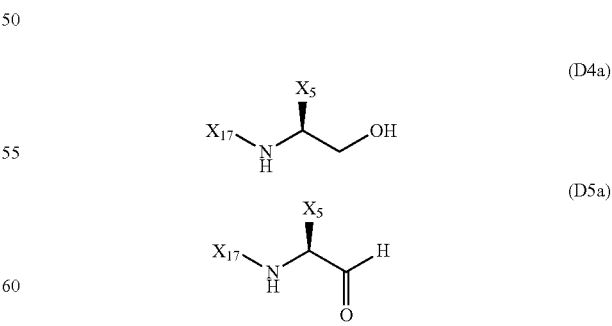

More preferably for the subsequent steps of the process for obtaining the compound (D), (D7aa) is used.

In step s2-f) the protecting group $X_{17}$ is removed by suspending compound (D7), or the corresponding isomers, in an aqueous solution of a strong acid. The acid can be used also concentrated. At the end of the reaction, an organic solvent, for example ethyl acetate, is added, the aqueous phase is recovered and concentrated under a reduced pressure. The residue is solubilized in an organic solvent and subjected to a methylation reaction. At the end of the reaction, the solvent is removed under reduced pressure, yielding the compound of formula (D) wherein $X_8$=H.

A suitable acid is for example HCl, for example 6N HCl. A suitable organic solvent is for example ethyl acetate. The reaction is carried out at the solvent reflux temperature. The reaction time can range from 1 to 14 hours. A suitable solvent for solubilising the residue, after the removal of the protecting group, is for example methanol. Methylation can for example be carried out with 2,2-dimethoxypropane and concentrated HCl (37% w/w). The reaction is carried out at a temperature comprised between 40° C. and 70° C. The methylation reaction time is generally comprised between 8 and 20 hours. In step s2-f) preferably the isomers (Deal) are obtained by flash chromatography of the reaction mixture, in particular the isomer (Daa2) is preferably isolated.

Optionally at the end of step s2-f), compound (D) or the corresponding isomers, are obtained in salified form with AnionH.

In step s2-g) (D2) is dissolved in an inert organic solvent, for example dichloromethane, and reacted with an aliphatic iodide of formula $X_7$,—I. The reaction temperature is comprised between −10° C. and 40° C. Generally the reaction time is in the range 10-20 hours. At the end the solvent is evaporated, the residue is solubilised in an inert organic solvent, for example toluene, and it is treated with an aqueous solution of a strong inorganic base, for example NaOH. The organic phase is then separated, dehydrated, evaporated yielding compound (D3).

When $X_8$ is different from H and has the meanings indicated in (A), the synthesis of compound (D) is carried out by carrying out step s2-c) to obtain compound (D5), compound (D) is then obtained by carrying out the following steps, depending on the meaning of $X_8$, see Scheme 3.

When $X_8$=OH the following steps are carried out: s2'-b) reaction of compound (05) with a compound of formula (DX), yielding compound (D1'). In compound (DX), X7 is as defined in formula (A) and $X_{19}$ is an alkylene optionally substituted with a linear or branched alkyl, s2'-c) compound (D1') is deacetylated yielding the aminoacid of formula (D'2), s2'-d) the protecting group $X_{17}$ and subsequent methylation of the hydroxy group is performed to yield compound (D).

When $X_8$ has the meaning of halogen, SH, OCH3, step s2'-b) is carried out and, in sequence, the following steps:

s2'-e) reaction of the hydroxyl group of compound (D1') with the corresponding precursor of the halogen, SH, $OCH_3$ groups, obtaining the compounds (D1'a), steps s2'-c) and s2'-d) are repeated but using (D1'a).

When $X_8$ has the meaning of alkyl, alkenyl, after step s2'-b). the following steps are carried out in sequence:

s2'-cA) oxidation of the hydroxyl group of compound (D1') to a keto group obtaining compound (D1"), then s2'-cB) obtaining (D1'a), then it is proceeded as indicated above.

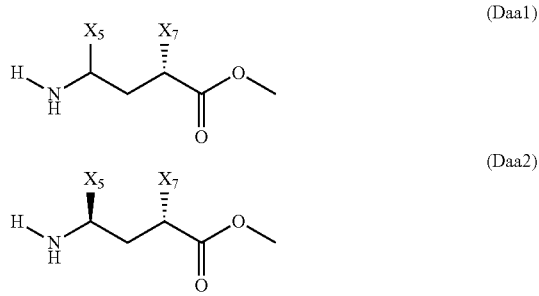

(Daa1)

(Daa2)

SCHEME 3

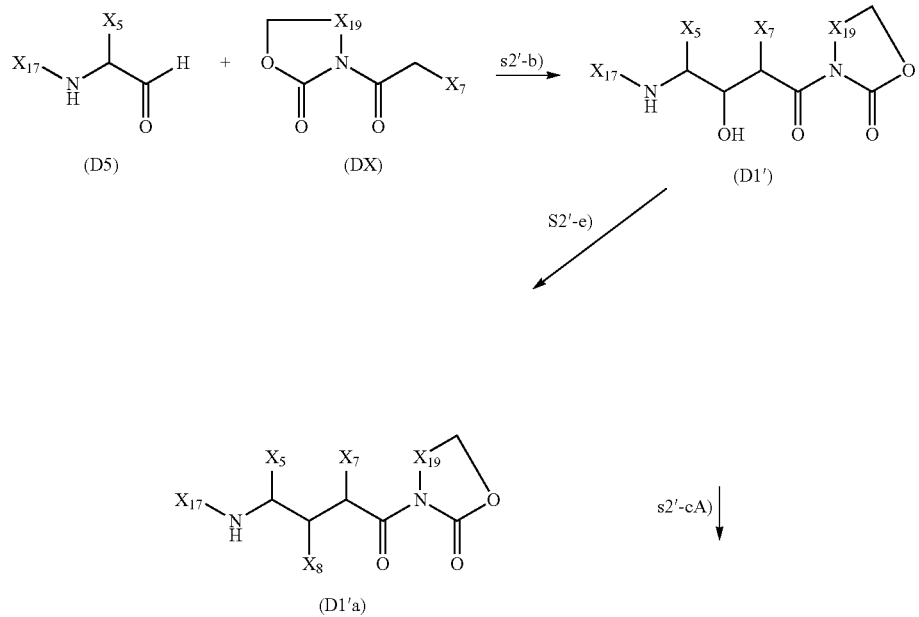

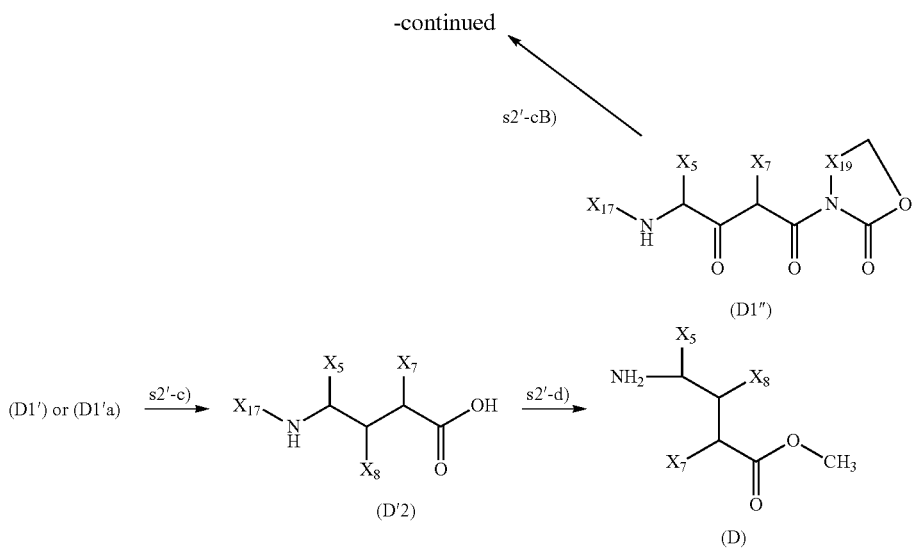

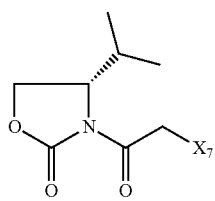

when (D1'a) is obtained from (D1') $X_8$-halogen, SH and $OCH_3$;

when (D1'a) is obtained from (D1") $X_8$=alkyl, alkenyl.

In step s2'-b) a suitable organic solvent that can be used is for example anhydrous THF, preferably in the presence of lithium diisopropylamide (LDA). The reaction is carried out at temperatures in the range −80° C.--−20° C., more preferably between −80° C.--−60° C., more preferably −80° C.-−70° C. Preferably the compound of formula (DX) has the following formula (DX'):

In step s2'-e) the substitution of the hydroxyl group with, respectively, halogen, SH or $OCH_3$, is carried out by using the same reaction conditions described in step s1-f).

In step s2'-cA) suitable oxidants are for example an oxalylchloride/DMSO/triethylamine mixture, or a $H_2SO_4/CrO_3$ mixture of pyridiniumchlorochromate.

In step s2'-cB) the keto group of compound (Di") is converted to alkyl or alkenyl by using the reactions described in step s1-d).

In step s2'-c) deacetylation can be carried out by using for example a mixture of THF and water. The reaction is preferably carried out by using a strong base, preferably Li(OH), optionally in the presence of hydrogen peroxide.

Step s2'-d) is carried out by submitting to an acid hydrolysis the group $X_{17}$—NH— of compound (D'2), for instance by using an HCl aqueous concentrated solution or by using $CF_3COOH$ in dichloromethane, followed by methylation of the group —C(O)OH by a methylating agent, for instance 2,2-dimethoxy propane in methanol and concentrated HCl.

Compound (D) can be obtained from compound (D1') or (D1'a) by treatment with a concentrated strong acid aqueous solution, for instance using as acid HCl, at the reflux temperature, and subsequent methylation of the carboxylic group by a methylating agent, for instance 2,2-dimethoxy propane in methanol and concentrated HCl.

Preferably in the synthesis of compound (D), when $X_8$ is different from H, for obtaining compound (D5) it is used the isomeric form (D4a) of compound (D4) (step s2-c) of Scheme 2). In step s2'-c) isomer (D'2a) of (D'2) is preferably obtained by flash chromatography, more preferably the further isomer (D'2aa) of (D'2) is obtained by flash chromatography (see the examples). These isomers are preferably reacted in step s2'-d) to obtain compound (D).

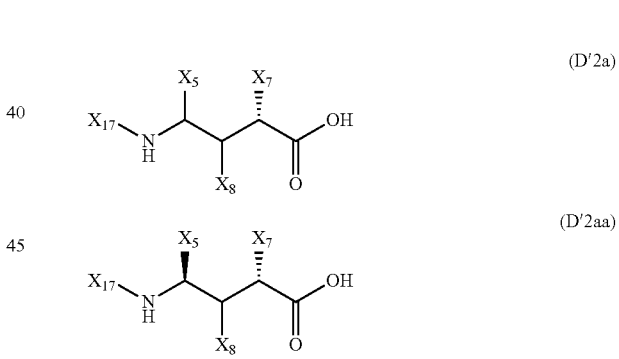

As said, the process of the present invention surprisingly and unexpectedly allows to obtain the compounds of formula (A) in high yields.

It is a further object of the present invention conjugated compounds comprising the compounds of formula (A) and polymers and/or pharmaceutically acceptable biomolecules. Preferably the conjugated compounds have the following formulae:

-continued

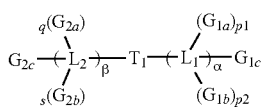
(C2)

wherein:
the p1, p2, q and s indexes, equal to or different from each other, are integers equal to 0 or 1,
T is a monovalent radical of the compounds of formula (A),
$T_1$ is a bivalent radical of the compounds of formula (A),
$G_{1a}$, $G_{1b}$, $G_{1c}$, $G_{2a}$, $G_{2b}$, $G_{2c}$, equal to or different from each other, are polymers or pharmaceutically acceptable biomolecules,
$L_1$ and $L_2$, equal to or different from each other, are linkers joining the radical T, or the radical $T_1$ of the compound of formula (A), to $G_{1a}$, $G_{1b}$, $G_{1c}$, $G_{2a}$, $G_{2b}$, $G_{2c}$, respectively. α and β are integers equal to zero or 1, with the proviso that when α=β=0, p1, p2, q and are equal to zero; when α and/or β=1, the part of $L_1$ and/or $L_2$ bound to groups Gi (i=1a, 1s, 1b, 2a, 2b, 2c) can be monovalent, bivalent or trivalent, depending on the values of p1, p2, s and q.

The linkers that can be used according to the present invention are those stable in biological fluids such as blood plasma and that are pharmaceutically acceptable. Preferably said linkers are metabolically cleavable.

As preferred linkers $L_1$, $L_2$, equal to or different from each other, the following can be mentioned: alkylene, alkenylene, alkynylene, heteroalkylene, arylene, heteroarylene, cycloalkylene, alkylcycloalkylene, heterolkylcycloalkylene, heterocycloalkylene, alkylenearyl, aryialkylene, alkylene-arylalkylene, heteroarylalkylene, alkyleneheteroaryl as defined above, optionally containing S—S bonds and/or N—N bonds, and/or the bivalent linkers of formula (DXI) and/or (DXII) (formulae reported hereinbelow), peptide chains, optionally containing S—S bonds and/or N—N bonds, and/or the bivalent linkers of formula (DXI) and/or (DXII).

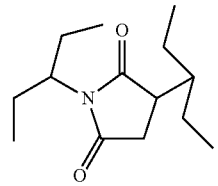
(DXI)

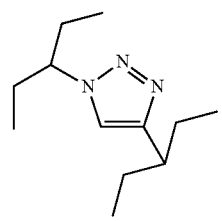
(DXII)

Examples of preferred linkers are those reported hereinafter (formulae from (XYZ1) to (XYZ22)):

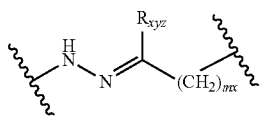
(XYZ1)

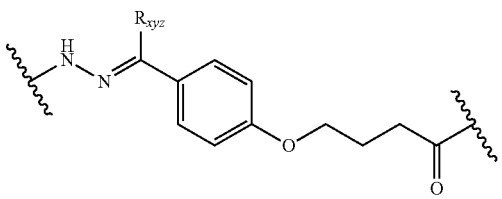
(XYZ2)

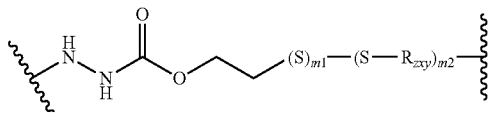
(XYZ3)

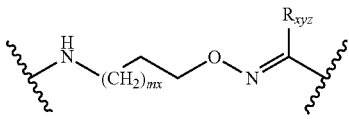
(XYZ4)

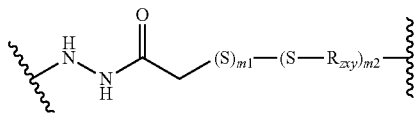
(XYZ5)

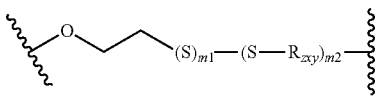
(XYZ6)

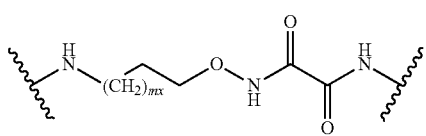
(XYZ7)

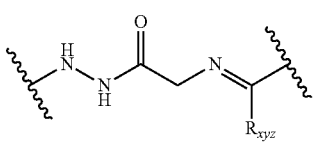
(XYZ8)

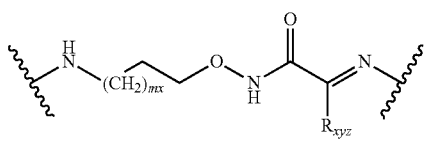
(XYZ9)

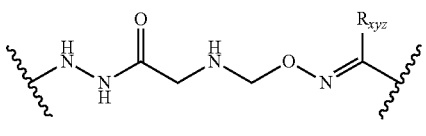
(XYZ10)

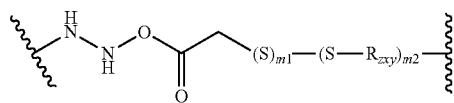
(XYZ11)
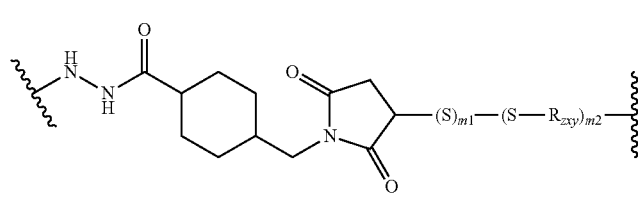
(XYZ12)
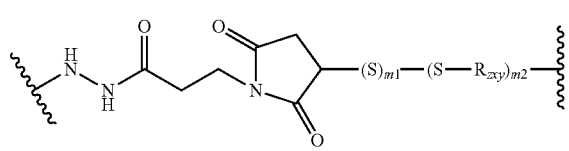
(XYZ13)
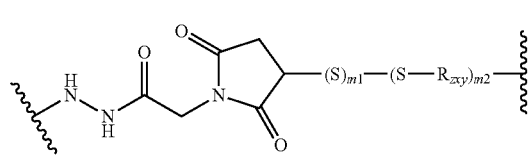
(XYZ14)
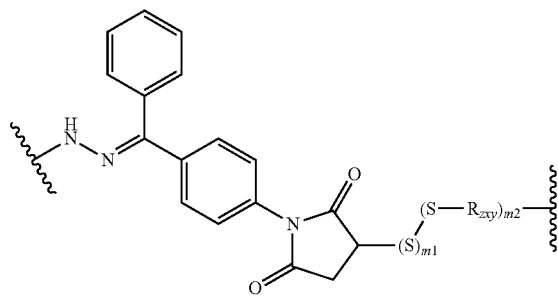
(XYZ15)
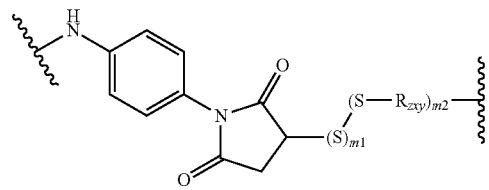
(XYZ16)
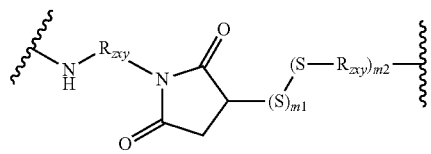
(XYZ17)
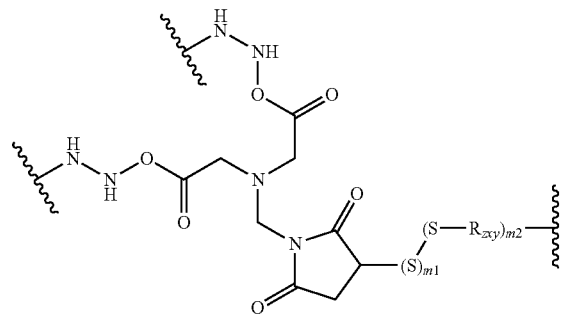
(XYZ18)
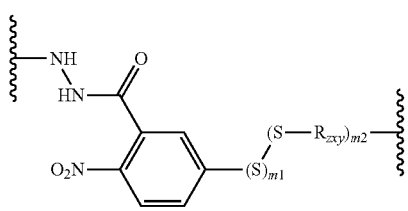
(XYZ19)

-continued

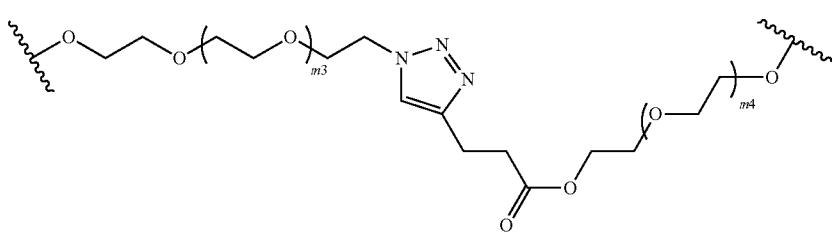
(XYZ20)

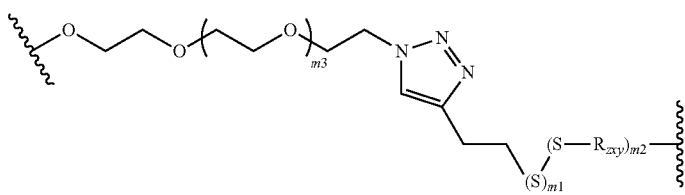
(XYZ21)

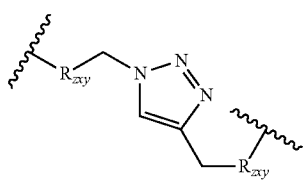
(XYZ22)

wherein:
the free valence present at the end, preferably on the right side of the linker formula is linked to $G_{1a}, G_{1b}, G_{1c}, G_{2a}, G_{2b}, G_{2c}$,
mx is an integer from 0 to 20, preferably between 0 and 6, m1 and m2, equal to or different from each other, are zero or 1, m3 and m4, equal to or different from each other, are an integer from 0 to 200, preferably from 0 to 50, more preferably from 0 to 10,
$R_{xyz}$ id selected from H or alkyl wherein alkyl is preferably a linear or when possible branched $C_1$-$C_5$ chain,
$R_{xyz}$ is selected from alkylene, alkynylene, alkynylene, heteroalkylene, arylene, heteroarylene, cycloalkylehe, alkylcycloalkylene, heteroalkylcycloalkylene, heterocyclo-alkylene, arylalkylene or heteroarylalkylene.

The polymers and the pharmaceutically acceptable biomolecules which can be used in the conjugated compounds of the invention are preferably selected from the following: proteins, as albumin, glycoproteins, lypoproteins, epidermal growth factor (EGF), lectin, transferrin, optionally peghilated by functionalization with compounds having polyethylenglycol (PEG) chains,
hormones,
aptamers, as for example those reported in Expert Opin. Drug Deliv. 2009, 6(3) 285-304, for example: MUC-1, PSMA Aptamer (A9,A10), A30, AS-1411, CTLA-4-Aptamer, Clone 5, TTA1, PDGF-r Aptamert, 111.1, PEGAPTANIB,
polysaccharides, as for example chitosan, dextran, amide and derivatives as for example hydroxyethyl starch (HES),
antibodies or their fragments, such as those reported in Expert Opin. Drug Deliv. 2009, 6(3) 285-304; News Physiol. Sci., 2001, 16, 191-194; British Journal of Cancer, 2007, 96, 1862-1870; preferably the antibodies are capable to link to angiogenesis markers as for example those able to selectively link to neovasculature markers, such as those joining integrins with particular reference to integrins αvβ3 and αvβ5,
endoglin,
vascular endothelial growth factor (VEGF),
VEGF receptors,
antigens expressed in the prostate cancer (PSMA: Prostate-specific membrane antigen, See for example S.A: Kularatne at al. Molecular Pharmaceutics vol. 6, n. 3, 780-789, 2009),
the cell adhesion CD44 receptor,
extradominiori B (ED-B) of fibronectin (FN),
tenascin C,
more preferably selective antibodies for the ED-B dominion of fibronectin known as L19 such as L19-SIP, monoclonal antibodies such as Trastuzumab (Herceptin®), Rituximab (Rituxan®), Alemtuzumab (Campath®), Gemtuzumab ozogamicin (Mylotarg®, Ibritumomab tiuxetan (Zevalin®), Tositumomab (Bexxar®), Gefitinib (Iressa®, Cetiximab (Erbitux®), Bevacizumab (Avastin®), Panitumumab (Vectibix®).

Peptide chains or peptides, such as those described in the above reported article of Expert Opinion Drug Delivery of 2009 and those described in patent application WO 2006/067, 633 can also be used as Gi, wherein i is 1a, 1b, 1c, 2a, 2b, 2c. For example VEGE peptides, vasoactive intestinal peptides (VIP: vasoactive intestinal peptide), somatostatin peptides, peptides comprising deamination products of peptides comprising an asparagine-glycine-arginine sequence (NGR) (NOR motif), or a DGR sequence (DGR motif), comprising $_D$Asp ($_D$D) and/or $_L$isoAsp ($_L$isoD) or a mixture thereof and that can comprise furthermore $_L$Asp ($_L$D) and $_D$isoAsp ($_D$isoD). The isoAsp and Asp terms are isoaspartic acid and aspartic acid, respectively. Among the deamination peptides, the deamination products of proteins of extracellular matrix, such as fibronectin, vitronectin, collagen or laminin, can for example be mentioned. Said peptides are optionally modified with GVRY end groups. Preferably the optionally modified deamination products comprise the following sequences (Seq):
$X_A$NGRX$_B$, wherein X$_A$ is a group comprising one or more of the following aminoacids: L, V, A, C, G, Y, P, H, K, Q, I and X$_B$ is a group comprising one or more of the following aminoacids: C, G, H, L, E, T, Q, R, S, P, V, Y, CNGRCVSGCAGRC, NGRAHA, GNGRG, CVLNGRMEC, CNGRC, CNGRCG, LNGRE, YNGRT, LQCISTGNGRGEWKCE, LQCISTGNGRGEWKCE, CICTGNGRGEWKC, CISTGNGRGEWKC, MRCTCVGNGRGEWTCY, MRCTSVGN-GRGEWTCY, CTCVGNGRGEWTC, CTSVGN-GRGEWTC,
CNGRCGVRY
cycloCVL wherein $G_1$ and $G_2$, equal to or different from each other, have the following meanings:

hydrogen,

OH, when the valence of the linkers to which $G_1$ and $G_2$ are linked is not on one oxygen atom, P1, P2, q and s are as defined in formulae (C1) and (C2), Con-2) reaction between the polymers or biomolecules $G_{1a}$, $G_{1b}$, $G_{1c}$, $G_{2a}$, $G_{2b}$, $G_{2c}$ and the compounds of formula (C1a) or (C2a) obtaining the conjugated compounds of formula (C1) or (C2), respectively.

when $\alpha=\beta=0$ Con-1) is absent and con-2 is carried out but using compound (A) instead of compound (C1a) or (C2a);

when one of the indexes $\alpha$ or $\beta$ is equal to zero,

Con-1) and Con-2) are carried out for obtaining the compound, or the group in the molecule, having the index that is different from zero, Con-2) is carried out for obtaining the compound, or the group in the molecule, having the index equal to zero, but using compound (A) instead of compounds (C1a) or (C2a).

In step Con-1) suitable linker precursors are compounds that by reaction of one of their functional groups, for example OH, SH, COOH, ester, amide, amino, with one or two functional groups of the compounds of formula (A), for example OH, SH, alkenyl, $OC(O)R_7$, $NR_6R_7$, $X_6$, are converted into the linkers $L_1$ and $L_2$, with formation of ester, thioester, amide groups, etc. When the reacting functional group of (A) is a double bond of an alkenyl substituent, the double bond can react with a double bond present on the linker precursor, for example by metathesis reaction or Diels Alder cycloaddition. When the reacting double bond of (A) is a conjugated double bond, such as for example a double bond on the carbon atom in alpha to a group C—O, the double bond can for example react through a Michael reaction, for example with SH or NH groups of the linker precursor.

Generally the linker precursors have in the molecule two functional groups.

The reaction is carried out at temperatures comprised between −80° C. and 15° C., preferably between −78° C. and 80° C., still more preferably between 0° C. and 70° C. As suitable inert organic solvents, for example DMF, THF, can be used.

When in the compounds of formula (A), or in the precursors of the linkers $L_1$ and $L_2$ the reacting group is a functional COOH group, this functional group it is previously activated by converting it into one of the following reactive groups: acyl chloride, anhydride, mixed anhydride, imidazolide, ester-amide adduct, linear or branched $C_1$-$C_4$ alkyl ester, linear or branched when possible.

When the precursor of the linkers $L_1$ or $L_2$ is a peptide prepared by solid phase synthesis on resin, as for example a functionalized polystyrene resin, in the process of the present invention said linker precursor can be used still attached to the resin by one of the two reactive groups. The second functional group of the peptide is reacted with the compound of formula (A). The reaction is carried out in the presence of an activator, for example O-(Benzotriazol-1-yl)-N,N,N',N'-tetramethyluronium tetrafluoroborate (TBTU), and of an organic base, for example diphenylethylamine (DIPEA).

From the compounds T-L-resin or resin-$L_2$-$T_1$-$L_1$-resin, (C1) or (C2), compounds (C1a) or (C2a) are obtained for example by treatment with hexafluoropropanol.

In step Con-2) the reaction between the functional group of the linker and the reactive functional groups of the polymers or of the biomolecules takes place under the same conditions indicated for step Con-1).

The reactive functional groups of the polymers or of the biomolecules are for example OH, SH, alkenyl, ester, amino, amido, azide, COOH.

The reactive functional groups of the linkers L and $L_2$, are the same as those mentioned above in step Con-1).

When the reactive group of the polymers or biomolecules is a .COOH group, it is previously activated by converting it into one of the reactive groups of group COOH indicated in step Con-1).

When $G_{1a}$, $G_{1b}$, $G_{1c}$, $G_{2a}$, $G_{2b}$, $G_{2c}$, are peptides synthesized in solid phase on resin, thus bound with a chain end group to the resin, step Con-2) can be carried out by reacting the end group of the peptides not linked to the resin with the compounds of formula (C1a) or (C2a), obtaining the precursors of the compounds of formula (C1) or (C2). The compounds (C1) or (C2) are obtained by treatment with hexafluoropropanol.

An alternative process is the following comprising the following steps:

Con-3) reaction between the polymers or biomolecules $G_{1a}$, $G_{1b}$, $G_{1c}$, $G_{2a}$ $G_{2c}$ and the precursors of linkers $L_1$ and $L_2$ according to the methods and in the reaction conditions described in Con-2), obtaining the compounds of formulae (C1b) or (C2b):

wherein $G_1$, $G_2$, $G_{1a}$, $G_{1b}$, $G_{1c}$, $G_{2a}$, $G_{2b}$, $G_{2c}$, p1, p2 q, s $L_1$ and $L_2$ are as defined above, Con-4) reaction between the compound of formula (A) and the compounds of formula (C1b) and/or (C2b) obtaining the compounds having formula (C1) or (C2), by using the methods and reaction conditions reported in Con-1).

Optionally the compounds obtained in each of the steps Con-1), Con-2), Con-3), Con-4) can be purified, for example by preparative chromatography, or preparative HPLC, or liquid/liquid, or solid/liquid extraction, or crystallization.

It is a further object of the present invention a compound obtainable by reacting the compounds of formula '(A) of the invention with at least one precursor of linkers $L_1$ or $L_2$. These compounds can be used for the same uses of the compounds of formula (A) of the invention.

Preferably these compounds have the formulae (C1a) and (C2a) defined above.

A further object of the present invention is represented by pharmaceutical compositions comprising the compounds and/or the conjugated compounds of the invention and/or compounds obtainable by reacting the compounds of formula (A) with at least one precursor of linkers $L_1$ or $L_2$.

By pharmaceutical compositions, preparations are meant wherein the compounds and/or conjugated compounds and/or the compounds obtainable by reacting the compounds of formula (A) with at least one precursor of the linkers $L_1$ or $L_2$, are mixed with excipients, carriers, dyestuffs, preservatives, aromas, and other additives the use of which in the pharmaceutical field is known.

The pharmaceutical compositions can be administered by oral, subcutaneous, sublingual, intramuscular, intravenous, topic, transdermal, rectal, ophthalmic, intranasal route. Said pharmaceutical compositions comprise for example dispersions, solutions, emulsions, microemulsions, powders, microparticles, nanoparticles, liposomes, capsules, aerosols, suppositories, tablets, syrups, elixirs, creams, gels, ointments, plasters.

They can be obtained according to known processes of the pharmaceutical technology, for example they are obtainable starting from emulsions and microemulsions, wherein the compounds or conjugated compounds of the invention are mixed with an aqueous phase and optionally with an oil phase in the presence of surfactants and other additives.

It is a further object of the present invention pharmaceutical formulations formed of microemulsions or emulsions, or comprising microemulsions or emulsions, comprising the following components (% by weight):

S) from 0.01 to 95% of one or more pharmaceutically acceptable compounds, selected from the following classes:
  surfactants selected from non-ionic, anionic, cationic and amphotheric, optionally containing fluorine atoms,
  polymers (Pol) forming organized structures such as aggregates, micelles, liquid crystals, vesicles, in the liquid in which they are solubilized,
O) from 0 to 95% of one or more oils selected from the following classes of pharmaceutically acceptable compounds:
  esters of $C_4$-$C_{32}$ carboxylic acids, optionally containing one or more unsaturations of ethylene type,
  $C_4$-$C_{32}$ carboxylic acids optionally containing one or more unsaturations of ethylene type, usable when the final composition has a pH comprised between 3 and 5,
PA) from 0.001 to 90% of compounds of formula (A) and/or of conjugated compounds of the invention, and/or of the compounds obtainable by reacting the compounds of formula (A) with at least one precursor of the linkers $L_1$ or $L_2$,
AD) from 0 to 60% by weight of one or more compounds selected from the following classes:
  modifiers of the water and/or oil polarity,
  modifiers of the film curvature of component S),
  co-surfactants,
WA) from 0.001 to 99.9% of water or of a saline aqueous solution, optionally buffered, the sum of the components being 100%.

The compositions of the invention in the form of microemulsions are limpid and transparent, preferably liquid. When the viscosity is very high, the microemulsions of the invention are in the gel form, optionally formed of liquid crystals.

In component S) the surfactants containing fluorine atoms can have (per)fluorinated chains, for example (per)fluoropolyether chains.

The liquids wherein the polymers of component S) are solubilized or dissolved to form the organized structures are water and/or oil. The usable oils are listed further on herein below and can be of both natural and synthetic origin.

By microemulsion a system is meant formed of two or more phases immiscible among each other, that is transparent, isotropic, comprising at least one aqueous phase and at least one oil phase, wherein the various phases are stabilized by component S), optionally in the presence of one or more compounds AD), for example co-surfactants. See for example R. K. Mitre, Physicochemical investigations of microemulsification of eucalyptus oil and water using mixed surfactants (AOT+Brij-35) and butanol, J. Colloid and Interface Science, 283 (2005) 565-577. Sometimes the oil phase in the microemulsions for pharmaceutical use is formed only by the active principle, when it is lipophilic and thus insoluble in water or in an aqueous phase.

By emulsion it is meant a system formed of the same components of the microemulsion but of an opalescent or milky appearance, or it is in the form of a cream.

The processes for preparing the microemulsions of the invention or the emulsions of the invention are described hereinafter.

Preferred microemulsions or emulsions according to the present invention have the following composition (% by weight):
from 0.01 to 90% of component S) as defined above,
from 0 to 90% of one or more oils of component O),
from 0.001 to 50% of compounds component PA),
from 0 to 30% of component AD),
from 0.1 to 99.9% of component WA),
the sum of the components being 100%.

More preferred microemulsions or emulsions have the following composition (% by weight):
from 0.01 to 80% of component S),
from 0 to 70% of one or more oils of component O),
from 0.05 to 40% of compounds component PA),
from 0 to 20% of component AD),
from 10 to 99.9% of component WA),
the sum of the components being 100%.

Still more preferred microemulsions or emulsions have the following composition (% by weight):
from 0.01 to 70% of component S),
from 0 to 50% of one or more oils of component O),
from 0.05 to 30% of compounds component PA),
from 0 to 15% of component AD),
from 20 to 99.9% of component WA),
the sum of the components being 100%.

Preferably the oil in the microemulsions/emulsions is not lower than 0.001%.

The preferred surfactants component S) are the non-ionic and anionic ones. Among the non-ionic surfactants, the most preferred are those containing polyoxyalkylene chains, preferably polyoxyethylene chains. The following ones can for example be mentioned:
polyoxyl 35 castor oil, known for example under the trademark Cremophor® EL (BASF), prepared by ethoxylation of castor oil, polyoxyl 40 hydrogenated castor oil, known for example under the trademark Cremophor® RH40 (BASF), prepared by ethoxylation of hydrogenated castor oil,
polyethylenglycol 15 hydroxystearate, known for example under the trademark Solutol® HS15 (BASF), prepared by reaction of 15 moles of ethylene oxide with 1 mole of 12-hydroxystearic acid, polyoxyethylene polysorbate, such as Tween® 80, Tween® 20, Tween® 60, Tween® 85,
sorbitan esters of fatty acids, as for instance sorbitan monolaurate and sorbitan monostearate, commercialized for example under the name Span® 20 and Span® 60, respectively,
vitamin E/TPGS: tocopheryl propylenglycol 1000 succinate, polyoxyethylen ethers of fatty acids, as for instance those of the series Brij®, such as Brij® 35, Brij® 76, Brij® 98,
PEG-12-acyloxy-stearates, see for example C. E. McNamee et al. in "Physicochemical Characterization of PEG 1500-12-acyloxy-stearate micelles and liquid crystalline phases", Langmuir, 2005, 21, 8146-8154. Among these the following can for example be mentioned:
PEG 1500 mono-12-capryioyloxy stearate (PEG 1500-$C_{18}C_8$)
PEG 1500 mono-12-caproyloxy stearate (PEG 1500-$C_{18}C_{10}$)

PEG 1500 mono-12-lauroyloxy stearate (PEG 1500-$C_{18}C_{12}$)
PEG 1500 mono-12-myristoyloxy stearate (PEG 1500-$C_{18}C_{14}$)
PEG 1500 mono-12-palmitoyloxy stearate (PEG 1500-$C_{18}C_{16}$).

Among the anionic surfactants the following can for example be mentioned: soya lecithin, for example known under the trademark Epikuron® 200, bis-2-ethylhexyl-suiphosuccinate (ACT), sodium taurocholate.

Among cationic surfactants, hexadecyltrimethylammonium bromide (CTAB) and didodecylammonium bromide (DDAB) can for example be mentioned.

The polymers, hereinafter called also Pol, which can be used as component S) must be soluble in the aqueous phase and/or in the oily phase. By soluble it is meant that the polymers must reach in the phase in which they are soluble concentrations at least equal to those allowing the formation of organized structures as aggregates, micelles, liquid crystals, vesicles. The presence of the mentioned organized structures can be detected by specific techniques of the physical chemistry of the dispersed systems, as for example Laser Light Scattering (LLS), Neutron Scattering, microscopy.

As said, the polymers component S) can be used also in combination with the mentioned surfactants. Also in this case the concentration of the solubilized polymer in the liquid phase used must be such to lead to the formation of the above mentioned organized structures.

The polymers component S) are for example polyvinylpyrrolidone and vinylpyrrolidone/vinyl acetate copolymers, commercialized for example under the trademark Kollidon®, as Kollidon® 12 PF and Kollidon® 17 PF (BASF), and the block copolymers containing polyoxyalkylene chains, more preferably containing polyoxyethylene chains (PEO), as for example the block copolymers PEO with polyoxypropylene chains (PPO) characterized by PEO-PPO-PEO structures, commercially available for example under the trademark Pluronic® or Poloxamer® or Lutrol®, as Lutrol® F68 and Lutrol® F127 commercialized by Basf.

In component O) the acid esters are preferably obtained by esterification of the corresponding acid, preferably aliphatic carboxylic acid, with an alcohol having an aliphatic chain, preferably $C_1$-$C_5$, or having a polyoxyethylene chain, or with glycerine. In this case mono-, di- or triglycerides are obtained.

The following can for example be mentioned:
oleoyl macrogol 6 glyceride (unsaturated polyglycosylated glyceride), commercialized for example under the trademark Labrafil® 1944 CS, (Gattefosse),
propylenglycol caprylate caprate, known for example under the trademark Labrafac® PG (Gattefosse),
propylenglycol monoester of the caprylic acid, commercialized for example under the trademark Capmul® PG-8 (Abitec),
glycerol oleate (for example Peceol® (Gattefossé)),
medium chain mono- and diglycerides, for example capric and caprylic acid glycerides (for example Capmul® MCM (Abitec), Imwitor® 308 (Sasol)),
polyglycerol oleate (for example Pluro® oleic (Gattefossé)),
capric/caprylic acid triglycerides (for example Miglyol® 812 and Miglyol® 810 (Sasol), Labrafac® CC CS (Gattefossé)),
ethyl butyrate, ethyl caprylate, ethyl oleate,
tripalmitine, commercialized for example under the trademark DYNASAN® 116 by Sasol.

Vegetable oils having a pharmaceutical purity containing one or more of the above mentioned esters can also be used. The soya oil is for example mentioned.

Among the acids component O) the carboxylic aliphatic acids are preferred, stearic acid, the omega-3 and omega-6 acids can for example be mentioned.

In component AD) the modifiers of the water and/or oil polarity can for example be polyethylenglycols. Lutrol®E300 and Lutrol® E400 (BASF) can be mentioned. Aliphatic alcohols, for example ethanol, can also be used.

In component AD) the modifiers of the film curvature of component S) are for example aliphatic alcohols, preferably $C_2$-$C_5$.

In component AD) the co-surfactants can for example be the surfactant compounds as defined above, or aliphatic alcohols, preferably having a chain with at least 6 carbon. atoms. The following compounds can be mentioned, for example:
propylen glycol monolaurate, known for example under the trademark Capmul®PG12 (Gattefosse) or Lauroglycol® 90 (Gattefossé),
Caprylocaproyl macrogol 8 glyceride (saturated ethyldiglycosylated glyceride) commercialized for example under the trademarks Labrasol®, Gelucire 44-14 (Gattefossé),
diethylenglycol monoethyl ether, known for example under the trademark Transcutol® (Gattefossé).

The compositions formed of microemulsions are stable in a wide range of temperature, generally from 0° C. to 80° C., preferably from 4° C. to 45° C.

The microemulsions of the present invention can be prepared with a a process comprising the following steps:
(IP) optional solubilization of the compound component PA) in oil,
(IIP) addition of component S) to component PA) or to its solution in oil obtained in (IP),
(IIIP) optional addition of component AD) to the phase obtained in (IIP),
(IVP) addition, under stirring, of water or of a saline aqueous solution to the phase obtained in (IIP) or optionally (IIIP), obtaining a limpid solution.

The steps of the process can be carried out at temperatures in the range 0° C.-80° C.

It is possible to obtain a microemulsion in the form of a limpid solution also by varying the order of implementation of the above mentioned steps, or, for example, by proceeding as follows:
(IP') optional solubilization of the compound component PA) in oil,
(IIP') addition of component S) to water or to a saline aqueous solution,
(IMP') optional addition of component AD) to the aqueous phase,
(IVP') mixing under stirring of component PA) or of the oily solution of step (IP') with the aqueous phase of step (IIP') or optionally step (IIIP').

The temperature range of this process is the same as that indicated in the previous process.

The emulsions of the present invention can be prepared by a process comprising the following steps:
(IP") optional solubilization of the compound component PA) in oil, optionally in the presence of component AD),
(IIP") heating of component PA) or of the oily solution obtained in (IP") at temperatures in the range 35° C.-80° C., more preferably 45-70° C.,
(IIIP") addition of component S) to water or to a saline aqueous solution, optionally containing component AD),
(IVP") heating of the obtained aqueous phase at temperatures in the range 35° C.-80° C., more preferably 45-70° C.,
(VP") addition, under stirring, of the phase obtained in step (IIP") to the aqueous phase obtained in step (IVP"), thus forming an emulsion, (VIP") cooling of the emulsion at temperatures comprised between 0° C. and 30° C. Step (VP") preferably is performed by using turboemulsifiers.

The emulsions obtained in steps (VP") and (IVP") can optionally be subjected to a further homogeneization step at high pressure.

The emulsions can also be obtained by dilution of microemulsions with water, or with aqueous solutions, or with component O). Optionally, the used water, the aqueous solutions and component O) can contain component AD).

Additional pharmaceutical compositions can be obtained according to the procedures described in U.S. Pat. No. 6,028, 084, herein incorporated by reference.

The pharmaceutical compositions can also be prepared by using the methods and the additives indicated in patent application US 2003/0003145. In these formulations sodium alkylsulphate, or other surfactants commonly used in the pharmaceutical field, can be used. For example pharmaceutical compositions usable for the oral administration of the compounds or of the conjugated compounds of the invention, comprise (% by weight):

0.5-20% of one or more compounds and/or conjugated compounds of the invention and/or the compounds obtainable by reacting the compounds of formula (A) with at least a precursor of linkers $L_1$ or $L_2$, 0.05-0.5% of a surfactant, preferably sodium alkylsulphate, 2.5-10% of a disgregating agent, for example cellulose, sodium carboxymethylcellulose or other cellulose derivative, the difference to 100% being the other vehicles of excipients commonly used in oral dosage forms.

Pharmaceutical formulations usable for the oral administration comprise the compounds or the conjugated compounds of the invention, and hydroxypropylmethylcellulose. In particular they comprise (% by weight):

0.1 to 20% of the compounds of formula (A) and/or of the conjugated compounds of the invention and/or the compounds obtainable by reacting the compounds of formula (A) with at least one precursor of linkers $L_1$ or $L_2$ 0.5 to 10% of hydroxypropylmethylcellulose (HPMC), the difference to 100% being the other vehicles, excipients commonly used in oral dosage forms.

Specific pharmaceutical formulations for oral administration in the form of capsules or tablets comprise the compounds or the conjugated compounds of the invention, hydroxypropylmethylcellulose, other excipients, such as monohydrate lactose, magnesium stearate, microcrystalline cellulose, titanium oxide. In these preparations HPMC can be present in the capsule or in the tablet core, and/or in the tablet shell, when a coating is present.

Other pharmaceutical formulations comprising the compounds of formula (A) and/or the conjugated compounds of the invention are those formed by or, comprising micro- and/or nano-particles of silica, or of lipids or of Pol-A compounds as defined above, pharmaceutically acceptable, wherein the compounds or the conjugated compounds of the invention, present in concentrations comprised between 0.1 and 60% by weight with respect to silica, lipid and/or compound Pol-A, are incorporated inside and/or on the surface of the particles.

The compounds Pol-A have been described above in the part relating to the conjugated compounds of the present invention.

As lipid particles, those based on fatty acids or esters thereof having a melting point higher than 40° C., more preferably higher than 50° C. can be mentioned. Suitable examples are, for instance, triglycerides of fatty acids, such as tripalmitine and lanolin. The particles can also be formed of mixtures of fatty acids or fatty acid esters having a melting point higher than 40° C. and an oil liquid at room temperature (20-25° C.), selected from medium chain triglycerides, such as vegetable oils, Miglyol® 812 and Miglyol® 810 commercialized by Sasol. Alternatively these particles can be formed of a surface layer of soya lecithin englobing a liquid lipidic core, constituted for example by medium chain triglycerides, such as vegetable oils, Miglyol® 812 and Miglyol® 810. As polymeric particles, those formed of the polymers mentioned above in the description of the conjugated compounds of the invention, can for example be mentioned.

The silica particles are preferably formed of hydrophilic silica. They can optionally contain one or more compounds component O) described for the emulsions and microemulsions, and/or lipids used for preparing the above described lipid particles. For example the particles of LipoCeramic™ described by Simovic et al. in Mol. Pharmaceutics, 2009, 861-872, can be used.

The particles containing the compounds of formula (A) or the conjugated compounds of the invention can optionally be surface-modified to ease, for example, the passage through physiological barriers, such as the haematoencephalic barrier, and/or to increase the residence time in the blood circulation system of the compounds of formula (A) or of the conjugated compounds of the invention, and/or to selectively target tumoural cells or tissues. The surface modification of the particles can be carried out both by chemico-physical adsorption of one or more surface modifiers, and by chemical functionalization of the polymers with one or more specific modifiers. In the latter case the modifiers are linked with covalent bond to the particles. For the particle modification reference is made to what stated above on the modification of the polymers Pol-A components of the conjugated compounds of the invention.

Among the modifiers, those previously indicated for the modification of the polymers Pol-A, described above under the conjugated compounds of the invention, can for example be mentioned.

The pharmaceutical formulations of the invention can contain hyaluronic acid and/or cyclodextrins, such as alpha, beta 'or gamma cyclodextrins or the modified cyclodextrins, for example containing alkyl chains and/or PEG.

The pharmaceutical compositions of the invention can optionally contain magnetic compounds, such as iron oxides.

The compounds of formula (A), the conjugated compounds of the invention and the compounds obtainable by reacting the compounds of formula (A) with at least one precursor of the linkers $L_1$ or $L_2$, and the pharmaceutical compositions thereof, show a high cytotoxicity towards tumoural cell lines.

It is a further object of the present invention compounds of formula (A) and/or conjugated compounds of the invention and/or the compounds obtainable by reacting the compounds of formula (A) with at least one precursor of linkers $L_1$ or $L_2$, and/or their pharmaceutical compositions, for use as a medicament.

The present invention relates also to the use of compounds of formula (A) and/or of the conjugated compounds of the invention and/or the compounds obtainable by reacting the compounds of formula (A) with at least one precursor of the linkers $L_1$ or $L_2$ and/or their pharmaceutical compositions, for preparing drugs for the treatment in mammals and in human beings of tumoural diseases and/or diseases associated to angiogenesis.

The compounds of the invention can be used as tubuline binders and inhibit tubuline polymerization. This is contrary to the conventional anticancer agents such as Epothilones and Taxol.

The use of the compounds of formula (A) and/or of the conjugated compounds of the present invention and/or of the compounds obtainable by reacting the compounds of formula (A) with at least one precursor of the linkers $L_1$ or $L_2$ and/or or the related pharmaceutical compositions, can be implemented by using the known methods employed for the treatment of said pathologies.

Optionally, the treatment can be carried out in association with other drugs or with other therapies, in particular with other drugs or tumoural therapies, for example radiotherapy. Examples of antitumoural drugs usable in combination with those of the present invention are those belonging to the classes described hereinbelow:

Alkylating agents, for example Nitrogen mustard analogues (for example Cyclophosphamide, Chlorambucil, Melphalan, Chlormethine, Iphosphamide, Trophosphamide, Prednimustine), Alkyl sulphonates (for example Busulfan, treosulfan, Mannosulfan), Ethylene imines (for example Thiotepa, Triaziquinone, Carboquone), Nitrosoureas (for example Carmustine, Lomustine, Semustine, Streptozocin, Fotemustine, Nimustine, Ranimustine), Epoxides (for example Etoglucid), Mitobronitol, Pipobroman, Antimetabolites, for example the analogues of the folic acid (for example Methotrexate, Paltitrexid, Raltitrexed), the analogues of purines (for examples Mercaptopurine, Tioguanine, Cladribine, Fludarabine), the analogues of pyrimidines (Cytarabine, Fluorouracil, Tegafur, Carmofur, Gemcitabine), natural alkaloids and other natural compounds, for example alkaloids of vinca (for example Vinblastine, Vincristine, Vindesine, Vinorelbine and mixtures thereof), the derivatives of Podophyllotoxin (for example Etoposide and Teniposide), the derivatives of the Colchicines (for example Demecolcine), Taxani (for example Paclitaxel and Docetaxel), Cytotoxic antibiotics and correlated substances, for example Actinomycines (for example Dactinomycin), Anthracyclines and related substances (for example Doxorubicin, Daunorubicin, Epirubicin, Aclarubicin, Zorubicin, Idraubicin, Mitoxantrone, Piraubicin), Bleomycin, Plicaycin, Mitomycin, Topoisomerase inhibitors, such as camptothecins (for example Irinotecan and Topotecan), topoisomerase inhibitors of type II (for example Amsacrine, Etoposide Phosphate and other derivatives of natural alkaloids of Podophyllum peltatum), other antineoplastic agents, such as Cisplatin, Carboplatin, Procrbazine, Asparginase, Altretamine, Hydroxycarbamide, Lonidamine, Pentostatin, Miltefosine, Masoprocol, Estramustine, Dacarbazine, Tretinoin, Porfimer sodium, Mitoguazone, Tiazofurine, tamoxifen.

In particular the administration of the compounds of formula (A) and/or of the conjugated compounds of the invention and/or of the compounds obtainable by reacting the compounds of formula (A) with at least one precursor of the linkers $L_1$ or $L_2$ must be carried out in a sufficiently effective amount for the specific treatment. Similarly the dosages, the administration route and the posology will be determined depending on the disease level, on the pathologpy severity, on the physical conditions and characteristics of the patient (for example age, weight, response to the active principle), on the pharmacokinetics and toxicology of the compounds or of the conjugated compounds of the invention selected for the specific treatment.

The preferred daily dosage is 0.01-1,000 mg of compound of formula (A) or of the conjugated compounds of the invention or of the compounds obtainable by reacting the compounds of formula (A) with at least one precursor of the linkers $L_1$ or $L_2$, per Kg of body weight of the mammal to be treated. In human beings, the preferred daily dosage range is 0.01-1,000 mg for Kg of body weight, still more preferred from: 1 to 800 mg.

The following examples are reported for a better understanding of the present invention but are not meant to be limitative of the scope of the invention.

EXAMPLES

Example 1.1

Synthesis of (2S,3R)-2-azido-N-benzyl-3-methylpentanamide

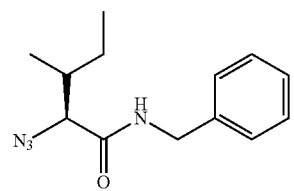 [SMILES: CCC(C)[C@H](N=[N+]=[N-])C(=O)NCc1ccccc1]

To a solution of benzylamine (19.0 mmoles, 2.0 ml) in dichloromethane (20 ml), maintained at a temperature of 0° C., diphenylethylamine (15.9 mmoles, 2.7 ml) and a solution in dichloromethane (5 ml) of the acyl chloride of the acid of formula (DD) (6.35 mmoles) are added (DD)

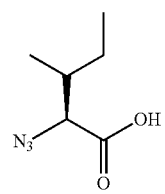

prepared according to the method described in J. Am. Chem. Soc., 128, 2006, 16018-16019. The reaction mixture is stirred for 30 minutes. At the end a saturated $NH_4Cl$ aqueous solution (30 ml) is added and the organic phase is extracted with dichloromethane (3×10 ml). The extracts are dehydrated over Na2SO4, the mixture is filtered and the solvent is evaporated under a reduced pressure. 1.26 g of (2S,3R)-2-azido-N-benzyl-3-methylpentanamide (80% yield) are recovered.

$R_f$=0.36 (n-hexane/ethyl acetate 8/2 volume/volume); $^1H$ NMR (400 MHz, $CDCl_3$) δ: 7.40-7.19 (m, 5H), 6.62 (br s, 1H), 4.45 J=5.8 Hz, 1H), 3.89 (d, J=4.4 Hz, 1H), 2.17-2.04 (m, 1H), 1.54-1.41 (m, 1H), 1.33-1.17 (m, 1H), 1.04 (d, J=6.9 Hz, 3H), 0.91 (t, J=7.4 Hz, 3H); $^{13}C$ NMR (101 MHz, $CDCl_3$) δ: 168.71, 137.74, 128.72, 127.78, 127.62, 69.97, 43.47, 38.30, 24.33, 16.0, 11.5; Mass (ESI) m/z: 269 ($M^+$+Na).

Example 1.2

Synthesis of ethyl 2-(3-((2S,3R-2-azido-N-benzyl⁻3⁻ methyl pentanamido-4-methypentanol)thiazol⁻4⁻ carboxylate

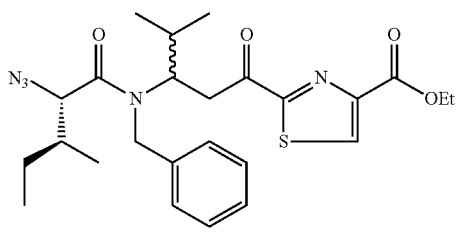 [SMILES: CCOC(=O)c1csc(C(=O)CC(C(C)C)N(Cc2ccccc2)C(=O)[C@@H](N=[N+]=[N-])[C@@H](C)CC)n1]

To a solution of the compound obtained in example 1.1 (4.9 mmoles) in anhydrous THF (40 ml), kept at −78° C., a KHMDS 0.5 N solution in toluene (4.9 mmoles, 9.8 ml) is added. The reaction mixture is stirred for 15 minutes. Then, a solution in anhydrous THF of the enone compound of the following formula (DD1) (3.3 mmoles in 10 ml of THF) is added.

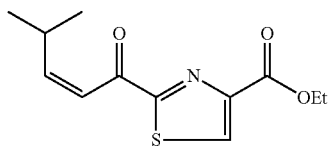

(DD1)

Compound (DD1) has been prepared as described in Angew. Chem. Int. Ed., 46, 2007, 3526-3529. The reaction mixture is stirred for one hour at −78° C. Then a saturated NH$_4$Cl aqueous solution (100 ml) is added and the organic phase is extracted with ethyl acetate (3×30 ml). The organic extracts are dehydrated over Na$_2$SO$_4$, the mixture is filtered and the solvent is evaporated under a reduced pressure. The crude product is purified by flash chromatography in n-hexane/ethyl acetate 85/15 volume/volume. 999 mg of ethyl 2-(3-((2S,3R)=2-azido-N-benzyl-3-methylpentanamido)-4-methypentanoyl)thiazol4-carboxylate (60% yield) are recovered.

$R_f$=0.39 (n-hexane/ethyl acetate 8/2 volume/volume); $^1$H NMR (400 MHz, CDCl$_3$) δ: 8.32 (s, 1H), 7.29-6.90 (m, 5H), 4.74 (td, J=9.3, 3.6 Hz, 1H), 4.62 (d, J=17.6 Hz, 1H), 4.50-4.36 (m, 4H), 3.52 (dd, J=17.9, 3.8 Hz, 1H), 3.39 (dd, J=18.0, 8.9 Hz, 1H), 3.25 (d, J=9.9 Hz, 1H), 2.28-2.05 (m, 4H), 1.74-1.62 (m, 1H), 1.41 (t, J=7.3 Hz, 3H), 1.18-1.07 (m, 1H), 1.05-0.77 (m, 12H); $^{13}$C NMR (101 MHz, CDCl$_3$) δ: 191.06, 169.71, 166.61, 160.43, 148.14, 136.58, 132.89, 128.41, 127.24, 126.24, 63.41, 61.44, 48.30, 39.34, 34.67, 30.33, 24.70, 20.12, 19.96, 19.20, 15.74, 14.06, 10.26; Mass (ESI) m/z: 522.1 (M$^+$+Na).

Example 1.3

Synthesis of ethyl 2-((1R,3R)-3-((2S,3R)-2-azido-N-benzyl-3-methylpentanamido-1-hydroxy-4-methyl-pentyl)thiazol-4-carboxylate

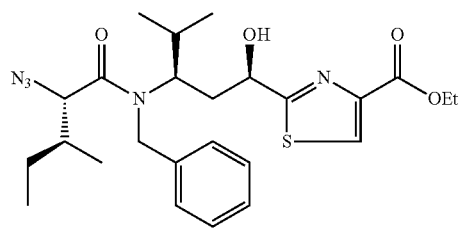 [SMILES: CCOC(=O)c1csc([C@H](O)C[C@H](C(C)C)N(Cc2ccccc2)C(=O)[C@@H](N=[N+]=[N-])[C@@H](C)CC)n1]

To a solution of the chiral catalyst (S)—CBS (0.38 mmoles, 105 mg) in anhydrous THF (10 ml), a 10 M solution of BH$_3$*Me$_2$S (2.3 mmoles, 230 pl) is added. After the temperature has been lowered to 0° C., a solution of the compound obtained in example 1.2 (1.9 mmoles) in anhydrous THF (5 ml) is added. The reaction mixture is stirred for one hour at 0° C. and then 4 hours at room temperature. At the end methanol (1 ml) is added, the solvents are evaporated under a reduced pressure and the crude product is purified by flash chromatography in n-hexane/ethyl acetate 75/25 volume/volume. 569 mg of the compound ethyl 2-((1R,3R)-3-((2S,3R)-2-azido-N-benzyl-3-methylpentanamido)-1-hydroxy-4-methylpentyl)thiazol-4-carboxylate (60% yield) are recovered.

$R_f$=0.42 (n-hexane/ethyl acetate 7/3 volume/volume); $^1$H NMR 400 MHz, CDCl$_3$) δ: 8.08 (d, J=1.0 Hz, 1H), 7.50-7.10 (m, 5H), 4.87 (d, J=10.8 Hz, 1H), 4.77 (d, J=4.0 Hz, 1H), 4.55 (s, 2H), 4.42 4.30 (m, 3H), 3.45 (d, J=10.0 Hz, 1H), 2.40-2.27 (m, 2H), 2.20 1.90 (m, 1H), 1.89-1.70 (m, 1H), 1.69-1.55 (m, 1H), 1.43-1.33 (t, J=7.3 Hz, 3H), 1.23-1.03 (m, 1H), 1.02-0.87 (m, 6H), 0.86-0.71 (m, 3H), 0.65 (d, J=6.6 Hz, 3H); $^{13}$C NMR (101 MHz, CDCl$_3$) δ: 175.61, 173.01, 161.37, 161.25, 146.85, 138.38, 136.83, 129.04, 127.27, 127.12, 68.93, 63.67, 61.63, 61.08, 37.82, 34.78, 29.87, 24.82, 20.58, 20.07, 15.62, 14.22, 10.19; Mass (ESI) m/z: 524.2 (M$^+$+-1-Na).

Example 1.4

Synthesis of 2-((1R,3R)-3-(2S,3R)-2-azido-N-benzyl-3-methylpentanamido)-1-hydroxy-4-methylpentyl)thiazol-4-carboxylic acid

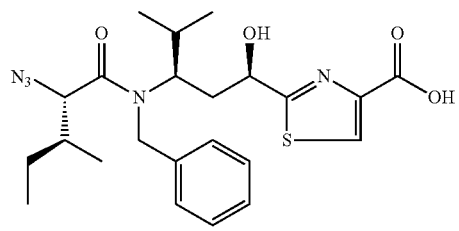 [SMILES: CC[C@H](C)[C@H](N=[N+]=[N-])C(=O)N(Cc1ccccc1)[C@H](C[C@@H](O)c1nc(C(=O)O)cs1)C(C)C]

The compound obtained in example 1.3 (1.09 mmoles) is dispersed in a THF/water 4/1 volume/volume (10 ml) mixture. Then Li(OH) (1.64 mmoles) is added. The reaction mixture is stirred for 12 hours. Water (5 ml) is then added and the organic phase is extracted with ethyl acetate (1×10 ml). The aqueous phase is recovered and acidified with a HCl 1N solution to a pH of 2. The aqueous phase is then extracted with ethyl acetate (3×10 ml), the organic extracts are pooled and dehydrated on Na$_2$SO$_4$. Na$_2$SO$_4$ is then removed by filtration and the solvent evaporated under a reduced pressure to yield 338 mg of 2-((1R,3R)-3-((2S,3R)-2-azido-Nbenzyl-3-methylpentanamido)-1-hydroxy-4-methylpentyl)thiazol-4-carboxylic acid (60% yield).

R$_f$=0.42 (dichloromethane/MeOH 9/1 volume/volume); $^1$H NMR (400 MHz, CD$_3$OD) δ: 8.25 (s, 1H), 7.52-7.01 (m, 10H), 4.91 (dd, J=10.0, 2.5 Hz, 1H), 4.69-4.49 (m, 3H), 3.54 (d, J-9.8 Hz, 1H), 2.36-2.02 (m, 3H), 1.91 (m, 1H), 1.63 (m, 1H), 1.13 (m, 1H), 0.97 (m, 6H), 0.86-0.69 (m, 6H); $^{13}$C NMR (101 MHz, CD$_3$OD) δ: 178.88, 173.36, 169.71, 163.9, 148.13, 138.86, 129.90, 129.36, 128.28, 69.98, 64.80, 60.06, 46.97, 39.05, 36.41, 31.88, 25.79, 20.54, 20.48, 16.01, 10.57; Mass (EST) m/z: 496.1 (M$^+$+Na), 518.1 (M$^+$+K).

Example 1.5

Synthesis of acid bromo acetic 2-isopropyl-5-methyl-cyclohexyl ester

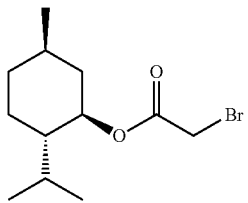

To a solution of (−) Menthol (2.75 mmoles) in anhydrous THF (5 ml), Et$_3$N (2.75 mmoles) is added under stirring. The solution temperature is lowered to 0° C. and bromo-acetyl-bromide (2.5 mmoles) added. The solution temperature is then allowed to raise to room temperature and the reaction mixture is stirred for 2 hours. An HCl 1N (2 ml) aqueous solution is added and the organic phase is extracted with ethyl acetate (3×5 ml). The pooled organic phases are washed with a saturated aqueous NaCl solution (1×15 ml), dehydrated on Na$_2$SO$_4$ and filtered. The solvent is evaporated under a reduced pressure and the crude product is purified by flash chromatography in n-hexane/ethyl acetate 97/3 volume/volume. 388 mg of 2-isopropyl-5-methyl-cyclohexyl ester of the bromo acetic acid (51% yield) are recovered.

$^1$H NMR (400 MHz, CDCl$_3$) δ: 4.78-4.60 (m, 1H), 3.86-3.69 (m, 1H), 1.95-1.83 (m, 1H), 1.74-1.59 (m, 2H), 1.16-0.95 (m, 2H), 0.87 (m, 6H), 0.77 (d, J=7.0 Hz, 3H); Mass (ESI): 299.0 (M$^+$H—Na).

Example 1.6

Synthesis of acid (Triphenyl-λ$^5$-phosphaniliden)-acetic 2-sopropyl-5-methyl-cyclohexyl ester

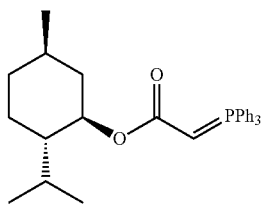

To a solution of the compound prepared in example 1.5 (0.36 moles) in anhydrous THF (3 ml), triphenylphosphine PPh$_3$ (0.37 mmoles) is added. The reaction mixture is heated at reflux for 2 hours. The solvent is evaporated under reduced pressure and the resulting solid is washed with hexane (10 ml) and filtered off. The solid is then solubilised in toluene (3.5 ml) and a 0.38 N of Na(OH) aqueous solution (1.26 mmoles, 3.3 ml) is added. The reaction mixture is stirred for one hour. The organic phase is separated, dried on Na$_2$SO$_4$ and filtered. The solvent is evaporated under a reduced pressure. 185 mg of 2-isopropyl-5-methyl-cyclohexyl ester of the (Triphenyl-λ$^5$-phosphaniliden)-acetic acid are recovered. The yield is quantitative.

Mass (ESI) m/z: 459.2 (M$^+$+H$^+$), the spectrum is in accordance with that reported in Tetrahedron, 1992, 6929-6952.

Example 1.7

Synthesis of acid (Triphenyl-λ$^5$-phosphaniliden)-propionic 2-isopropyl-5-methyl-cyclohexyl ester

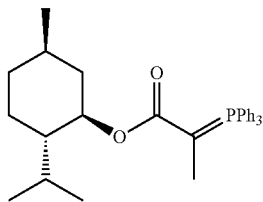

0.36 mmoles of the compound obtained in example 1.6 are solubilized in 2 ml of dichloromethane, under stirring. The solution is then cooled at 0° C. and methyl iodide (0.54 mmoles) is added. The temperature of the reaction mixture is then allowed to raise up to room temperature and stirring is continued for further 12 hours. The solvent is evaporated under a reduced pressure and the crude product is dissolved in toluene (5 ml). A 0.38 N Na(OH) aqueous solution (1.26 mmoles) is added and stirring is continued for further 2 hours. The organic phase is separated, dehydrated on Na$_2$SO$_4$ and filtered. The solvent is evaporated under a reduced pressure. 160 mg of 2$^-$isopropyl-5-methyl-cyclohexyl ester of 2-(Triphenyl-λ$^5$-phosphaniliden)-propionic acid (94% yield) are recovered.

$^1$H NMR (400 MHz, CDCl$_3$) δ: 7.97-7.14 (m, 16H), 4.72-4.32 (m, 1H), 2.33-1.90 (m, 1H), 1.74-1.10 (m, 5H), 1.08-0.19 (m, 12H); $^1$H NMR (101 MHz, CDCl$_3$) δ: 133.50, 133.41, 131.27, 128.20, 128.08, 70.83, 46.76, 40.99, 34.14, 30.94, 24.66, 22.41, 21.78, 20.95, 15.37; Mass (ESI) m/z: 473.2 (M$^+$+H$^+$).

Example 1.8

Synthesis of di(S)terbutyl-1-oxo-3-phenyl propan-2-yl-carbamate

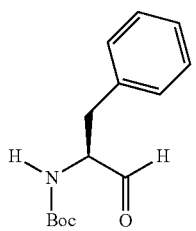 [SMILES: CC(C)(C)OC(=O)N[C@H](C=O)Cc1ccccc1]

To a solution of Boc-phenylalaminol (0.6 mmoles) in dichloromethane (6 ml), NaHCO$_3$ (12.0 mmoles) and Dess-Martin periodinane (0.9 mmoles) are added. The reaction mixture is stirred for 2 hours. Et$_2$O (10 ml) is added and stirring is continued for 15 minutes. The reaction mixture is poured into an aqueous solution of saturated NaHCO$_3$/Na$_2$S$_2$O$_3$ (20 ml). Dichloromethane (20 ml) is added and the organic phase is separated, dehydrated on Na$_2$SO$_4$ and filtered. The solvent is evaporated under a reduced pressure. 163 mg of the compound (S)terbutyl-1-oxo-3-phenyl propan-2-yl-carbamate (98% yield) are recovered.

$^1$H NMR (400 MHz, CDCl$_3$) δ: 9.68 (s, 1H), 7.53-6.89 (m, dH), 5.11-5.03 (m, 1H), 4.50-4.42 (m, 1H), 3.16 (d, J=6.4 Hz, 2H), 1.48 (s, 9H).

Example 1.9

Synthesis of (S,E)-((1R,2S,5R)-2-isopropyl-5-methylcyclohexyl)4-(tert-butoxy carbonyl amino)-2-methyl-5-phenylpent-2-enoate

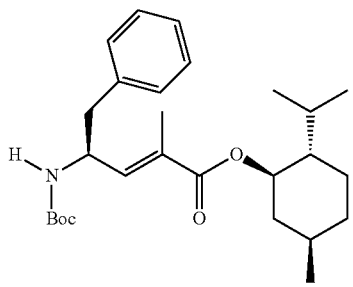 [SMILES: C/C(=C\[C@H](Cc1ccccc1)NC(=O)OC(C)(C)C)C(=O)O[C@@H]1C[C@H](C)CC[C@H]1C(C)C]

To a solution in dichloromethane of the compound obtained in example 1.7 (0.48 mmoles in 5 ml), cooled at 0° C., 0.32 moles of the aldehyde obtained in example 1.8 are added. The temperature of the organic solution is then allowed to raise up to room temperature and stirring is continued for further 2 hours. An 1 N NaHSO$_4$ aqueous solution (10 ml) is added, the organic phase is separated, and the aqueous solution further extracted with dichloromethane (2×10 ml). The pooled organic extracts phases are washed with an aqueous NaCl saturated solution (1×10 ml), dehydrated on Na2SO$_4$ and filtered. The solvent is evaporated under a reduced pressure and the crude product is purified by flash chromatography in n-hexane/ethyl acetate 85/15 volume/volume. 150 mg of (S,E)-((1R,2S,5R)-2-isopropyl-5-methylcyclohexyl)4-(tert-butoxy carbonyl amino)-2-methyl-5-phenylpent-2-enoate are recovered. The yield is quantitative.

R$_f$=0.47 (n-hexane/ethyl acetate 97/3 volume/volume); $^1$H NMR (400 MHz, CDCl$_3$) δ: 7.38-7.04 (m, 5H), 6.46 (d, J=9.2 Hz, 1H), 4.79-4.62 (m, 2H), 4.50-4.56 (m, 1H), 2.93 (dd, J=13.3, 5.6 Hz, 1H), 2.84-2.74 (m, 1H), 2.08-1.98 (m, 1H), 1.93-1.74 (m, 1H), 1.76-1.65 (m, 4H), 1.61-1.45 (m, 2H), 1.45 (s, 10H), 0.97-0.81 (m, 6H), 0.77 (d, J=6.9 Hz, 3H). Mass (ESI) m/z: 444.3 (M$^+$+H$^+$).

Example 1.10

Synthesis of (2S,4R)-((1R,2S,5R)-2-isopropyl-5-methylcyclo-hexyl)4$^-$(tert-butoxycarbonylamino)-2-methyl-5-phenylpentanoate To a solution of the compound obtained in example 1.9 (0.32 mmoles) in ethyl acetate (6 ml), a catalytic amount of Pd/C is added. The reaction mixture is kept under stirring under an hydrogen atmosphere for 2 hours. At the end the organic solution is filtered on celite and the solvent is evaporated under a reduced pressure. Compound (DD2) is obtained. It is formed of a mixture of two diastereoisomers (DD2A) and (DD2B)

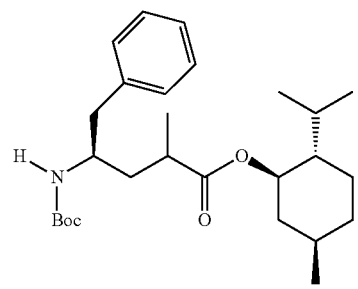
(DD2)

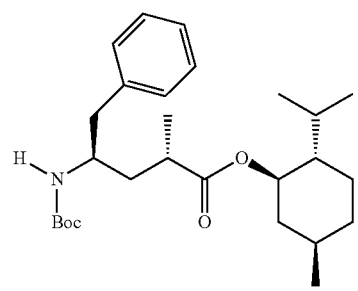
(DD2A)

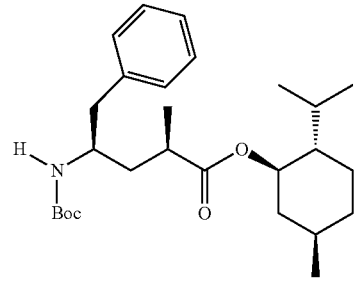
(DD2B)

The two diastereoisomers (DD2A) and (DD2B) are separated by flash chromatography in n-hexane/ethyl acetate 8/2 volume/volume. 89 mg of compound (DD2A) and 37 mg of compound (DD2B) (88% yield) are recovered.

(DD2A): R$_f$=0.7 (ethyl acetate/hexane 1/4 volume/volume); $^1$H-NMR (400 MHz, CDCl$_3$) δ: 7.30-7.26 (m, 2H), 7.22-7.15 (m, 3H), 4.64 (dt, J=10.8 Hz, 4.3 Hz, 1H), 4.34 (s, 1H), 3.95-3.80 (m, 1H), 2.83-2.73 (m, 2H), 2.50-2.41 (m, 1H), 1.98-1.92 (m, 1H), 1.86-1.60 (m, 4H), 1.54-1.31 (m, 4H), 1.39 (s, 9H), 1.13 (d, J=7.0 Hz, 3H), 1.10-1.00 (m, 1H), 0.92-0.80 (m, 1H), 0.89 (d, J=6.4 Hz, 3H), 0.88 (d, 6.9 Hz, 3H,), 0.74 (d, J=6.8 Hz, 3H,); $^{13}$C-NMR (100 MHz, CDCl$_3$) 176.0, 155.3, 137.8, 129.4, 128.2, 126.2, 74.0, 49.7, 46.9, 42.0, 40.7, 37.2, 36.8, 34.1, 31.3, 29.6, 28.2, 26.1, 23.3, 21.9, 20.7, 16.7, 16.1; Mass (ESI) m/z 446.3 (M$^+$-4-H$^+$), 468.3 (M$^+$+Na).

(DD2B): R$_f$=0.62 (ethyl acetate/hexane 1/4 volume/volume); $^1$H-NMR (400 MHz, CDCl$_3$) δ: 7.29-7.26 (m, 2H), 7.22-7.16 (m, 3H), 4.66 (m, J=10.8 Hz, 4.3 Hz, 1H), 4.34 (s, 1H), 3.92-3.80 (m, 1H), 2.80-2.70 (m, 2H), 2.62-2.50 (m, 1H), 2.02-1.96 (1H, 1H), 1.91-1.81 (m, 2H), 1.71-1.64 (m, 2H), 1.54-1.33 (m, 4H), 1.39 (s, 9H), 1.15 (d, J=7.0 Hz, 3H), 1.10-1.00 (m, 2H), 0.90 (d, J=6.4 Hz, 3H), 0.89 (d, J=6.9 Hz, 3H), 0.75 (d, J=6.9 Hz, 3H); $^{13}$C-NMR (100 MHz, CDCl$_3$) 175.7, 155.1, 137.9, 129.5, 128.3, 126.3, 74.1, 49.9, 47.1, 41.2, 40.8, 37.7, 36.7, 34.3, 31.4, 29.7, 28.4, 26.2, 23.4, 22.0, 20.8, 17.7, 16.1; Mass (ESI) m/z 446.3 (M$^+$+H$^+$), 468.3 (M$^+$+Na).

Example 1.11

Synthesis of (2S,4R)-methyl 4⁻amino-2-methyl-5-phenyl-pentanoate hydrochloride

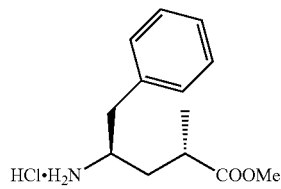

2.28 mmoles of compound (DD2A) obtained in example 1.10 are dispersed in an HCl 6N aqueous solution (25 ml) and the dispersion heated at reflux for one hour. After cooling to room temperature, ethyl acetate (30 ml) is added, and the aqueous phase is separated, concentrated under a reduced pressure. The solid residue is dissolved in methanol (10 ml). 2,2-dimethoxypropane (4.56 mmoles) and concentrated HCl (37%, 0.024 mmoles, 2 μl) are added and the reaction mixture is heated to 50° C. for 12 hours. The solvent is then evaporated under a reduced pressure. 580 mmg of the hydrochloride of (2S,4R)-methyl 4-amino-2-methyl-5-phenylpentanoate (99% yield) are recovered.

R$_f$=0.3 (dichloromethane/methanol 9/1 volume/volume); $^1$H NMR (400 MHz, CD$_3$OD) δ: 7.46-7.15 (m, 5H), 3.63 (s, 3H), 3.59-3.47 (m, 1H), 2.57-2.50 (m, 1H), 3.04 (dd, J=19.9 and 6.2 Hz, 1H), 2.91 (dd, J=13.7 and 7.7 Hz, 1H), 2.79-2.65 (m, 1H), 2.08-1.95 (m, 1H), 1.75-1.63 (m, 1H), 1.16 (d, J=6.9 Hz, 3H,); $^{13}$C NMR (100.5 MHz, CD$_3$OD) δ: 178.1, 137.8, 131.3, 130.9, 129.3, 53.3, 41.1, 37.9, 18.7; Mass (ESI) m/z 258.2 M$^+$+H$^+$).

Example 1.12

Synthesis of (2S,4R)-methyl 4⁻(2⁻((1R,3R)-3-((2S,3R)-2-azidoN-benzyl-3-methyl pentanamido)-1-hydroxy-4-methyl pentyl)-thiazol-4-carboxamido)-2-methyl-5-phenyl pentanoate

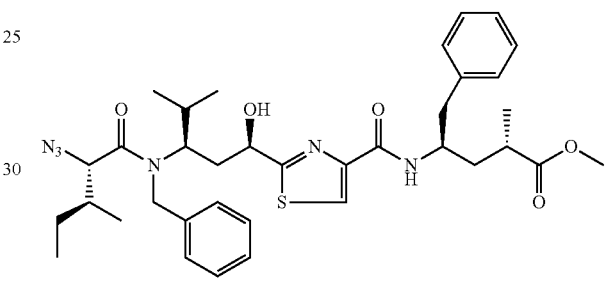

To a solution of the compound obtained in example 1.11 (0.65 mmoles) in DMF (5 ml) HOAt (0.715 mmoles), HATS (0.715 mmoles), triethylamine (1.36 mmoles) and the compound obtained in example 1.4 (0.65 mmoles) are added in the order. The reaction is stirred for 2 hours. Water (10 ml) is added and the organic phase is extracted with ethyl ether (3×10 ml). The extracted pooled organic phases are then washed, in sequence, with an HCl 1N aqueous solution (1×10 ml), an aqueous NaHCO$_3$ saturated solution (1×10 ml) and an aqueous NaCl saturated solution (1×10 ml). The organic phase is separated and dehydrated on Na2SO4. Na2SO4 is then removed by filtration and the solvent evaporated under a reduced pressure. 326 mg of (2S,4R)-methyl-4-(2-((1R,3R)-3-((2S,3R)-2⁻azido-N-benzyl-3-methylpentanamido)-1-hydroxy-4-methyl-pentyl)thiazol-4-carboxyamido)-2-methyl-5-phenyl pentanoate (74% yield) are recovered.

R$_f$=0.44 (n-hexane/ethyl acetate 1/1 volume/volume); $^1$H NMR (400 MHz, CDCl$_3$) δ: 7.96 (s, 1H), 7.34-7.08 (m, 10H), 6.98 (d, J=9.2 Hz, 1H), 4.94-4.75 (m, 2H), 4.63 (d, J=17.2 Hz, 1H), 4.49 (d, J=17.2 Hz, 1H), 4.40-4.26 (m, 2H), 3.88 3.75 (m, 1H), 3.63 (s, 3H), 3.46 (d, J=9.8 Hz, 1H), 3.02 2.74 (m, 2H), 2.67-2.53 (m, 1H), 2.45-2.25 (m, 1H), 2.23-1.87 (m, 4H), 1.61 (m, 2H), 1.22-1.07 (m, 4H), f.06-0.90 (m, 6H), 0.81 (m, 3H), 0.74-0.61 (m, 3H); $^{13}$C NMR (101 MHz, CDCl$_3$) δ: 176.39, 175.01, 171.90, 171.25, 160.68, 149.68, 137.51, 137.23, 128.90, 128.50, 128.41, 128.26, 127.92, 126.29, 122.85, 68.83, 63.68, 61.74, 59.32, 51.70, 48.32, 47.86, 45.22, 41.73, 37.95, 37.80, 36.43, 34.33, 30.15, 24.77, 20.42, 20.04, 17.73, 15.74, 10.14; Mass (ESI) m/z: 677.3 (M$^+$+H$^+$), 699.3 (M+Na).

Example 1.13

Synthesis of (2S,4R)-methyl 4⁻(2-((1R,3R)-3-((2S,3R)—N-benzyl-3-methyl-2-(1-methyl piperidin-2-carboxamido)pentanamido)-1-hydroxy-4-methyl pentyl)thiazol-4-carboxamido)-2-methyl-5-phenyl pentanoate

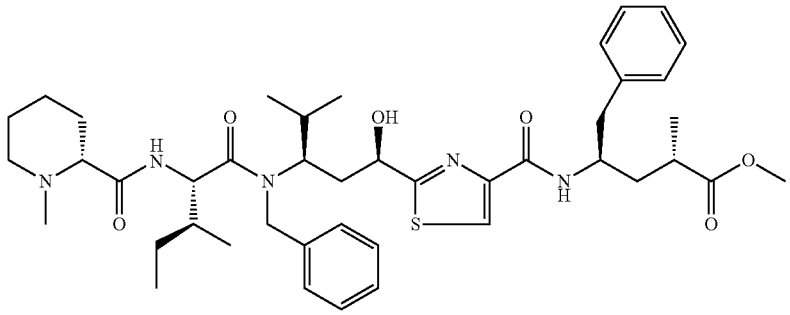 [SMILES: CC[C@H](C)[C@H](NC(=O)[C@H]1CCCCN1C)C(=O)N(Cc1ccccc1)[C@H](C[C@@H](O)c1nc(C(=O)N[C@@H](Cc2ccccc2)C[C@H](C)C(=O)OC)cs1)C(C)C]

0.44 moles of the compound obtained in example 1.12 are solubilized in methanol (10 ml); a catalytic amount of Pd/C 10% is added to the solution. The reaction is stirred under an hydrogen atmosphere for 12 hours. At the end the suspension is filtered on celite and the solvent is evaporated under a reduced pressure. 0.46 mmoles of the obtained product are added, under stirring, to a suspension of N-methyl pipecolinic acid (0.69 mmoles) in dichloromethane (10 ml) containing HOAt (0.73 mmoless), HATU (0.73 mmoles) and triethylamine (0.73 mmoles). The reaction is stirred for 4 hours. Water (10 ml) is added and the organic phase is extracted with dichloromethane (3×10 ml). The organic extracts are separated, pooled and dehydrated on sodium sulphate. After filtration, the solvent is evaporated under a reduced pressure. The crude product is purified by flash chromatography in dichloromethane/methanol 95/5 volume/volume. 270 mg of (2S,4R)-methyl 4-(2-((1R,3R)-3-((2S,3R)—N-benzyl-3-methyl-2-(1-methylpiperidin-2-carbo-xamido)pentana-mido)-1-hydroxy-4-methyl pentyl)thiazo-4-carboxamido)-2-methyl-5-phenyl pentanoate (total yield on the two steps: 79%) are recovered.

$R_f$=0.30 (dichloromethane/methanol 95/5 volume/volume); $^1$H NMR (400 MHz, CD$_3$OD) δ: 8.05 (s, 1H), 7.60-7.02 (m, 5H), 5.14 (d, J=16.6 Hz, 1H), 4.87 (m, 1H), 4.80 (d, J=10.5 Hz, 1H), 4.32 (m, 3H), 3.96 (m, 1H), 3.61 (s, 3H), 2.97-2.76 (m, 3H), 2.71 (dd, J=11.0, 2.8 Hz, 1H), 2.67-2.55 (m, 2H), 2.48-2.42 (m, 2H), 2.21 (s, 3H), 2.18-1.95 (m, 5H), 1.94-1.39 (m, 8H), 1.37-1.21 (m, 2H), 1.20-1.13 (m, 3H), 1.12-1.04 (m, 3H), 1.03-0.90 (m, 4H), 0.83 (d, J=6.5 Hz, 3H), 0.71 (t, J=7.4 Hz, 3H); $^{13}$C NMR (101 MHz, CD$_3$OD) δ: 178.85, 177.90, 175.23, 174.75, 162.81, 150.62, 140.03, 139.15, 139.01, 130.39, 130.30, 129.64, 129.25, 127.41, 70.47, 69.87, 62.27, 56.48, 55.57, 52.17, 50.09, 46.52, 44.91, 42.08, 39.29, 39.11, 38.13, 37.65, 32.34, 31.42, 26.10, 25.27, 24.24, 24.14, 21.11, 21.02, 20.92, 18.26, 16.83, 10.66; Mass (ESI) m/z: 776.4 (M⁺+H⁺), 798.4 (M+Na).

Example 1.14

Synthesis of 2,2,2-trifluoroacetic salt of (2S,4R)-4-(2-((1R,3R)-3-((2S,3R)—N-benzyl-3-methyl-2-(1-methylpiperidin-2-carboxamido)pentanamido)-1-hydroxy-4-methyl pentyl)thiazol-4-carboxamido)-2-methyl-5-phenylpentanoic acid

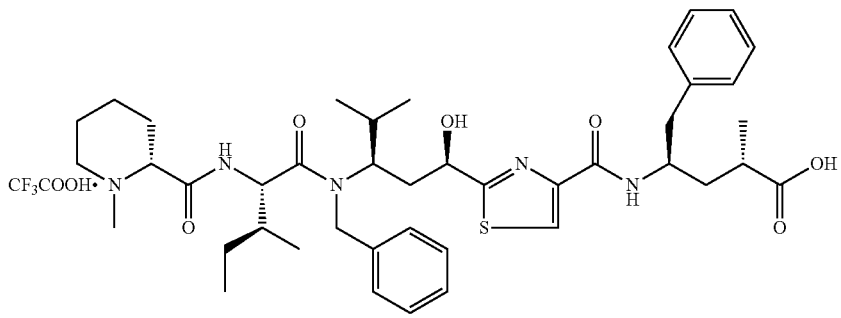 [SMILES: CC[C@H](C)[C@H](NC(=O)[C@H]1CCCCN1C)C(=O)N(Cc1ccccc1)[C@H](C[C@@H](O)c1nc(C(=O)N[C@@H](Cc2ccccc2)C[C@H](C)C(=O)O)cs1)C(C)C]

0.26 mmoles of the compound obtained in example 1.13 are solubilized in THF (5 ml). To the obtained solution an 1N Li(OH) aqueous solution (0.773 mmoles) is added. The solution is stirred for 48 hours. Water (2 ml) and trifluoroacetic acid are then added in an amount to give a pH of 2. The organic phase is extracted with ethyl acetate (3×5 ml) and the pooled organic extracts are dehydrated on Na$_2$SO$_4$. After filtration, the solvents are evaporated under a reduced pressure. 250 mg of 2,2,2-trifluoroacetic salt of (2S,4R)-4-(2⁻((1R,3R)-3-((2S,3R)—N-benzyl-3-methyl-2-(1-methylpiperidin2-carboxamido)pentanamido)-1-hydroxy-4-methyl pentyl)thiazol4-carboxamido)-2-methyl-5-phenylpentanoic acid (90% yield) are recovered.

$R_f$=0.15 (dichloromethane/methanol 95/5 volume/volume); $^1$H NMR (400 MHz, CD$_3$OD) δ: 8.06 (s, 1H), 7.36-7.03 (m, 10H), 5.15 (d, J=10.3 Hz, 2H), 5.03 (d, J=16.4 Hz, 1H), 4.94-4.82 (m, 2H), 4.74 (d, J=8.5 Hz, 1H), 4.59 (d, J=16.7 Hz, 1H), 4.51-4.26 (m, 4H), 3.96 (dd, J=20.8, 10.9 Hz, 2H), 3.86 (d, J=10.8 Hz, 1H), 3.50 (t, J=12.7 Hz, 2H), 3.08 (dd, J=27.4, 13.7 Hz, 2H), 2.94-2.68 (m, 11H), 2.48 (dd, J=34.9, 15.4, 5.6 Hz, 3H), 2.30-1.74 (m, 22H), 1.72 1.46 (m, 6H), 1.34 (dd, J=19.4, 13.6 Hz, 2H), 1.26-1.15 (m, 8H), 1.09 (dd, J=18.7, 5.1 Hz, 7H), 0.97 (dd, J=21.5, 12.9, 7.1 Hz, 11H), 0.85 (d, J=6.5 Hz, 3H), 0.71 (t, J=7.3 Hz, 3H), 0.57 (d, J=6.5 Hz, 3H). $^{13}$C NMR (101 MHz, CD$_3$OD) δ: 180.62, 179.68, 175.12, 171.62, 169.86, 163.96, 161.94 (q, J=38.4 Hz), 151.55, 140.80, 140.07, 131.31, 130.66, 130.14, 129.87, 128.31, 117.96 (q, J=287.3 Wz), 70.97, 69.51, 62.88, 58.81, 57.20, 51.58, 47.90, 44.05, 42.88, 40.74, 40.21, 38.74, 38.49, 33.34, 31.20, 28.78, 25.90, 24.61, 23.10, 21.82, 21.69, 19.43, 17.38, 16.96, 12.96, 11.52; Mass (ESI) m/z: 762.4 (M$^+$+H$^+$), 784.4 (M$^+$+Na).

Example 1.15

Synthesis of (2S,4R)-4-(2-((1R,3R)-1-acetoxy-3-((2S,3R)—N-benzyl-3-methyl-2-(1-methyl piperidin-2-carboxamido)pentanamido)-4-methylpentyl) thiazol-4-carboxamido)-2-methyl-5-phenylpentanoic acid

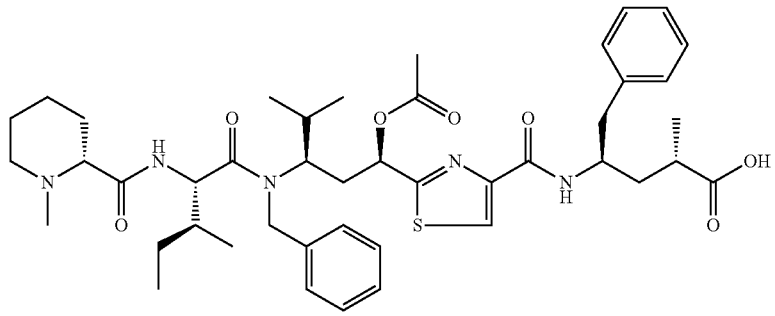 [SMILES: CC[C@H](C)[C@H](NC(=O)[C@H]1CCCCN1C)C(=O)N(Cc1ccccc1)[C@H](C[C@@H](OC(C)=O)c1nc(C(=O)N[C@@H](Cc2ccccc2)C[C@H](C)C(=O)O)cs1)C(C)C]

To a solution of the compound obtained in example 1.14 (0.27 mmoles) in pyridine (4 ml), acetic anhydride (2 ml) is added. The reaction mixture is stirred for 12 hours. The solvent is evaporated under a reduced pressure and the crude product is purified by flash chromatography in a first run with dichloromethane/methanol 98/2 volume/volume and in a second run with dichloromethane/methanol 9:1 volume/volume. 159 mg of (2S,4R)-4-(2-((1R,3R)-1-acetoxy-3-((2S,3R)—N-benzyl-3-methyl-2-(1-methyl piperidin-2-carboxamido) pentanamido)-4-methylpentyl)thiazol-4-carboxamido)-2-methyl-5-phenyl-pentanoic acid (74% yield) are recovered.

R$_f$=0.25 (DCM/MeOH 95/5); $^1$H NMR (400 MHz, CD$_3$OD) δ: 8.07 (s, 1H), 7.57-7.01 (m, 10H), 5.95-5.85 (m, 1H), 5.06 (d, J=16.8 Hz, 1H), 4.74 (d, J=9.0 Hz, 1H), 4.45 (d, J=16.8 Hz, 1H), 4.41-4.30 (m, 2H), 3.18-3.09 (m, 1H), 2.99 (dd, J-11.1, 2.6 Hz, 1H), 2.96-2.80 (m, 2H), 2.60-2.51 (m, 1H), 2.49-2.27 (m, 6H), 2.16 (s, 3H), 2.11-1.86 (m, 4H), 1.85-1.56 (m, 5H), 1.56-1.25 (m, 2H), 1.19 (d, J=6.9 Hz, 3H), 1.13-0.98 (m, 4H), 0.99-0.95 (m, 1H), 0.86 (d, J=6.6 Hz, 3H), 0.76 (t, J=7.4 Hz, 3H), 0.70 (d, J=6.8 Hz, 3H); $^{13}$C NMR (101 MHz, CD$_3$OD) δ: 175.79, 173.33, 171.70, 171.15, 162.54, 150.88, 139.45, 139.41, 130.43, 129.90, 129.26, 128.94, 127.34, 71.28, 69.68, 59.54, 56.34, 55.37, 50.96, 44.32, 41.88, 39.42, 37.83, 36.29, 31.88, 31.16, 25.45, 25.22, 23.60, 20.93, 20.81, 20.62, 18.78, 16.29, 10.80; Mass (ESI) m/z: 804.4 (M$^+$+H$^+$), 826.4 (M$^+$+Na).

Example 2.1

Synthesis of compound Boc-4-phenyl-phenylalaninol

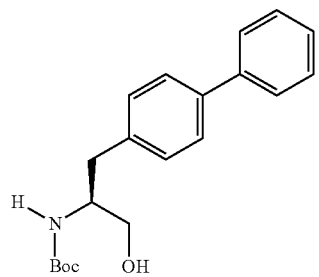 [SMILES: CC(C)(C)OC(=O)N[C@H](CO)Cc1ccc(-c2ccccc2)cc1]

To a solution of the commercial product Boc-4-phenylphenylalanine (0.43 mmoles) in THF (4 ml), Et$_3$N (0.51 mmoles) is added under stirring. The temperature is lowered to 0° C. and EtO$_2$Cl (0.51 mmoles) is added. The reaction mixture is stirred for 30 minutes and then filtered on celite. The filtrate is added to a solution of NaBH$_4$ (0.64 mmoles) in H$_2$O (1 ml), cooled at 0° C. The temperature is allowed to raise up to room temperature and the reaction mixture is kept under stirring for further 10 minutes. At the end a 1N HCl aqueous solution (1 ml) is added and the organic phase is extracted with ethyl acetate (3×5 ml). The solvent is evaporated under a reduced pressure and the crude product is purified by flash chromatography in n-hexane/ethyl acetate 6/4 volume/volume. 123 mg of Boc-4-phenyl-phenylaminol (87% yield) are recovered.

R$_f$=0.23 (n-hexane/ethyl acetate 6/4 volume/volume); $^1$H NMR (400 MHz, CDCl$_3$) δ: 7.60-7.50 (m, 4H), 7.46-7.39 (m, 2H), 7.37-7.25 (m, 3H), 4.80 (d, J=8.1 Hz, 1H), 3.98-3.85 (m, 1H), 3.75-3.64 (m, 1H), 3.64-3.56 (m, 1H), 2 89 (d, J=7.1 Hz, 2H), 2.46-2.38 (m, 1H), 1.43 (s, 9H); $^{13}$C NMR (101 MHz, CDCl$_3$) δ: 140.88, 139.52, 136.94, 129.72, 128.73, 127.24, 126.98, 64.32, 54.2, 37.3, 28.35.

Example 2.2

Synthesis of a Compound of Formula (A)

The examples from 1.1 to 1.15 have been repeated, but using in example 1.8 instead of compound Boc-phenylalaminol the compound obtained in example 2.1.

At the end of the synthesis the compound (DD3) was isolated

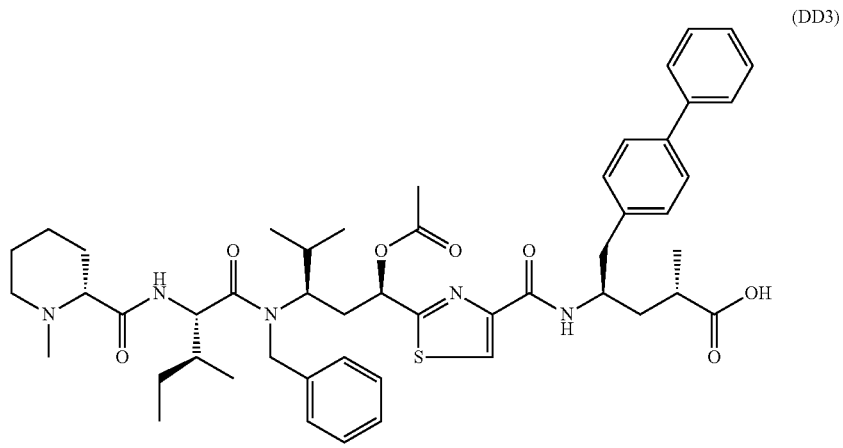 [SMILES: CC[C@H](C)[C@H](NC(=O)[C@H]1CCCCN1C)C(=O)N(Cc1ccccc1)[C@H](C[C@@H](OC(C)=O)c1nc(C(=O)N[C@@H](Cc2ccc(-c3ccccc3)cc2)C[C@H](C)C(=O)O)cs1)C(C)C]

(DD3)

¹H NMR (400 MHz, 09309) δ: 8.08 (s, 1H), 7.51-7.19 (m, 10H), 5.96-6.04 (m, 1H), 4.96 (d, J=16.7 Hz, 1H), 4.65 (d, J=10.3 Hz, 1H), 4.45 (d, J=16.7 Hz, 1H), 4.40-4.27 (m, 2H), 3.58-3.53 (m, 1H), 3.34-3.26 (m, 1H), 3.03-2.92 (m, 2H), 2.73-2.65 (m, 2H), 2.48-2.43 (m, 3H), 2.29 (s, 3H), 2.15 (s, 4H), 2.05-1.46 (m, 11H), 1.19 (m, 3H), 1.09-0.96 (m, 12H). ¹³C NMR (100 MHz, CD₃OD) δ: 179.61, 172.65, 172.45, 170.80, 166.51, 160.88, 150.29, 140.59, 140.48, 138.87, 137.37, 131.07, 128.93, 128.69, 128.51, 128.35, 128.33, 127.75, 127.33, 126.13, 66.81, 61.60, 55.74, 55.21, 54.39, 53.30, 47.95, 43.21, 39.37, 37.50, 37.06, 36.49, 35.53, 31.70, 27.31, 24.95, 24.81, 22.14, 21.24, 18.60, 18.28, 16.28, 11.56; Mass (ESI) m/z: 880.5 (M⁺+H⁺), 902.5 (M⁺+Na).

Example 3

The examples from 1.1 to 1.15 were repeated but using in example 1.8 instead of compound Boc-phenylalaminol the compound Boc-4-fluoro-phenylalanine.

At the end of the process, compound (904) was isolated.

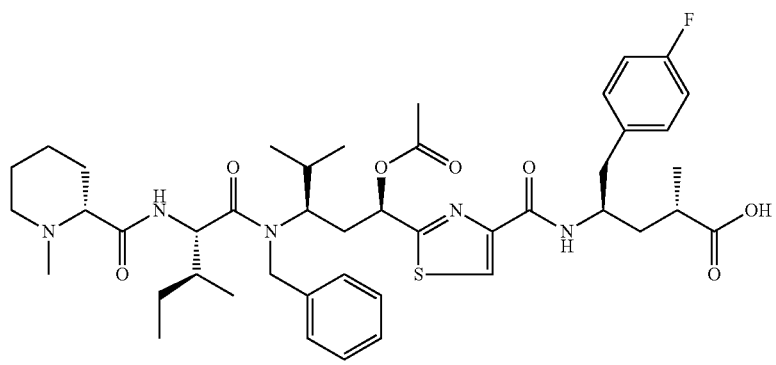

(DD4)

¹H NMR (400 MHz, CD₃OD) δ: 7.02 (m, 9H), 6.28-6.20 (m, 8.07 (s, 1H), 8.42 (s, 1H), 7.42-1H), 5.02 (d, J=17.7 Hz, 1H), 4.72 (d, J=10.0 Hz, 1H), 4.45 (d, J=17.7 Hz, 1H), 4.43-4.29 (m, 2H), 3.47-3.42 (m, 1H), 3.33-3.28 (m, 1H), 3.08-3.00 (m, 1H), 2.92-2.86 (m, 2H), 2.74-2.68 (m, 1H), 2.64 (s, 1H), 2.42 (s, 3H), 2.39-2.30 (m, 3H), 2.15 (s, 3H), 2.05-1.85

(m, 5H), 1.84-1.76 (m, 5H), 1.52-1.30 (m, 3H), 1.21 m, 3H), 1.13-0.80 (m, 14H). $^{13}$C NMR (100 MHz, CD$_3$OD) δ: 179.61, 172.66, 170.80, 166.51, 162.89, 160.88, 150.29, 137.37, 134.03, 133.99, 130.75, 128.69, 128.69, 128.51, 127.75, 126.13, 116.11, 116.00, 66.81, 61.60, 55.74, 55.21, 54.39, 53.29, 47.95, 43.21, 39.36, 37.50, 37.05, 36.49, 35.52, 31.70, 27.30, 24.95, 24.81, 22.14, 21.23, 18.59, 18.28, 16.28, 11.56. Mass (ESI) m/z: 822.4 (M$^+$+H$^+$), 844.3 (M$^+$+Na).

Example 4

The examples from 1.1 to 1.15 were repeated but using in example 1.8 instead of compound Boc-phenylalaminol compound Boc-4-methoxy-phenylalanine. At the end of the process, compound (DD5) was isolated.

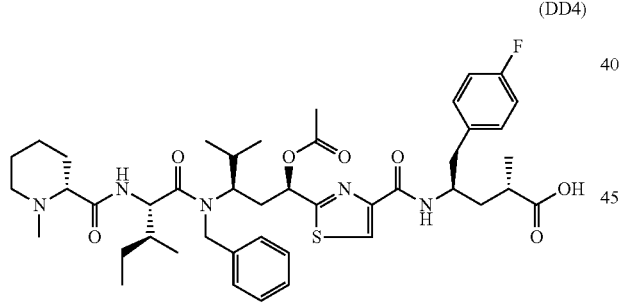
(DD4)

$^1$H NMR (400 MHz, CD$_3$OD) δ: 8.08 (s, 1H), 7.38-7.23 7.20-7.05 (m, 2H), 6.94-6.80 (m, 2H), 6.02-5.94 5.00 (d, J=17.7 Hz, 1H), 4.70 (d, J-10.0 Hz, (d, J=17.7 Hz, 1H), 4.45-4.27 (m, 2H), 3.88 3.32-3.26 (m, 2H), 3.08-3.02 (m, 2H), 2.76 (s, 1H), 2.71-2.48 (m, 2H), 2.31 (s, 3H), 2.16 (s, 5H), 2.06-2.02 (m, 1H), 1.88-1.79 (m, 3H), 1.68-1.47 (m, 8H), 1.24 (m, 3H), 1.10-0.96 (m, 12H). $^{13}$C NMR (100 MHz, CD$_3$OD) δ: 179.61, 172.65, 172.45, 170.80, 166.51, 160.88, 157.66, 150.29, 137.37, 130.09, 129.65, 128.69, 128.51, 127.75, 126.13, 114.93, 66.81, 61.60, 56.04, 55.74, 55.21, 54.39, 53.30, 47.95, 43.21, 39.37, 37.50, 37.06, 36.49, 35.53, 31.70, 27.31, 24.95, 24.81, 22.14, 21.24, 18.60, 18.28, 16.28, 11.56; Mass (ESI) m/z: 832.3 (M$^+$+H$^+$), 854.3 (M$^+$+Na).

Example 5

The examples from 1.1 to 1.15 were repeated, but using in example 1.8 instead of compound Boc-phenylalaminol the compound Boc-4-trifluoromethyl-phenylalanine. At the end of the process, compound (DD6) was isolated.

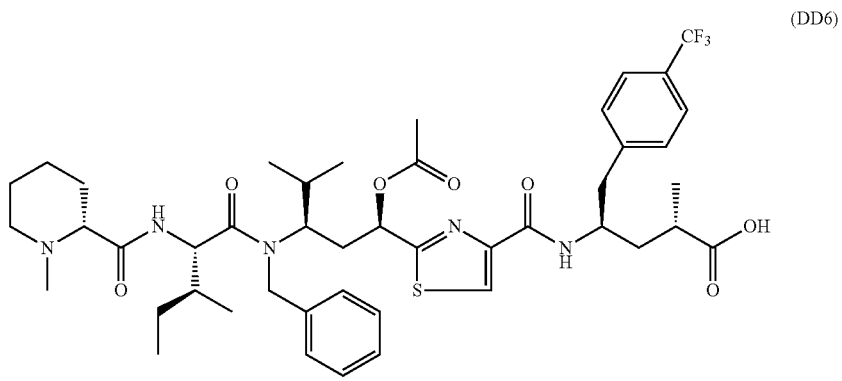 [SMILES: CC[C@H](C)[C@H](NC(=O)[C@H]1CCCCN1C)C(=O)N(Cc1ccccc1)[C@H](C[C@@H](OC(C)=O)c1nc(C(=O)N[C@@H](Cc2ccc(C(F)(F)F)cc2)C[C@H](C)C(=O)O)cs1)C(C)C]
(DD6)

$^1$H NMR (400 MHz, CD$_3$OD) δ: 8.06 (s, 1H), 7.65-7.52 (m, 2H), 7.34-7.27 (m, 5H), 7.09-6.95 (m, 2H), 5.80-5.70 (m, 1H), 4.90 (d, J=16.7 Hz, 1H), 4.60 (d, J=10.3 Hz, 1H), 4.40 (d, J=16.7 Hz, 1H), 4.39-4.25 (m, 2H), 3.59-3.51 (m, 1H), 3.30-2.96 (m, 2H), 2.75-2.48 (m, 4H), 2.28 (s, 4H), 2.14 (s, 4H), 1.98-1.92 (m, 1H), 1.81-1.46 (m, 8H), 1.21 (m, 3H), 1.13-0.98 (m, 12H). $^{13}$C NMR (100 MHz, CD$_3$OD) δ 179.61, 172.65, 172.45, 170.80, 166.51, 160.88, 150.29, 142.71, 137.37, 131.58, 130.97, 128.69, 128.51, 127.78, 127.75, 126.13, 124.37, 66.81, 61.60, 55.74, 55.21, 54.39, 53.30, 47.95, 43.21, 39.37, 37.50, 37.06, 36.49, 35.53, 31.70, 27.31, 24.95, 24.81, 22.14, 21.24, 18.60, 18.28, 16.28, 11.56; Mass (ESI) m/z: 872.4 (M$^+$+H$^+$), 894.4 (M$^+$+Na).

Example 6.1

Synthesis of (2S,3R)2-azido-N-(2-methoxyethyl)-3-methyl-pentanamide

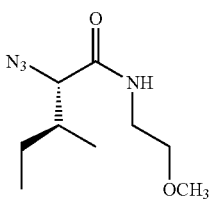

Example 1.1 was repeated but using the amine of formula NH$_2$CH$_2$CH$_2$OCH$_3$ instead of benzylamine. At the end of the synthesis, compound (2S,3R)-2-azido-N-(2-methoxyethyl)-3-methylpentanamide was isolated (74% yield).

R$_f$=0.27 (n-hexane/ethyl acetate 7/3 volume/volume); $^1$H NMR 400 MHz, CDCl$_3$) δ: $^1$H NMR (400 MHz, CDCl$_3$) 6.62 (br s, 1H), 3.81 (d, J=4.5 Hz, 1H), 3.54-3.36 (m, 4H), 3.29 (d, J=30.7 Hz, 3H), 2.15-1.95 (m, 1H), 1.50-1.34 (m, 1H), 1.32-1.13 (m, 1H), 1.00 (d, J=6.9 Hz, 3H), 0.88 (t, J-7.4 Hz, 3H); $^{13}$C NMR (101 MHz, CDCl$_3$) δ: 168.89, 70.91, 69.92, 58.66, 39.05, 38.13, 24.25, 15.94, 11.40; Mass (ESI) m/z: 237.0 (M$^+$+Na).

Example 6.2

Synthesis of ethyl 2-(3-((2S,3R)-2-azido-N-(2-methoxyethyl-3-methylpentanamido)-4-methylpentanoyl)thiazol-4-carboxylate

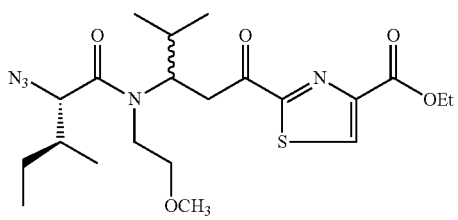 [SMILES: CCOC(=O)c1csc(C(=O)CC(C(C)C)N(CCOC)C(=O)[C@@H](N=[N+]=[N-])[C@@H](C)CC)n1]

Example 1.2 was repeated but using the compound obtained in example 6.1 instead of the compound obtained in example 1.1. The compound ethyl 2-(3-((2S,3R)-2-azido-N-(2-methoxyethyl)-3-methylpentanamido)-4-methylpentanoyl)thiazol-4-carboxylate was isolated (41% yield).

$R_f$=0.45 (n-hexane/ethyl acetate 7/3 volume/volume); $^1$H NMR (400 MHz, CDCl$_3$) δ: 8.40 (s, 1H), 4.45 (m, 2H), 4.27-4.20 (m, 1H), 3.78 (dd, J=17.0, 4.2 Hz, 1H), 3.67-3.36 (m, 6H), 3.26 (s, 3H), 2.34-2.18 (m, 1H), 2.15-2.05 (m, 1H), 1.80-1.65 (m, 2H), 1.43 (t, J=7.1 Hz, 3H), 1.02-0.81 (m, 12H); $^{13}$C NMR (101 MHz, CDCl$_3$) δ: 191.60, 170.04, 166.88, 160.66, 148.54, 133.24, 122.09, 71.08, 65.63, 63.07, 61.55, 58.48, 46.55, 40.27, 35.09, 30.30, 24.85, 20.23, 19.48, 15.32, 15.05, 14.08, 10.39; Mass (ESI) m/z: 490.1 (M$^+$+Na).

Example 6.3

Synthesis of ethyl 2-((1R,3R)-3-((2S,3R)-2-azido-N-(2-methoxy ethyl-3-methylpentanamido)-1-hydroxy-4-methylpentyl)thiazol-4-carboxylate

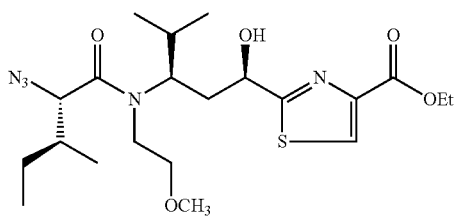 [SMILES: CCOC(=O)c1csc([C@H](O)C[C@H](C(C)C)N(CCOC)C(=O)[C@@H](N=[N+]=[N-])[C@@H](C)CC)n1]

Example 1.3 was repeated but using the compound obtained in example 6.2 instead of the compound obtained in example 1.2. ethyl 2-((1R,3R)-3-((2S,3R)-2-azido-N-(2-methoxyethyl)-3-methylpentanamido)-1-hydroxy-4-methylpentyl)-thiazol-4-carboxylate was isolated (77% yield).

$R_f$=0.42 (n-hexane/ethyl acetate 7/3 volume/volume); $^1$H NMR (400 MHz, CDCl$_3$) δ: 8.06 (s, 1H), 4.78-4.69 (m, 2H), 4.46-4.18 (m, 3H), 3.83 (d, J=10.2 Hz, 1H), 3.77-3.50 (m, 4H), 3.39-3.33 (m, 1H), 3.31 (s, 3H), 2.39-2.07 (m, 2H), 2.07-1.79 (m, 2H), 1.75-1.69 (m, 1H), 1.41-1.29 (m, 3H), 1.29-1.18 (m, 2H), 1.03-0.77 (m, 12H); $^{13}$C NMR (101 MHz, CDCl$_3$) δ: 175.61, 172.48, 161.35, 146.79, 127.23, 127.15, 71.33, 68.76, 63.29, 60.99, 58.59, 39.03, 34.57, 29.60, 24.99, 20.28, 19.74, 15.67, 14.16, 10.37; Mass (ESI) m/z: 492.2 (M$^+$+Na).

Example 6.4

Synthesis of 2-((1R,3R)-3-((2S,3R)-2-azido-N-(2-methoxy ethyl)-3-methylpentanamido)-1-hydroxy-4-methylpentyl)thiazol4-carboxylic acid

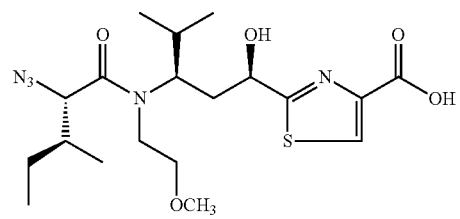 [SMILES: CC[C@H](C)[C@H](N=[N+]=[N-])C(=O)N(CCOC)[C@H](C[C@@H](O)c1nc(C(=O)O)cs1)C(C)C]

Example 1.4 was repeated but using the compound obtained in example 6.3 instead of the compound obtained in example 1.3. 2-((1R,3R)-3-((2S,3R)-2-azido-N-(2-methoxyethyl)-3-methylpentanamido)-1-hydroxy-4-methylpentyl)thiazol-4-carboxylic acid was isolated (75% yield).

$R_f$=0.35 (dichloromethane/methanol 9/1 volume/volume); $^1$H NMR (400 MHz, CD$_3$OD) δ: 8.28 (s, 1H), 4.80-4.72 (m, 1H), 4.05-3.45 (m, 5H), 3.35 (s, 3H), 2.47-2.24 (m, 1H), 2.19-1.89 (m, 3H), 1.81-1.67 (m, 1H), 1.38-1.23 (m, 1H), 1.08-0.86 (m, 12H); $^{13}$C NMR (101 MHz, CD$_3$OD) δ: 179.27, 172.98, 164.15, 148.33, 129.03, 69.63, 64.56, 58.93, 4.21, 49.00, 48.79, 39.38, 36.30, 31.35, 26.04, 20.88, 15.95, 10.82; Mass (ESI) m/z: 464.1 (M$^+$+Na), 486.1 (M$^+$+K).

Example 6.5

Synthesis of (2S,4R)-methyl-4-(2-((1R,3R)-3-((2S,3R)-2-azido-N-(2-methoxyethyl)-3-methylpentanamido)-1-hydroxy-4-methyl-pentyl thiazol-4-carboxamide-2-metil-5-phenylpentanoate

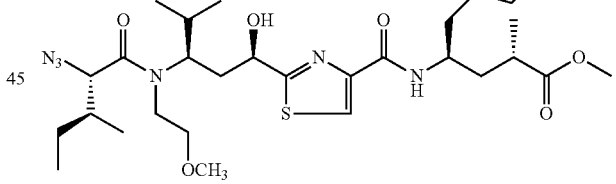

Example 1.12 was repeated but using the compound obtained in example 6.4 instead of the compound obtained in example 1.4. (2S,4R)-methyl-4-(2-((1R,3R)-3-((2S,3R)-2-azido-N-(2-methoxyethyl)-3-methylpentanamido)-1-hydroxy-4-methyl-pentyl)-thiazol-4-carboxamido)-2-methyl-5-phenylpentanoate was isolated (72% yield).

$R_f$=0.31 (n-hexane/ethyl acetate 1:1 volume/volume); $^1$H NMR (400 MHz, CDCl$_3$ δ: 7.89 (s, 1H), 7.31-6.92 (m, 6H), 4.82-4.67 (m, 2H), 4.47-4.21 (m, 2H), 3.82-3.63 (m, 2H), 3.57 (s, 3H), 3.52-3.28 (m, 3H), 3.21 (s, 3H), 3.00-2.70 (m, 2H), 2.65-2.43 (1H), 1.63-1.37 (m, 1H), 1.37-1.19 (m, 1H), 1.17-0.66 (m, 15H); $^{13}$C NMR (101 MHz, CDCl$_3$) δ: 176.38, 175.04, 170.80, 160.64, 149.55, 137.45, 129.50, 128.23, 126.33, 122.85, 71.34, 68.63, 63.24, 58.49, 51.55, 48.23, 40.94, 39.18, 37.72, 36.39, 34.46, 29.76, 25.00, 20.41, 17.63, 15.66, 10.39; Mass (ESI) m/z: 651.3 (M$^+$+H$^+$), 673.3 (M$^+$+Na).

Example 6.6

Synthesis of (2S,4R)⁻methyl-4-(2-((1R,3R)-1-hydroxy-3-((2S,3R)⁻N⁻(2⁻methoxyethyl)-3-methyl-2-(1-methylpiperidin-2-carboxamido)pentanamido)-4-methylpentyl)thiazol-4-carbox-amido)-2-methyl-5-phenylpentanoate

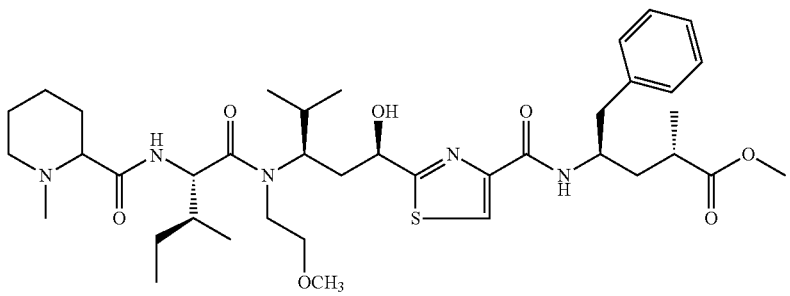 [SMILES: CC[C@H](C)[C@H](NC(=O)C1CCCCN1C)C(=O)N(CCOC)[C@H](C[C@@H](O)c1nc(C(=O)N[C@@H](Cc2ccccc2)C[C@H](C)C(=O)OC)cs1)C(C)C]

Example 1.13 was repeated but using the compound obtained in example 6.5 instead of the compound obtained in example 1.12. (2S,4R)⁻methyl-4-(2-H1R,3S)-1-hydroxy-3-((2S,3S)—N-(2-methoxyethyl)-3-methyl-2-(1-methylpiperidine-2-carboxamido)-pentanamido)⁻4⁻methylpentyl)thiazol-4-carboxamido)-2-methyl5-phenylpentanoate was isolated (77% yield).

$R_f$ NMR=0.32 (400 (dichloromethane/methanol 95/5 volume/volume); ¹H MHz, CD₃OD) δ: 8.02 (s, 1H), 7.33-7.02 (m, 5H), 4.89-4.74 (m, 2H), 4.42-4.29 (m, 2H), 3.80-3.65 (m, 3H), 3.58 (s, 3H), 3.54-3.31 (m, 3H), 3.22 (s, 3H), 2.71-2.55 (m, 3H), 2.49-2.42 (m, 2H), 2.23 (s, 3H), 2.20-1.94 (m, 5H), 1:95-1.39 (m, 8H), 1.39-1.24 (m, 2H), 1.21-1.13 (m, 3H), 1.12-1.04 (m, 3H), 1.02-0.93 (m, 4H), 0.83-0.70 (m, 6H); ¹³C NMR (101 MHz, CD₃OD) δ: 176.80, 174.30, 172.45, 169.54, 160.88, 150.29, 138.39, 129.26, 128.97, 126.91, 126.13, 71.55, 66.81, 62.88, 57.81, 55.73, 55.21, 54.39, 53.30, 52.17, 43.21, 42.53, 39.37, 38.44, 37.98, 37.14, 35.53, 31.70, 27.31, 24.95, 24.81, 22.14, 18.60, 17.86, 16.28, 11.56; Mass (ESI) m/z: 744.4 (M⁺+H⁺), 766.4 (M⁺+Na).

Example 1.14 was repeated but using the compound obtained in example 6.6 instead of the compound obtained in example 1.13. Yield 87%; $R_f$=0.17 (dichloromethane/methanol 95/5 volume/volume); ¹H NMR (400 MHz, CD₃OD) δ: 8.07 (s, 1H), 7.32-7.04 (m, 5H), 4.82 (m, 1H), 4.73 (d, J=9.4 Hz, 1H), 4.39 (m, 1H), 4.24-4.04 (m, 1H), 3.89-3.40 (m, 4H), 3.37 (s, 3H), 3.21 (s, 3H), 3.16-2.99 (m, 1H), 2.98-2.87 (m, 2H), 2.80 (s, 3H), 2.69-2.50 (m, 2H), 2.44-2.25 (m, 1H), 2.28-1.50 (m, 12H), 1.24-0.70 (m, 15H), ¹³C NMR (101 MHz, CD₃OD) δ: 179.61, 174.30, 172.45, 169.54, 160.88, 160, 60 (q, J-38.4 Hz), 150.29, 138.39, 129.26, 128.97, 126.91, 126.13, 118.96 (q, J=38.4 Hz), 71.55, 66.81, 62.88, 57.81, 55.73, 55.21, 54.39, 53.30, 43.21, 42.53, 39.37, 37.98, 37.50, 37.06, 35.53, 31.70, 27.31, 24.95, 24.81, 22.14, 18.60, 18.28, 16.28, 11.56; Mass (ESI) m/z: 731.4 (M⁺+H⁺), 753.4 (W+Na)

Example 6.7

Synthesis of the trifluoroacetic acid salt of (2S,4R)-4-(2-(1R,3R)-1-hydroxy-3-((2S3R)—N-(2-methoxyethyl)-3-methyl-2-(1-methylpiperidine-2-carboxamido)pentan-amide)-4-methyl-pentyl)thiazol-4-carboxamido)-2-mehyil-5-phenylpentanoic acid

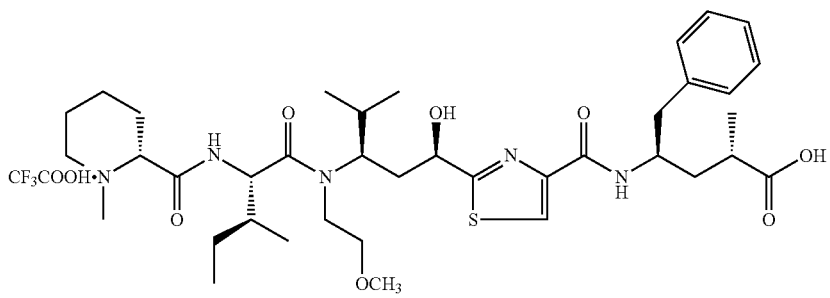

Example 6.8

Synthesis of (2S,4R)-4-(2-((1R,3R)-1-acetoxy-3-((2S,3R)—N(2-methoxyethyl)-3-methyl-2-(1-methyl piperidine-2-carboxamido)pentanamido)-4-methyl-pentyl)thiazol-4-carboxamido)-2-methyl-5-phenyl-pentanoic acid

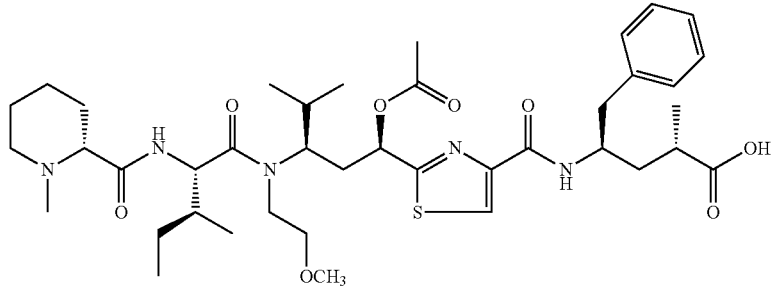 [SMILES: CC[C@H](C)[C@H](NC(=O)[C@H]1CCCCN1C)C(=O)N(CCOC)[C@H](C[C@@H](OC(C)=O)c1nc(C(=O)N[C@@H](Cc2ccccc2)C[C@H](C)C(=O)O)cs1)C(C)C]

Example 1.15 was repeated but using the compound obtained in example 6.7 instead of the compound obtained in example 1.14. Yield 78%; $R_f$=0.28 (dichloromethane/methanol 95/5 volume/volume); $^1$H NMR (400 MHz, CD$_3$OD) δ: 8.07 (s, 1H), 7.31-7.05 (m, 5H), 5.84 (d, J=12.7 Hz, 1H), 4.38 (m, 1H), 4.23 (m, 2H), 3.70-3.61 (m, 2H), 3.22 (s, 3H), 3.12-3.06 (m, 1H), 2.99-2.88 (m, 3H), 2.57-2.48 (m, 2H), 2.42-2.30 (m, 2H), 2.42-2.30 (m, 5H), 2.22 (s, 3H), 2.09-1.81 (m, 5H), 1.83-1.51 (m, 6H), 1.39-1.30 (m, 1H), 1.26-1.09 (m, 4H), 1.03 (d, J=17.3, 3H), 1.01-0.87 (m, 6H), 0.84 (d, J=6.6 Hz, 3H); $^{13}$C NMR (101 MHz, CD$_3$OD) δ: 171.97, 171.69, 162.78, 150.98, 139.68, 130.57, 129.38, 127.44, 73.08, 71.40, 69.83, 59.16, 56.44, 55.09, 51.05, 44.37, 41.99, 38.03, 36.27, 31.63, 31.24, 28.03, 25.62, 25.57, 23.69, 21.06, 20.92, 20.53, 18.78, 16.41, 11.03, 11.02; Mass (551) m/z: 772.4 (M$^+$+H$^+$), 794.4 (M$^+$+Na).

Example 7

Synthesis of the conjugated compound (compound example 1.15)-(Ala-Leu-Ala-Leu-βAla-βAla-Cys-Asn-Gly⁻Arg⁻Cys⁻Gly⁻Val⁻ArgTyrCOOH)

7a: Synthesis of the Biomolecule on Resin NH2βAla-βAla-Cys-Asn-Gly-Arg-Cys-Gly-Val-Arq-TyrQCOO⁻Resin The peptide synthesis on resin was carried out with an automatic instrument (Abi-433 Applied Biosystems) by using a polystyrene resin functionalized with a linker Cl-tritylChloride and preloaded with 300 microequivalents of tyrosine, the resin having 0.5 meg of active sites/g resin. The synthesis was carried out so as to obtain 300 μMoles of peptide.

The synthesis was of the FastMoc type (Fmoc-tBu) and was carried out in accordance with Atherton E. and Sheppard R. C. (1987) in Udenfriend S and Meienhofer J (eds) The Peptides, vol. 9: 1-39, Academic Press, San Diego, Calif., and by Fields G. B. e Noble R. L. (1990) in Int. J. Peptide Protein Res., 35: 161-214. As activator 0-(Benzotriazol-1-yl)-N,N,N',N'-tetramethyluronium tetrafluoroborate (TBTU) was used. The other reaction conditions adopted were:

excess of reactants for the "coupling"×4;
molar ratio between aminoacid/activator/DIPEA 1/1/2;
DeFmoc reactant: Piperidine in Dimethylformamide (DMF) 20%.

7b: Synthesis of the peptide (linker) on resin NH$_2$-Ala-Leu-Ala-Leu-COO-resin The peptide synthesis on resin was carried out with an automatic instrument (Abi-433) by using a polystyrene resin functionalized with Cl-trityl-Chloride linker and preloaded with leucine, the resin having 0.5 meg of active sites/g resin. The synthesis was carried out so as to obtain 300 μMoles of peptide.

The synthesis was of the FastMoc type (Fmoc-tBu) and carried out under the same conditions adopted in example 7a.

7c: Synthesis of the conjugated compound T-L$_1$ (compound example 1.15)-(Ala-Leu-Ala-Leu-COOH)

To a solution in DMF (200 μl) of the compound obtained in example 1.15 (35 mg, 0.043 mmoles), TBTU (14 mg, 0.043 mmoles) and DIPEA (15 μl) are added. The obtained solution is added to the compound NH$_2$-Ala-Leu-Ala-Leu-COO-resin prepared in example 7b (43 mg, 0.0215 mmoles), suspended in DMF (200 μl). Stirring was continued for 18 hours.

The conjugated compound was then removed from the resin by adding hexafluoropropanol, precipitated in TBME (tertbutylmethyl ether), the solid recovered by centrifugation and washed ten times with TBME.

7d: Synthesis of the conjugated compound T-L$_1$-G$_{1c}$ (compound example 1.15)-(Ala-Leu-Ala-Leu-βAla-βAla-Cys-Asn-Gly-Arg-Cys-Gly-Val-Arq-Tyr-COOH)

To a solution in DMF (200 μl) of the conjugated compound (compound Example 1.15)-(Ala-Leu-Ala-Leu-COOH) (0.0215 mmoles), obtained in example 7c, TBTU (7 mg) and DIPEA (7.5 μl) are added. The resulting solution is added to a suspension in DMF (200 μl) of the compound NH$_2$βAla-βAla-Cys-Asn-Gly-ArgCys-Gly-Val-Arg-TyrCOO-Resin (25 mg, 0.0107 mmol) obtained in example 7a, and stirred for 18 hours.

The peptide was then removed from the resin and deprotected at the side chains by using a mixture of trifluoroacetic acid added of phenol (scavenger). The removal was carried out also by using, instead of phenol, other scavengers as water, thioanisol or ethandithiol, triisopropylsilane. The peptide was then precipitated in tert-butylmethyl ether, the solid recovered by centrifugation and washed ten times with TBME.

The product was then purified by inverse phase semi-preparative HPLC(RP-HPLC), under the following conditions:
semipreparative column Phenomenex, Jupiter 10 micron Proteo 90 A model, 20×250 mm size; Fluent A: 97% water, 3% acetonitrile+1/1000 trifluoroacetic acid; Fluent B: 30% water, 70% acetonitrile+1/1000 trifluoroacetic acid; the column was eluted with a mixture of the two solvents, according to a linear elution gradient, from an initial mixture at 80% v of A to a final mixture containing 20% v of A, in a time of 50 minutes.

The oxidative folding (bridge formation of S—S) was carried out under the following conditions: peptide solution: 0.2 mM in buffer TRIS 20 mM pH 7.5, oxidizing agent: $H_2O_2$, reaction stoichiometry: 2 µMoles of $H_2O_2$/1 µM of peptide. The "oxidative folding" was controlled by analytical RP-HPLC by using the same chromatographic conditions reported above, but that the linear elution gradient used was from 80% v of A (initial) to 20% v of A (final) in 14 minutes. The retention time of the compound was of 12.439 minutes.

Folding resulted completed after 60 minutes. The reaction was followed by titrating the residual SH-groups with DTNB (5,5'-Dithio-bis(2-nitrobenzoic acid)). The peptide was subjected to semipreparative RP-HPLC under the same conditions reported above, and then lyophilized, obtaining 18 mg of product (37% yield, calculated on the basis of the coupling with $NH_2$-AlaLeu-Ala-Leu-COO-resin).

MASS (ESI) m/z: 1167.9 (M+2H$^+$), 778.6 (M+3H$^+$).

Example 8

Synthesis of the conjugated compound (compound Example 1.15)-(Gly-Phe-Leu-Gly-βAla-βAla-Cys-Asn-Gly-Arg-Cys-Gly-Val-ArgTyrCOOH)

8a: Synthesis of the peptide (linker) on resin $NH_2$-Gly-Phe-Leu-Gly-COO-resin

The peptide synthesis on the resin was carried out with automatic instrument (Abi-433) by using a polystyrene resin functionalized with Cl-trityl-Chloride linker and preloaded with glycine. The resin is characterized by 0.5 meq of active sites/g. The synthesis was carried out so as to obtain 300 µMoles of peptide.

The synthesis was of the FastMoc (Fmoc-tBu) type, carried out under the same conditions used in example 7a.

8b: Synthesis of the Conjugated Compound T-L$_1$ (Compound of Formula (A) of Example 1.15)-(Gly-Phe-Leu-Gly-COOH)

Example 7c was repeated, but using the resin obtained in example 8a instead of the compound $NH_2$-Ala-Leu-Ala-Leu-COO-resin, prepared in example 7b.

8c: Synthesis of the Conjugated Compound T-L$_1$-G$_{10}$ (Compound of Formula (A) of example 1.15)-(Gly-Phe-Leu-Gly-(βAla-βAla-Cys-Asn-Gly-Arg-Cys-Gly-Val-Arg-TyrCOOH)

Example 7d was repeated, but using the conjugated compound prepared in example 8b instead of that obtained in example 7c. Yield 38% calculated on the basis of the coupling with $NH_2^-$-Gly-Phe-Leu-Gly-COO-resin.

MASS (ESI) m/z: 1170.9 (M+2H$^+$), 780.6 (M+3H$^+$).

Example 9

Preparation of Nanoparticles of Polylactate-Polyglycolate Containing the Compound of Example 1.15

10 mg of the compound obtained in example 1.15 and 100 mg of copolymer PLA-PLGA 50:50 having an average molecular weight 40,000-75,000, commercialized by Sigma Aldrich®, were dissolved in 4 ml of dichloromethane. The obtained organic solution was emulsified in 8 ml of an aqueous solution at 5% by weight of Solutol® HS15 (Basf®) by treatment for 30 minutes with an ultraturrax Politron® emulsifier (10,000 rpm with a 7 mm probe).

The organic solvent (dichloromethane) was then removed from the emulsion by heating to 50° C. in a rotating evaporator. An aqueous dispersion of PLA-PLGA particles containing the compound of example 1.15 was obtained. The aqueous dispersion was subjected to three washing cycles by centrifuging with centrifuge AMICON™ test tubes, having membranes with 100,000 MWCO cut off. Each washing cycle was carried out at 4,000 rpm for 20 minutes, by adding each time 15 ml of distilled water in the upper compartment of the test tubes containing the nanoparticles.

At the end of the washings the particle aqueous dispersion was lyophilized under the following conditions: temperature: −40° C., pressure: 5×10$^{-2}$ mbar, duration: 24 hours.

The obtained nanoparticles were characterized by both transmission electronic microscopy (TEM), and by Photon Correlation Spettroscopy (PCS). The nanoparticle average diameters were the following: 120±25 nm (TEM), 146±10 nm (PCS).

The active principle content englobed in the particles was determined by solubilising in dichloromethane a known amount of the final sample and analyzing then by UV/visible spectrophotometry the organic solution. The amount of compound of example 1.15 determined in the sample of the lyophilized nanoparticles was equal to 58% of that initially dissolved in dichloromethane.

Example 10

Preparation of the Nanoparticles of Polylactate-Polyglycolate Containing the Compound of Example 6.8

The process reported in example 9 was repeated, but using: the compound of formula (A) obtained in example 6.8 instead of the compound prepared in example 1.15, polyvinyl alcohol instead of Solutol® HS15.

The preparation steps were the same as those reported in the previous example. The characterization has given the following results: the particle average diameter was 135±20 nm (TEM), 157±17 nm (PCS), the amount of compound of example 6.8 contained in the particles was equal to 60% of that initially dissolved in dichloromethane.

Example 11

Preparation of Lipidic Nanoparticles (t Palmitine) Containing Compound Obtained in Example 1.15

50 mg of the compound obtained in example 1.15 were mixed with 1 g of tripalmitine (DYNASAN® 116, Sasol) at the temperature of 70° C. The oily phase was then emulsified at the same temperature with an aqueous solution of 4 g of Solutol® HS15 in 60 ml of distilled water (60 ml), under stirring by means of an ultraturrax Politron turboemulsifier at 8,000 rpm for 20 minutes. The obtained emulsion was cooled to room temperature. A dispersion was formed having a lipid (tripalmitine) aqueous base containing the compound of example 1.15, stabilized by the surfactant Solutol® HS15. The dispersion was then subjected to 4 treatment cycles in a Microfluidics 1105 device (high pressure homogenizer) at the pressure of 120 psi.

The obtained dispersion was characterized by Photon Correlation Spectroscopy (PCS). The average diameters determined for the lipid particles were of 160±15 nm.

The aqueous dispersion was subjected to three washing cycles by centrifugation by using centrifuge AMICON test tubes having membrane with 100,000 MWCO cut off. Each washing cycle was carried out at 4,000 rpm for 20 minutes, by adding each time 15 ml of distilled water in the upper compartment of the test tubes, containing the nanoparticles.

At the end of the washing process, the aqueous dispersion was lyophilised under the following conditions: temperature −40° C., pressure $5 \times 10^{-2}$ mbar, time 24 hours.

The content of the compound of example 1.15 englobed in the nanoparticles was determined as described in example 9.

The compound amount contained in the lyophilized sample of nanoparticles is equal to 40% of that initially solubilised in tripalmitine.

Example 12

Preparation of Particles of (MePEG cyano acrylate-co-alkylcyanoacrylate) Containing the Compound of Example 1.15 a. Preparation of MePEG (Polyethylenglycol Methylether) Cyanoacetate

The MePEG esterification reaction was carried out under an inert atmosphere (Argon), by adding to a solution of cyanoacetic acid (0.9357 g) and of MePEG (11 g) in 25 ml of anhydrous dichloromethane, 5 ml of anhydrous dichloromethane containing 2.2696 g of dicyclohexylcarbodiimide (DCC) and 50 mg of 4-(dimethylamino) pyridine (DMAP). The reaction mixture was stirred for 6 hours at room temperature. The solid residue was separated by filtration under vacuum and washed with dichloromethane (3×20 ml). The filtrate was concentrated under reduced pressure, obtaining a viscous, pale yellow-coloured product, which was subsequently purified by crystallization from isopropanol. After recrystallization 11 g of a beige-coloured solid were obtained.

b. Preparation of Hexadecyl Cyanoacetate

The esterification reaction of hexadecanol was carried out under an inert atmosphere (Argon). To a solution of cyanoacetic acid (7.4853 g) and of hexadecanol (10.6674 g) in 50 ml of anhydrous dichloromethane and 5 ml of ethyl acetate, 50 ml of anhydrous dichloromethane containing 9.9864 g of dicyclohexylcarbodiimide (DCC) and 50 mg of 4-(dimethylamino)pyridine (DMAP) were added. The reaction mixture was stirred for 24 hours at room temperature. Then 50 ml of anhydrous hexane were added. The formed solid residue was separated by filtration under vacuum and washed with n-hexane (70 ml). The filtrate was concentrated under reduced pressure until obtaining an amorphous yellow solid, subsequently purified by flash chromatography (ligroin/ethyl acetate 9/1 v/v), yielding 14 g of a white solid.

c. Copolymerization

The condensation reaction of the two esters was carried out under an inert atmosphere (Argon). To a solution of hexadecyl cyanoacetate (1.238 g) and MePEG cyanoacetate (2.067 g) in 10 ml of absolute ethanol and 20 ml of anhydrous dichloromethane, 2 ml of formaline 37% w/v and 1 ml of dimethylamine 40% w/v were added. The reaction was carried out under magnetic stirring for 25 hours at room temperature and the obtained mixture was concentrated under reduced pressure until obtaining a yellow waxy solid. The compound was dispersed in water and extracted with dichloromethane. The organic solvent was recovered, dehydrated on sodium sulphate and dried under pressure. 3.4 g of poly (MePEG cyano acrylate-co-alkylcyanoacrylate) were obtained as a waxy pale yellow-coloured solid.

d. Particle Preparation 30 mg of poly(MePEG cyano acrylate-co-alkylcyanoacrylate) and 5 mg of the compound of example 1.15 were dissolved in 6 ml of acetone. The organic solution was added dropwise to 12 ml of distilled water under magnetic stirring. The organic solvent was then removed by evaporation obtaining an aqueous dispersion of nanoparticles, that was lyophilized under the following conditions: temperature −40° C., pressure $5 \times 10^{-2}$ mbar, time 24 hours.

The obtained nanoparticles were characterized by both transmission electronic microscopy (TEM) and Photon Correlation Spectroscopy (PCS). The average diameters were of 175±20 nm (TEM) and 193±10 nm (PCS).

The active principle content englobed in the particles was determined by solubilising in acetone a known amount of the final sample and analyzing by UV/visible spectrophotometry the organic solution. The amount of the compound of example 1.15 determined in the lyophilized sample of nanoparticles is equal to 55% with respect to that initially dissolved in acetone.

Example 13

Preparation of Lipidic Nanoparticles of Lecithin with a Liquid Core, Containing the Compound of Example 6.8

2.65 g of aqueous solution at 3% by weight NaCl, 1.1 g of Miglyol® 812S, 1.25 g of a mixture of surfactants formed of Solutol HS15 and Soya Lecithin (Epikuron 200) in a 5:1 w/w ratio, 0.005 g of the compound of example 6.8 were admixed at the temperature of 70° C. The obtained liquid oily phase at the same temperature, was dropwise added (1 drop/second) to 50 ml of distilled water maintained at 4° C. under continuous stirring by means of an Ultraturrax Politron® at a rate of 7,000 rpm. At the end of the addition, the dispersion containing the nanoparticles was left under stirring at 4° C. for further 15 minutes. Subsequently, the dispersion was sonicated for 5 minutes and then filtered on 0.45 micron PTFE filters.

The nanoparticles were separated from the aqueous medium by centrifugation in a centrifuge "Amicon® Ultra"

filters (100,000 MWCO cut off), by using four washing cycles (30 minutes, 4,000 rpm, 4° C.). At the end of the washing cycles the nanoparticles have been redispersed in water and sonicated for ten minutes. The nanoparticle aqueous dispersion was lyophilised under the following conditions: temperature −40° C., pressure $5 \times 10^2$ mbar, time 24 hours.

The nanoparticles were characterized by Photon Correlation Spectroscopy (PCS). The average particle diameters were of $65 \pm 10$ nm.

The active principle content englobed in the particles was determined by solubilising in dichloromethane a known amount of the final sample and analyzing by UV/visible spectrophotometry the organic solution. The amount of compound of formula (A) determined on the lyophilized sample of nano-particles is equal to 45% with respect to that added to the starting oily phase.

Example 14

Tests In Vitro for Evaluating the Cytotoxicity of the Compounds of Formula (A)

The cytotoxic effects of the compounds of formula (A) were evaluated by treating 3 cell lines with different concentrations of the compounds under screening. The following cell lines were used: A2780 (human ovarian carcinoma), HL60 (human leukaemia), C6 (rat glioma) and HT29 (adenocarcinoma of human colon). The cell lines have been obtained by ECACC (European Collection of Cell Cultures).

The cell lines have been cultured in 75 cm² flasks with culture medium DMEM (Dulbecco's Medium Eagle Modified, Sigma Aldrich®) and the following additives (Sigma Aldrich®): L-Glutamine 2 mM, 10% Fetal Bovine Serum, Penicillin/-Streptomycin, Fungizone, Gentamycin. The incubation was carried out in modified atmosphere incubators (37° C., 5% $CO_2$). When cell confluence was obtained, the cells were propagated by dilution in a ratio 1:3/1:5 by using a Trypsin-EDTA 1× solution and then transferred into 96 well plates in the suitable culture medium. The cells were then treated for 72 hours with different concentrations ($10^{-13} \div 10^{-4}$ M) of the compounds under examination. For the tests in vitro the compounds obtained in the examples 1.15 and 6.8 were solubilised in dimethylsulphoxide (DMSO). All the tests were performed with a constant DMSO concentration equal to 0.1% by weight.

In order to control the cellular viability, the ATPlite test (Perkin Elmer) was used. The APTlite test evaluates the ATP production. APT is a marker of cellular viability as it is present in all the metabolically active cells. The test' is based on the chemiluminiscence due to the ATP reaction with the luciferase and the D-luciferin. The emitted light is proportional to the ATP concentration. For the reading the Victor 3 instrument by Perkin Elmer was used.

Four readings were taken for each sample solution. The results (average values) for the cytotoxicity of the compounds of formula (A) obtained in examples 1.15 and 6.8 are reported respectively in Tables 1 and 2. It is noted that the $GI_{50}$ values determined by means of the cellular viability values are lower than 2 nM. This confirms the high cytotoxicity of the compound of formula (A).

The high cytotoxicity values found above are an index that the tubulysines of this example are endowed with antimitotic and/or antiangiogenic properties.

TABLE 1

Evaluation of the cytotoxicity of the compound of formula (A) obtained in example 1.15 by determining cellular viability (ATPlite Perkin Elmer test)

| Cellular Line | Concentration of the compound of example 1.15 (mole/litre) | | | | | | | | | | $GI_{50} \times 10^9$ (moles/litre) |
|---|---|---|---|---|---|---|---|---|---|---|---|
| | $10^{-13}$ | $10^{-12}$ | $10^{-11}$ | $10^{-10}$ | $10^{-9}$ | $10^{-8}$ | $10^{-7}$ | $10^{-6}$ | $10^{-5}$ | $10^{-4}$ | |
| HL60 | 98.98 | 34.26 | 22.65 | 8.29 | 3.66 | 2.94 | 2.69 | 2.99 | 2.57 | 0.47 | 0.0004 |
| HT29 | 104.5 | 103.2 | 102.2 | 99.08 | 20.77 | 17.55 | 16.85 | 15.43 | 14.55 | 15.14 | 0.3122 |
| A2780 | 100.1 | 65.66 | 32.71 | 25.04 | 25.08 | 11.78 | 10.60 | 9.60 | 7.23 | 3.10 | 0.0018 |

TABLE 2

Evaluation of the cytotoxicity of the compound of formula (A) obtained in example 6.8 by determining cellular viability (ATPlite Perkin Elmer test)

| Cellular line | Concentration of the compound of example 6.8 (mole/litre) | | | | | | | | | | $GI_{50} \times 10^9$ |
|---|---|---|---|---|---|---|---|---|---|---|---|
| | $10^{-13}$ | $10^{-12}$ | $10^{-11}$ | $10^{-10}$ | $10^{-9}$ | $10^{-8}$ | $10^{-7}$ | $10^{-6}$ | $10^{-5}$ | $10^{-4}$ | |
| HL60 | 100.9 | 102.0 | 56.38 | 3.53 | 1.36 | 1.04 | 1.14 | 1.25 | 1.22 | 0.75 | 0.0108 |
| HT29 | 108.0 | 107.5 | 115.6 | 95.7 | 24.49 | 20.38 | 17.68 | 18.08 | 11.46 | 11.55 | 0.2781 |
| A2780 | 104.0 | 104.1 | 109.7 | 106.7 | 64.56 | 22.80 | 9.11 | 9.11 | 8.41 | 3.08 | 1.537 |
| C6 | 101.2 | 99.13 | 96.68 | 64.15 | 39.57 | 25.60 | 20.70 | 19.58 | 20.19 | 19.10 | 0.1471 |

Example 15

Comparative

Example 15.1

Synthesis of 2-((1R,3R)-3-((2S,3S)-2-azido-N-(2-methoxy ethyl)-3-methylpentanamido)-1-hydroxy-4-methylpentyl)-N-methylthiazole-carboxamide

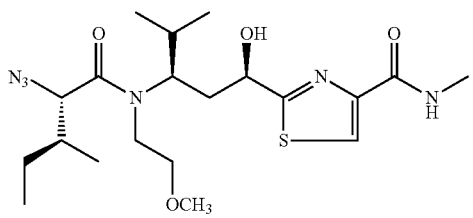 [SMILES: CC[C@H](C)[C@H](N=[N+]=[N-])C(=O)N(CCOC)[C@H](C[C@@H](O)c1nc(C(=O)NC)cs1)C(C)C]

To a solution of the compound obtained in example 6.4 (0.2 mmole, 88 mg) in DMF (5 mL) were added, in the order, of HOAt (0.22 mmol, 30 mg), HATU (0.22 mmole, 84 mg) and of Et$_3$N (0.42 mmole, 58 µL). After stirring for 5 minutes, methylamine hydrochloride (0.22 mmole, 15 mg) was added. The reaction mixture was stirred for further 4 hours. At the end the reaction mixture was diluted with H$_2$O (10 mL) and extracted with Et$_2$O (3×5 mL). The organic phases were pooled and washed, in the order, with 1N HCl aqueous solution (1×10 mL), with a NaHCO$_3$ saturated aqueous solution (1×10 mL) and with brine (1×10 mL). The organic phase was dried over Na$_2$SO$_4$, filtered and concentrated under vacuum to give 90 mg (99% yield) of pure 2-((1R,3R)-3-((2S,3S)-2-azido-N-(2-methoxyethyl)-3-methyl-pentanamido)-1-hydroxy-4-methylpentyl)-N-methylthiazole-4-carboxamide. R$_f$=0.35 (petroleum ether/ethyl acetate 1/1 volume/volume).

Example 15.2

Synthesis of (1R,3R)-3-((2S,3S)-2-azido-N-(2-methoxyethyl)-3-methylpentanamido)-4-methyl-1-(4-(methylcarbamoyl)thiazol-2-yl)pentyl acetate

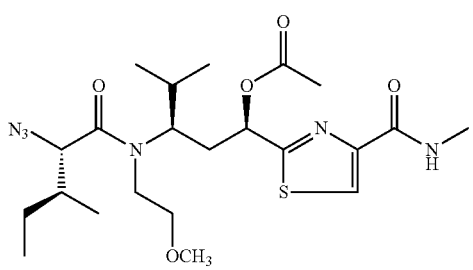 [SMILES: CC[C@H](C)[C@H](N=[N+]=[N-])C(=O)N(CCOC)[C@H](C[C@@H](OC(C)=O)c1nc(C(=O)NC)cs1)C(C)C]

To a solution of the compound obtained in example 15.1 (0.2 mmole, 90 mg) in dichloromethane (8 mL), kept under stirring, were added acetic anhydride (1 mmole, 94 µL), pyridine (0.5 mmole, 40 µL) and a catalytic amount of DMAP. Stirring was continued for 3 hours. At the end the reaction mixture was diluted with H$_2$O (10 mL) and extracted with dichloromethane (2×5 mL). The organic phases were pooled and washed, in the order, with a NaHCO$_3$ saturated aqueous solution (1×10 mL), with a 1N aqueous solution of HCl (1×10 mL) and with brine (1×10 mL). The organic phase were dried over Na$_2$SO$_4$, filtered and concentrated under vacuum to give 92 mg (93% yield) of (1R,3R)-3-((2S,3S)-2-azido-N-(2-methoxyethyl)-3-methylpentanamido)⁻⁴⁻methyl-1-(4-(methylcarbamoyl)thiazol-2-yl)pentyl acetate. R$_f$=0.32 (petroleum ether/ethyl acetate 1/1 volume/volume).

Example 15.3

Synthesis of (1R,3R)-3-((2S,3S)-2-amino-N-(2-methoxyethyl)-3-methylpentanamido)-4-methyl-1-(4-(methylcarbamoyl)thiazol-2-yl)pentyl acetate

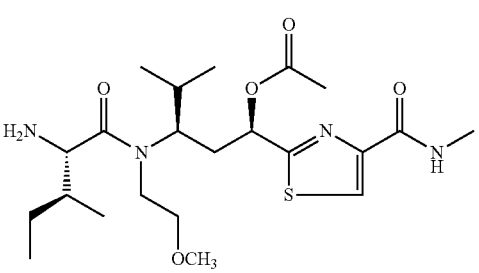 [SMILES: CC[C@H](C)[C@H](N)C(=O)N(CCOC)[C@H](C[C@@H](OC(C)=O)c1nc(C(=O)NC)cs1)C(C)C]

To a solution of the compound obtained in example 15.2 (0.18 mmole, 92 mg) in methanol (10 mL) were subsequently added, under stirring, a catalytic amount of palladium on charcoal 10% and formic acid (3.7 mmole, 0.14 mL). Stirring was continued for 1 hour under an inert atmosphere. The reaction mixture was filtered through celite and the solvent was removed under vacuum. The crude product was solubilized in dichloromethane (10 mL) and washed with a saturated aqueous solution of NaHCO$_3$ (1×10 mL). The organic phase were dried over Na$_2$SO$_4$, filtered and concentrated under vacuum. 46 mg (52% yield) of (1R,3R)-3-((2S,3S)-2-amino-N-(2-methoxyethyl)-3-methylpentanamido)-4-methyl-1-(4-(methylcarbamoyl)thiazol-2-yl) pentyl acetate were recovered. R$_f$=0.30 (chloroform/methanol 97:3 volume/volume).

Example 15.4

Synthesis of (1R,3R)-3-((2S,3S)—N-(2-methoxyethyl)-3-methyl-2-((R)-1-methylpiperidine-2-carboxamido)pentanamido)-4-methyl-1-(4-(methyl carbamoyl)thiazol-2-yl)pentyl acetate

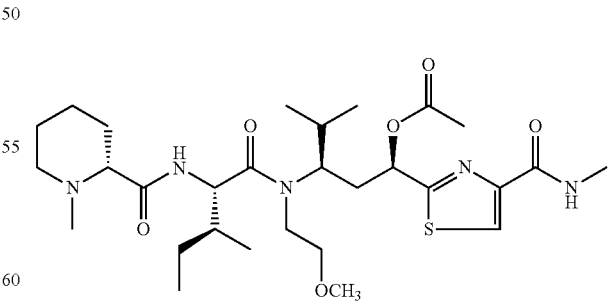

To a suspension of N-methyl pipecolinic acid (0.15 mmole, 21 mg) in dichloromethane (5 mL) were subsequently added, in the order, HOAt (0.11 mmole, 15 mg), HATU (0.11 mmole, 42 mg) and Et$_3$N (0.21 mmole, 29 µL). After stirring for 5 minutes, a solution in dichloromethane (1 mL) of the compound obtained in example 15.3 (0.1 mmole, 46 mg) was added. The reaction mixture was stirred for 4 hours, At the end dichloromethane was removed under vacuum. The crude product was dissolved in ethyl acetate (10 mL) and washed, in the order, with a NaHCO$_3$ saturated aqueous solution (1×10 mL) and with brine (1×10 mL). The organic phase were dried over Na$_2$SO$_4$, filtered and concentrated under vacuum. The product was purified by flash chromatography (eluent chloroform:methanol 97:3 volume/volume). 58 mg (99% yield) of pure 2-((1R,3R)-3-((2S,3S)-2-azido-N-(2-methoxyethyl)-3-methylpentanamido)-1-hydroxy-4-methylpentyl)-N-methylthiazole-4-carboxamide were isolated. R$_f$=0.37 (chloroform/methanol 97:3 volume/volume). $^1$HNMR (400 MHz, CDCl$_3$) δ: 8.07 (s, 1H), 7.62 (m, 1H), 7.57 (m, 1H), 5.75 (dd, 1H), 4.61 (dd, 1H), 4.11 (m, 1H), 3.70-3.48 (m, 4H), 3.22 (s, 3H), 3, 20-3.08 (m, 1H), 2.92 (m, 3H), 2.88-2.78 (m, 1H), 2.40 (m, 1H), 2.2-2.09 (m, 6H), 2.09-1.81 (m, 5H), 1.69-1.48 (m, 5H), 1.39-1.30 (m, 1H), 1.26-1.09 (m, 1H), 1.08-0.86 (m, 12H).

Example 15.5

Comparative

The compound obtained in example 15.4 Comparative has been evaluated in the same test in vitro described in example 14, using the cell line HL60, determining cell viability up to $10^{-10}$ mole/liter.

99.8 and 96% values of cell viability were obtained at a concentration of $10^{-11}$ mole/liter and $10^{-10}$ mole/liter, respectively.

Tables 1 and 2 shows that at the above concentrations by using the compounds of the present invention cell viability is markedly lower than 99.8 and 96%, respectively. Therefore the compounds of the present invention are markedly more cytotoxic than the compound of the comparative example.

The citotoxicity, expressed as GI$_{50}$, was of 1×10$^{-8}$ mole/liter. It is noted that the citotoxicity on the same cell line of the compounds of the present invention was at least of 1.08×10$^{-11}$ mole/liter. See Table 2 of the description. Therefore the compound of example 15.4 comparative is 10$^3$ times less toxic than the compounds of the present invention.

Example 16

Comparative

Example 16.1

Synthesis of tert-butyl-(4-methoxyphenyl)-(phenylsulphonyl)-methyl carbamate

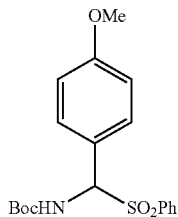

To a solution of tert-butyl carbamate (12.7 mmoles, 1.5 g) in a MeOH/water mixture 2/1 volume/volume (30 ml), p-anisaldehyde (25.5 mmoles, 3.1 ml), sodium benzensulphinate (25.5 mmoles, 4.2 g) and formic acid (25.5 mmoles, 0.96 ml), in the order, are added. The reaction mixture is kept under stirring for 12 hours. The precipitated solid is filtered, washed with water and dried.

3.09 g of tert-butyl-(4-methoxyphenyl)-(phenylsulphonyl)-methyl carbamate (64% yield) are obtained.

$^1$H NMR (400 MHz, CDCl$_3$) δ: 8.06-6.84 (m, 9H), 5.84 (br s, 1H), 3.88 (s, 1H), 3.81 (s, 3H), 1.25 (s, 9H); $^{13}$C NMR (101 MHz, CDCl$_3$) δ: 161.24, 153.89, 134.17, 132.36, 130.58, 129.85, 129.37, 122.25, 114.73, 114.65, 55.72, 28.37.

Example 16.2

Synthesis of ethyl 2-(3-(tertbutoxyarbonylamino)-3-(4-(methoxyphenyl)propanoyl)thiazol-4-carboxylate

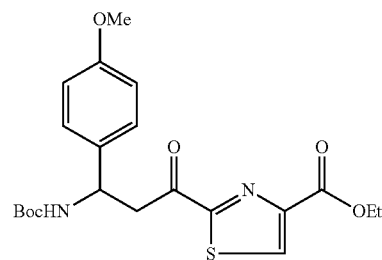 [SMILES: CCOC(=O)c1csc(C(=O)CC(NC(=O)OC(C)(C)C)c2ccc(OC)cc2)n1]

To a suspension of sodium hydride at 60% (w/w) in mineral oil (8.3 mmoles, 332 mg) in anhydrous THF (20 ml), a solution in anhydrous THF of the compound acetyl thiazole of the following formula (5.0 mmoles in 10 ml of THF) (ethyl-2-acetyl-thiazol-4-carboxylate) is added

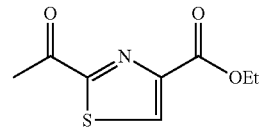

The compound has been prepared by the method described in Angew. Chem. Int. Ed., 46, 2007, 3526-3529. The reaction mixture is kept under stirring for 15 minutes and then a solution of the compound obtained in example 16.1 in anhydrous THF (3.3 mmoles in 10 ml of THF) is dripped in 30 minutes. The reaction mixture is stirred for 2 hours. Then an aqueous NH$_4$Cl saturated solution (50 ml) is added and the organic phase extracted with ethyl acetate (3×30 ml). The organic extracts are dried on Na$_2$SO$_4$, the mixture is filtered and the solvent evaporated under a reduced pressure. The crude product is purified by flash chromatography in n-hexane/ethyl acetate 70/30 volume/volume. 740 mg of ethyl-2-(3-(tertbutoxy-carbonylamino)-3-(4-(methoxyphenyl)propanoyl)-thiazol-4-carboxylate (52% yield) are obtained.

R$_f$=0.35 (n-hexane/ethyl acetate 65/35 volume/volume); $^1$H NMR (400 MHz, CDCl$_3$) δ: 8.40 (s, 1H), 7.50-6.62 (m, 4H), 5.26 (br s, 1H), 4.44 (q, J=7.1 Hz, 2H), 3.76 (s, 3H), 1.42 (t, J=7.1 Hz, 3H), 1.38 (s, 9H); $^{13}$C NMR (101 MHz, CDCl$_3$) δ: 191.79, 167.45, 161.14, 159.27, 157.18, 155.35, 149.04, 133.82, 128.02, 114.39, 80.02, 62.25, 55.65, 51.03, 45.24, 28.70, 14.72; Mass (ESI): m/z 457.0 (M+Na).

Example 16.3

Synthesis of ethyl 2-H1R,3R)-3-(tert-butoxycarbonylamino)-1-hydroxy-3-(4-methoxyphenyl)propyl) thiazol-4-carboxylate

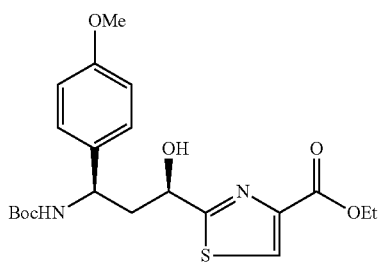 [SMILES: CCOC(=O)c1csc([C@H](O)C[C@@H](NC(=O)OC(C)(C)C)c2ccc(OC)cc2)n1]

To a solution of the chiral catalyst (S)—CBS (0.24 mmoles, 68 mg) in anhydrous THF (10 ml) a solution of 10 M of BH₃'Me₂S (2.2 mmoles, 221 μl) is added. The temperature of the liquid phase is lowered to 0° C., and a solution of the compound obtained in example 16.2 (2.2 mmoles) in anhydrous THF (5 ml) is added. The reaction mixture is stirred for one hour at 0° C. and then 4 hours at room temperature. At the end methanol (1 ml) is added, the solvents are evaporated at a reduced pressure and the crude product is purified by flash chromatography in n-hexane/ethyl acetate 7/3 volume/volume. 495 mg of the compound of ethyl 2-((1R,3R)-3-(tert-butoxycarbonylamino)-1-hydroxy-3-(4-methoxyphenyl)propyl)thiazol-4-carboxylate (51% yield) are obtained.

$R_f$=0.29 (n-hexane/ethyl acetate 7/3 volume/volume); $^1$H NMR (400 MHz, CDCl₃) δ: 8.07 (s, 1H), 7.21 (d, J=8.5 Hz, 2H), 6.81 (d, J=8.5 Hz, 2H), 5.31 (br s, 1H), 5.15-5.07 (m, 1H), 4.98-4.93 (m, 1H), 4.37 (q, J-7.1 Hz, 2H), 3.74 (s, 3H), 2.53-2.47 (m, 1H), 2.03-1.97 (m, 1H), 1.40 (s, 9H), 1.35 (t, J=7.1 Hz, 3H); $^{13}$C NMR (101 MHz, CDCl₃) δ: 176.74, 161.86, 159.43, 157.49, 147.26, 133.44, 128.13, 127.61, 114.60, 80.80, 69.43, 61.66, 55.64, 51.26, 45.67, 28.68, 14.71; Mass (ESI): m/z 459.0 (M⁺+Na).

Example 16.4

Synthesis of ethyl 2-((1R,3R)-3-((2S,3R)-2-(tert-butoxy-carbonylamino)-3-methylpentanamido)-1-hydroxy-3-(4-methoxy-phenyl)propyl)thiazol-4-carboxylate

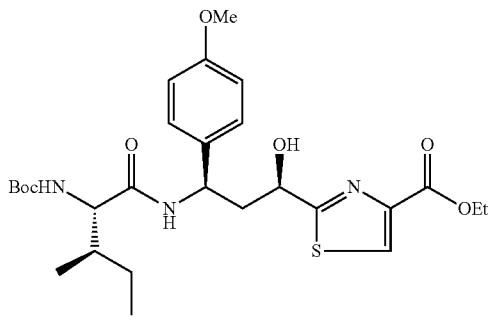 [SMILES: CCOC(=O)c1csc([C@H](O)C[C@@H](NC(=O)[C@@H](NC(=O)OC(C)(C)C)[C@H](C)CC)c2ccc(OC)cc2)n1]

To a solution of tert-butoxycarbonyl-isoleucine (0.97 mmoles, 225 mg) in DMF (5 ml), HOBt (1.07 mmoles), hydrochloride HOC (1.07 mmoles, sin-collidine (2.14 mmoles) and the compound obtained in example 16.3 (0.97 mmoles) are added in the order. The reaction mixture is stirred for 2 hours. Water (10 ml) is added and the organic phase is extracted with ethyl ether (3×10 ml). The extracted organic phase is then washed, in sequence, with an HCl 1N aqueous solution (1×10 ml), with an aqueous NaHCO₃ saturated solution (1×10 ml) and with an aqueous NaCl saturated solution (1×10 ml). The organic phase is recovered and dried on Na₂SO₄, the mixture is filtered and the solvent evaporated under a reduced pressure. 338 mg of ethyl 2-((1R,3R)-3-((2S,3R)-2-(tert-butoxycarbonylamino)-3-methylpentanamido)-1-hydroxy-3-(4-methoxy⁻phenyl)propyl)thiazol-4-carboxylate (63% yield) are obtained.

$R_f$=0.22 (n-hexane/ethyl acetate 1/1 volume/volume); $^1$H NMR (400 MHz, CDCl₃) δ: 8.09 (s, 1H), 7.23 (d, J=8.7 Hz, 2H), 6.84 (d, J=8.7 Hz, 2H), 6.73 (br s, 1H), 5.41 (br s, 1H), 5.29-5.21 (m, 1H), 5.08-4.87 (m, 2H), 4.39 (q, J=7.1 Hz, 2H), 3.99-3.92 (m, 1H), 3.77 (s, 3H), 2.69-2.62 (m, 1H), 2.11-2.04 (m, 1H), 1.97-1.90 (m, 1H), 1.38 (s, 9H), 1.35 (t, J=7.1 Hz, 3H), 1.18-1.10 (m, 1H), 0.94 (d, J=68 Hz, 3H), 0.89 (t, J=7.4 Hz, 3H); $^{13}$C NMR (101 MHz, CDCl₂) δ: 176.38, 173.40, 161.88, 159.69, 147.38, 132.84, 128.33, 127.72, 122.70, 114.72, 69.24, 61.66, 59.97, 55.67, 50.53, 44.22, 36.67, 30.03, 28.60, 25.07, 16.30, 14.71, 11.62; Mass (ESI): m/z 572.2 (M⁺+Na).

Example 16.5

Synthesis of 2-((1R,3R)-3-((2S,3R)-2-(tert-butoxycarbonylamino)-3-methylpentanamido)-1-hydroxy-3-(4-methoxy-phenyl)propyl)thiazol-4-carboxylic acid

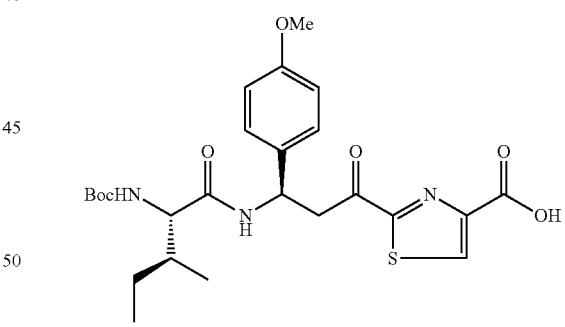

The compound obtained in example 16.4 (0.59 mmoles) is dispersed in a THF/water mixture 4/1 volume/volume (10 ml). Then Li(OH) (0.87 mmoles) is added. The reaction mixture is stirred for 5 hours. Water (5 ml) is added and the organic phase is extracted with ethyl acetate (1×10 ml). The aqueous phase is recovered and acidified with an HCl 1N solution to pH=2. Then it is extracted with ethyl acetate (3×10 ml) and the organic extracts are pooled and dried on Na₂SO₄, the mixture is filtered and the solvent evaporated under a reduced pressure obtaining 307 mg of 2-((1R,3R)-3-((2S,3R)-2-(tertbutoxycarbonylamino)-3-methyl-pentanamido)-1-hydroxy-3-(4-methoxyphenyl)propyl)thiazol-4-carboxylic acid (quantitative yield).

$R_f$=0.40 (dichloromethane/methanol 9/1 volume/volume); $^1$H NMR (400 MHz, CDCl$_3$) δ: 8.09 (s, 1H), 7.23 (d, J=8.7 Hz, 2H), 6.84 (d, J=8.7 Hz, 2H), 6.73 (br s, 1H), 5.41 (br s, 1H), 5.29-5.21 (m, 1H), 5.08-4.87 (m, 2H), 4.39 (q, J=7.1 Hz, 2H), 3.99-3.92 (m, 1H), 3.77 (s, 3H), 2.69-2.62 (m, 1H), 2.11-2.04 (m, 1H), 1.97-1.90 (m, 1H), 1.38 (s, 9H), 1.35 (t, J=7.1 Hz, 3H), 1.18-1.10 (m, 1H), 0.94 (d, J=6.8 Hz, 3H), 0.89 (t, J=7.4 Hz, 3H); $^{13}$C NMR (101 MHz, CDCl$_3$) δ: 176.38, 173.40, 161.88, 159.69, 147.38, 132.84, 128.33, 127.72, 122.70, 114.72, 69.24, 61.66, 59.97, 55.67, 50.53, 44.22, 36.67, 30.03, 28.60, 25.07, 16.30, 14.71, 11.62; Mass (ESI): m/z 572.2 (M$^+$+Na).

392 mg of (2S,4R)-methyl 4-(2-((1R,3R)-3-((2S,3S)-2-(tert-butoxy carbonylamino)-3-methylpentanamido)-1-hydroxy-3-(4-methoxy-phenyl)propyl)thiazol-4-carboxamido)-2-methyl-5-phenyl-pentanoate (97% yield) are obtained. $R_f$=0.41 (n-hexane/ethyl acetate 4/6 volume/volume); $^1$H NMR (400 MHz, CDCl$_3$) δ: 7.99 (s, 1H), 7.33-7.05 (m, 9H), 6.90 (br s, 1H), 6.80 (d, J=7.4 Hz, 1H), 5.41-5.21 (m, 2H), 4.93 (t, J=10.0 Hz, 2H), 4.43-4.32 (m, 1H), 3.98 (t, J=7.1 Hz, 1H), 3.80 (s, 3H), 3.61 (s, 3H), 3.00-2.80 (m, 2H), 2.64-2.54 (m, 1H), 2.46 (t, J=12.6 Hz, 1H), 2.14 (t, J=12.2 Hz, 1H), 2.04-1.88 (m, (m, 2H), 1.38 (s, 9H), 1.14 (d, J=6.9 Hz, =6.6 Hz, 3H), 0.90 (t, J=7.2 Hz, 3H); $^{13}$C CDCl$_3$) δ: 176.92, 175.12, 173.21, 161.12, 159.74, 156.56, 150.18, 137.90, 137.80, 132.98, 129.98, 128.72, 128.16, 126.84, 123.50, 114.79, 68.95, 55.71, 52.03, 5029, 48.65, 44.51, 41.50, 38.22, 36.89, 36.57, 30.04, 28.60, 25.15, 18.12, 17.24, 16.32, 11.66. Mass (ESI): m/z 747.2 (M$^+$+Na).

Example 16.6

Synthesis of (2S,4R)-methyl 4-(2-((1R,3R)-3-((2S,3S)-2-(tert-butoxy carbonylamino)-3-methylpentanamido)-1-hydroxy-3-(4-methoxy-phenyl)propyl)thiazol-4-carboxamido)-2-methyl-5-phenylpentanoate Example 16.7

Synthesis of (2S,4R)-methyl 4-(2-((1R,3R)-1-hydroxy-3-(4-methoxyphenyl)-3-((2S,3S)-3-methyl-2-((R)-1-methylpiperidin-2-carboxamido)pentanamido)propyl)thiazol-4-carboxamido)-2-methyl-5-phenylpentanoate

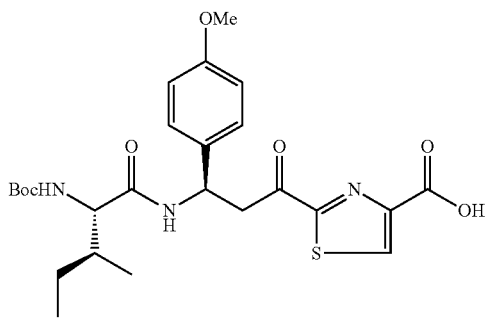 [SMILES: CC[C@H](C)[C@H](NC(=O)OC(C)(C)C)C(=O)N[C@H](CC(=O)c1nc(C(=O)O)cs1)c1ccc(OC)cc1]

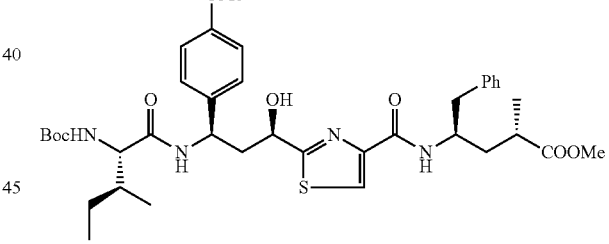

To a solution of the compound obtained in example 16.5 (0.56 mmoles) in DMF (5 ml), HOAt (0.61 mmoles), HATU (0.61 mmoles), triethylamine (1.11 mmoles) and the compound obtained in example 1.11 (0.56 mmoles) are added, in the order. The reaction is stirred for 2 hours. Water (10 ml) is added and the organic phase extracted with ethyl ether (3×10 ml). The extracted organic phase is then washed, in sequence, with an aqueous HCl 1N solution (1×10 ml), with an aqueous NaHCO$_3$ saturated solution (1×10 ml) and with an aqueous NaCl saturated solution (1×10 ml). The organic phase is recovered and dried on Na$_2$SO$_4$, the mixture is filtered and the solvent evaporated under a reduced pressure.

0.53 moles of the compound obtained in example 16.6 are dissolved in DCM (10 ml); to this solution TFA (1 ml) is added. The reaction is stirred for 2 hours. The solvent is evaporated under a reduced pressure. 0.51 mmoles of the obtained product are added, under stirring to a suspension of N-methyl pipecolinic acid (0.56 mmoles) in dichloromethane (10 ml) containing HOAt (0.56 mmoles), HATU (0.56 mmoles) and triethylamine (1.02 mmoles). The reaction is stirred for 4 hours. Water (10 ml) is added and the organic phase is extracted with dichloromethane (3×10 ml). The pooled organic extracts are dried over anhydrous sodium sulphate, then the mixture filtered and the solvent evaporated under a reduced pressure. The crude product is purified by flash chromatography in dichloromethane/methanol 95/5 volume/volume. 289 mg of (2S,4R)-methyl 4-(2-((1R,3R)-1-hydroxy-3-(4-methoxyphenyl)-3-((2S,3S)-3-methyl-2-((R)-1-methylpiperidin-2-carboxamido)pentanamido)propyl)-thiazol-4-carboxamido)-2-methyl-5-phenylpentanoate (75% yield) are obtained. R$_f$=0.40 (dichloromethane/methanol 9/1 volume/volume); $^1$H NMR (400 MHz, CD$_3$OD) δ: 8.02 (s, 1H), 7.36-6.78 (m, 9H), 5.28 (dd, J=9.6, 3.8 Hz, 1H), 4.90 (dd, J=9.5, 3.4 Hz, 1H), 4.36-4.31 (m, 1H), 4.28-4.22 (m, 1H), 3.74 (s, 3H), 3.56 (s, 3H), 2.96-2.83 (m, 3H), 2.65-2.39 (m, 2H), 2.21-2.12 (m, 1H), 2.10 (s, 3H), 2.05-1.80 (m, 3H), 1.73-1.42 (m, 6H), 1.32-1.16 (m, 4H), 1.12 (d, J=7.1 Hz, 3H), 0.97 (d, J=6.7 Hz, 3H), 0.90 (t, J=7.3 Hz, 3H); $^{13}$(2 NMR (101 MHz, CD$_3$OD) δ: 181.60, 181.13, 178.67, 175.93, 165.94, 163.29, 153.66, 142.23, 138.41, 133.43, 132.33, 131.72, 130.44, 127.61, 117.94, 73.51, 62.13, 59.51, 55.18, 53.92, 52.64, 52.42, 52.21, 52.00, 51.79, 51.57, 47.70, 45.28, 41.94, 40.63, 34.40, 29.05, 27.20, 21.11, 19.15, 14.01; Mass (ESI): m/z 750.3 (M$^+$+H$^+$), 772.3 (M$^+$+Na).

Example 16.8

Synthesis of the 2,2,2-trifluoroacetic salt of (2S,4R)-4-(2-H1R,3R)-1-hydroxy-3-(4-methoxyphenyl)-3-((2S,3S)-3-methyl-2-((R)-1-methylpiperidin-2-carboxamido)pentan-amido)-propyl)-thiazol-4-carboxamido)-2-methyl-5-phenylpentanoic acid

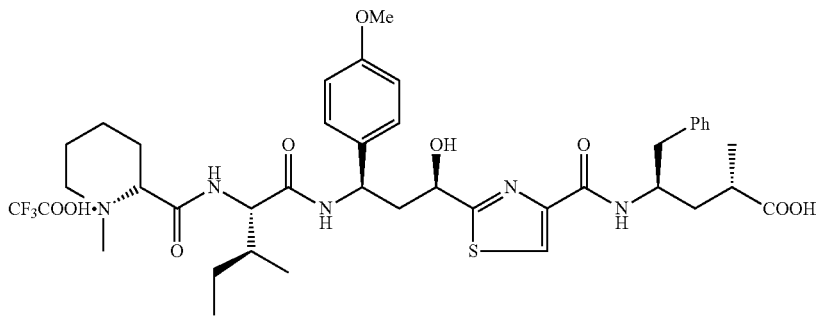

0.36 mmoles of the compound obtained in example 16.7 are solubilized in THF (5 ml), to this solution a 1N aqueous solution of Li(OH) (0.72 mmoles) is added. The reaction is stirred for 48 hours. Water (2 ml) and then trifluoroacetic acid to pH=2 are added. The organic phase is extracted with ethyl acetate (3×5 ml) and the pooled organic extracts are dried on Na$_2$SO$_4$ and then filtered. The solvents are evaporated under a reduced pressure. 261 mg of the 2,2,2-trifluoroacetic salt of (2S,4R)-4-(2-((1R,3R)-1-hydroxy-3-(4-methoxyphenyl)-3-((2S,3S)-3-methyl-2-((R)-1-methyl-piperidin-2-carboxamido)-pentanamido)propyl)thiazol-4-carboxami-do)-2-methyl-5-phenylpentanoic acid (99% yield) are obtained.

R$_f$=0.35 (dichloromethane/methanol 9/1 volume/volume); $^1$H NMR (400 MHz, CD$_3$OD) δ: 8.00 (s, 1H), 7.41-6.76 (m, 9H), 5.23 (dd, J=9.6, 4.0 Hz, 1H), 4.91 (dd, J=9.6, 3.9 Hz, 1H), 4.41-4.32 (m, 1H), 4.31-4.19 (m, 1H), 3.79 (s, 3H), 3.03 (q, J=12.7 Hz, 1H), 2.88 (d, J=5.5 Hz, 2H), 2.61 (s, 3H), 2.55-2.47 (m, 2H), 2.17-2.10 (m, 1H), 2.02-1.83 (m, 3H), 1.78-1.52 (m, 6H), 1.34-1.20 (m, 4H), 1.15 (d, J=7.1 Hz, 3H), 0.97 (d, J=6.7 Hz, 3H), 0.92-0.87 (m, 3H); $^{13}$C NMR (101 MHz, CD$_3$OD) δ: 182.80, 181.42, 175.74, 172.32, 166.02, 163.26, 153.68, 142.18, 138.50, 133.49, 132.36, 131.80, 130.46, 122.70, 117.95, 72.66, 63.05, 59.30, 58.89, 54.18, 52.81, 52.59, 52.37, 52.16, 51.95, 51.73, 46.07, 45.18, 40.49, 33.12, 29.00, 26.97, 25.28, 19.20, 14.34. Mass (ESI): m/z 736.2 (M$^+$+H$^+$).

Example 16.9

Synthesis of (2S,4R)-4-(2-((1R,3R)-1-acetoxy-3-(4-methoxy-phenyl)-3-((2S,3S)-3-methyl-2-((R)-1-methylpiperidin-2-carbox-amido)pentanamido)propyl) thiazol-4-carboxamido)-2-methyl-5-phenylpentanoic acid

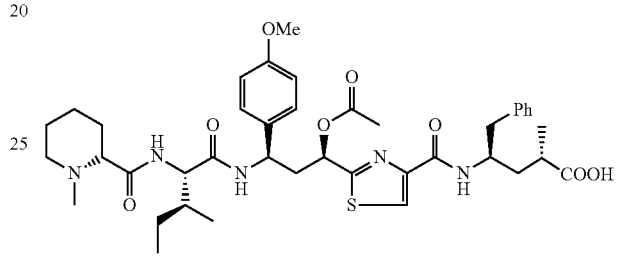

To a solution of the compound obtained in example 16.8 (0.35 mmoles) in piridine (4 ml), acetic anhydride (2 ml) is added. The reaction mixture is stirred for 12 hours. The solvent is evaporated under a reduced pressure and the crude product is purified by flash chromatography in dichloromethane/methanol 94/6 volume/volume and, in a second run, with dichloromethane/methanol 9:1 volume/volume. 264 mg of (2S,4R)-4-(2-((1R,3R)-1-acetoxy-3-(4-methoxyphenyl)-3-((2S,3S)-3-methyl-2-((R)-1-methyl piperidin-2-carboxamido)-pentanamido)propyl)-thiazol-4-carboxamido)-2-metil-5-phenil-pentanoic acid (96% yield) are obtained.

R$_f$=0.37 (dichloromethane/methanol 95/5 volume/volume); $^1$H NMR (400 MHz, CD$_3$OD) δ: 8.13 (s, 1H), 7.32-6.78 (m, 9H), 6.04 (dd, J=9.7, 3.8 Hz, 1H), 5.12 (dd, J=10.0, 4.8 Hz, 1H), 4.40-4.30 (m, 1H), 4.32-4.20 (m, 1H), 3.74 (s, 3H), 3.23 (t, J=12.8 Hz, 1H), 2.86 (d, J=6.1 Hz, 2H), 2.72-2.42 (m, 2H), 2.41 (s, 3H), 2.11 (s, 3H), 2.05-1.14 (m, 7H), 1.11 (d, J=6.7 Hz, 3H), 0.94 (d, J=6.7 Hz, 3H), 0.89 (t, J=7.1

Hz, 3H); $^{13}$C NMR (101 MHz, CD$_3$OD) δ: 182.60, 181.40, 175.78, 174.54, 173.92, 166.10, 163.50, 153.54, 142.36, 137.91, 133.38, 132.24, 131.91, 130.44, 122.70, 118.03, 73.98, 62.43, 59.20, 58.78, 53.80, 52.64, 52.21, 52.00, 51.79, 51.57, 46.46, 45.22, 43.52, 40.49, 33.44, 28.87, 23.70, 19.11, 14.10; Mass (ESI): m/z 778.2 (M$^+$+H$^+$), 800.2 (M$_+$+Na).

Example 16.10

Comparative

The compound obtained in example 16.9 has been evaluated with the cytotoxicity test in vitro on cellular lines. The cellular lines used were the following: HL60, A 2780, C6.

By using the cellular lines HL 60 and C6, GI$_{50}$ values higher than 10$^{-5}$ moles/liter were obtained.

By using the cellular line A 2780, a GI$_{50}$ value higher than 10$^{-4}$ moles/liter was obtained.

These values show that the compound of the example 16.9 in vitro, depending on the used cellular lines, were about from 10,000 times to about 100,000 times less toxic than the compounds of the present invention.

Example 17

Comparative

Example 17.1

Synthesis of tertbutyl cyclohexyl(phenylsulphonyl)-methylcarbamate

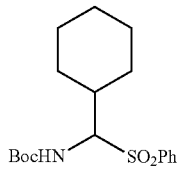

Example 16.1 was repeated but using the cyclohexancarboxyaldehyde in place of p-anisaldehyde. At the end of the process the compound tertbutyl cyclohexyl(phenyllsulphonyl)methylcarbamate was obtained with a 96% yield.

R$_f$=0.35 (n-hexane/ethyl acetate 4/6 volume/volume); $^1$H NMR (400 MHz, CDCl$_3$) δ: 1.42 (t, J=7.1 Hz, 3H), 1.38 (s, 9H); $^{13}$C NMR (101 MHz, CDCl$_3$) δ: 191.79, 167.45, 161.14, 159.27, 157.18, 155.35, 149.04, 133.82, 128.02, 114.39, 80.02, 62.25, 55.65, 51.03, 45.24, 28.70, 14.72; Mass (ESI): m/z 457.0 (M$_+$+Na).

Example 17.2

Synthesis of ethyl 2-(3-(tert-butoxycarbonylamino)-3-cyclohexyl propanoyl)thiazol-4-carboxylate

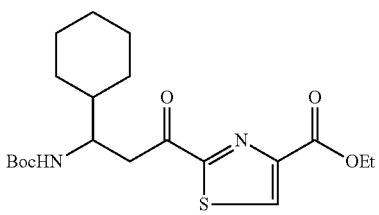 [SMILES: CCOC(=O)c1csc(C(=O)CC(NC(=O)OC(C)(C)C)C2CCCCC2)n1]

Example 16.2 was repeated but using the compound obtained in example 17.1 instead of the compound obtained in example 16.1. At the end of the process the compound ethyl 2-(3-(tertbutoxycarbonylamino)-3-cyclohexyl propanoyl)thiazol-4-carboxylate was obtained in a 62% yield.

R$_f$=0.41 (n-hexane/ethyl acetate 3/7 volume/volume); $^1$H NMR (400 MHz, CDCl$_3$) δ: 8.37 (s, 1H), 4.79 (br s, 1H), 4.39 (q, J=7.1 Hz, 2H), 3.96 (m, 1H), 3.38—3.22 (m, 2H), 1.80-1.48 (m, 6H), 1.37 (t, J=7.1 Hz, 3H), 1.32 (s, 9H), 1.22-0.96 (m, 5H); $^{13}$C NMR (101 MHz, CDCl$_3$) δ: 192.84, 167.75, 161.09, 155.81, 149.03, 133.49, 79.35, 62.02, 52.74, 42.35, 41.72, 30.20, 29.22, 28.64, 26.60, 26.42, 26.38, 14.61; Mass (ESI): m/z 433.1 (M$^+$+Na).

Example 17.3

Synthesis of ethyl 2-((1R,3R)-3-(tert-butoxycarbonylamino)-3-cyclohexyl-1-hydroxypropyl)thiazol-4-carboxylate

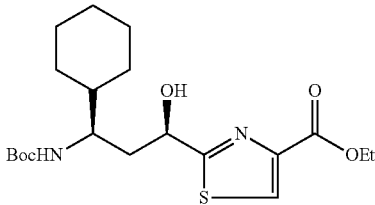 [SMILES: CCOC(=O)c1csc([C@H](O)C[C@@H](NC(=O)OC(C)(C)C)C2CCCCC2)n1]

Example 16.3 was repeated but using the compound obtained in example 17.2 instead of the compound obtained in example 16'.2. At the end of the process the compound ethyl 2-((1R,3R)-3-(tertbutoxycarbonylamino)-3-cyclohexyl-1-hydroxy-propyl)-thiazol-4-carboxylate was obtained with a 51% yield.

R$_f$=0.34 (n-hexane/ethyl acetate 55/45 volume/volume); $^1$H NMR (400 MHz, CDCl$_3$) δ: 8.06 (s, 1H), 5.10 (br s, 1H), 4.96-490 (m, 1H), 4.70-4.56 (m, 1H), 4.37 (q, J=7.1 Hz, 2H), 3.67-3.60 (m, 1H), 2.36-2.33 (m, 1H), 1.96-1.63 (m, 6H), 1.37 (s, 9H), 1.35 (t, J=7.1 Hz, 3H), 1.30-0.80 (m, 5H); $^{13}$C NMR (100.5 MHz, CDCl$_3$) δ 177.83, 161.88, 157.08, 146.94, 127.69, 80.29, 71.55, 61.64, 53.57, 43.06, 41.62, 30.03, 28.74, 28.44, 26.66, 26.53, 26.50, 14.69; Mass (ESI) m/z: 435.1 (M++Na).

Example 17.4

Synthesis of ethyl 2-((1R,3R)-3-((2S,3R)-2-(tert-butoxy-carbonylamino)-3-methyl-pentanamido)-3-cyclohexyl-1-hydroxy-propyl)-thiazol-4-carboxylate

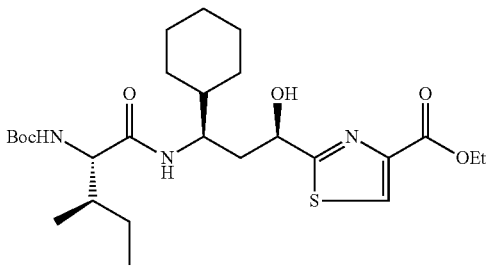

Example 16.4 was repeated but using the compound obtained in example 17.3 instead of the compound obtained in example 16.3. At the end of the process the compound ethyl 2-((1R,3R)-3-((2S,3R)⁻2-(tert-butoxycarbonylamino)-3-methyl-pentanamido)-3-cyclohexyl-1-hydroxypropyl)thiazol-4-carboxylate was obtained with a 97% yield.

$R_f$=0.52 (n-hexane/ethyl acetate 1/1 volume/volume); $^1$H NMR (40.0 MHz, CDCl$_3$) δ: 8.05 (s, 1H), 6.45 (br s, 1H), 5.67 (br s, 1H), 5.23 (d, J=8.2 Hz, 1H), 4.97 (d, J=8.3 Hz, 1H), 4.37 (q, J=7.1 Hz, 2H), 4.01 (s, 1H), 3.70 (t, J=7.1 Hz, 1H), 2.47-2.38 (m, 1H), 1.90-1.38 (m, 9H), 1.36 (s, 9H), 1.35 (t, J=7.1 Hz, 3H), 1.30-0.95 (m, 5H), 0.92 (d, J=6.7 Hz, 3H), 0.86 (t, J=7.9 Hz, 3H); $^{13}$C NMR (101 MHz, CDCl$_3$) δ: 178.28, 172.74, 161.92, 156.91, 147.42, 127.78, 80.75, 71.40, 61.63, 60.66, 53.56, 42.93, 41.24, 36.83, 30.08, 28.74, 28.64, 26.70, 26.53, 26.46, 19.64, 16.12, 14.68, 14.40, 11.4; Mass (ESI) m/z: 548.2 (M++Na).

Example 17.5

Synthesis of 2-((1R,3R)-3-((2S,3R)-2-(tert-butoxy-carbonyl amino)-3-methylpentanamido)-3-cyclohexyl⁻1⁻hydroxypropyl)⁻thiazol-4-carboxylic acid

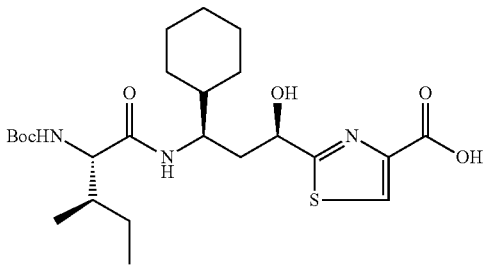 [SMILES: CCOC(=O)c1csc([C@H](O)C[C@@H](NC(=O)[C@@H](NC(=O)OC(C)(C)C)[C@H](C)CC)C2CCCCC2)n1]

Example 16.5 was repeated but using the compound obtained in example 17.4 instead of the compound obtained in example 16.4. At the end of the process the compound 2-((1R,3R)-3-((2S,3R)⁻2-(tert-butoxycarbonyl amino)-3-methylpentanamido)⁻3⁻cyclohexyl-1-hydroxy propyl)thiazol-4-carboxylic acid was obtained with a 98% yield.

$R_f$-0.40 (dichloromethane/methanol 9/1 volume/volume); $^1$H NMR (400 MHz, CDCl$_3$) δ: 9.09 (br s, 1H), 8.00 (s, 1H), 6.88 (br s, 1H), 5.75 (br s, 1H), 5.08-5.01 (m, 1H), 4.98-4.95 (m, 1H), 4.02-3.80 (m, 2H), 2.25-2.13 (m, 1H), 1.93-1.45 (m, 9H), 1.36 (s, 9H), 1.28-0.93 (m, 5H), 0.91 (d, J=6.7 Hz, 3H), 0.85 (t, J=79 Hz, 3H); $^{13}$C NMR (101 52.77, 42.62, 36.93, 30.01, 29.92, 28.64, 26.68, 26.47, 25.19, 21.22, 16.07, 14.55, 1134; Mass (ESI): m/z 520.2 (M+Na).

Example 17.6

Synthesis of (2S,4R)-methyl 4-(2-((1R,3R)-3-((2S,3S)-2-(tertbutoxycarbonylamino)-3-methylpentanamido)-3-cyclohexyl-1-hydroxypropyl)thiazol-4-carboxyamido-2-methyl-5-phenylpentanoate

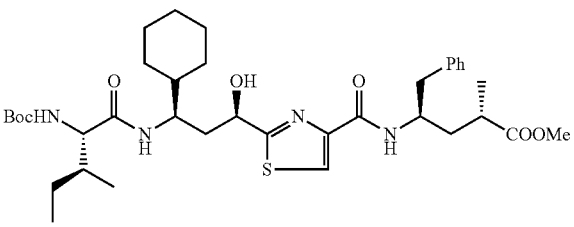 [SMILES: CC[C@H](C)[C@H](NC(=O)OC(C)(C)C)C(=O)N[C@H](C[C@@H](O)c1nc(C(=O)N[C@@H](Cc2ccccc2)C[C@H](C)C(=O)OC)cs1)C1CCCCC1]

Example 16.6 was repeated but using the compound of example 17.5 instead of the compound obtained in example 16.5. At the end of the process the compound (2S,4R)-methyl-4-(2-((1R,3R)-3-((2S,3S)-2-(tert-butoxycarbonylamino)-3-methylpent-anamido)⁻3⁻cyclohexyl-1-hydroxypropyl)thiazol-4-carboxyamido)-2-methyl-5-phenylpentanoate was obtained with a 75% yield. $R_f$=0.47 (n-hexane/ethyl acetate 35/65 volume/volume);

$^1$H NMR (400 MHz, CDCl$_3$) δ 7.94 (s, 1H), 7.35-7.11 (m, 5H), 6.44 (br s, 1H), 5.41 (br s, 1H), 5.25 (d, J=7.1 Hz, 1H), 4.74-4.84 (m, 1H), 4.42-4.31 (m, 1H), 4.16-4.05 (m, 1H), 3.77-3.66 (m, 1H), 3.61 (s, 3H), 2.98-2.84 (m, 2H), 2.66-2.54 (m, 1H), 2.26 (d, J=14.5 Hz, 1H), 2.11-1.96 (m, 2H), 1.95-1.41 (m, 9H), 1.36 (s, 9H), 1.30-0.95 (m, 5H), 1.15 (d, J=7.1 Hz, 3H), 0.97 (d, J=6.6 Hz, 3H), 0.89 (t, J=7.3 Hz, 8H); $^{13}$O NMR (101 MHz, CDCl$_3$) δ: 177.01, 176.61, 172.59, 161.28, 150.42, 138.20, 129.93, 128.65, 126.76, 123.16, 80.77, 70.95, 60.85, 53.22, 52.02, 48.88, 43.28, 41.50, 41.13, 38.38, 36.94, 30.09, 28.92, 28.62, 26.76, 26.58, 26.53, 25.46, 18.10, 16.19, 14.41, 11.38; Mass (EST) m/z: 723.2 (M++Na).

Example 17.7

Synthesis of (2S,4R)-methyl 4-(2-((1R,3R)-3-cyclohexyl-1-hydroxy-3-((2S,3S)-3-methyl-2-((R)-1-methy piperidin-2-carboxyamido)pentanamido)propyl)thiazol-4-carboxamido)-2-methyl-5-phenylpentanoate

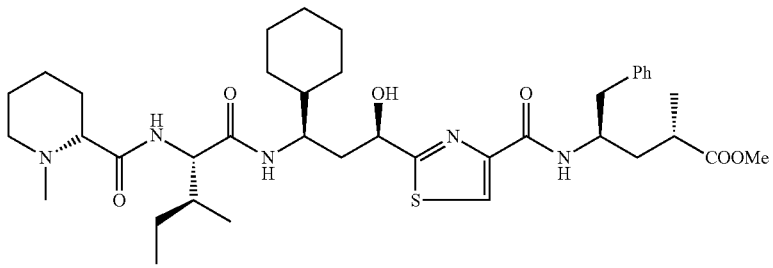

Example 16.7 was repeated but using the compound obtained in example 17.6 in place of the compound obtained in example 16.6. At the end of the process the compound (2S,4R)-methyl 4-(2-((1R,3R)-3-cyclohexyl-1-hydroxy-3-((2S,3S)-3-methyl-2-((R)-1-methyl piperi-din-2-carboxamido)pentanamido)propyl)-thiazol-4-carboxamido)-2-methyl-5-phenyl pentanoate was obtained with a 97% yield.

$R_f$=0.47 (dichloromethane/methanol 9/1 volume/volume); $^1$H NMR (400 MHz, CD$_3$OD) δ 7.89 (s, 1H), 7.33-7.07 (m, 5H), 4.85 4.81 (m, 1H), 4.34-4.26 (m, 1H), 4.24-4.14 (m, 1H), 4.16-4.10 (m, 1H), 3.61 (s, 3H), 3.31-3.29 (m, 1H), 3.01-2.80 (m, 3H), 2.71-2.59 (m, 1H), 2.55-2.43 (m, 1H), 2.14 (s, 3H), 2.07-0.71 (m, 24H), 1.17 (d, J=7.1 Hz, 3H), 0.98 (dd, J=6.6 Hz, 3H), 0.90 (t, J=7.4 Hz, 3H); $^{13}$C NMR (101 MHz, CD$_3$OD) δ 181.62, 180.73, 178.94, 175.48, 166.09, 165.94, 142.53, 133.54, 132.20, 130.41, 122.70, 73.62, 73.31, 55.55, 53.07, 52.86, 52.64, 52.43, 52.22, 52.00, 51.79, 48.23, 47.04, 45.34, 44.04, 42.51, 40.92, 40.69, 34.49, 32.72, 30.38, 29.16, 29.05, 27.26, 21.71, 19.55, 14.37; Mass (ESI) m/z: 749.3 (M$^+$+Na).

Example 16.8 was repeated but using the compound obtained in example 17.7 instead of the compound obtained in example 16.7. At the end of the process the compound 2,2,2-trifluoroacetic salt of the (2S,4R)-methyl 4-(2-((1R,3R)-3-cyclohexyl-1-hydroxy-3-((2S,3S)-3-methyl-2-((R)-1-methyl-piperidin-2-carboxyamido)pentanamido) propyl) thiazol-4-carboxamido)-2-methyl-5-phenyl pen-tanoic acid was obtained with a 82% yield.

$R_f$=0.35 (dichloromethane/methanol 9/1 volume/volume); $^1$H NMR (400 MHz, CD$_3$OD) δ: 7.99 (s, 1H), 7.32-7.08 (m, 5H), 4.80-4.67 (m, 1H), 4.29-4.15 (m, 1H), 4.10-3.98 (m, 1H), 3.30 3.26 (m, 1H), 3.02-2.88 (m, 1H), 2.74-2.61 (m, 1H), 2.54-2.42 (m, 1H), 2.13 (s, 3H), 2.08-0.78 (m, 24H), 1.18 (d, J=7.0 Hz, 3H), 0.96 (d, J=6.8 Hz, 3H), 0.90 (t, J=7.1 Hz, 3H); $^{13}$C NMR (101 MHz, CD$_3$OD) δ: 183.17, 180.73, 179.27, 175.44, 166.14, 153.56, 142.48, 133.51, 132.32, 130.44, 127.06, 73.39, 73.33, 55.54, 53.02, 52.81, 52.59, 52.38, 52.17, 51.95, 51.74, 47.12, 45.06, 44.03, 42.39, 40.93, 40.59, 33.93, 32.90, 30.31, 29.05, 28.99, 27.00, 21.27, 19.49, 14.66; Mass (ESI) m/z: 734.2 (M$^+$+Na).

Example 17.8

Synthesis of the 2,2,2-trifluoroacetic salt of (2S,4R)-methyl 4-(2-((1R,3R)-3-cyclohexyl-hydroxy-3-((2S,3S)-3-methyl-2-((R)-1-methylpiperidin-2-carboxyamido)pentanamido)-propyl)thiazol-4-carboxamido)-2-methyl-5-phenylpentanoic acid

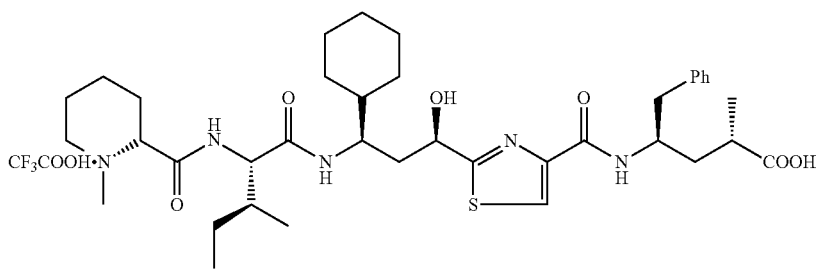

Example 17.9

Synthesis of (2S,4R)-4-(2-((1R,3R)-1-acetoxy-3-cyclohexyl-3-((2S',3S-3-methyl-2-((R)-1-methylpiperidin-2-carboxamido)pentan-amido)propyl)thiazol-4-carboxamido)-2-methyl-5-phenyl pentanoic acid

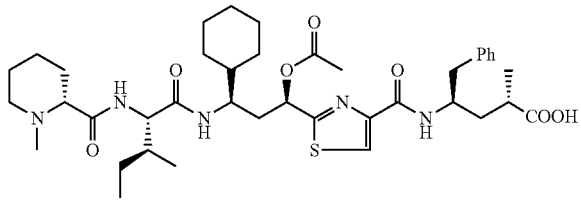 [SMILES: CC[C@H](C)[C@H](NC(=O)[C@H]1CCCCN1C)C(=O)N[C@H](C[C@@H](OC(C)=O)c1nc(C(=O)N[C@@H](Cc2ccccc2)C[C@H](C)C(=O)O)cs1)C1CCCCC1]

Example 16.9 was repeated but using the compound obtained in example 17.8 instead of the compound obtained in example 16.8. At the end of the process the compound (2S,4R)-4-(2-((1R,3R)-1-acetoxy-3-cyclohexyl-3-((2S,3S)-3-methyl-2-((R)-1-methyl-piperidin-2-carboxamido)pentanamido)propyl)thiazol-4-carboxamido)-2-methyl-5-phenyl pentanoic acid was obtained with a 91% yield.

$R_f$=0.38 (dichloromethane/methanol 9/1 volume/volume); $^1$H NMR (400 MHz, CD$_3$OD) δ: 7.99 (s, 1H), 7.26-7.09 (m, 5H), 4.46-4.31 (m, 1H), 4.30-1.19 (m, 1H), 4.09-3.95 (m, 1H), 3.23-3.12 (m, 1H), 3.02-2.86 (m, 1H), 2.77-2.54 (m, 1H), 2.53-2.41 (m, 1H), 2.48 (s, 3H), 2.12 (s, 3H), 2.08-0.87 (m, 24H), 1.19 (d, J=6.9 Hz, 3H), 0.99 (d, J=6.9 Hz, 3H), 0.91 (t, J-7.2 Hz, 3H); $^{13}$C NMR (101 MHz, CD$_3$OD) δ: 175.51, 175.20, 173.75, 173.20, 165.45, 165.26, 153.49, 142.52, 133.07, 131.65, 129.74, 127.11, 74.88, 72.18, 58.85, 54.03, 53.56, 52.15, 51.94, 51.72, 51.51, 51.30, 51.09, 50.87, 46.55, 46.50, 44.24, 42.57, 40.65, 40.29, 33.38, 33.20, 32.41, 31.31, 30.02, 29.79, 28.50, 27.64, 23.32, 21.11, 18.72, 13.60; Mass (ESI) m/z: 776.7 (M$^+$+Na).

Example 17.10

Comparative

The cytotoxicity of the compound of the example 17.9 comparative was evaluated as described in example 16.10 comparative for the compound 16.9.

A GI$_{50}$ value of 10$^{-5}$ Moles/liter was found. This value is 10,000 times higher than the GI$_{50}$ of the compounds of the invention. The same comments reported in the example 16.10 Comparative can be repeated.

---

The invention claimed is:

1. Tubulysin compounds of formula (A) having a high cytotoxicity

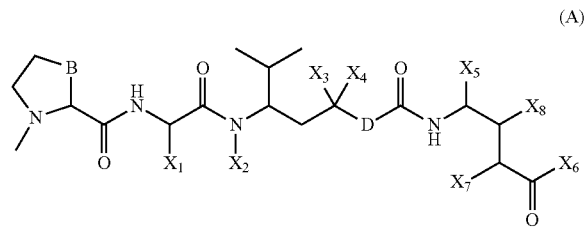

wherein:
B is selected from $CH_2$, $CH_2$—$CH_2$ or $CH_2$—$CH_2$—$CH_2$,
D is a heteroaryl having 5 or 6 atoms in the ring,
$X_1$ is alkyl or alkenyl,
$X_2$ is selected from the following groups:
  $X_{2a}$, substituted or non substituted, is selected from: aryl, heteroaryl, arylalkyl, cycloalkylalkyl, heterocycloalkylalkyl, or heteroarylalkyl, and
  $X_{2b}$: alkylene-O-alkyl, wherein alkylene is $C_2$-$C_{10}$,
$X_3$ is H,
$X_4$ is selected from OH, $(OR_5)_n$—$OR_6$, $OC(O)R_7$,
$R_5$ is an alkylene,
n is zero or an integer from 1 to 10,
$R_6$ and $R_7$, equal to or different from each other, have the following meanings:
  z1: H, alkyl,
  z2 substituted or non substituted: aryl, heteroaryl, cycloalkyl, heterocycloalkyl, arylalkyl, hetero-arylalkyl, cycloalkylalkyl, heterocycloalkylalkyl,
$X_5$ is substituted or non-substituted aryl or arylalkyl,
$X_6$ is OH,
$X_7$ is H, alkyl or alkenyl,
$X_8$ is selected from H, alkyl or alkenyl,
and their hydrates, solvates and pharmaceutically acceptable salts.

2. Compounds according to claim 1 in the form of geometrical isomers and stereoisomers, or their mixtures.

3. Compounds according to claim 1 wherein the atoms are in their isotopic forms.

4. Compounds according to claim 1, wherein D has the meaning of formula (V):

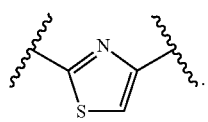

5. Compounds according to claim 1 wherein:
B is $CH_2$—$CH_2$,
D is an heteroaryl of formula (V),
$X_1$ is a $C_1$-$C_6$ alkyl,
$X_2$ is selected from the following groups:
  monocyclic aryl, monocyclic heteroaryl, monocyclic arylalkyl, monocyclic cycloalkylalkyl, monocyclic heterocycloalkylalkyl, or monocyclic heteroarylalkyl,
  alkylene-O-alkyl, wherein alkylene is $C_2$-$C_4$,
$X_3$ is H,
$X_4$ is selected from $(OR_5)_n$—$OR_6$, $OC(O)R_7$,
$R_5$ is a $C_1$-$C_2$ alkylene,
n is zero or an integer from 1 to 4,
$R_6$ and $R_7$, equal to or different from each other, are selected from H or $C_1$-$C_6$ alkyl,
$X_5$ is monocyclic arylalkyl,
$X_6$ is OH,
$X_7$ is selected from $C_1$-$C_6$ alkyl or $C_2$-$C_6$ alkenyl,
$X_8$ has the meaning of H.

6. Compounds according to claim 1 having formula (A1):

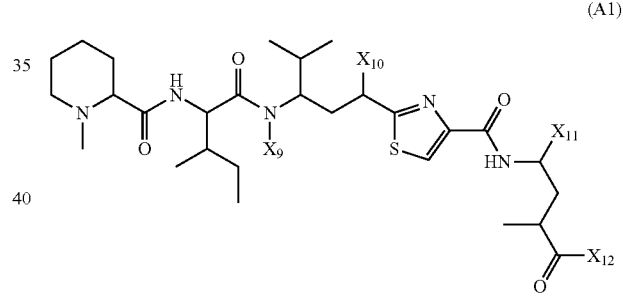

$X_9$ is selected from:
  monocyclic arylalkyl, monocyclic cycloalkylalkyl, monocyclic heterocycloalkylalkyl, or monocyclic heteroarylalkyl, non substituted or substituted with the groups which are substituents of $X_{2a}$,
  CH—$CH_2$O-alkyl wherein alkyl is $C_1$-$C_3$, wherein $C_3$ is linear or branched,
$X_{10}$ is $(OR_{10})_m$—$OR_{11}$ or $OC(O)R_{12}$,
$R_{10}$ is a $C_1$-$C_2$ alkylene,
m is zero or an integer from 1 to 3,
$R_{11}$ and $R_{12}$, equal to or different from each other, are selected from H or $CH_3$,
$X_{11}$ is substituted or non-substituted monocyclic arylalkyl,
$X_{12}$ is OH.

7. Compounds according to claim 1 having the following formulae:

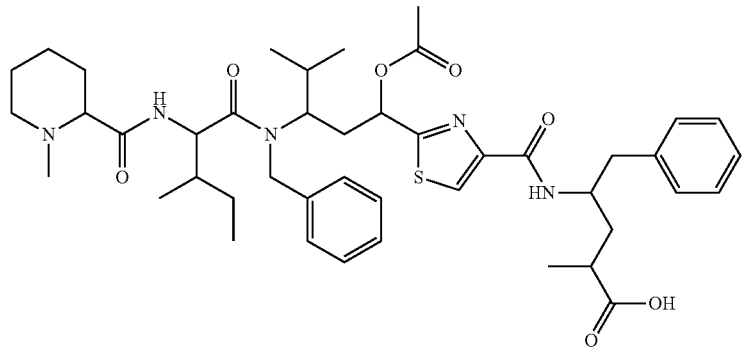
(AI)
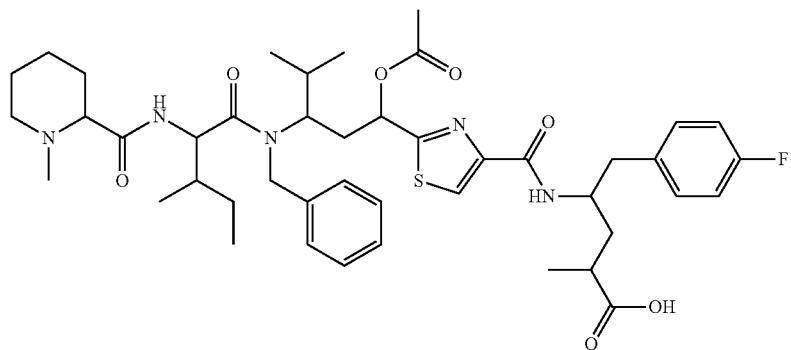
(AII)
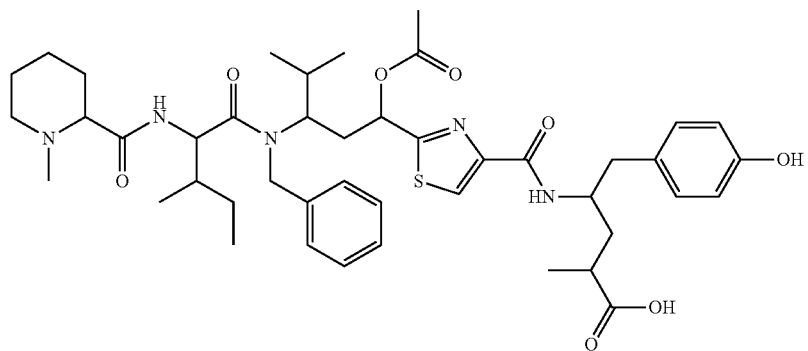
(AIII)
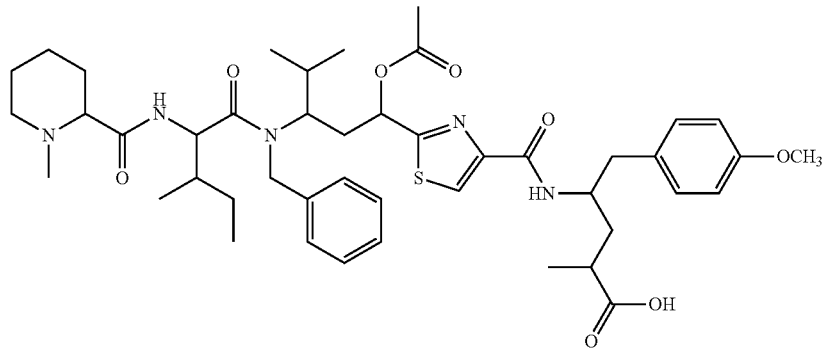
(AIV)

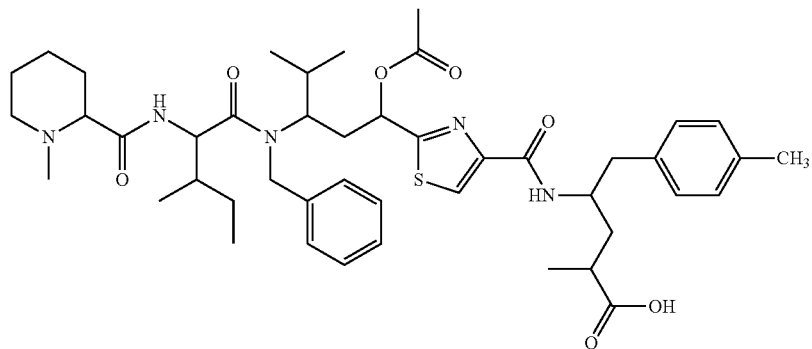
(AV)
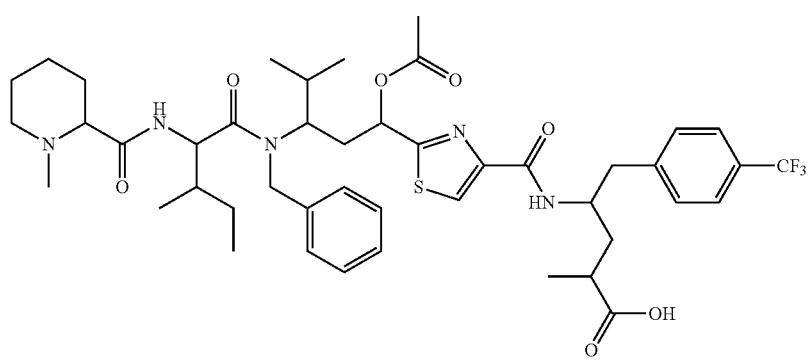
(AVI)
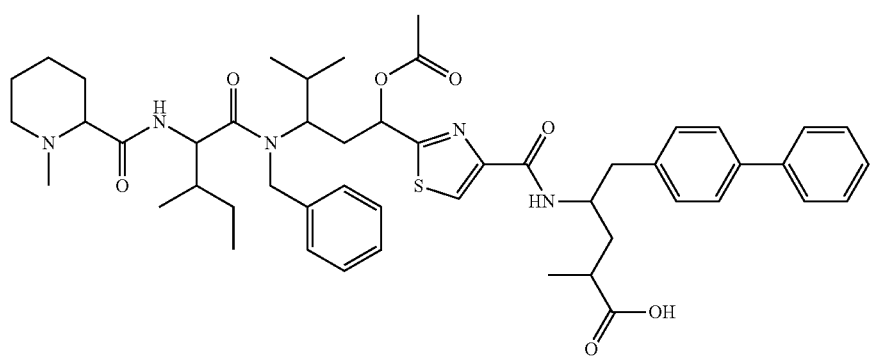
(AVII)
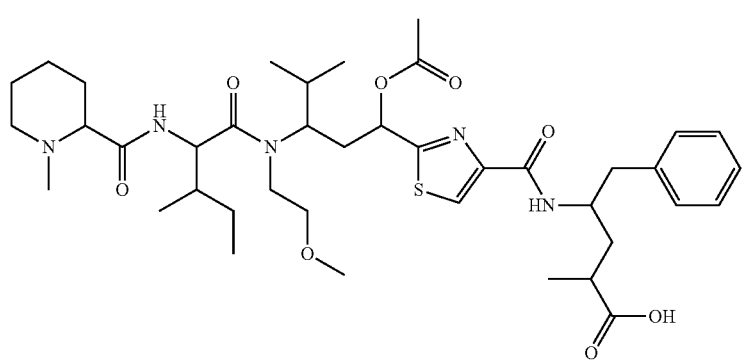
(AVIII)

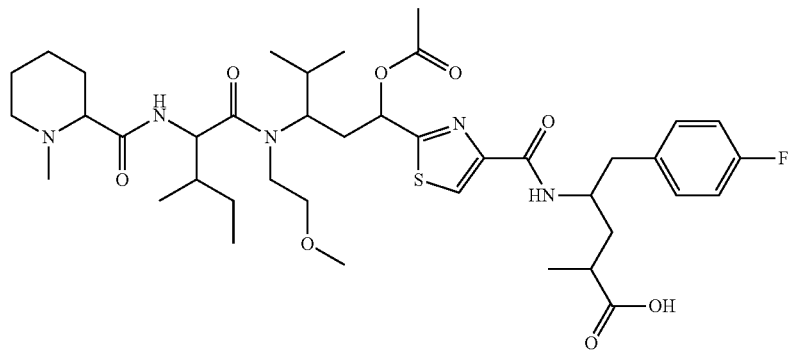
(AIX)
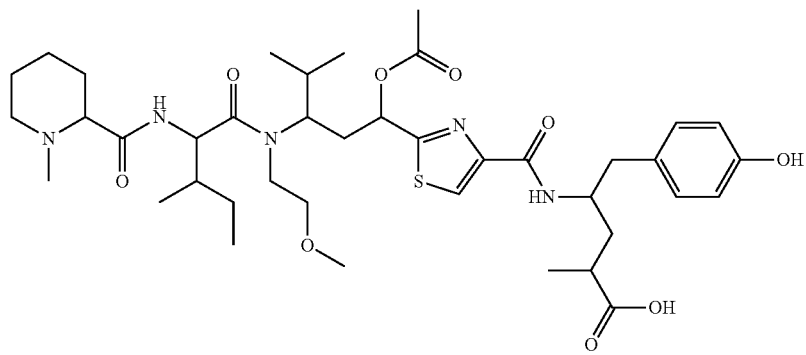
(AX)
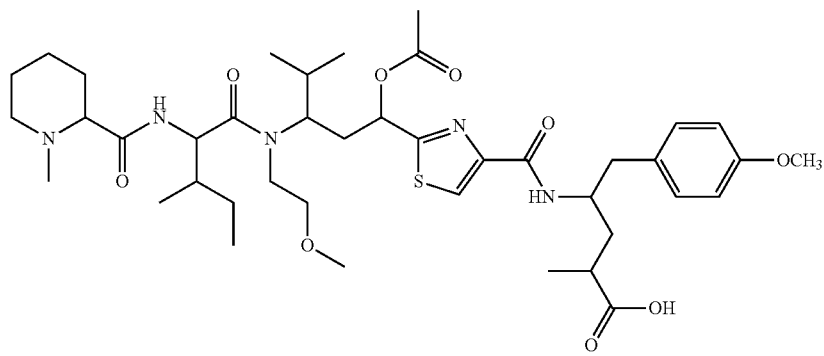
(AXI)
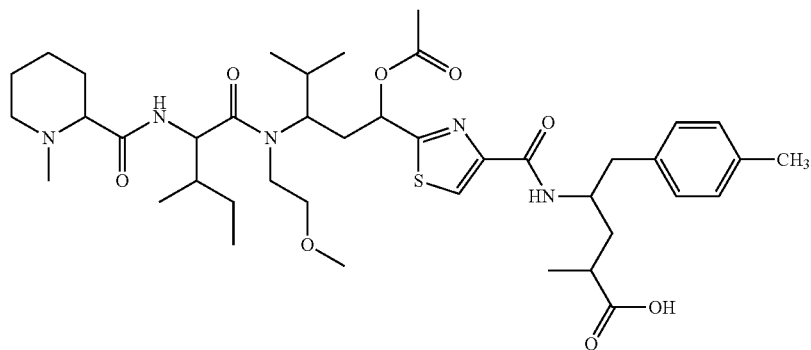
(AXII)

(AXIII)
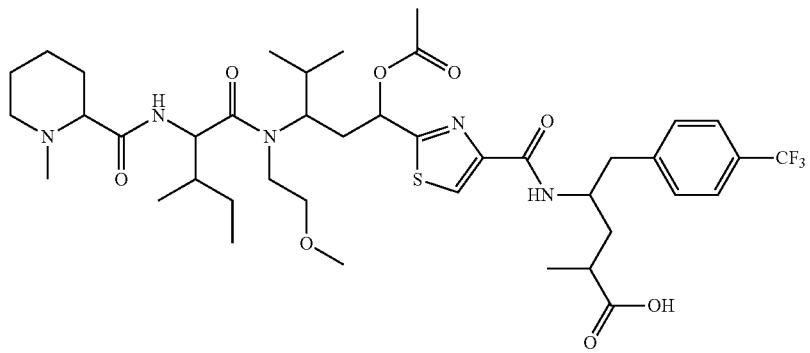
(AXIV)
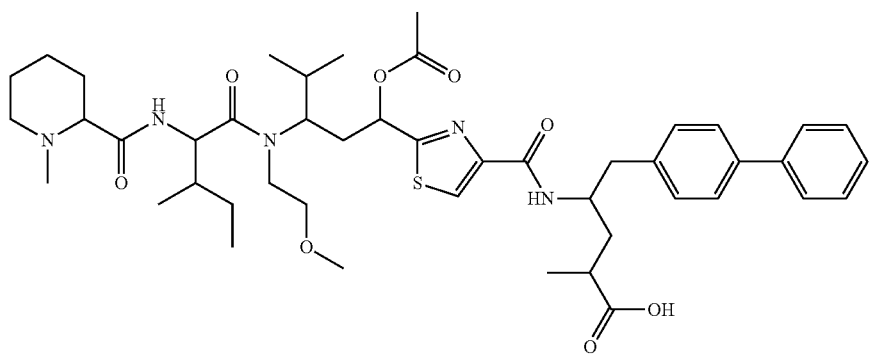
(AXV)
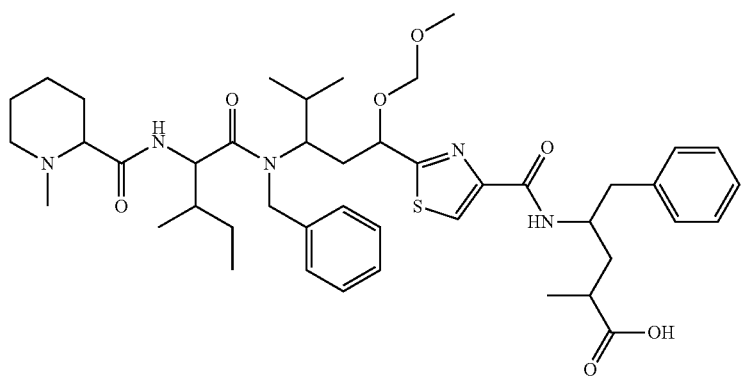
(AXVI)
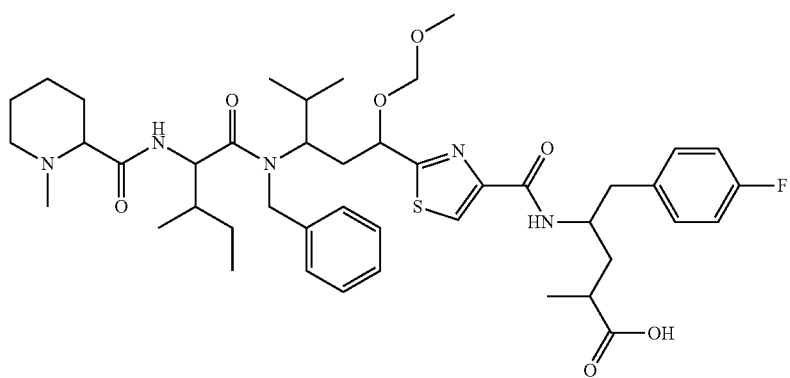

-continued
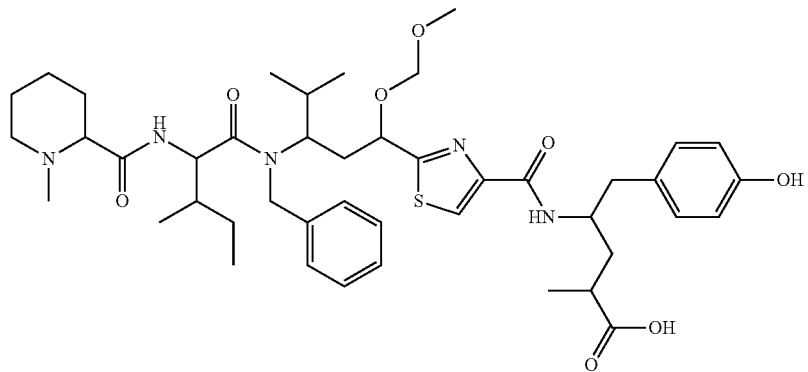
(AXVII)
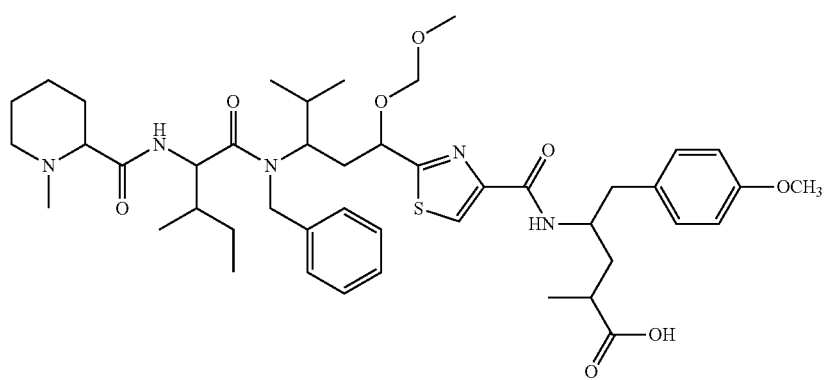
(AXVIII)
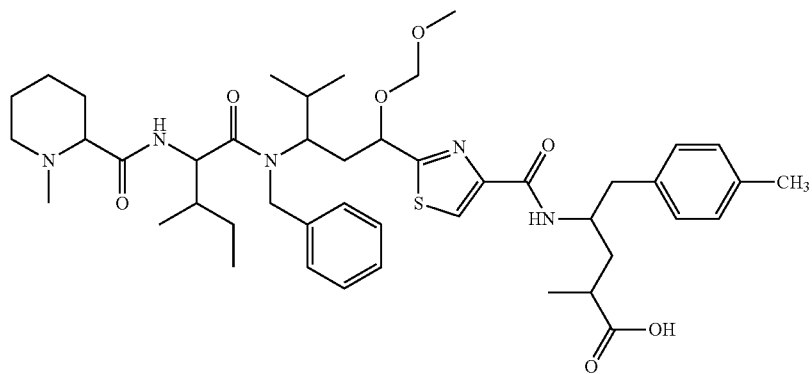
(AXIX)
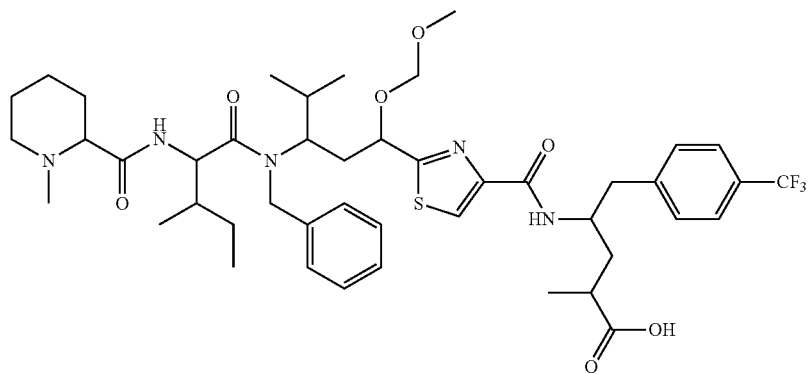
(AXX)

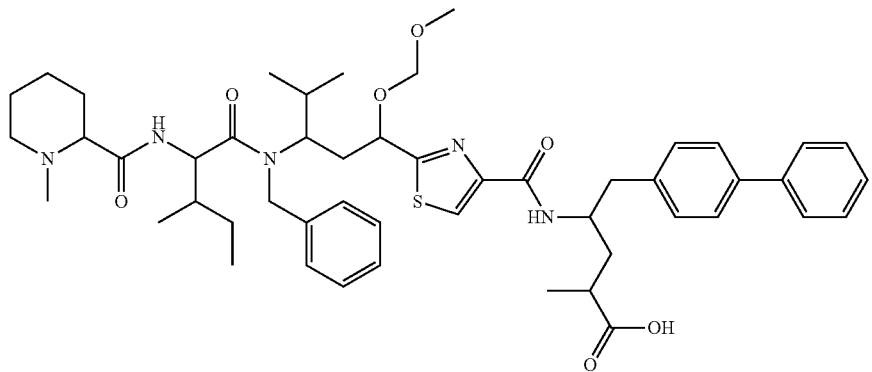
(AXXI)
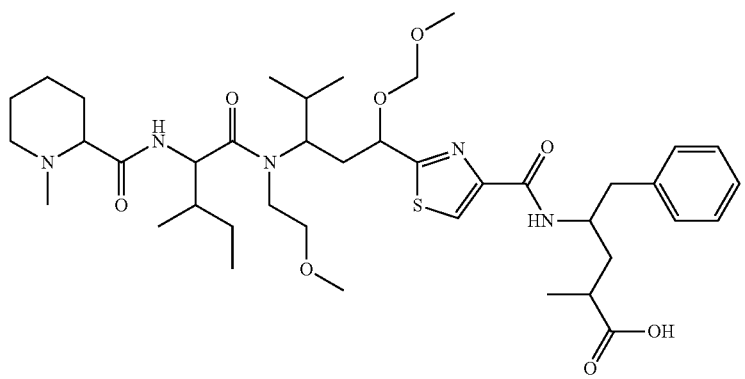
(AXXII)
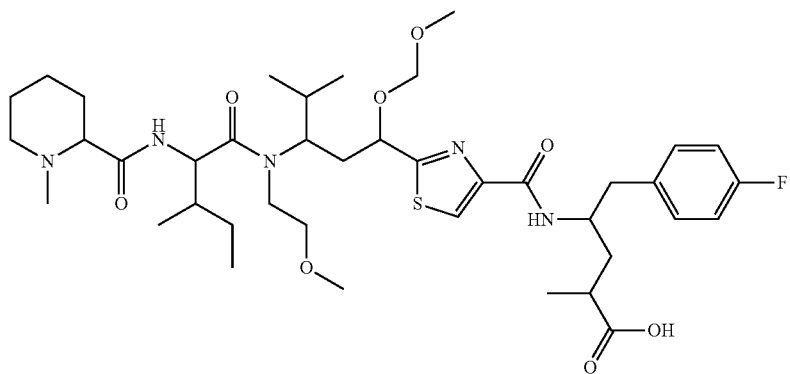
(AXXIII)
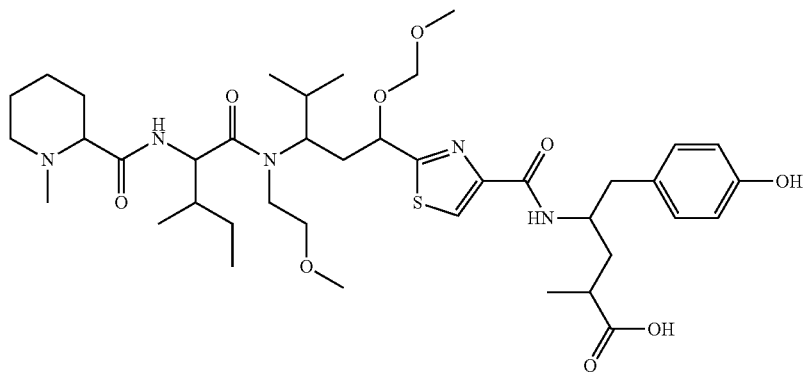
(AXXIV)

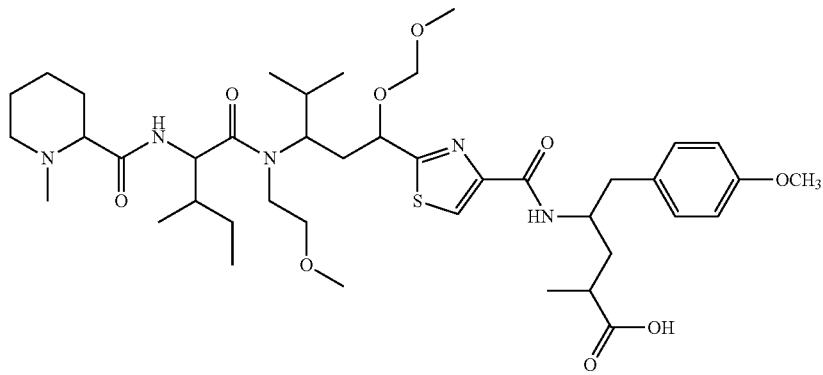
(AXXV)
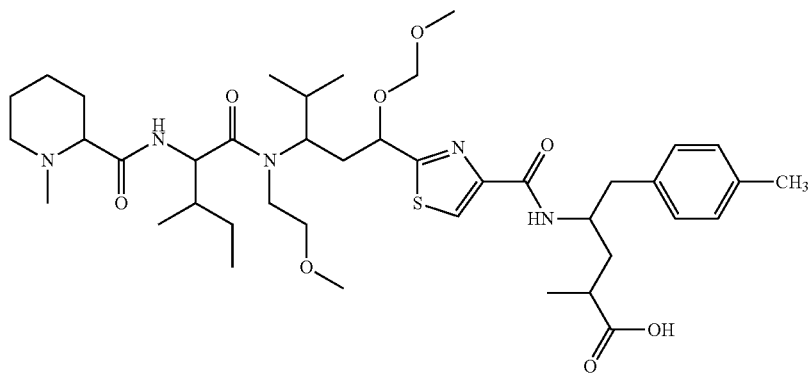
(AXXVI)
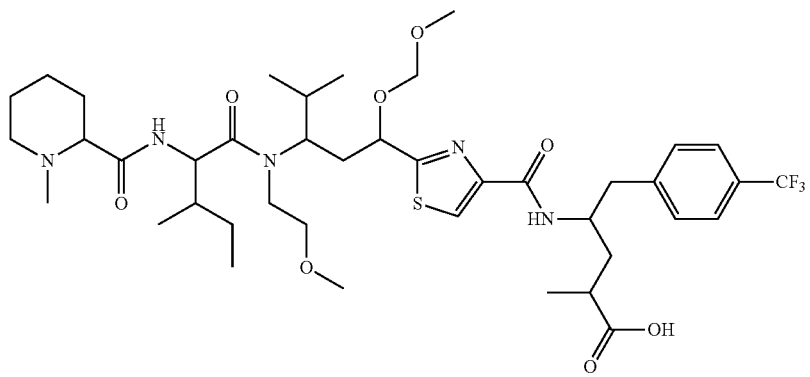
(AXXVII)
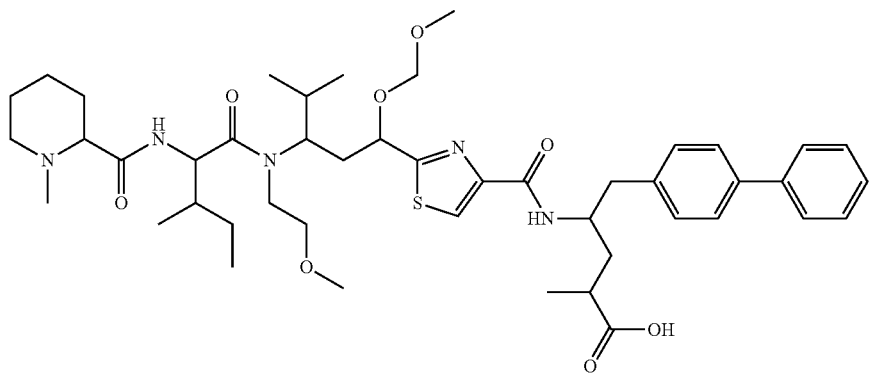
(AXXVIII)

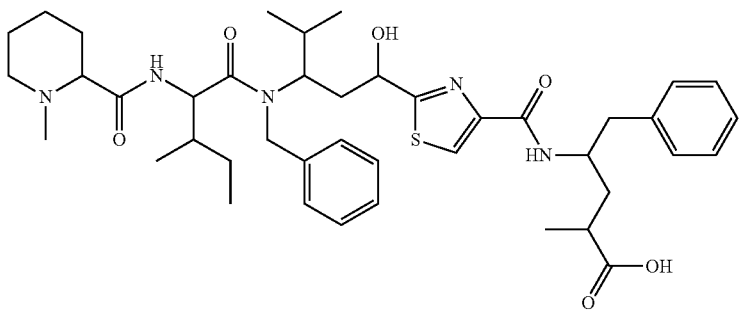
(AXXIX)
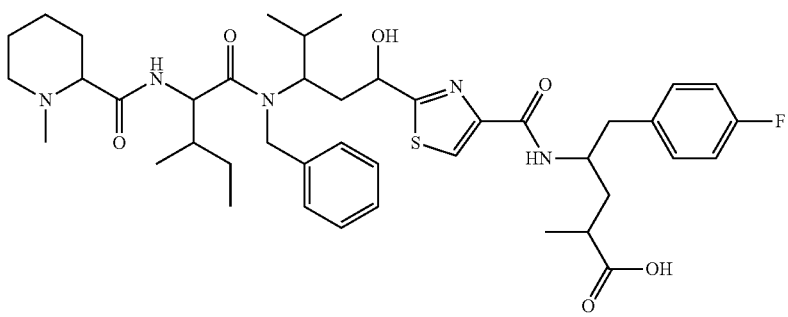
(AXXX)
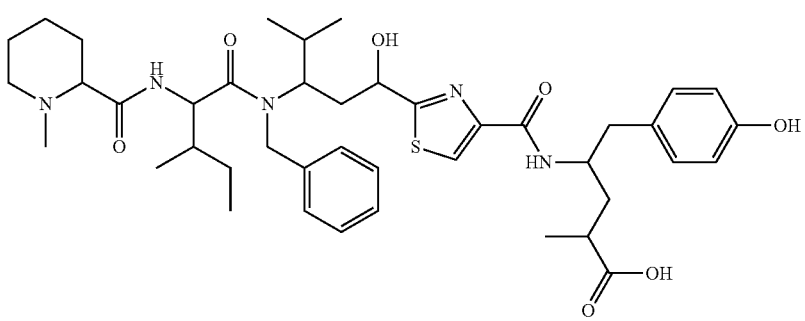
(AXXXI)
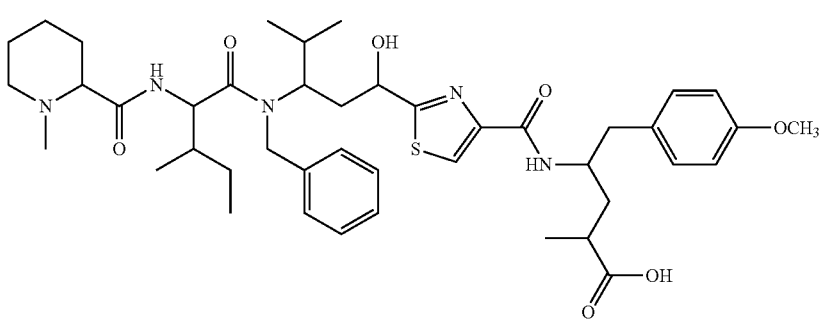
(AXXXII)
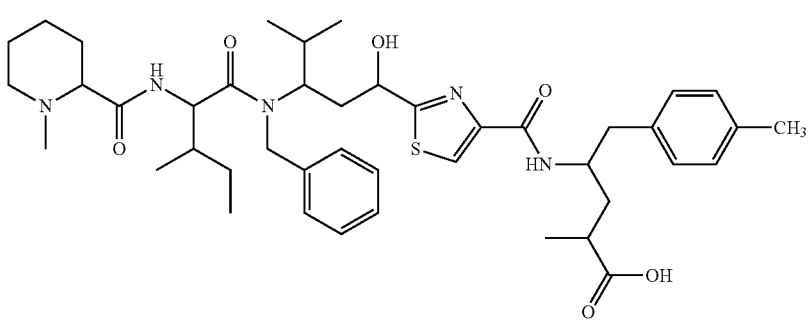
(AXXXIII)

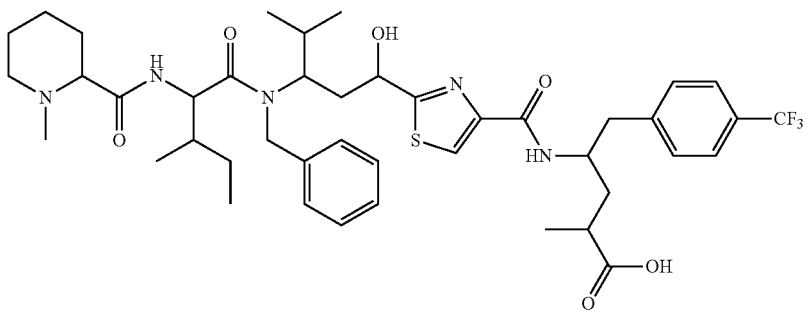
(AXXXIV)
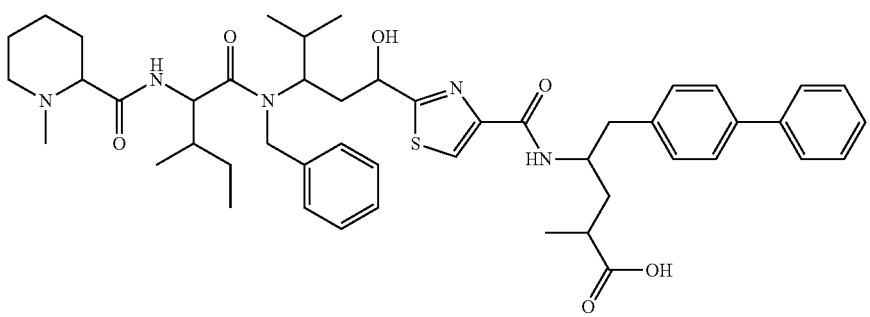
(AXXXV)
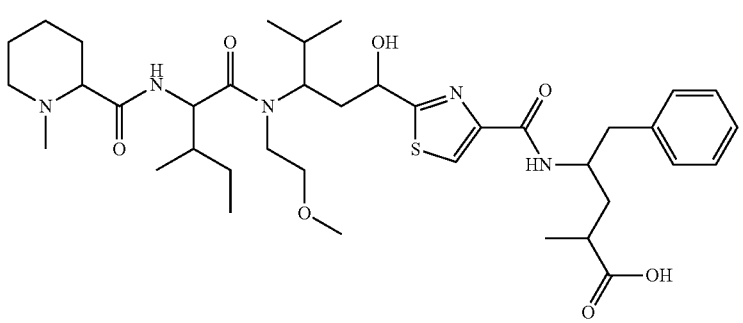
(AXXXVI)
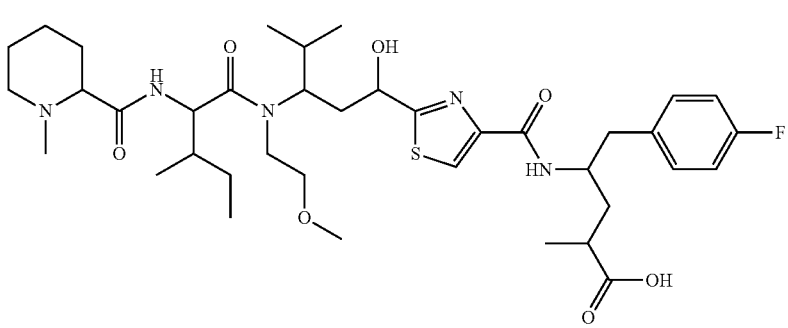
(AXXXVII)
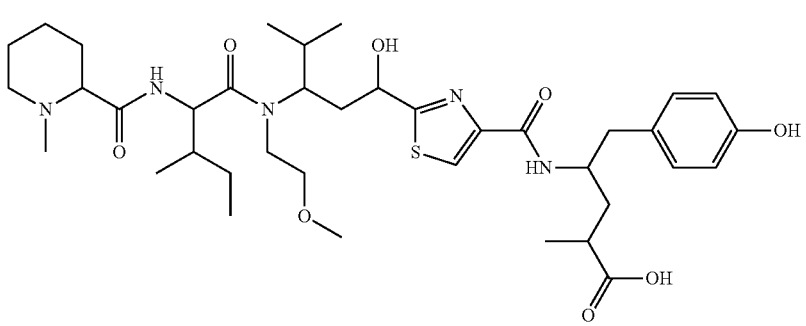
(AXXXVIII)

(AXXXIX)
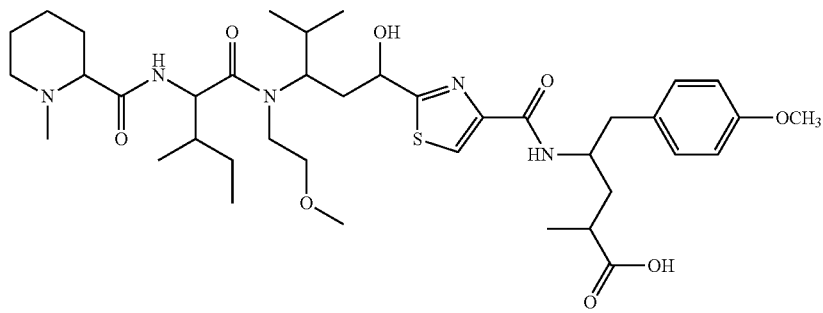
(AXL)
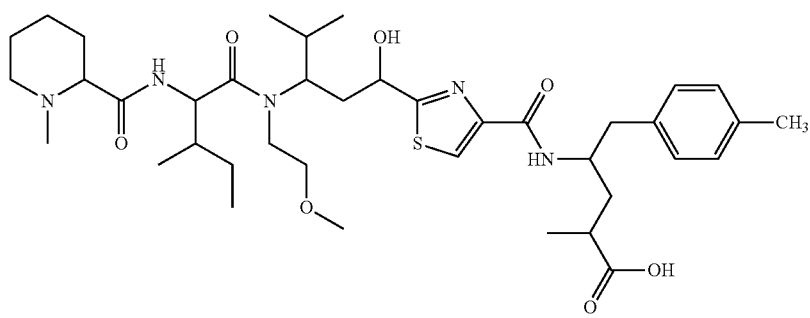
(AXLI)
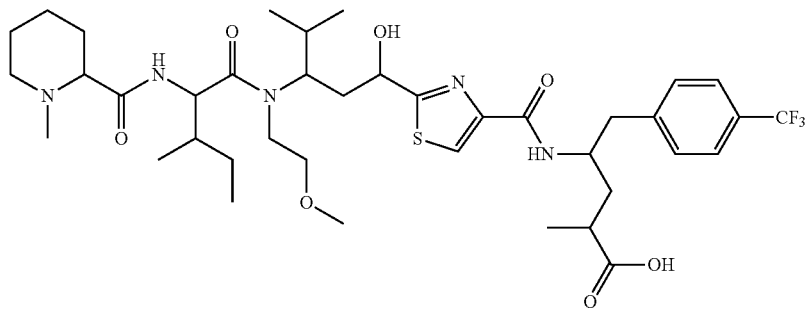
(AXLII)
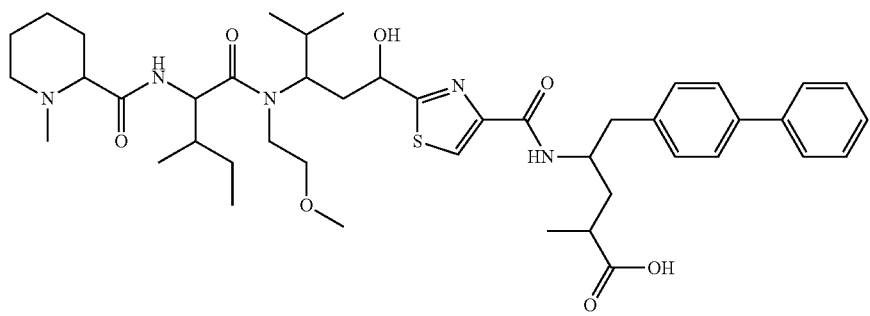
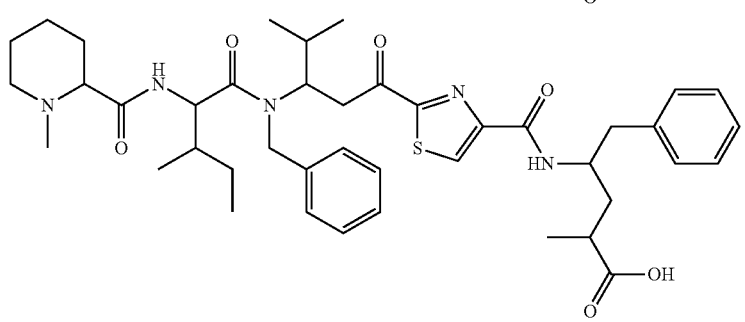

-continued
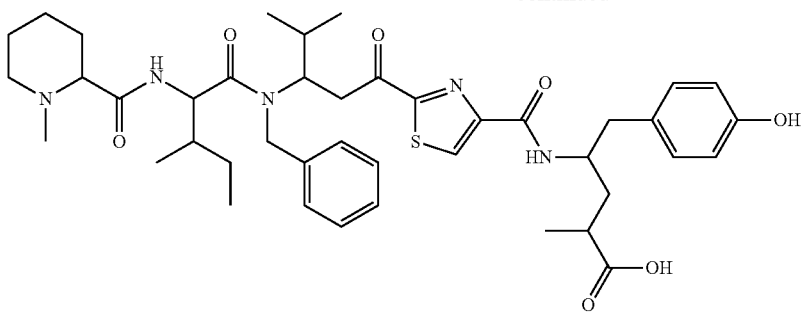
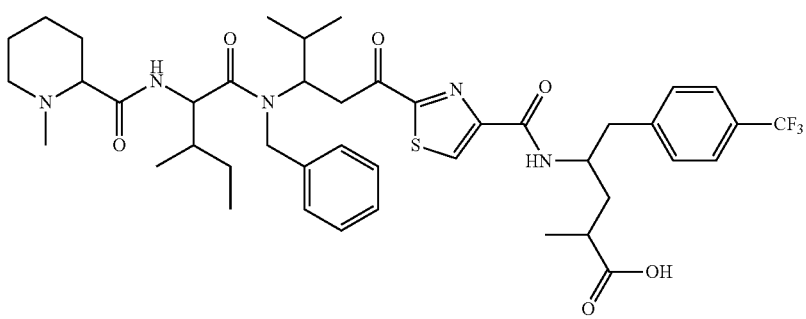
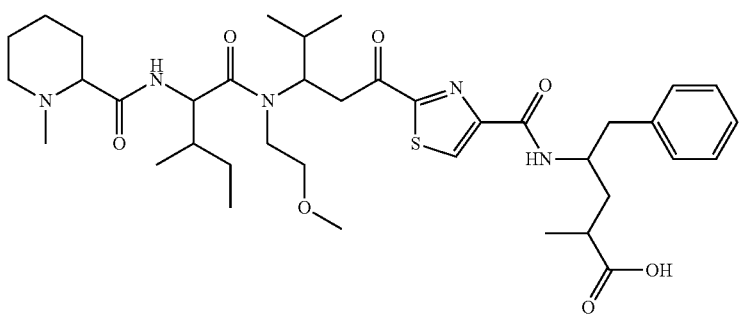
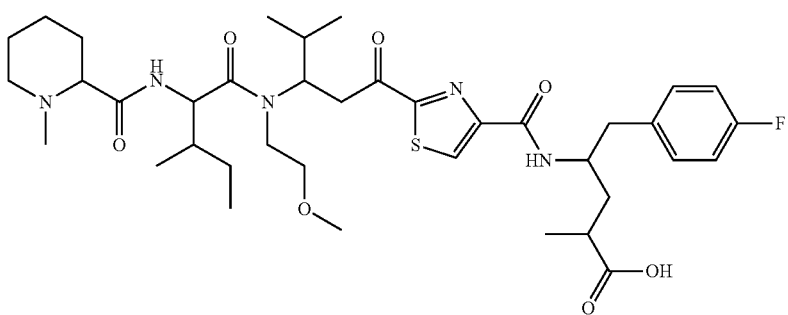
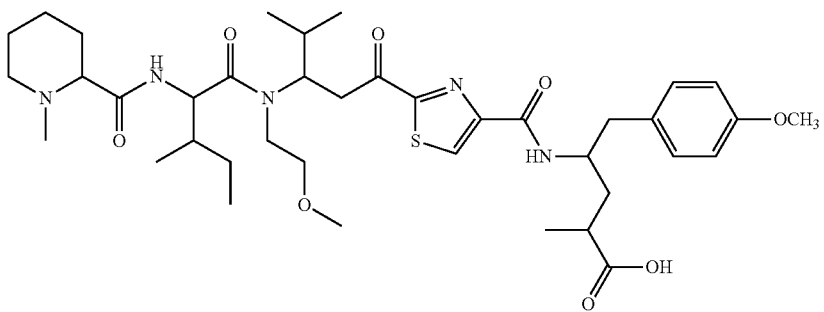

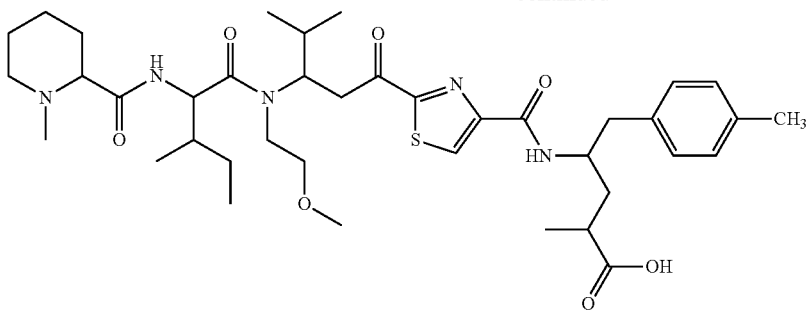
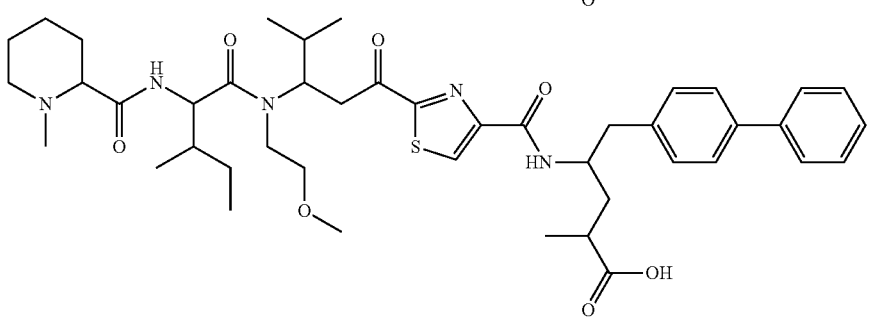
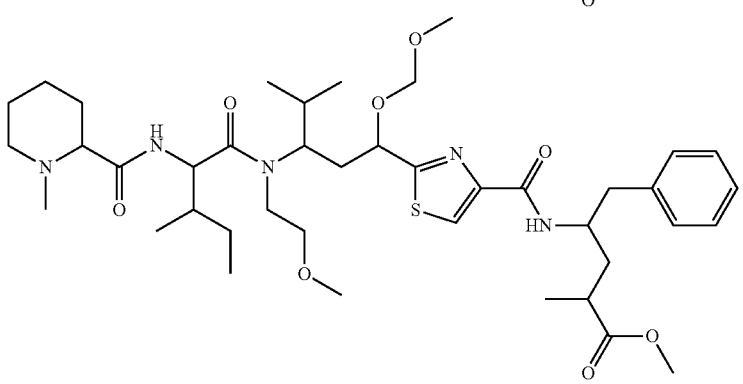
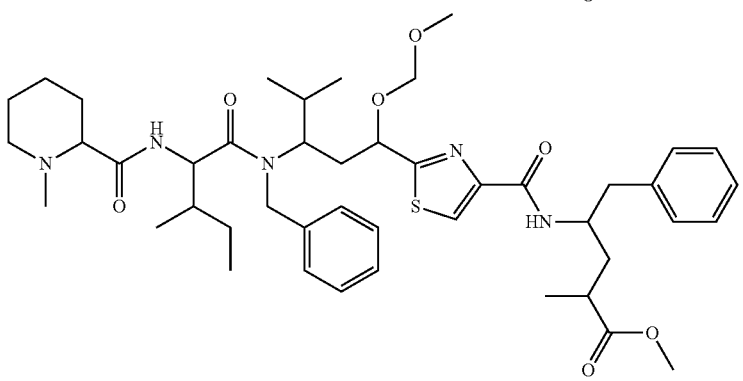
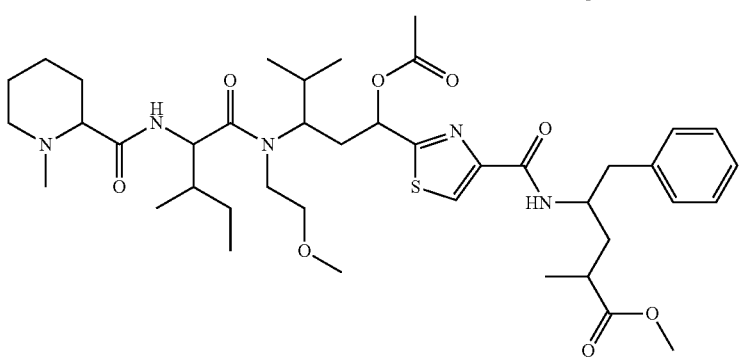

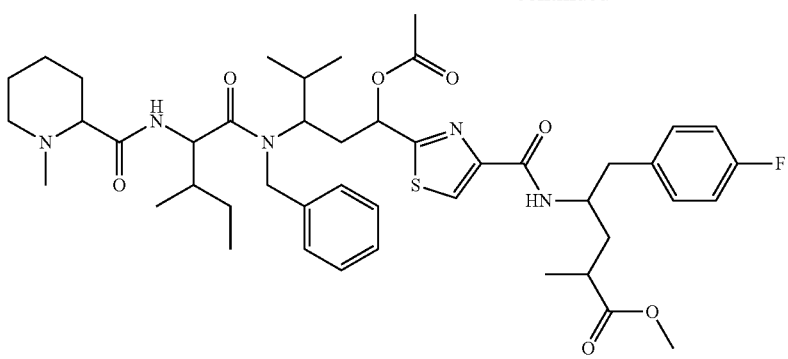
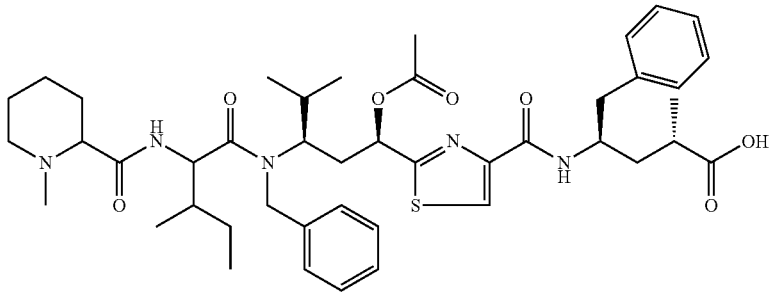
(ALXI)
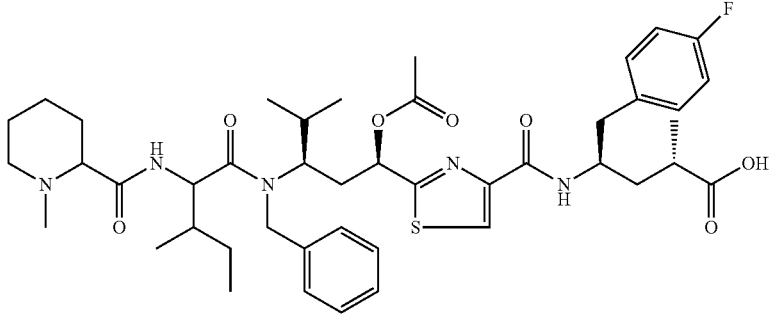
(ALXII)
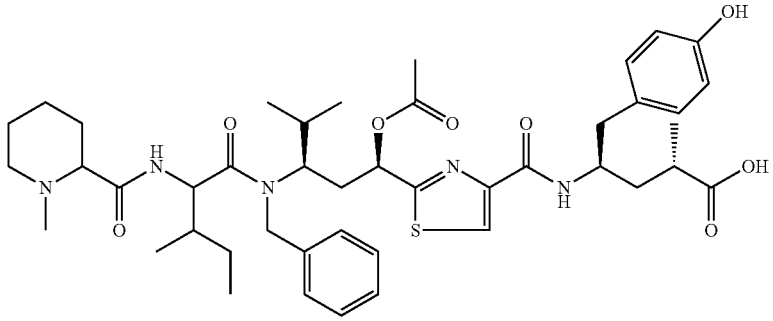
(ALXIII)
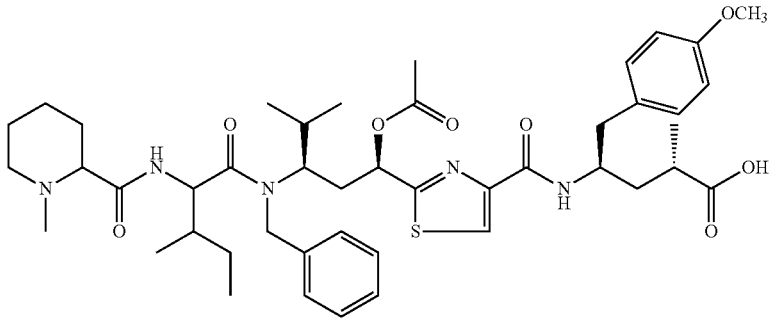
(ALXIV)

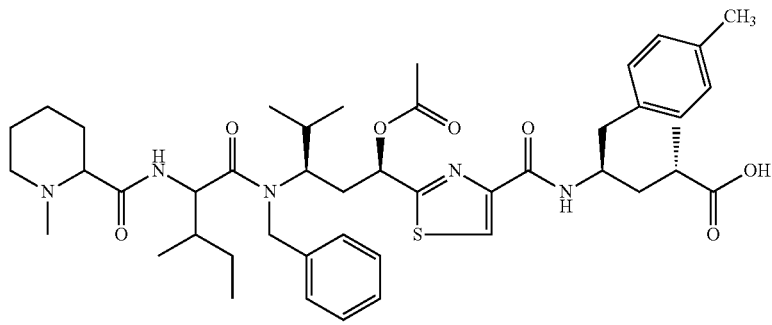
(ALXV)
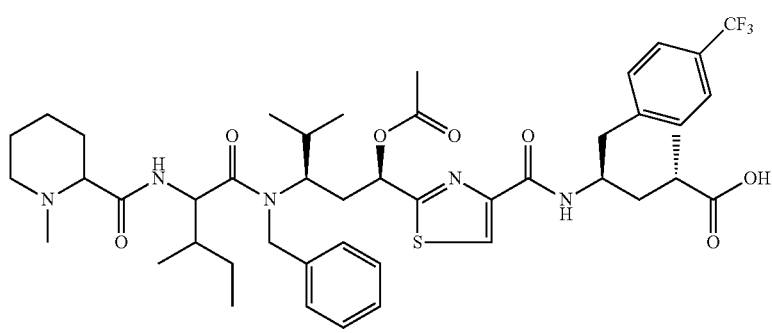
(ALXVI)
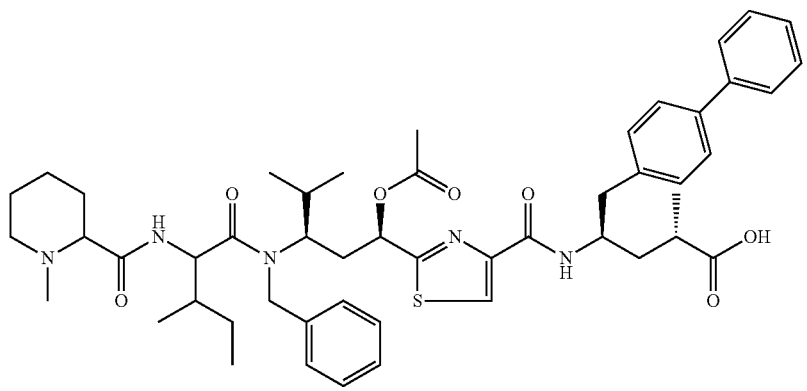
(ALXVII)
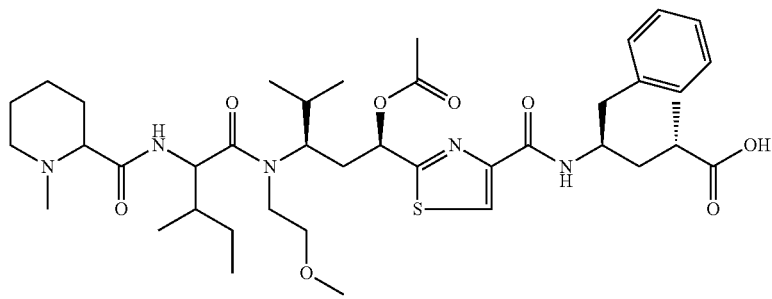
(ALXVIII)

-continued
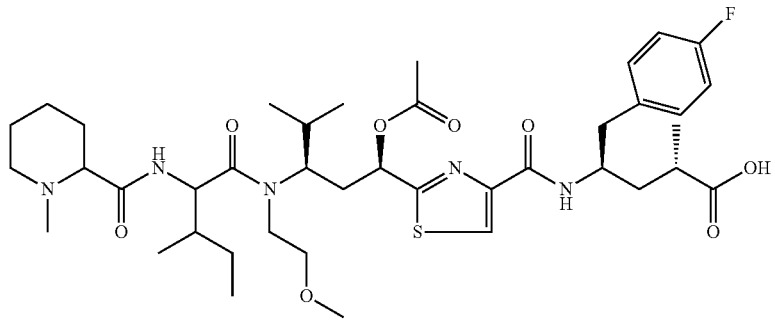
(ALXIX)
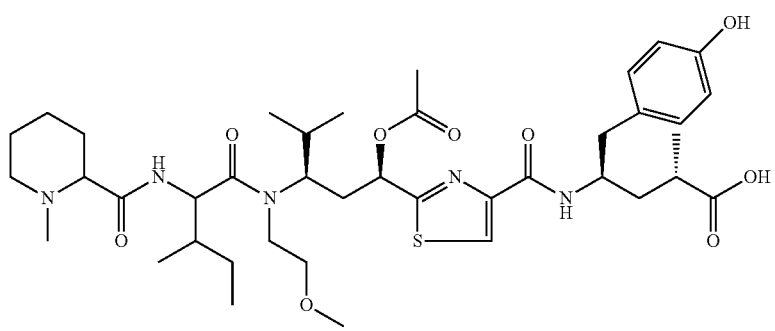
(ALXX)
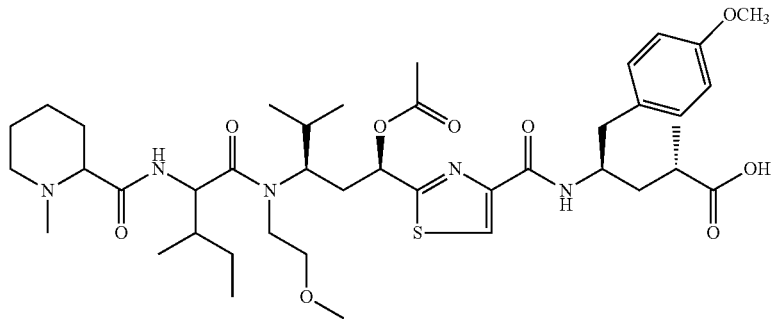
(ALXXI)
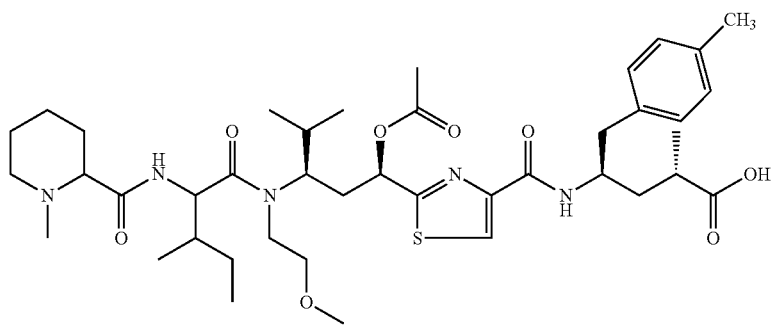
(ALXXII)
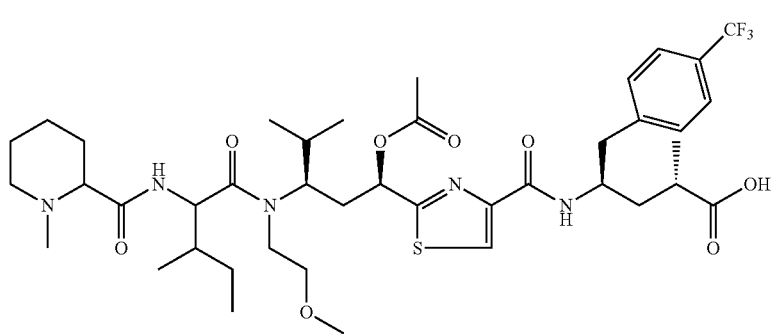
(ALXXIII)

(ALXXIV)
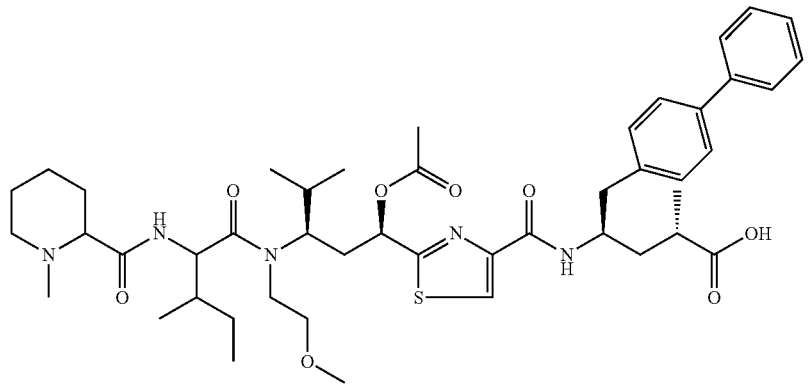
(ALXXV)
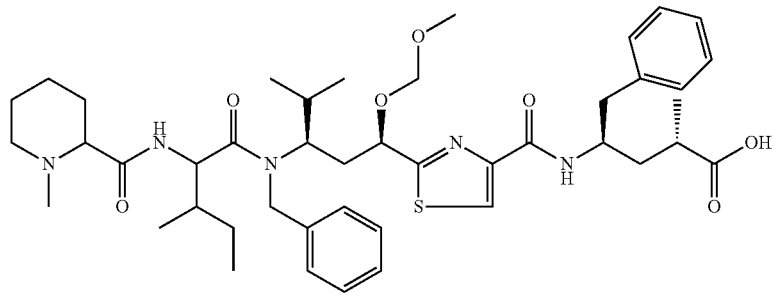
(ALXXVI)
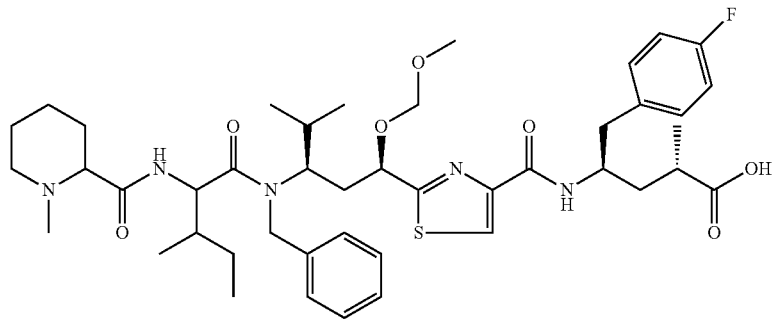
(ALXXVII)
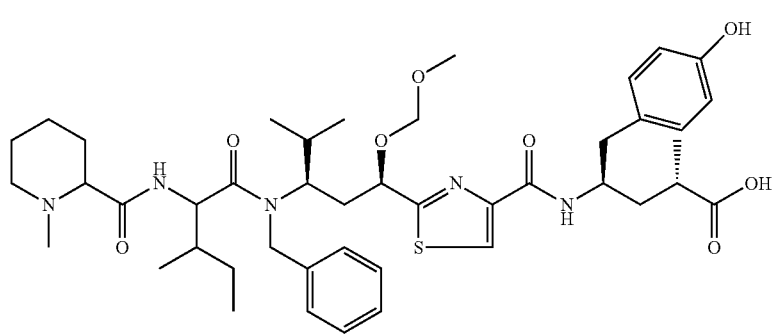

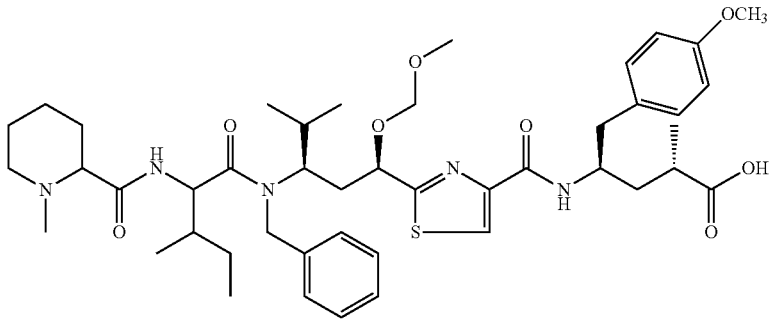
(ALXXVIII)
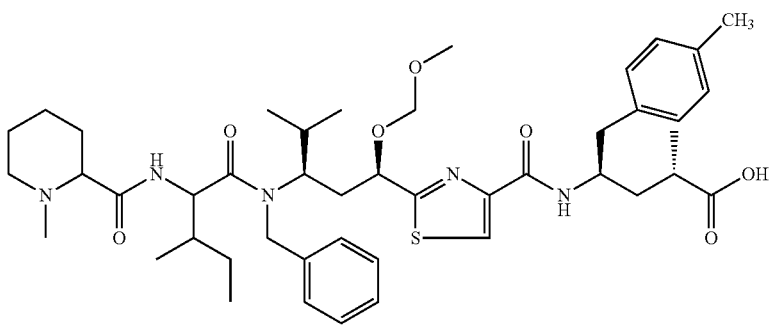
(ALXXIX)
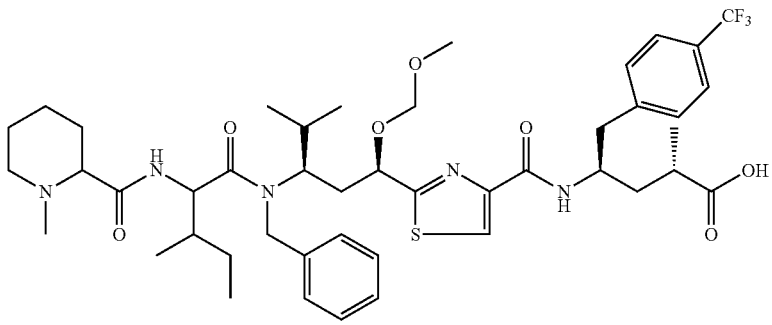
(ALXXX)
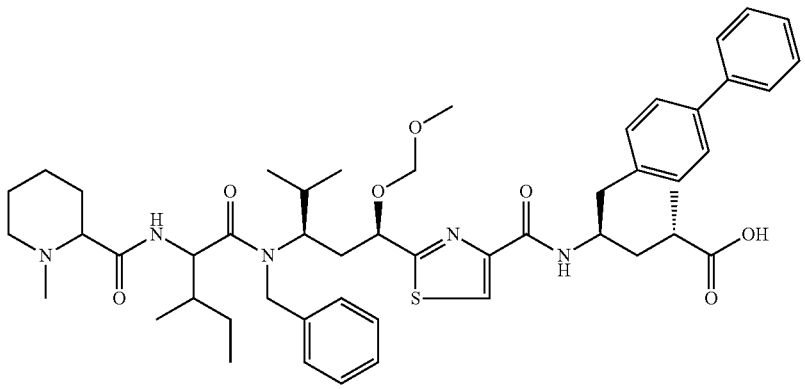
(ALXXXI)

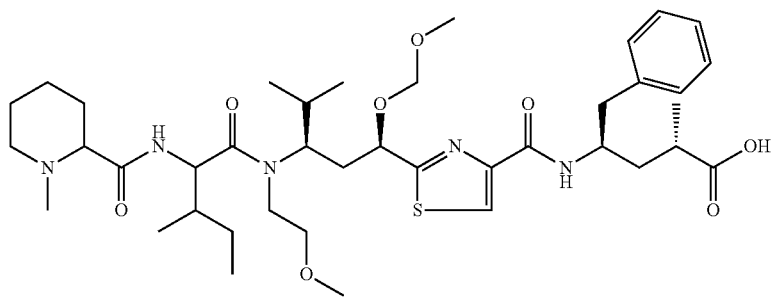
(ALXXXII)
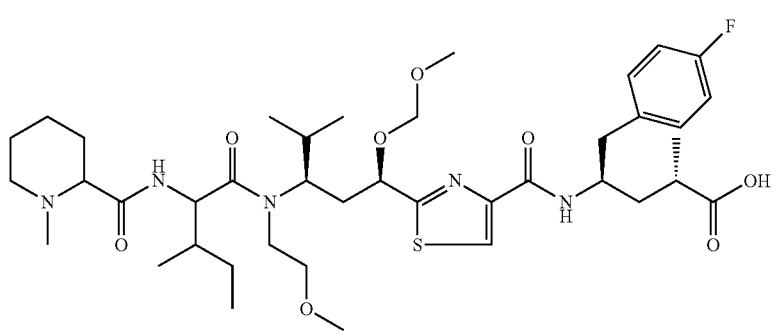
(ALXXXIII)
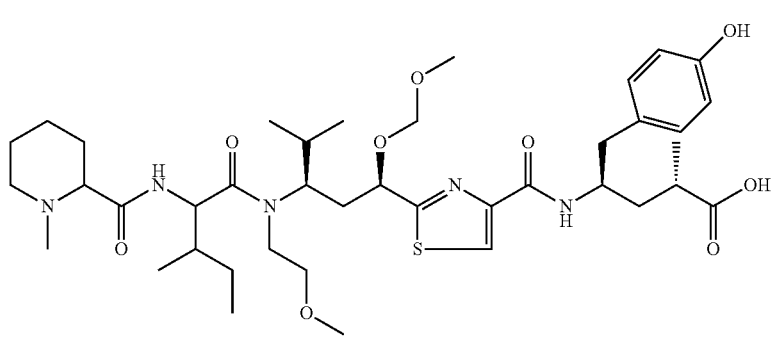
(ALXXXIV)
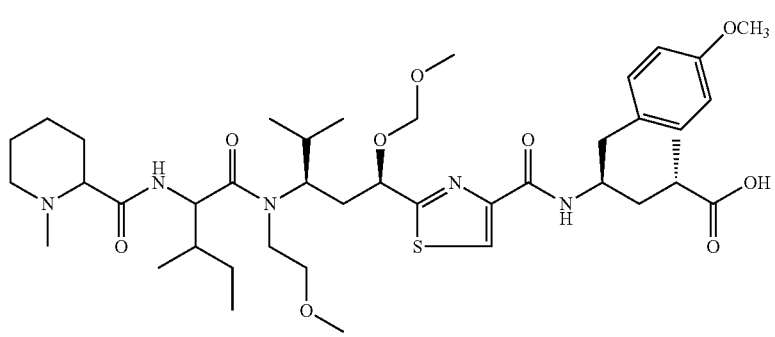
(ALXXXV)
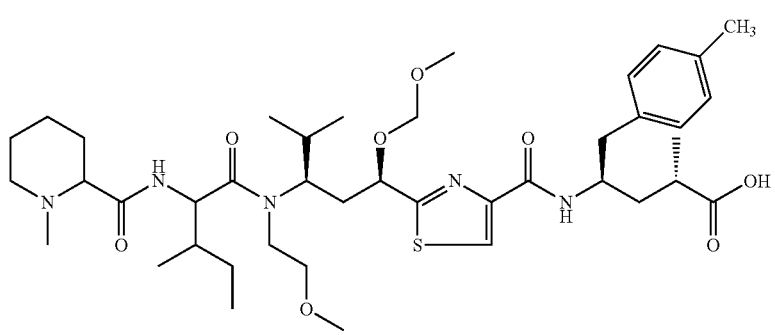
(ALXXXVI)

(ALXXXVII)
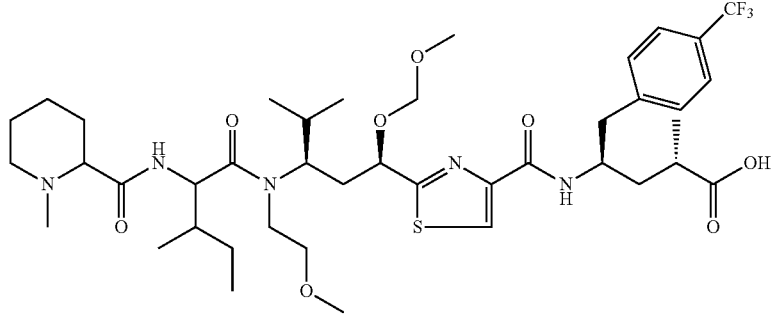
(ALXXXVIII)
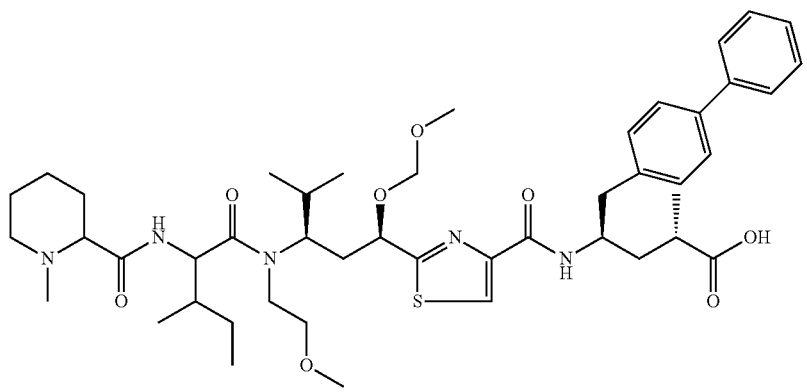
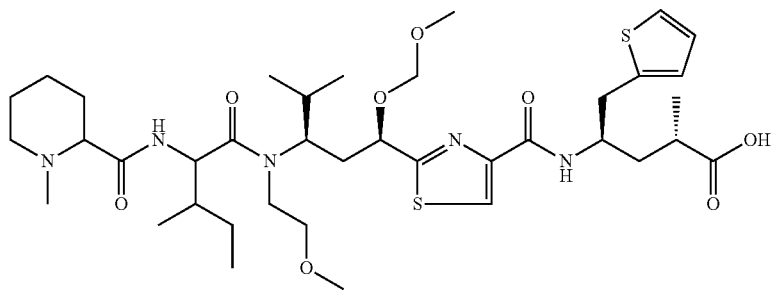
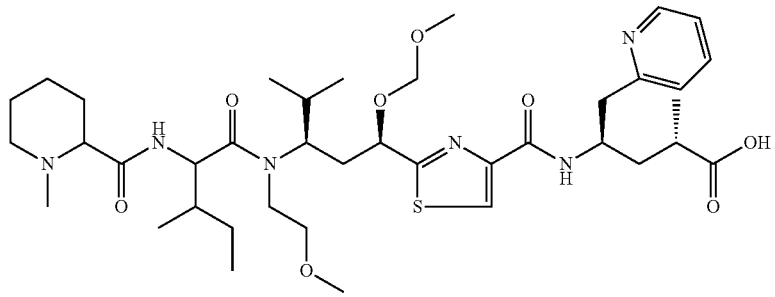
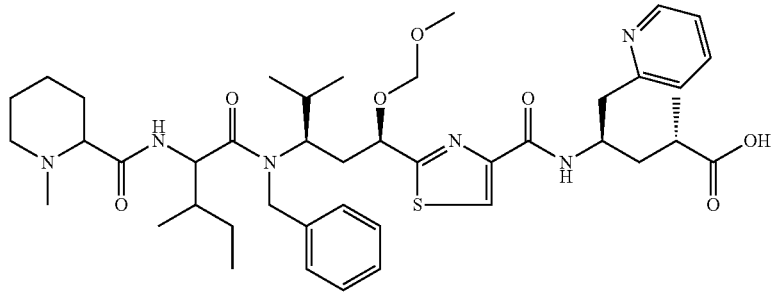

-continued
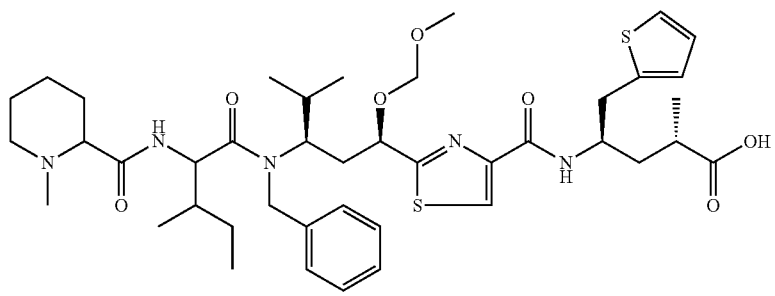
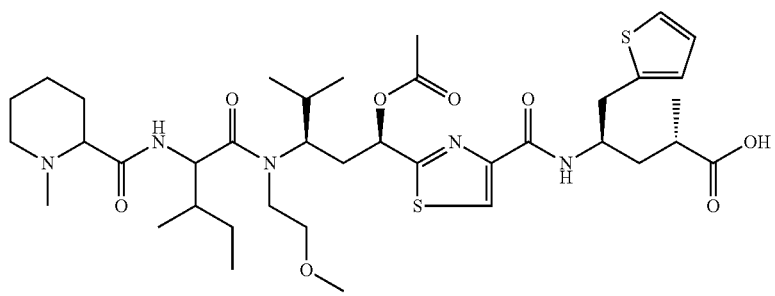
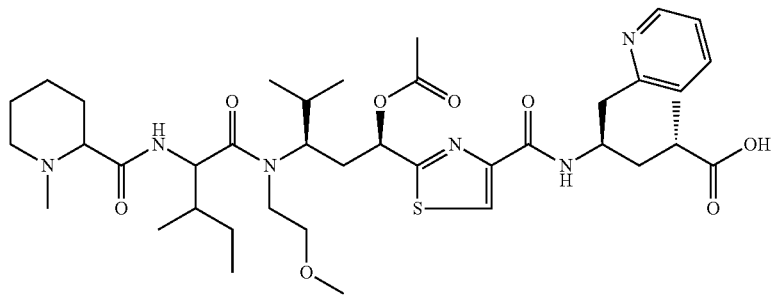
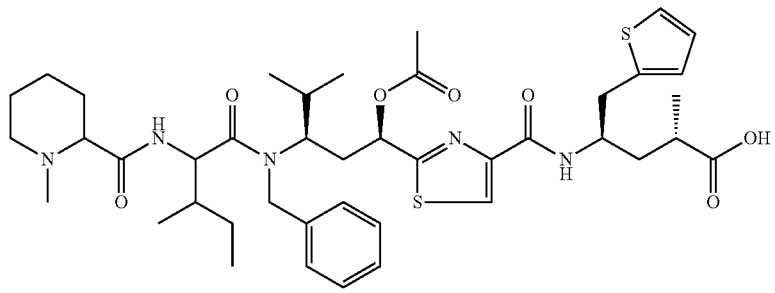
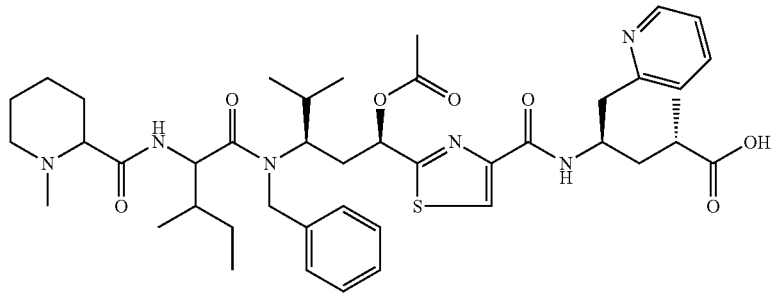

-continued
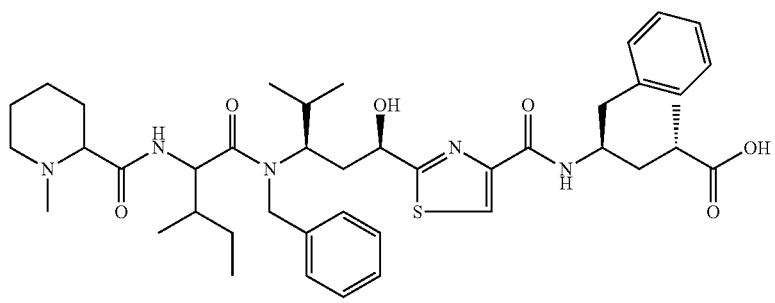
(AXCVII)
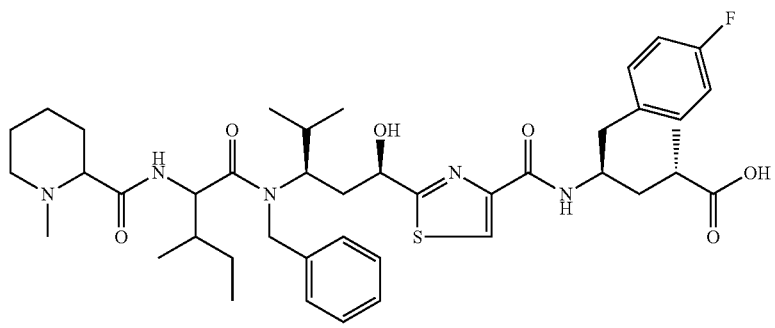
(AXCVIII)
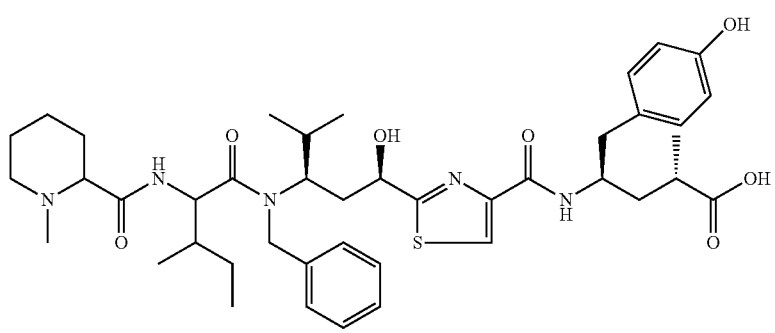
(AIC)
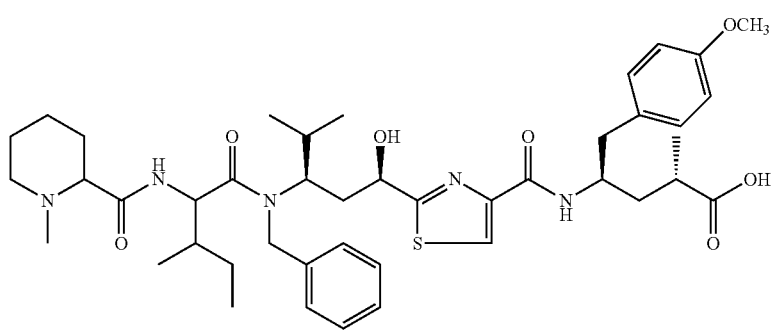
(AC)
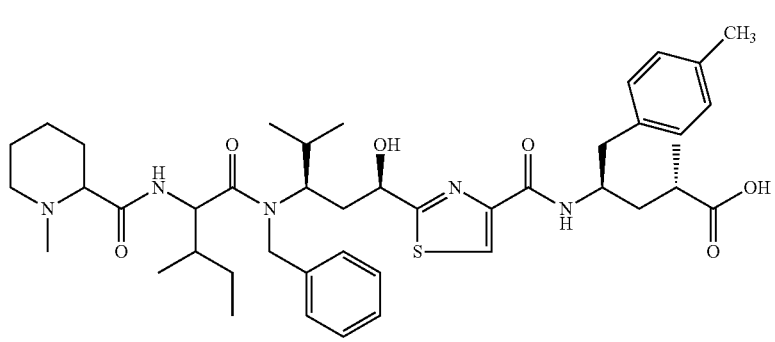
(ACI)

-continued
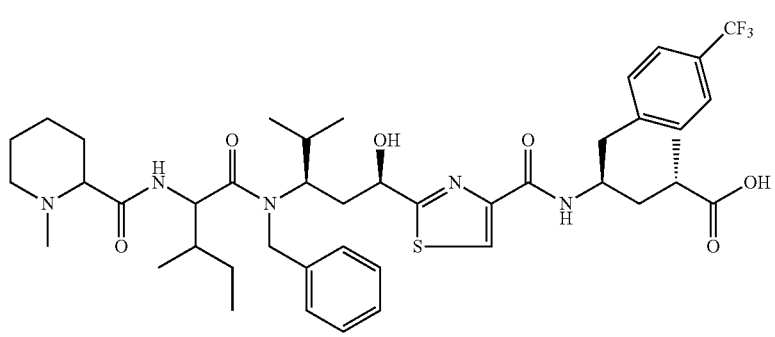
(ACII)
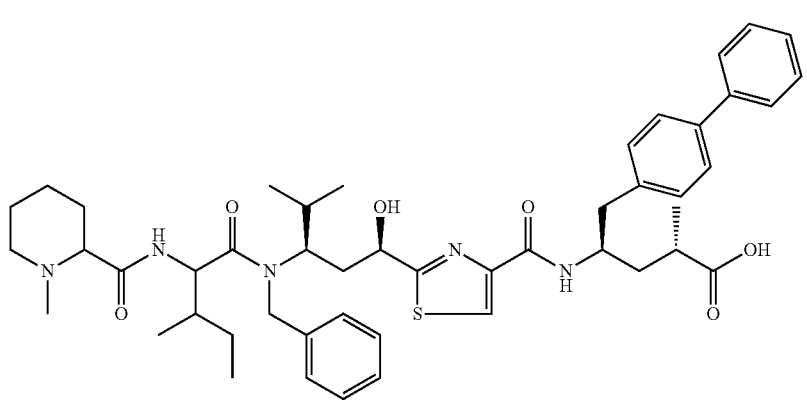
(ACIII)
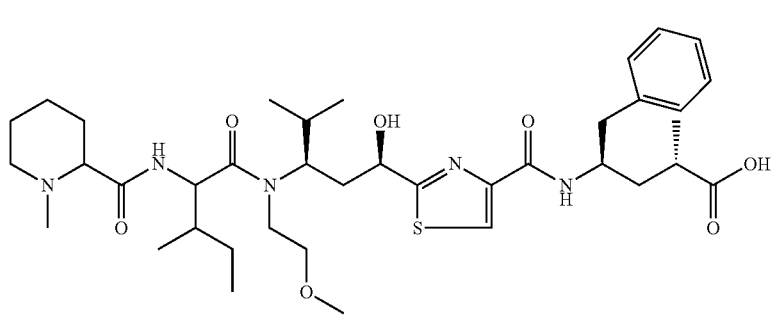
(ACIV)
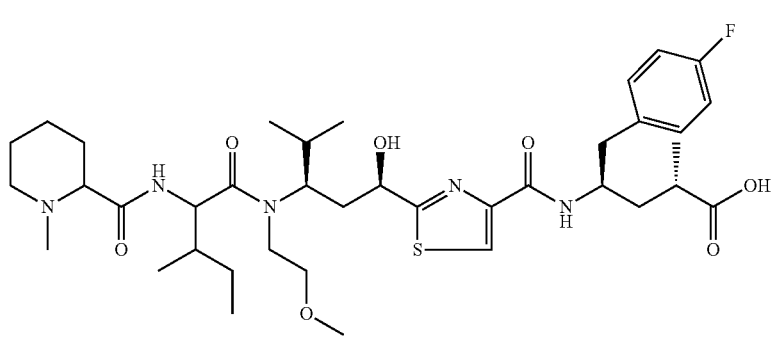
(ACV)

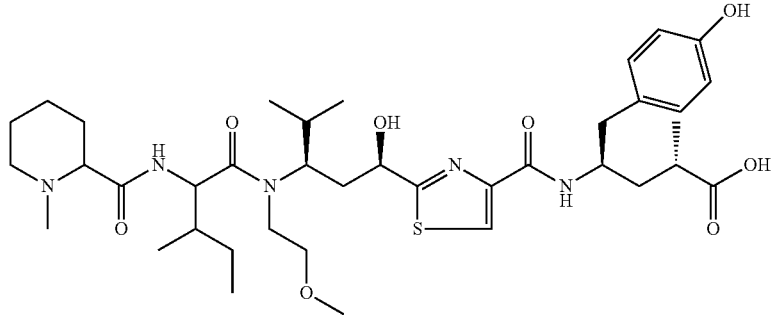
(ACVI)
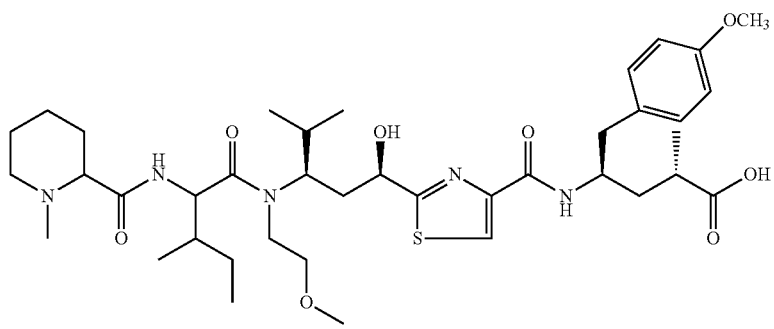
(ACVII)
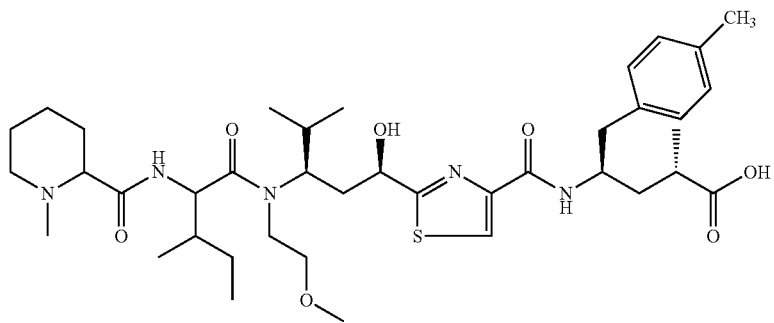
(ACVIII)
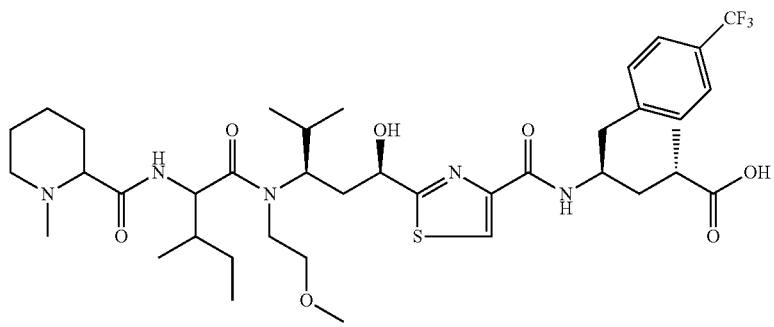
(ACIX)

-continued
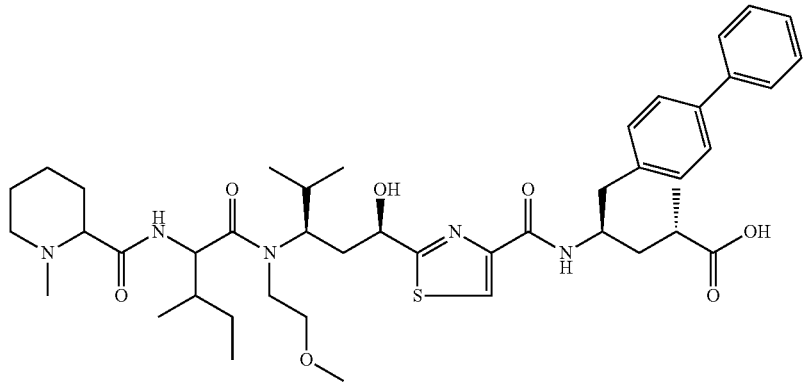
(ACX)
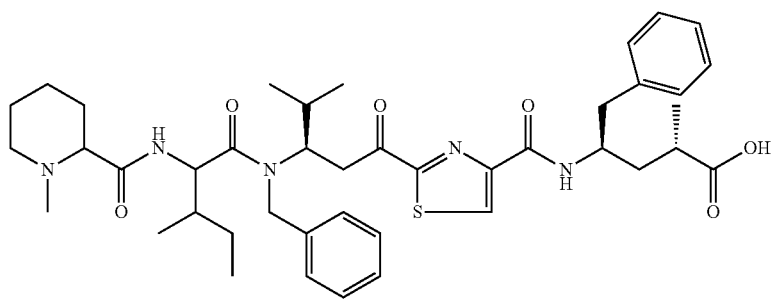
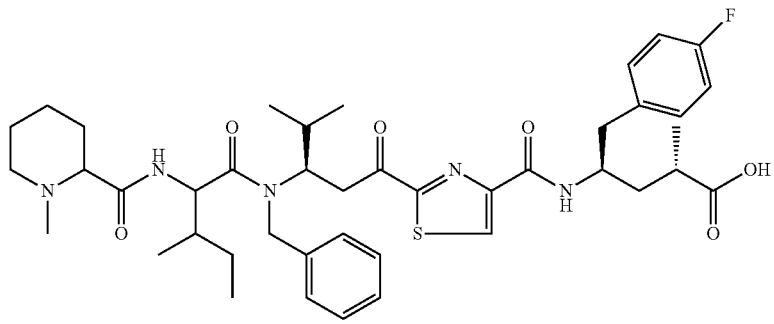
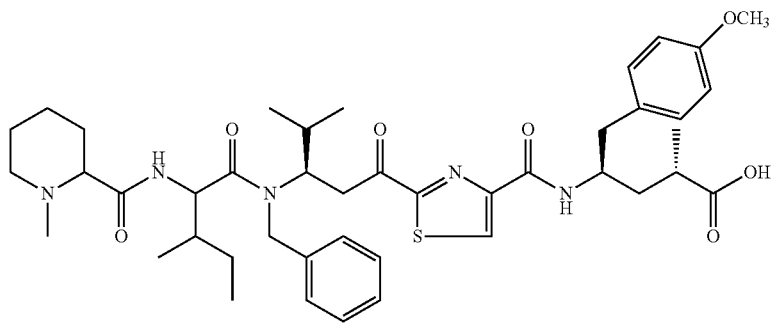
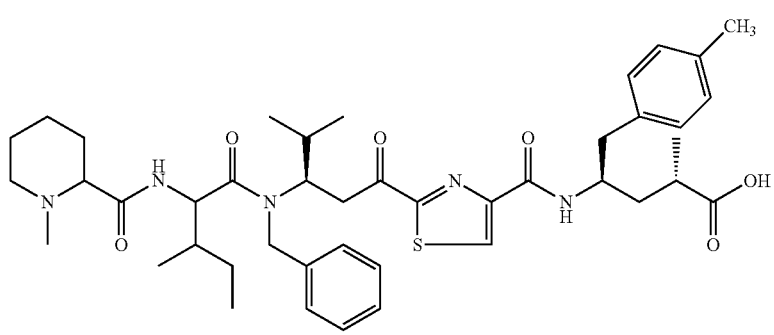

-continued
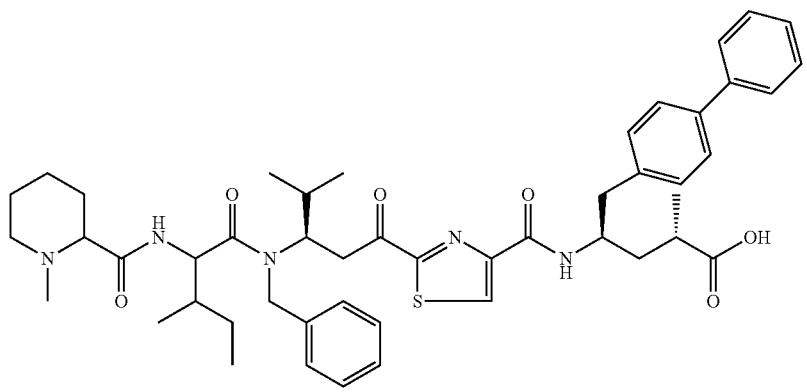
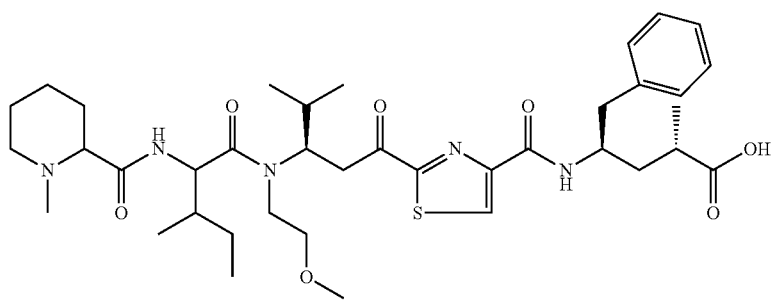
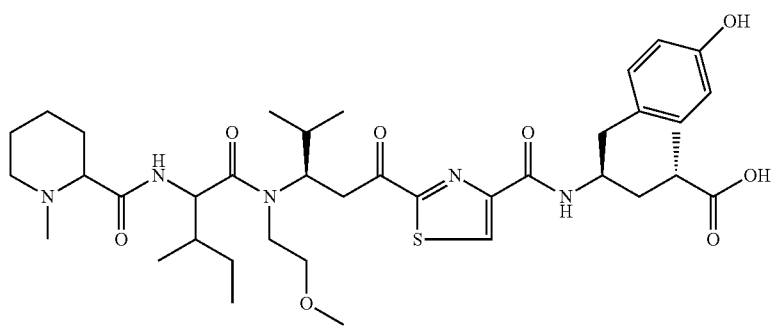
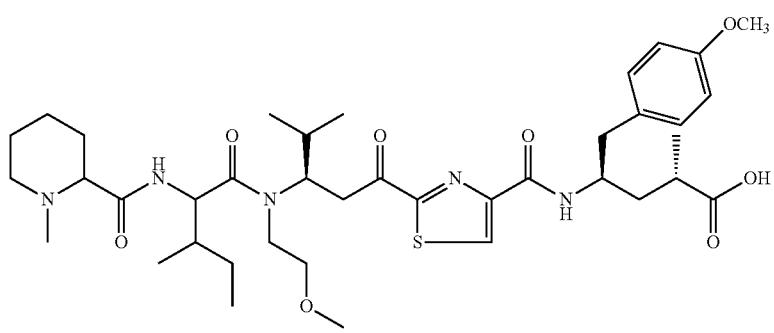
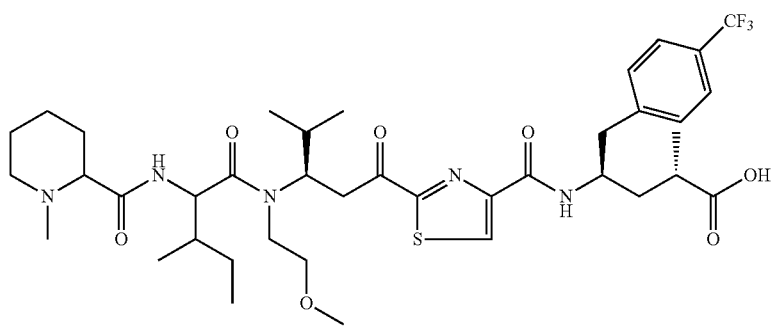

-continued
(ACXX)
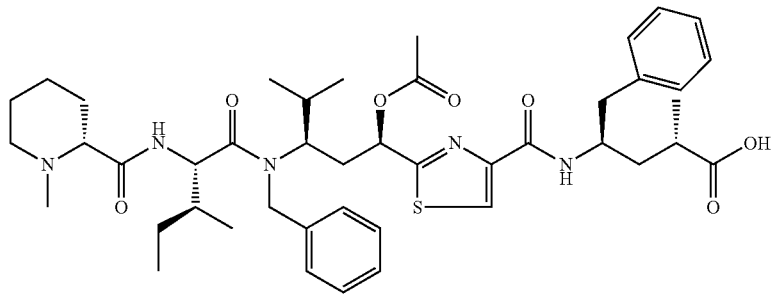
(ACXXI)
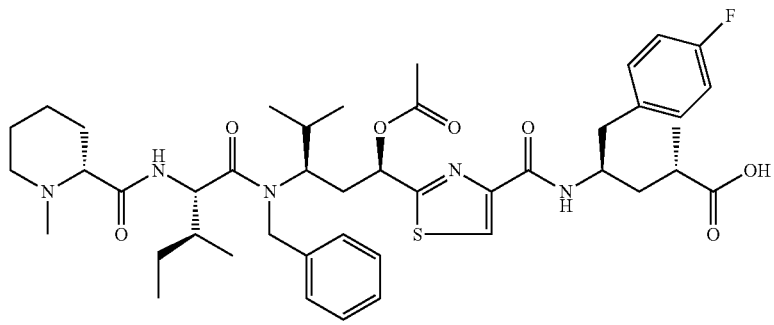
(ACXXII)
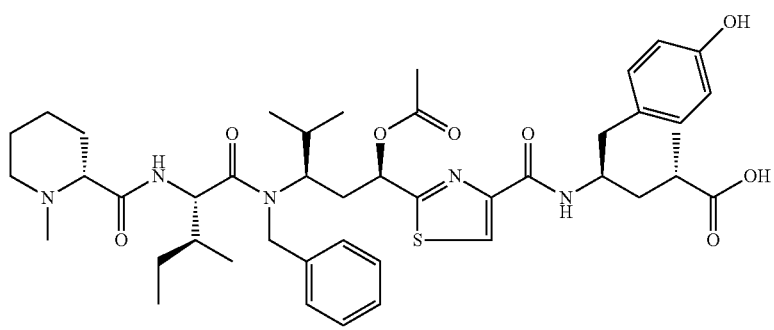
(ACXXIII)
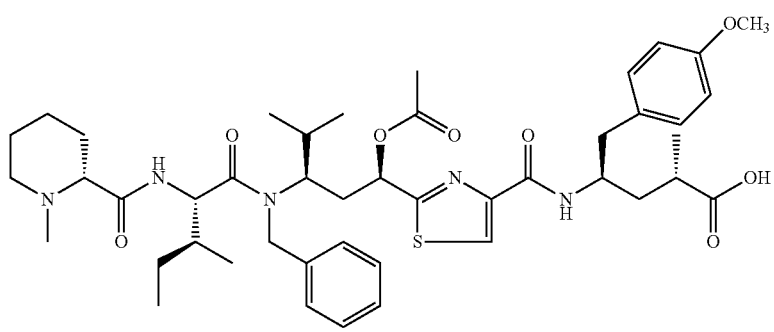
(ACXXIV)
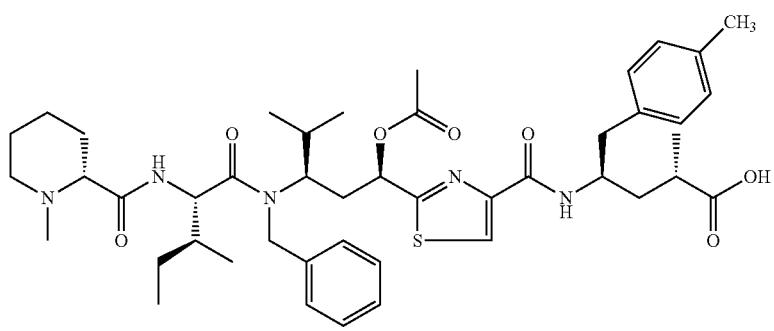

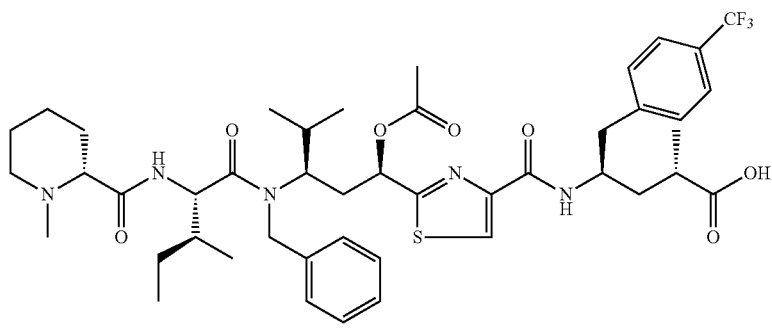
(ACXXV)
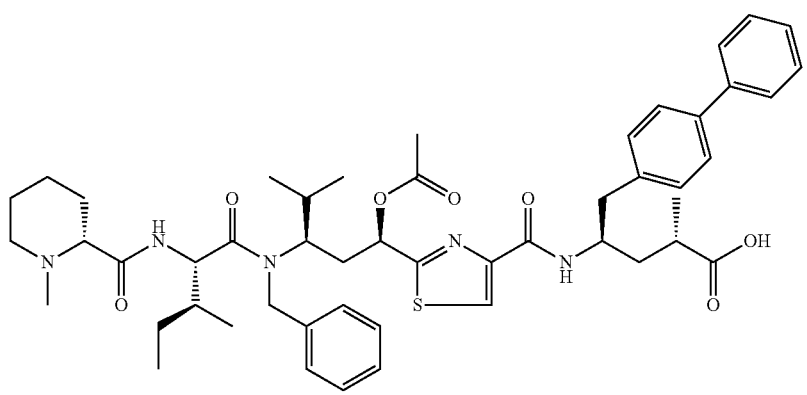
(ACXXVI)
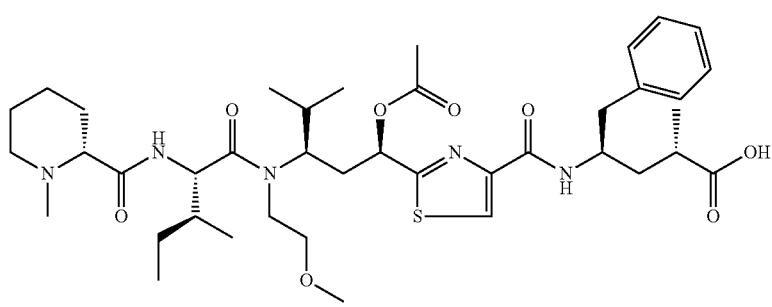
(ACXXVII)
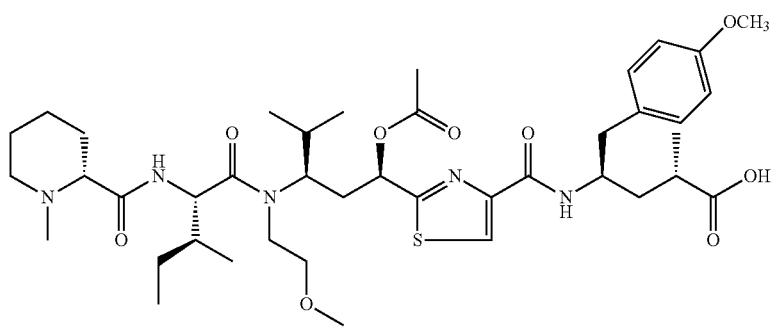
(ACXXVIII)

-continued
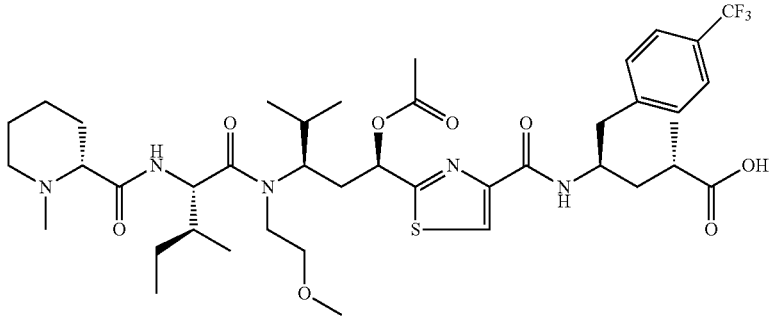
(ACXXIX)
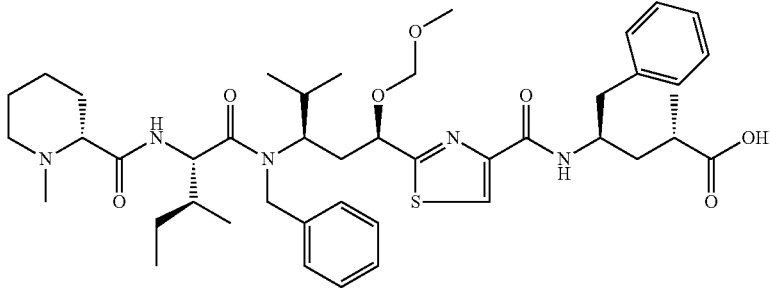
(ACXXX)
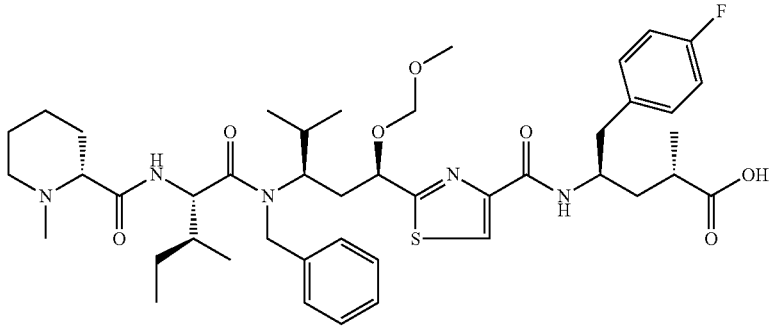
(ACXXXI)
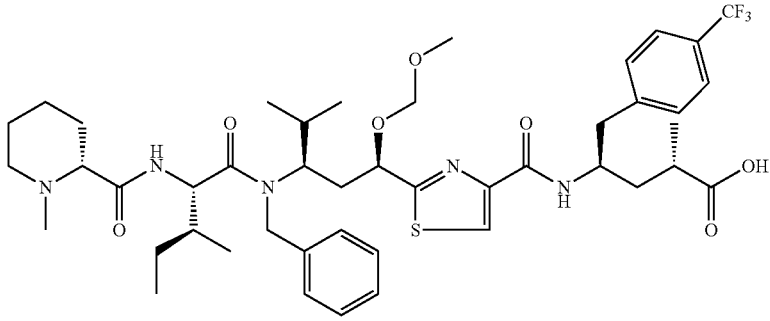
(ACXXXII)
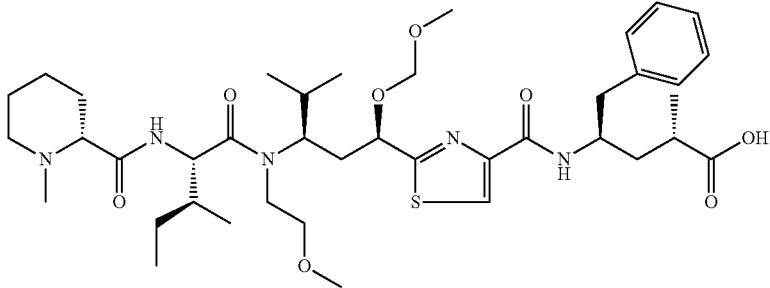
(ACXXXIII)

-continued
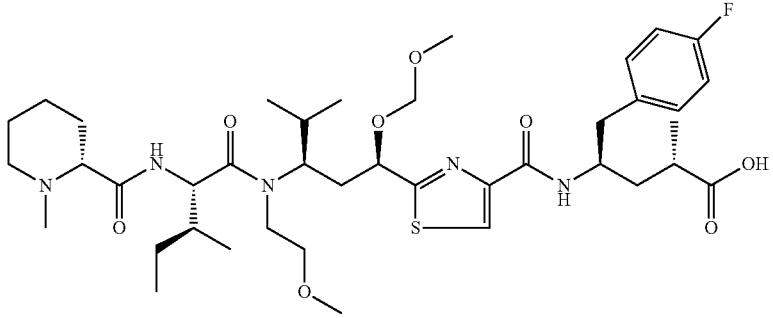
(ACXXXIV)
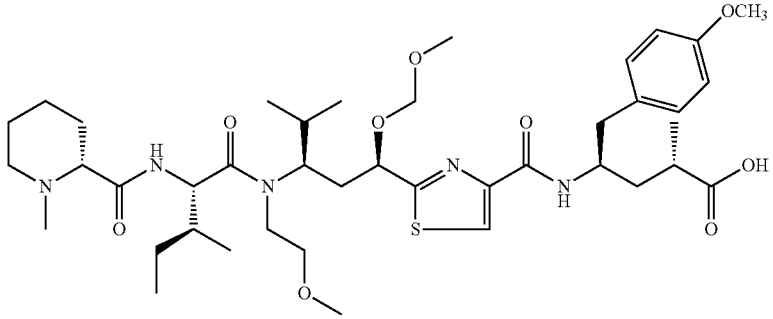
(ACXXXV)
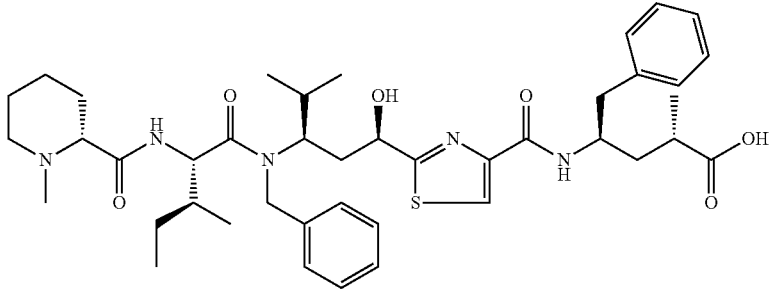
(ACXXXVI)
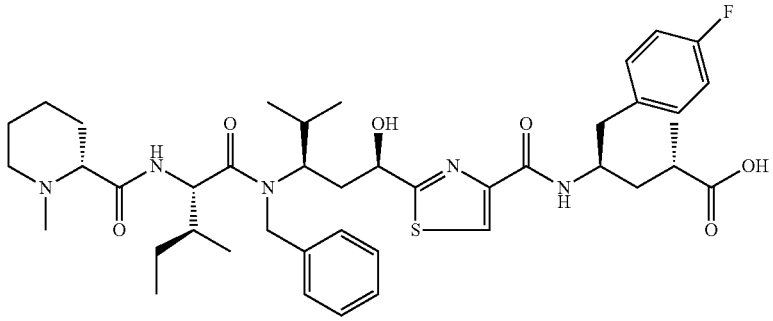
(ACXXXVII)
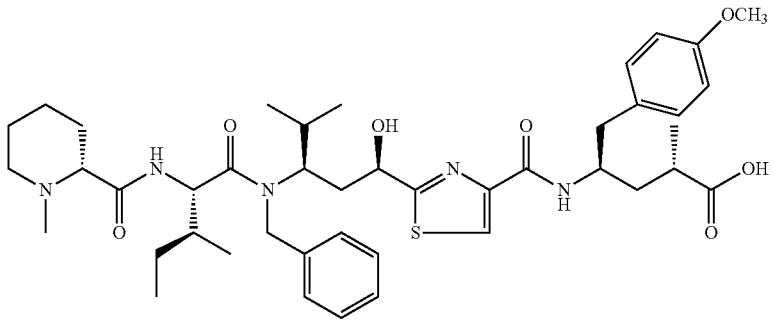
(ACXXXVIII)

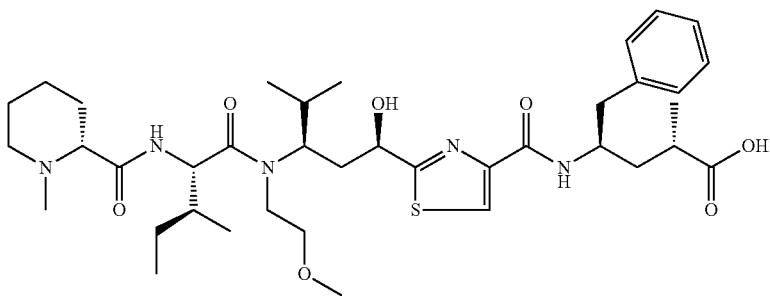
(ACIXL)

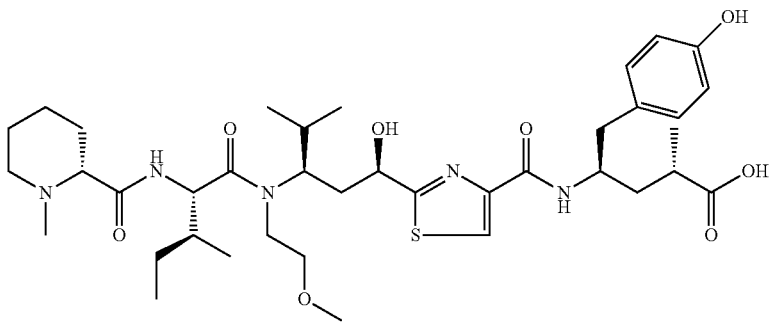
(ACXL)

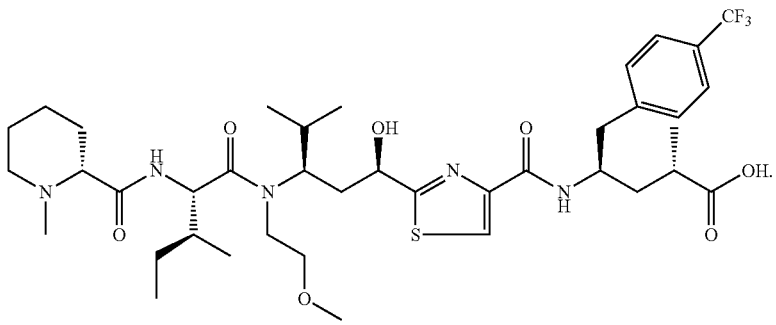
(ACXLI)

8. Pharmaceutical compositions comprising the compounds of claim 1.

9. Pharmaceutical compositions according to claim 8 in the form of microemulsions, emulsions, or comprising microemulsions or emulsions, comprising the following components (% by weight):
- S) from 0.01 to 95% of one or more pharmaceutically acceptable compounds, selected from the following classes:
  - surfactants selected from non-ionic, anionic, cationic and amphoteric surfactants, optionally containing fluorine atoms,
  - polymers which form organized structures as aggregates, micelles, liquid crystals, vesicles, in the liquid in which they are solubilized,
- O) from 0 to 95% of one or more oils selected from the following classes of pharmaceutically acceptable compounds:
  - esters of $C_4$-$C_{32}$ acids, optionally containing one or more ethylene unsaturations,
  - $C_4$-$C_{32}$ acids optionally containing one or more unsaturations of ethylene type, when the final composition has a pH such that the acid is not transformed into the corresponding salt,
- PA) from 0.001 to 90% of compounds of any one of claims 1, 6, and 7,
- AD) from 0 to 60% by weight of one or more compounds selected from the following classes:
  - modifiers of water and/or oil polarity,
  - modifiers of the film curvature of component S),
  - co-surfactants,
- WA) from 0.001 to 99.9% of water or of a saline aqueous solution, optionally buffered,
the sum of the components being 100%.

10. Pharmaceutical compositions according to claim 8 further comprising micro- and/or nano-particles of silica, or lipids and/or pharmaceutically acceptable polymers and/or biomolecules.

11. A method of treating a mammal or human being having a tumoral disease, comprising administering the compounds of claim 1 or pharmaceutical compositions thereof to the mammal or human being, wherein the tumoral disease is selected from the group consisting of: colon cancer, leukemia, glioma, ovarian cancer, breast cancer, gastric cancer, mesothelioma, and lung cancer.

* * * * *